(12) United States Patent
Wang et al.

(10) Patent No.: US 12,012,467 B2
(45) Date of Patent: Jun. 18, 2024

(54) SMALL MOLECULE DCN1 INHIBITORS AND THERAPEUTIC METHODS USING THE SAME

(71) Applicant: THE REGENTS OF THE UNIVERSITY OF MICHIGAN, Ann Arbor, MI (US)

(72) Inventors: Shaomeng Wang, Superior Township, MI (US); Haibin Zhou, Ann Arbor, MI (US); Jianfeng Lu, Ann Arbor, MI (US); Liu Liu, Ann Arbor, MI (US); Yi Sun, Superior Township, MI (US); Denzil Bernard, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1045 days.

(21) Appl. No.: 16/496,974

(22) PCT Filed: Mar. 28, 2018

(86) PCT No.: PCT/US2018/024708
§ 371 (c)(1),
(2) Date: Sep. 24, 2019

(87) PCT Pub. No.: WO2018/183411
PCT Pub. Date: Oct. 4, 2018

(65) Prior Publication Data
US 2020/0109167 A1    Apr. 9, 2020

Related U.S. Application Data

(60) Provisional application No. 62/477,498, filed on Mar. 28, 2017.

(51) Int. Cl.
| | | |
|---|---|---|
| A61K 31/426 | (2006.01) |
| A61K 31/427 | (2006.01) |
| A61K 31/428 | (2006.01) |
| A61K 31/454 | (2006.01) |
| A61K 31/5377 | (2006.01) |
| A61K 38/05 | (2006.01) |
| A61K 38/06 | (2006.01) |
| A61K 38/07 | (2006.01) |
| A61K 45/06 | (2006.01) |
| C07D 277/30 | (2006.01) |
| C07D 277/64 | (2006.01) |
| C07D 417/12 | (2006.01) |
| C07K 5/02 | (2006.01) |
| C07K 5/062 | (2006.01) |
| C07K 5/078 | (2006.01) |
| C07K 5/097 | (2006.01) |
| C07K 5/113 | (2006.01) |
| C07K 5/117 | (2006.01) |
| C07K 7/02 | (2006.01) |

(52) U.S. Cl.
CPC ......... *C07K 5/1021* (2013.01); *A61K 31/426* (2013.01); *A61K 31/427* (2013.01); *A61K 31/428* (2013.01); *A61K 31/454* (2013.01); *A61K 31/5377* (2013.01); *A61K 38/05* (2013.01); *A61K 38/06* (2013.01); *A61K 38/07* (2013.01); *A61K 45/06* (2013.01); *C07D 277/30* (2013.01); *C07D 277/64* (2013.01); *C07D 417/12* (2013.01); *C07K 5/02* (2013.01); *C07K 5/021* (2013.01); *C07K 5/06026* (2013.01); *C07K 5/06139* (2013.01); *C07K 5/0821* (2013.01); *C07K 5/1024* (2013.01); *C07K 7/02* (2013.01)

(58) Field of Classification Search
None
See application file for complete search history.

(56) References Cited

U.S. PATENT DOCUMENTS

| 5,430,022 A | 7/1995 | Hemmi et al. |
| 6,759,384 B1 | 7/2004 | Al-Obeidi et al. |

FOREIGN PATENT DOCUMENTS

| CN | 101544687 A | 9/2009 |
| EP | 0441191 A2 | 8/1991 |
| EP | 1584625 A1 | 10/2005 |

(Continued)

OTHER PUBLICATIONS

Database Registry Chemical Abstracts Service, Columbus, Ohio, Accession No. RN 1026406-22-3. Entered STN: Jun. 8, 2008.*

(Continued)

*Primary Examiner* — Samantha L Shterengarts
(74) *Attorney, Agent, or Firm* — MARSHALL, GERSTEIN & BORUN LLP

(57) ABSTRACT

Compounds of formula (I) as inhibitors of DCN1 and compositions containing the same are disclosed. Methods of using the DCN1 inhibitors in the treatment of diseases and conditions wherein inhibition of DCN1 provides a benefit, like oxidative stress-related diseases and conditions, neurodegenerative diseases and conditions, metabolic disorders, and muscular nerve degeneration, also are disclosed.

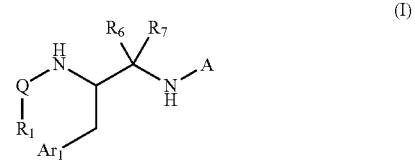

(I)

7 Claims, 4 Drawing Sheets

(56) References Cited

FOREIGN PATENT DOCUMENTS

| WO | WO-95/17423 A1 | 6/1995 |
|---|---|---|
| WO | WO-2009/130735 A1 | 10/2009 |
| WO | WO-2014/029022 A1 | 2/2014 |
| WO | WO-2017/049295 A1 | 3/2017 |

OTHER PUBLICATIONS

Database Registry Chemical Abstracts Service, Columbus, Ohio, Accession No. RN 1057707-01-3. Entered STN: Oct. 6, 2008.*
Database Registry Chemical Abstracts Service, Columbus, Ohio, Accession No. RN 2245888-15-5. Entered STN: Oct. 23, 2018.*
Andérica-Romero et al., Cullin 3 as a novel target in diverse pathologies, Redox Biol., 1:366-72 (2013).
Bedford et al., Ubiquitin-like protein conjugation and the ubiquitin-proteasome system as drug targets, Nat. Rev. Drug Discov., 10(1):29-46 (Jan. 2011).
Bomprezzi, Dimethyl fumarate in the treatment of relapsing-remitting multiple sclerosis: an overview, Ther. Adv. Neurol. Disord., 8(1):20-30 (2015).
Brownell et al., Substrate-assisted inhibition of ubiquitin-like protein-activating enzymes: the NEDD8 E1 inhibitor MLN4924 forms a NEDD8-AMP mimetic in situ, Mol. Cell, 37(1):102-11 (2010).
Buendia et al., Nrf2-ARE pathway: An emerging target against oxidative stress and neuroinflammation in neurodegenerative diseases, Pharmacol. Ther., 157:84-104 (2016).
Bulatov et al., Targeting Cullin-RING E3 ubiquitin ligases for drug discovery: structure, assembly and small-molecule modulation, Biochem. J., 467(3):365-86 (2015).
Canning et al., New strategies to inhibit KEAP1 and the Cul3-based E3 ubiquitin ligases, Biochem. Soc. Trans., 42(1):103-7 (2014).
Chemical Abstracts Service, Database accession No. 1026406-22-3 (Jun. 8, 2008).
Chemical Abstracts Service, Database accession No. 1281062-79-0 (Apr. 17, 2011).
Chemical Abstracts Service, Database accession No. 1978:136939 (1977).
Chemical Abstracts Service, Database accession No. 1030373-38-6 (Jun. 24, 2008).
Ciechanover et al., The ubiquitin-proteasome pathway: the complexity and myriad functions of proteins death, Proc. Natl. Acad. Sci. USA, 95(6):2727-30 (Mar. 1998).
Cullinan et al., The Keap1-BTB protein is an adaptor that bridges Nrf2 to a Cul3-based E3 ligase: oxidative stress sensing by a Cul3-Keap1 ligase, Mol. Cell Biol., 24(19):8477-86 (2004).
de Zeeuw et al., Bardoxolone methyl in type 2 diabetes and stage 4 chronic kidney disease, N. Engl. J. Med., 369(26):2492-503 (2013).
Deshaies et al., Control of cullin-ring ubiquitin ligase activity by nedd8, Subcell Biochem., 54:41-56 (2010).
Duda et al., Structural insights into NEDD8 activation of cullin-RING ligases: conformational control of conjugation, Cell, 134(6):995-1006 (2008).
Emsley et al., Coot: model-building tools for molecular graphics, Acta Crystallogr D Biol. Crystallogr., 60(Pt 12 Pt 1):2126-32 (Dec. 2004).
Genschik et al., The emerging family of CULLIN3-RING ubiquitin ligases (CRL3s): cellular functions and disease implications, EMBO J., 32(17):2307-20 (2013).
Gong et al., Identification of the activating and conjugating enzymes of the NEDD8 conjugation pathway, J. Biol. Chem., 274(17):12036-42 (1999).
Gorrini et al., Modulation of oxidative stress as an anticancer strategy, Nat. Rev. Drug Discov., 12(12):931-47 (2013).
Hayes et al., The Nrf2 regulatory network provides an interface between redox and intermediary metabolism, Trends Biochem. Sci., 39(4):199-218 (2014).
Hershko, The ubiquitin system for protein degradation and some of its roles in the control of the cell division cycle, Cell Death Differ., 12(9):1191-7 (Sep. 2005).
Huang et al., A unique E1-E2 interaction required for optimal conjugation of the ubiquitin-like protein NEDD8, Nat. Struct. Mol. Biol., 11(10):927-35 (2004).
International Application No. PCT/US2018/024708, International Search Report and Written Opinion, dated Jul. 6, 2018.
Janecka et al., Reduced-size antagonists of luteinizing hormone-releasing hormone active in vitro, J. Med. Chem., 38(15):2922-4 (Jul. 1995).
Kane et al., Bortezomib for the treatment of mantle cell lymphoma, Clin. Cancer Res., 13(18 Pt. 1):5291-4 (Sep. 2007).
Kane et al., Velcade: U.S. FDA approval for the treatment of multiple myeloma progressing on prior therapy, Oncologist, 8(6):508-13 (2003).
Keuss et al., Characterization of the mammalian family of DCN-type NEDD8 E3 ligases, J. Cell Sci., 129(7):1441-54 (2016).
Kim et al., SCCRO (DCUN1D1) is an essential component of the E3 complex for neddylation, J. Biol. Chem., 283(48):33211-20 (2008).
Kobayashi et al., Oxidative stress sensor Keap1 functions as an adaptor for Cul3-based E3 ligase to regulate proteasomal degradation of Nrf2, Mol. Cell Biol., 24(16):7130-9 (2004).
Kurz et al., Dcn1 functions as a scaffold-type E3 ligase for cullin neddylation, Mol. Cell., 29(1):23-35 (2008).
Liby et al., Synthetic oleanane triterpenoids: multifunctional drugs with a broad range of applications for prevention and treatment of chronic disease, Pharmacol. Rev., 64(4):972-1003 (2012).
Ma, Role of nrf2 in oxidative stress and toxicity, Annu. Rev. Pharmacol. Toxicol., 53:401-26 (2013).
Martinez Molina et al., Monitoring drug target engagement in cells and tissues using the cellular thermal shift assay, Science, 341(6141):84-7 (2013).
McCormack, Carfilzomib: in relapsed, or relapsed and refractory, multiple myeloma, Drugs, 72(15):2023-32 (Oct. 2012).
Monda et al., Structural conservation of distinctive N-terminal acetylation-dependent interactions across a family of mammalian NEDD8 ligation enzymes, Structure, 21(1):42-53 (2013).
Nalepa et al., Drug discovery in the ubiquitin-proteasome system, Nat. Rev. Drug Discov., 5(7):596-613 (Jul. 2006).
Nishitani et al., Two E3 ubiquitin ligases, SCF-Skp2 and DDB1-Cul4, target human Cdt1 for proteolysis, EMBO J., 25(5):1126-36 (2006).
Ojima et al., Synthesis of optically active N-(N-acetyl)-alpha-aminoacyl-beta-amino alcohols by homogeneous and heterogeneous asymmetric hydrogenations, Chem. Lett., pp. 1335-1338 (1982).
Otwinowski et al., Processing of X-ray diffraction data collected in oscillation mode, Methods Enzymol., 276:307-26 (1997).
Petroski et al., Function and regulation of cullin-RING ubiquitin ligases, Nat. Rev. Mol. Cell Biol., 6(1):9-20 (2005).
Scott et al., A dual E3 mechanism for Rub1 ligation to Cdc53, Mol. Cell, 39(5):784-96 (2010).
Scott et al., N-terminal acetylation acts as an avidity enhancer within an interconnected multiprotein complex, Science, 334(6056):674-8 (2011).
Scott et al., Structure of a RING E3 trapped in action reveals ligation mechanism for the ubiquitin-like protein NEDD8, Cell, 157(7):1671-84 (2014).
Soucy et al., An inhibitor of NEDD8-activating enzyme as a new approach to treat cancer, Nature, 458(7239):732-6 (2009).
Soucy et al., Targeting NEDD8-activated cullin-RING ligases for the treatment of cancer, Clin. Cancer Res., 15912):3912-6 (2009).
Soucy et al., The NEDD8 Conjugation Pathway and Its Relevance in Cancer Biology and Therapy, Genes Cancer, 1(7):708-16 (2010).
Sporn et al., NRF2 and cancer: the good, the bad and the importance of context, Nat. Rev. Cancer, 12(8):564-71 (2012).
Suzuki et al., Toward clinical application of the Keap1-Nrf2 pathway, Trends Pharmacol. Sci., 34(6):340-6 (2013).
Vagin et al., Molecular replacement with MOLREP, Acta Crystallogr. D Biol. Crystallogr., 66(Pt. 1):22-5 (Jan. 2010).
Venugopal et al., Nrf2 and Nrf1 in association with Jun proteins regulate antioxidant response element-mediated expression and coordinated induction of genes encoding detoxifying enzymes, Oncogene, 17(24):3145-56 (1998).

(56) References Cited

OTHER PUBLICATIONS

Wang et al., Enantioselective addition of vinylzinc reagents to 3,4-dihydroisoquinoline N-oxide, Org. Lett., 8(18):3979-82 (Aug. 2006).

Wang et al., How well does a restrained electrostatic potential (RESP) model perform in calculating conformational energies of organic and biological molecules?, J. Comput. Chem., 21(12):1019-74 (Sep. 2000).

Watson et al., NEDD8 pathways in cancer, Sine Quibus Non, Cancer Cell, 19(2):168-76 (2011).

Wu et al., Suramin inhibits cullin-RING E3 ubiquitin ligases, Proc. Natl. Acad. Sci. USA, 113(14):E2011-8 (Apr. 2016).

Yang et al., Analysis of Flexibility and Hotspots in Bcl-xL and Mcl-1 Proteins for the Design of Selective Small-Molecule Inhibitors, ACS Med. Chem. Lett., 3(4):308-12 (2012).

Yang et al., Computational analysis of protein hotspots, ACS Med. Chem. Lett., 1(3):125-9 (2010).

Yang et al., Hydrophobic Binding Hot Spots of Bcl-xL Protein-Protein Interfaces by Cosolvent Molecular Dynamics Simulation, ACS Med. Chem. Lett., 2(4):280-4 (2011).

Zhao et al., Cullin-RING Ligases as attractive anti-cancer targets, Curr. Pharm. Des., 19(18):3215-25 (2013).

Zhao et al., Targeting Neddylation pathways to inactivate cullin-RING ligases for anticancer therapy, Antioxid. Redox. Signal., 21(17):2383-400 (2014).

Zhu et al., Hydrolysis of DNA by a dipeptides containing histidine, Int. J. Peptide Res. Ther., 16(4):297-300 (Sep. 2010).

Holder et al., Structure-activity relationships of the melanocortin tetrapeptide Ac-His-DPhe-Arg-Trp-NH(2) at the mouse melanocortin receptors. 1. Modifications at the His position, J. Med. Chem., 45(13):2801-10 (2002).

European Patent Application No. 18718067.4, Communication Pursuant to Article 94(3) EPC, dated Nov. 24, 2020.

\* cited by examiner

SMALL MOLECULE DCN1 INHIBITORS AND THERAPEUTIC METHODS USING THE SAME

CROSS-REFERENCE TO RELATED APPLICATIONS

This application is the U.S. National Stage application of International Application No. PCT/US2018/024708, filed Mar. 28, 2018, which claims the benefit of U.S. Provisional Patent Application No. 62/477,498, filed Mar. 28, 2017, incorporated herein by reference in its entirety.

FIELD OF THE INVENTION

The present invention relates to small molecule DCN1 inhibitors and to therapeutic methods of treating conditions and diseases wherein inhibition of DCN1 provides a benefit.

BACKGROUND OF THE INVENTION

The regulated destruction of intracellular proteins is controlled by the ubiquitin-proteasome system (UPS) via tagging the ubiquitin on the proteins, and is essential to cellular protein homeostasis (1,2). The UPS has been extensively pursued as a drug target (3,4), with two proteasome inhibitors, Bortezomib and Carfilzomib, having been approved for the treatment of multiple myeloma (5-7).

The Cullin-Ring ligases (CRL), a central component of the UPS, regulate the turnover of approximately 20% of cellular proteins, and the dysregulation of CRLs plays a critical role in various human diseases, including cancer, cardiovascular diseases, neurodegenerative disorders, and viral infections (8-11). The activity of CRLs is controlled by NEDD8 (neural precursor cell expressed developmentally downregulated protein 8), a ubiquitin-like protein (9,10,12). Analogous to the process of ubiquitination, neddylation is a process by which the ubiquitin-like protein NEDD8 is conjugated to its target proteins.

The neddylation cascade begins with the activation of NEDD8 by an E1 enzyme, the NEDD8 activating enzyme (NAE), followed by transfer of the activated NEDD8 to one of two NEDD8-specific E2 enzymes, UBC12 and UBE2F. In the final step of this cascade, an E3 enzyme catalyzes the transfer of NEDD8 from E2 to target substrates (13). The enzymes of the NEDD8 pathway have been pursued as potential therapeutic targets (14-17) and MLN4924, an inhibitor of the E1 enzyme NAE, was shown to suppress tumor cell growth both in vitro and in vivo (18). Mechanistically, MLN4924 inhibits NAE enzymatic activity through formation of a covalent NEDD8-MLN4924 adduct, which in turn inactivates CRLs, leading to accumulation of CRL substrates (18,19). MLN4924 is currently being tested in clinical trials for the treatment of human cancers (20).

Schulman et al. have defined both the structural and biochemical mechanisms underlying the E1-E2-E3 cascade reaction in the NEDD8 pathway (13,21-23). Schulman et al. further demonstrated that DCN1, a scaffold-like E3 ligase, facilitates the transfer of NEDD8 from UBC12 to cullins through its interaction with UBC12 and greatly enhances the enzymatic activity of cullins (13,22,23). The co-crystal structure of the DCN1-UBC12 complex 22,23 reveals that UBC12 interacts with DCN1 through two distinct sites and the N-terminally acetylated UBC12 peptide binds to a well-defined pocket in DCN1.

To date, no small-molecule inhibitors of the DCN1-UBC12 interaction have been advanced into clinical development. Accordingly, a need still exists in the art for small molecule inhibitors of the UBC12-DCN1 protein-protein interaction, having physical and pharmacological properties that permit use of such inhibitors in a range of therapeutic applications in which modulation of the activity of cullins may have a therapeutic benefit.

SUMMARY OF THE INVENTION

The present invention is directed to small-molecule inhibitors designed to bind to the UBC12 binding site in DCN1 (hereafter called DCN1 inhibitors), to compositions comprising the inhibitors, and to methods of using the inhibitors in a therapeutic treatment of conditions and diseases wherein inhibition of the UBC12 binding site in DCN1 provides a benefit. In particularly, the present compounds are potent inhibitors of the DCN1-UBC12 protein-protein interaction. The inhibitors block neddylation of cullin 3. The inhibitors also block neddylation of other cullins, although at higher concentrations than those used for inhibition of the neddylation of cullin 3.

More particularly, the present invention is directed to compounds having a structural formula (I), wherein

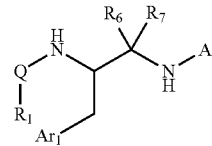

Q is C=O, C=S or $SO_2$;

$Ar_1$ is a five or six-membered aromatic or heteroaromatic ring or a polycyclic aromatic or heteroaromatic ring having 8-12 atoms, including up to four heteroatoms chosen from N, O and S, in a chemically stable arrangement, optionally substituted with up to four $R_2$ substitutes;

A is $CHR_8CH_2R_9$, $COR_{13}$, $CHR_8CONR_{14}R_{15}$, $CHR_8CONR_{16}CHR_{17}CONR_{14}R_{15}$ or $CHR_8CONR_{16}CHR_{17}CONR_{16}CHR_{18}CONR_{14}R_{15}$;

$R_1$ is selected from the group consisting of H, alkyl, substituted alkyl, alkenyl, cycloalkyl, cycloalkylmethylene, substituted cycloalkyl, $NR_3R_4$, and $OR_5$;

$R_2$ are independently selected from the group consisting of halogens, CN, $N_3$, $CF_3$, $NO_2$, H, alkyl, substituted alkyl, alkenyl, substituted alkenyl, alkynyl, substituted alkynyl, cycloalkyl, substituted cycloalkyl, cycloalkenyl substituted cycloalkenyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, alkyl, allyl, propargyl, cycloalkyl, heterocyclyl, aryl, heteroaryl, alkyl-cycloalkyl, alkyl-cycloalkenyl, alkyl-heterocyclyl, alkaryl, alkyl-heteroaryl, acyl, cycloalkylcarbonyl, heterocyclylcarbonyl, aroyl, heteroaroyl, or are taken together with the nitrogen atom to which they are attached to form a ring of four to seven members, optionally including any chemically stable combination of one to three O, C=O, $NR^5$ and S;

$R_5$ is selected from the group consisting of hydrogen, alkyl, allyl, propargyl, cycloalkyl, heterocyclyl, aryl, heteroaryl, alkyl-cycloalkyl, alkyl-cycloalkenyl, alkyl-heterocyclyl, alkaryl, alkyl-heteroaryl, lower acyl, cycloalkylcarbonyl, heterocyclylcarbonyl, aroyl, heteroaroyl, each optionally substituted with up to three substituents independently selected from halo, hydroxy, oxo, thio, thiono, amino, cyano, alkoxy, alkylthio, alkylamino, dialkylamino, heterocyclo, aryl, and heteroaryl;

$R_6$ and $R_7$, independently, are hydrogen or alkyl, or $R_6$ and $R_7$ are taken together to form =O, =S, or $R_6$ and $R_7$ are taken together with the carbon atom to which they are attached to form a three to six membered ring, optionally including any chemically stable combination of one to three O, C=O, S(O)$_x$, or NR$_5$;

$R_8$ is selected from the group consisting of alkyl, cycloalkyl, alkenyl, cycloalkenyl, heterocyclo, alkynyl, alkyl-cycloalkyl. alkyl-cycloalkenyl, alkyl-heterocyclo, aryl, alkylaryl, heteroaryl, alkyl-heteroaryl, bicycloalkyl and alkyl-bicycloalkyl;

$R_9$ is $NR_{10}R_{11}$, $NR_5CONR_{10}R_{11}$, $NR_5COR_{12}$, $NR_5SO_2R_{12}$, $OR_{12}$, or $S(O)_xR_{12}$, $R_{10}$, $R_{11}$, and $R_{12}$ are independently selected from the group consisting of H, optionally substituted alkyl, allyl, propargyl, cycloalkyl, cycloalkenyl, heterocyclo, alkyl-cycloalkyl. alkyl-cycloalkenyl, alkyl-heterocyclo, aryl, alkaryl, heteroaryl, alkylheteroaryl, acyl, acyl-cycloalkyl, acyl-heterocyclo, acyl-heterocyclo-heterocyclo, acyl-aryl, acyl-aryl-heterocyclyl, acyl-heterocyclo-aryl. acyl-heteroaryl, acyl-heteroaryl-heterocyclyl, acyl-heterocyclo-heteroaryl, or $R_{10}$ and $R_{11}$ are taken with the nitrogen atom to which they are attached to form a heterocyclic ring of four to seven atoms, optionally including any chemically stable combination of up to two of O, C=O NR$_5$ and S(O)$_x$;

$R_{13}$ is alkyl, cycloalkyl, cycloalkenyl, heterocyclo, alkyl-cycloalkyl, alkyl-cycloalkenyl, heterocyclo, alkyl-heterocyclo, aryl, alkylaryl, heteroaryl, alkyl-heteroaryl, alkenylaryl, alkenylheteroaryl, with these groups optionally substituted with up to five substituents independently selected from the group consisting of alkyl, halo, hydroxy, oxo, thio, thiono, amino, cyano, hydroxymethyl, aminomethyl, alkoxy, alkylamino, dialkylamino, alkylS(O)$_x$, aminoacyl, alkylaminosulfonyl, sulfonamido, heterocyclo(carbonyl), aryl, aroyl, heteroaryl, and heteroaroyl;

$R_{14}$ and $R_{15}$, independently, are selected from the group consisting of H, optionally substituted alkyl, cycloalkyl, heterocyclo, alkyl-heterocyclo, aminoalkyl, alkylamino-alkyl, aryl, alkaryl, heteroaryl, alkyl-heteroaryl, alkyl-di(hetero)aryl, bicycloaryl, partially saturated bicycloaryl, bicycloheteroaryl, partially saturated bicycloheteroaryl, heterocyclo-heterocyclyl, heterocyclo-aryl, aryl-heterocyclyl, heterocyclo-heteroaryl heteroaryl-heterocyclyl, or $R_{14}$ and $R_{15}$ are taken together with the nitrogen atom to which they are attached to form a heterocyclic ring of four to seven atoms, optionally containing any chemically stable combination of one to three O, C=O, NR$_5$, and S(O)$_x$;

$R_{16}$ is H or alkyl:

$R_{17}$ and $R_{18}$ are independently the side chains of the naturally occurring amino acids, alkylidenyl-NR$_3$R$_4$, or an $R_{16}$ may be taken in conjunction with either $R_{17}$ or $R_{18}$ to form a proline, or 3-hydroxyproline residue.

x is 0, 1, or 2;

or a pharmaceutically acceptable salt, hydrate, or solvate thereof.

In one embodiment, the present invention provides a method of treating a condition or disease by administering a therapeutically effective amount of a compound of structural formula (I) to an individual in need thereof. The disease or condition of interest is treatable by inhibition of DCN1, for example, an oxidative stress-related disease or a neurodegenerative disease.

Another embodiment of the present invention is to provide a composition comprising (a) a DCN1 inhibitor of structural formula (I) and (b) an excipient and/or pharmaceutically acceptable carrier useful in treating diseases or conditions wherein inhibition of DCN1 provides a benefit.

Another embodiment of the present invention is to utilize a composition comprising a compound of structural formula (I) and an optional second therapeutically active agent in a method of treating an individual for a disease or condition wherein inhibition of DCN provides a benefit.

In a further embodiment, the invention provides for use of a composition comprising a DCN1 inhibitor of structural formula (I) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a DCN inhibitor of structural formula (I), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

Another embodiment is a method of blocking an interaction between DCN1 and its binding partners, including, but not limited to, UBC12 and UBC2E, in cells comprising contacting the cells with a compound of structural formula (I).

In other embodiments, blocking the interaction between DCN1 and its binding partners in cells by contacting the cells with a compound of structural formula (I) leads to one or more of (a) selective inhibition of cullin 3 activity; (b) accumulation of protein substrates of cullin 3; (c) upregulation of NRF2, a known cullin 3 substrate; (d) modulation of a set of genes regulated by NRF2; (e) a therapeutic benefit in human diseases or conditions by modulation of the activity of cullin 3; and (f) a therapeutic benefit in human diseases or conditions by modulation of the activity of NRF2.

DETAILED DESCRIPTION OF THE INVENTION

Figure 1:
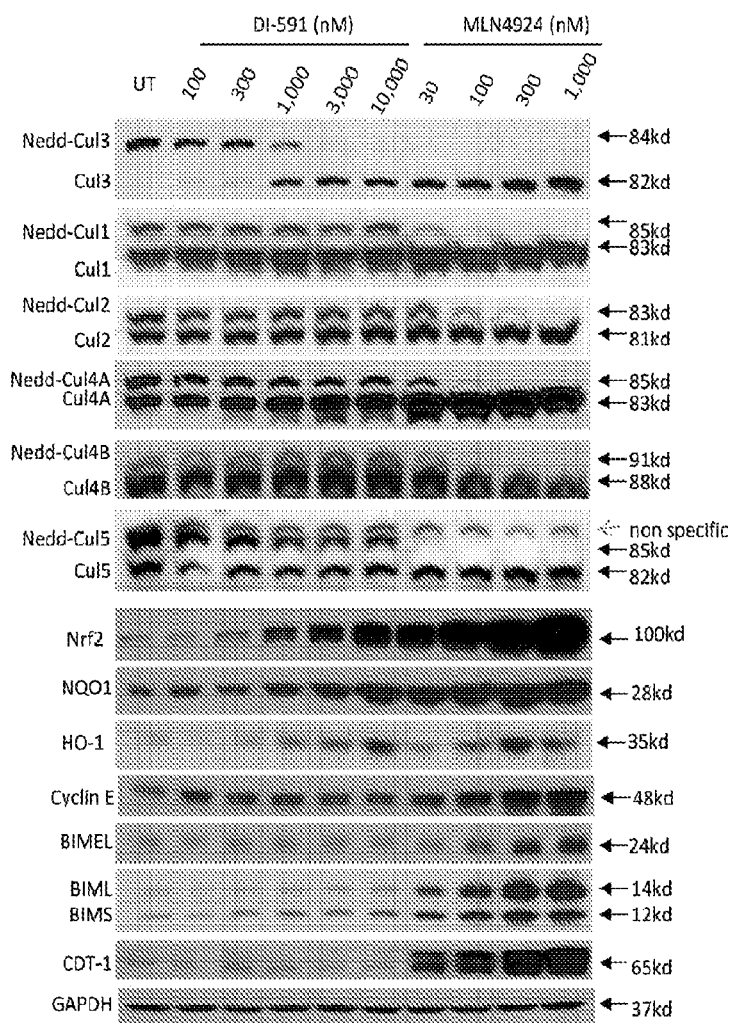
FIG. 1 shows that Example 58 (DI-591) selectively and dose-dependently inhibits the neddylation of cullin 3, and induces upregulation of cullin 3-dependent NRF2 and NRF2-regulated proteins in liver cells. Immortalized THLE2 liver cell line was treated by a dose-range of DCN1 inhibitor Example 58 or a dose-range of MLN4924 for 24 h. The protein levels of neddylated- and un-neddylated-cullin family proteins and several well-known substrates of cullins were examined by western blotting analysis. GAPDH was used as a loading control.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "DCN1" as used herein means a protein that functions as a Scaffold-Type E3 Ligase for cullin neddylation.

The term "a disease or condition wherein inhibition of DCN1 provides a benefit" pertains to a condition in which DCN1, and/or an action of DCN1, is important or necessary, e.g., for the onset, progress, expression of that disease or condition, or a disease or a condition which is known to be treated by a DCN1 inhibition. An example of such a condition includes, but is not limited to, an oxidative stress-related disease, a neurodegenerative disease, cancer, a cardiovascular disease, or tissue regeneration. One of ordinary skill in the art is readily able to determine whether a compound treats a disease or condition mediated by DCN1 for any particular cell type, for example, by assays which conveniently can be used to assess the activity of particular compounds.

The term "second therapeutic agent" refers to a therapeutic agent different from a DCN1 inhibitor of structural formula (I) and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, compounds of structural formula (I) are potent inhibitors of DCN1 and can be used in treating diseases and conditions wherein inhibition of DCN1 provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of structural formula (I) to an individual in need of such treatment.

Within the meaning of the invention, "treatment" includes the treatment of acute or chronic signs, symptoms, and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other oxidative stress-related disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce DCN1 interactions in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a DCN1 inhibitor of structural formula (I) can be administered at the same time or sequentially in any order at different points in time as a second therapeutic agent. A present DCN1 inhibitor and the second therapeutic agent can be administered separately, in any appropriate form and by any suitable route. When a present DCN1 inhibitor and the second therapeutic agent are not administered concurrently, it is understood that they can be administered in any order to a subject in need thereof. For example, a present DCN1 inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a DCN1 inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein are intended to merely serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

To date, most small-molecule modulators targeting UPS components contain a chemically reactive group and act as covalent inhibitors. These include FDA-approved Bortezomib (5,6), Carfilzomib (7), and dimethyl fumarate (38), and MLN4924 (18), RTA402 and RTA408 (39-41), which currently are in clinical development.

The present invention targets the DCN1-UBC12 protein-protein interaction as a strategy for modulation of protein turnover. DCN1 is a component of neddylation E3 ligase and plays a role in modulation of the activity of cullins. The co-crystal structure of DCN1 complexed with UBC12 revealed that the UBC12 peptide-binding pocket in DCN1 could accommodate a small-molecule inhibitor for blocking the DCN1-UBC12 protein-protein interaction. The present invention therefore is directed to a new class of potent inhibitors of the DCN1-UBC12 protein-protein interaction.

Recent evidence suggests that the dysfunction of cullin 3 is associated with various human diseases, including metabolic disorders, neurodegeneration, and cancer (42-44). Modulation of cullin 3 therefore can have a therapeutic potential for the treatment of human diseases. Compared to the global inhibition of neddylation of all cullins by MLN4924, a compound of structural formula (I) is a selective inhibitor of the neddylation of cellular CUL3. A compound of structural formula (I) increases the level of NRF2 protein, a well known substrate of cullin 3, leading to upregulation of two detoxification enzymes NQO1 and HO1. In comparison, MLN4924, a NAE inhibitor, globally increases the abundance of all cullin-targeted proteins examined. Therefore, compounds of structural formula (I) serves as excellent chemical probes for a study of cullin 3 and its role in different biological processes and human diseases.

As the master regulator of antioxidant responses, NRF2 regulates about 200 genes involved in cytoprotection, lipid metabolism, and gene transcription. Activation of NRF2 can have a therapeutic benefit against various oxidative stress-related diseases, including cancer, neurodegenerative disease, cardiovascular disease, acute lung injury, chronic obstructive pulmonary diseases, autoimmune disease, and inflammation (36,45,46,47). One NRF2 inducer, dimethyl fumarate, has recently been approved by the FDA as first-line therapy for relapsing-remitting multiple sclerosis (MS) (38). Another series of NRF2 inducers under clinical development are synthetic derivatives of oleanoic acid (39,40). A common mechanism of these compounds is that they are covalent modulators targeting Keap1. In comparison, a compound of structural formula (I) activates NRF2 by blocking the DCN1-UBC12 protein-protein interaction and selectively inhibiting the activity of cullin 3, thus engaging a different mechanism of action. The DCN1 inhibitors of the present invention therefore are useful in the treatment of a variety of diseases and conditions in subjects in need of such treatment.

The present invention is directed to compounds having a structural formula (I).

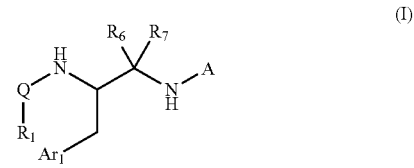

(I)

wherein

Q is C=O, C=S or $SO_2$;

$Ar_1$ is a five or six-membered aromatic or heteroaromatic ring or a polycyclic aromatic or heteroaromatic ring having 8-12 atoms, including up to four heteroatoms chosen from N, O and S, in a chemically stable arrangement, optionally substituted with up to four $R_2$ substitutes;

A is $CHR_8CH_2R_9$, $COR_{13}$, $CHR_8CONR_{14}R_{15}$, $CHR_8CONR_{16}CHR_{17}CONR_{14}R_{15}$ or $CHR_8CONR_{16}CHR_{17}CONR_{16}CHR_{18}CONR_{14}R_{15}$;

$R_1$ is selected from the group consisting of H, alkyl, substituted alkyl, alkenyl, cycloalkyl, cycloalkylmethylene, substituted cycloalkyl, $NR_3R_4$, and $OR_5$;

$R_2$ are independently selected from the group consisting of halo, CN, $N_3$, $CF_3$, $NO_2$, H, alkyl, substituted alkyl, alkenyl, substituted alkenyl, alkynyl, substituted alkynyl, cycloalkyl, substituted cycloalkyl, cycloalkenyl substituted cycloalkenyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, alkyl, allyl, propargyl, cycloalkyl, heterocyclyl, aryl, heteroaryl, alkyl-cycloalkyl, alkyl-cycloalkenyl, alkyl-heterocyclyl, alkaryl, alkyl-heteroaryl, acyl, cycloalkylcarbonyl, heterocyclylcarbonyl, aroyl, heteroaroyl, or are taken together with the nitrogen atom to which they are attached to form a ring of four to seven members, optionally including any chemically stable combination of one to three O, C=O, $NR^5$ and S;

$R_5$ is selected from the group consisting of hydrogen, alkyl, allyl, propargyl, cycloalkyl, heterocyclyl, aryl, heteroaryl, alkyl-cycloalkyl, alkyl-cycloalkenyl, alkyl-heterocyclyl, alkaryl, alkyl-heteroaryl, lower acyl, cycloalkylcarbonyl, heterocyclylcarbonyl, aroyl, heteroaroyl, each optionally substituted with up to three substituents independently selected from halo, hydroxy, oxo, thio, thiono, amino, cyano, alkoxy, alkylthio, alkylamino, dialkylamino, heterocyclo, aryl, and heteroaryl;

$R_6$ and $R_7$, independently, are hydrogen or alkyl, or $R_6$ and $R_7$ are taken together to form =O, =S, or $R_6$ and $R_7$ are taken together with the carbon atom to which they are attached to form a three to six membered ring, optionally including any chemically stable combination of one to three O, C=O, S(O)$_x$, or NR$_5$;

R$_8$ is selected from the group consisting of alkyl, cycloalkyl, alkenyl, cycloalkenyl, heterocyclo, alkynyl, alkyl-cycloalkyl. alkyl-cycloalkenyl, alkyl-heterocyclo, aryl, alkylaryl, heteroaryl, alkyl-heteroaryl, bicycloalkyl and alkyl-bicycloalkyl;

R$_9$ is NR$_{10}$R$_{11}$, NR$_5$CONR$_{10}$R$_{11}$, NR$_5$COR$_{12}$, NR$_5$SO$_2$R$_{12}$, OR$_{12}$, or S(O)$_x$R$_{12}$,

R$_{10}$, R$_{11}$, and R$_{12}$ are independently selected from the group consisting of H, optionally substituted alkyl, allyl, propargyl, cycloalkyl, cycloalkenyl, heterocyclo, alkyl-cycloalkyl. alkyl-cycloalkenyl, alkyl-heterocyclo, aryl, alkaryl, heteroaryl, alkylheteroaryl, acyl, acyl-cycloalkyl, acyl-heterocyclo, acyl-heterocyclo-heterocyclo, acyl-aryl, acyl-aryl-heterocyclyl, acyl-heterocyclo-aryl. acyl-heteroaryl, acyl-heteroaryl-heterocyclyl, acyl-heterocyclo-heteroaryl, or R$_{10}$ and R$_{11}$ are taken with the nitrogen atom to which they are attached to form a heterocyclic ring of four to seven atoms, optionally including any chemically stable combination of up to two of O, C=O NR$_5$ and S(O)$_x$;

R$_{13}$ is alkyl, cycloalkyl, cycloalkenyl, heterocyclo, alkylcycloalkyl, alkyl-cycloalkenyl, heterocyclo, alkyl-heterocyclo, aryl, alkylaryl, heteroaryl, alkyl-heteroaryl, alkenylaryl, alkenylheteroaryl, with these groups optionally substituted with up to five substituents independently selected from the group consisting of alkyl, halo, hydroxy, oxo, thio, thiono, amino, cyano, hydroxymethyl, aminomethyl, alkoxy, alkylamino, dialkylamino, alkylS(O)$_x$, aminoacyl, alkylaminosulfonyl, sulfonamido, heterocyclo(carbonyl), aryl, aroyl, heteroaryl, and heteroaroyl;

R$_{14}$ and R$_{15}$, independently, are selected from the group consisting of H, optionally substituted alkyl, cycloalkyl, heterocyclo, alkyl-heterocyclo, aminoalkyl, alkylamino-alkyl, aryl, alkaryl, heteroaryl, alkyl-heteroaryl, alkyl-di(hetero)aryl, bicycloaryl, partially saturated bicycloaryl, bicyclohetoroaryl, partially saturated bicycloheteroaryl, heterocyclo-heterocyclyl, heterocyclo-aryl, aryl-heterocyclyl, heterocyclo-heteroaryl heteroaryl-heterocyclyl, or R$_{14}$ and R$_{15}$ are taken together with the nitrogen atom to which they are attached to form a heterocyclic ring of four to seven atoms, optionally containing any chemically stable combination of one to three O, C=O, NR$_5$, and S(O)$_x$;

R$_{16}$ is H or alkyl:

R$_{17}$ and R$_{18}$ are independently the side chains of the naturally occurring amino acids, alkylidenyl-NR$_3$R$_4$, or an R$_{16}$ may be taken in conjunction with either R$_{17}$ or R$_{18}$ to form a proline, or 3-hydroxyproline residue.

x is 0, 1, or 2;

or a pharmaceutically acceptable salt, hydrate, or solvate thereof.

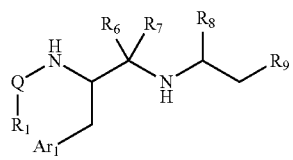

(II)

In a particular embodiment of the invention, the compounds are of formula (II) wherein;

Q is C=O, C=S or SO$_2$;

Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substitutes;

R$_1$ is selected from the group consisting of C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;

R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, or are taken together with the nitrogen atom to which they are attached to form a ring of four to seven members, optionally including any chemically stable combination of one to three O, C=O, NR$^5$ and S;

R$_5$ is selected from the group consisting of hydrogen, C$_{1-6}$ alkyl, allyl, propargyl, C$_{3-6}$ cycloalkyl, C$_{1-6}$ alkyl-C$_{46}$ cycloalkenyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-6}$ heterocyclo, aryl, and heteroaryl;

R$_6$ and R$_7$, independently, are hydrogen or C$_{1-6}$ alkyl, or R$_6$ and R$_7$ are taken together to form =O, =S, or R$_6$ and R$_7$ are taken together with the carbon atom to which they are attached to form a three to six membered ring, optionally including any chemically stable combination of one to three of O, C=O, S(O)$_x$ or NR$_5$;

R$_8$ is selected from the group consisting of C$_{1-6}$ alkyl, C$_{3-6}$ cycloalkyl, C$_{2-6}$ alkenyl, C$_{4-6}$ cycloalkenyl, C$_{4-6}$ heterocyclo, C$_{2-6}$ alkynyl, C$_{1-6}$ alkyl-C$_{3-6}$ cycloalkyl. C$_{1-6}$ alkyl-C$_{4-6}$ cycloalkenyl, C$_{1-6}$ alkyl-C$_{4-6}$ heterocyclo, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;

R$_9$ is NR$_{10}$R$_{11}$, NR$_5$CONR$_{10}$R$_{11}$, NR$_5$COR$_{12}$, NR$_5$SO$_2$R$_{12}$, OR$_{12}$, or S(O)$_x$R$_{12}$,

R$_{10}$, R$_{11}$, and R$_{12}$ are independently selected from the group consisting of H, optionally substituted C$_{1-6}$ alkyl, allyl, propargyl, C$_{3-6}$ cycloalkyl, C$_{4-6}$ cycloalkenyl, C$_{4-6}$ heterocyclo, C$_{1-6}$ alkyl-C$_{3-6}$ cycloalkyl. C$_{1-6}$ alkyl-C$_{4-6}$ cycloalkenyl, C$_{1-6}$ alkyl-C$_{4-6}$ heterocyclo, aryl, C$_{1-6}$ alkaryl, heteroaryl, C$_{1-6}$ alkylheteroaryl, C$_{1-6}$ acyl, C$_{1-6}$ acyl-C$_{3-6}$ cycloalkyl, C$_{1-6}$ acyl-C$_{1-6}$ heterocyclo, C$_{1-6}$ acyl-C$_{4-6}$ heterocyclo-C$_{4-6}$ heterocyclo, C$_{1-6}$ acyl-aryl, C$_{1-6}$ acyl-aryl-C$_{4-6}$ heterocyclyl, C$_{1-6}$ acyl-C$_{4-6}$ heterocyclo-aryl, C$_{1-6}$ acyl-heteroaryl, C$_{1-6}$ acyl-heteroaryl-C$_{4-6}$ heterocyclyl, C$_{1-6}$ acyl-C$_{4-6}$ heterocyclo-heteroaryl, or R$_{10}$ and R$_{11}$ are taken with the nitrogen atom to which they are attached to form a heterocyclic ring of four to seven atoms, optionally including any chemically stable combination of up to three of O, C=O NR$_5$ and S(O)$_x$;

x is 0, 1, or 2;

or a pharmaceutically acceptable salt, hydrate, or solvate thereof.

In a particular embodiment of the invention, the compounds are of formula (III)

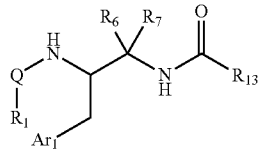

(III)

wherein;

Q is C=O, C=S or SO$_2$;

Ar$_t$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substitutes;

R$_1$ is selected from the group consisting of C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;

R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, or are taken together with the nitrogen atom to which they are attached to form a ring of four to seven members, optionally including any chemically stable combination of one to three O, C=O, NR$^5$ and S;

R$_5$ is selected from the group consisting of hydrogen, C$_{1-6}$ alkyl, allyl, propargyl, C$_{3-6}$ cycloalkyl, C$_{1-6}$ alkyl-C$_{4-6}$ cycloalkenyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-6}$ heterocyclo, aryl, and heteroaryl;

R$_6$ and R$_7$, independently, are hydrogen or C$_{1-6}$ alkyl, or R$_6$ and R$_7$ are taken together to form =O, =S, or R$_6$ and R$_7$ are taken together with the carbon atom to which they are attached to form a three to six membered ring, optionally including any chemically stable combination of one to three of O, C=O, S(O)$_x$ or NR$_5$;

R$_{13}$ is C$_{1-6}$ alkyl, C$_{3-6}$ cycloalkyl, C$_{4-6}$ cycloalkenyl, C$_{4-6}$ heterocyclo, C$_{1-6}$ alkyl-C$_{3-6}$ cycloalkyl, C$_{1-6}$ alkyl-C$_{4-6}$ cycloalkenyl, C$_{4-6}$ heterocyclo, C$_{1-6}$ alkyl-C$_{4-6}$ heterocyclo, aryl, C$_{1-6}$ alkylaryl, heteroaryl, C$_{1-6}$ alkyl-heteroaryl, C$_{2-4}$ alkenylaryl, C$_{2-4}$ alkenylheteroaryl, with these groups optionally substituted with up to five substituents independently selected from the group consisting of C$_{1-6}$ alkyl, halo, hydroxy, oxo, thio, thiono, amino, cyano, hydroxymethyl, aminomethyl, C$_{1-6}$ alkoxy, C$_{1-6}$ alkylamino, C$_{1-6}$ dialkylamino, C$_{1-6}$ alkylS(O)$_x$, C$_{1-6}$ aminoacyl, C$_{1-6}$ alkylamino-sulfonyl, sulfonamido, C$_{4-6}$ heterocyclo(carbonyl), aryl, aroyl, heteroaryl, and heteroaroyl;

x is 0, 1, or 2;

or a pharmaceutically acceptable salt, hydrate, or solvate thereof.

In a particular embodiment of the invention, the compounds are of formula (IV)

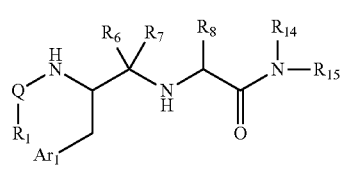

(IV)

wherein;

Q is C=O, C=S or SO$_2$;

Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substitutes;

R$_1$ is selected from the group consisting of C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;

R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, or are taken together with the nitrogen atom to which they are attached to form a ring of four to seven members, optionally including any chemically stable combination of one to three O, C=O, NR$^5$ and S;

R$_5$ is selected from the group consisting of hydrogen, C$_{1-6}$ alkyl, allyl, propargyl, C$_{3-6}$ cycloalkyl, C$_{1-6}$ alkyl-C$_{4-6}$ cycloalkenyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-6}$ heterocyclo, aryl, and heteroaryl;

R$_6$ and R$_7$, independently, are hydrogen or C$_{1-6}$ alkyl, or R$_6$ and R$_7$ are taken together to form =O, =S, or R$_6$ and R$_7$ are taken together with the carbon atom to which they are attached to form a three to six membered ring, optionally including any chemically stable combination of one to three of O, C=O, S(O)$_x$ or NR$_5$;

R$_8$ is selected from the group consisting of C$_{1-6}$ alkyl, C$_{3-6}$ cycloalkyl, C$_{2-6}$ alkenyl, C$_{4-6}$ cycloalkenyl, C$_{4-6}$ heterocyclo, C$_{2-6}$ alkynyl, C$_{1-6}$ alkyl-C$_{3-6}$ cycloalkyl. C$_{1-6}$ alkyl-C$_{4-6}$ cycloalkenyl, C$_{1-6}$ alkyl-C$_{4-6}$ heterocyclo, aryl, C$_{1-6}$ alkylaryl, heteroaryl, C$_{1-6}$ alkyl-heteroaryl, C$_{5-10}$ bicycloalkyl and C$_{1-6}$ alkyl-C$_{5-10}$ bicycloalkyl;

R$_{14}$ and R$_{15}$, independently, are selected from the group consisting of H, optionally substituted C$_{1-6}$ alkyl, C$_{3-6}$ cycloalkyl, C$_{4-6}$ heterocyclo, C$_{1-6}$ alkyl-C$_{4-6}$ heterocyclo, C$_{1-6}$ alkyl-C$_{3-6}$ cycloalkyl, C$_{1-6}$ alkyl-C$_{4-6}$ cycloalkenyl, C$_{1-6}$ aminoalkyl, C$_{1-6}$ alkylamino-C$_{1-6}$ alkyl, C$_{1-6}$ dialkylamino-C$_{1-6}$ alkyl, aryl, C$_{1-6}$ alkaryl, heteroaryl, C$_{1-6}$ alkyl-heteroaryl, C$_{1-2}$ alkyl-di(hetero)aryl, bicycloaryl, partially saturated bicycloaryl, bicyclohetoroaryl, partially saturated bicycloheteroaryl, C$_{4-6}$ heterocyclo-C$_{4-6}$ heterocyclyl, C$_{4-6}$ heterocyclo-aryl, aryl-C$_{4-6}$ heterocyclyl, C$_{4-6}$ heterocyclo-heteroaryl heteroaryl-C$_{4-6}$ heterocyclyl, or R$_{14}$ and R$_{15}$ are taken together with the nitrogen atom to which they are attached to form a heterocyclic ring of four to seven atoms, optionally containing any chemically stable combination of one to three O, C=O, NR$_5$, and S(O)$_x$;

x is 0, 1, or 2;

or a pharmaceutically acceptable salt, hydrate, or solvate thereof.

In a particular embodiment of the invention, the compounds are of formula (V) or (VI)

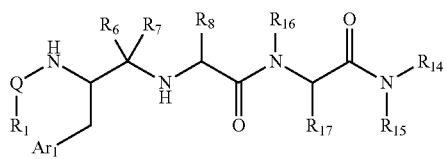

(V)

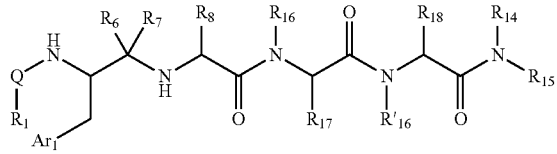

(VI)

wherein;

Q is C=O, C=S or SO$_2$;

Ar$_1$ is a five or six-membered aromatic or heteroaromatic ring or a bicyclic aromatic or heteroaromatic ring having 8-12 atoms, including up to four heteroatoms chosen from N, O and S, in a chemically stable arrangement, optionally substituted with up to four R$_2$ substitutes;

R$_1$ is selected from the group consisting of C$_{1-6}$ alkyl, C$_{3-6}$ cycloalkyl, C$_{3-6}$ cycloalkylmethylene, NHMe, N(Me)$_2$, NHEt, NH-cyclopropyl, OMe, OEt, O-cyclopropyl;

R$_2$ are independently selected from the group consisting of halo, CN, N$_3$, CF$_3$, NO$_2$, H, C$_{1-6}$ alkyl, substituted C$_{1-6}$ alkyl, C$_{2-6}$ alkenyl, substituted C$_{2-6}$ alkenyl, C$_{2-6}$ alkynyl, substituted C$_{2-6}$ alkynyl, C$_{3-6}$ cycloalkyl, substituted C$_{3-6}$ cycloalkyl, C$_{4-6}$ cycloalkenyl substituted C$_{4-6}$ cycloalkenyl, phenyl, substituted phenyl, monocyclic heteroaryl, substituted monocyclic heteroaryl, OR$_5$, NR$_3$R$_4$, COOR$_5$, CONR$_3$R$_4$;

R$_3$ and R$_4$, independently, are selected from the group consisting of hydrogen, C$_{1-6}$ alkyl, allyl, C$_{3-6}$ cycloalkyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ cycloalkenyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, or are taken together with the nitrogen atom to which they are attached to form a ring of four to seven members, optionally including any chemically stable combination of one to three O, C=O, NR$^5$ and S;

R$_5$ is selected from the group consisting of hydrogen, C$_{1-6}$ alkyl, allyl, propargyl, C$_{3-6}$ cycloalkyl, C$_{1-6}$ alkyl-C$_{4-6}$ cycloalkenyl, C$_{4-6}$ heterocyclyl, aryl, heteroaryl, C$_{1-6}$ alkyl-C$_{3-6}$ cycloalkyl, C$_{1-6}$ alkyl-C$_{4-6}$ heterocyclyl, C$_{1-6}$ alkaryl, C$_{1-6}$ alkyl-heteroaryl, C$_{1-6}$ acyl, C$_{3-6}$ cycloalkylcarbonyl, C$_{4-6}$ heterocyclylcarbonyl, aroyl, heteroaroyl, each optionally substituted with up to three substituents independently selected from halo, hydroxy, oxo, thio, thiono, amino, cyano, C$_{1-6}$ alkoxy, C$_{1-6}$ alkylthio, C$_{1-6}$ alkylamino, C$_{1-6}$ dialkylamino, C$_{4-6}$ heterocyclo, aryl, and heteroaryl;

R$_6$ and R$_7$, independently, are hydrogen or C$_{1-6}$ alkyl, or R$_6$ and R$_7$ are taken together to form =O, =S, or R$_6$ and R$_7$ are taken together with the carbon atom to which they are attached to form a three to six membered ring, optionally including any chemically stable combination of one to three of O, C=O, S(O)$_x$ or NR$_5$;

R$_{14}$ and R$_{15}$, independently, are selected from the group consisting of H, optionally substituted C$_{1-6}$ alkyl, C$_{3-6}$ cycloalkyl, C$_{4-6}$ heterocyclo, C$_{1-6}$ alkyl-C$_{4-6}$ heterocyclo, C$_{1-6}$ alkyl-C$_{3-6}$ cycloalkyl, C$_{1-6}$ alkyl-C$_{4-6}$ cycloalkenyl, C$_{1-6}$ aminoalkyl, C$_{1-6}$ alkylamino-C$_{1-6}$ alkyl, C$_{1-6}$ dialkylamino-C$_{1-6}$ alkyl, aryl, C$_{1-6}$ alkaryl, heteroaryl, C$_{1-6}$ alkyl-heteroaryl, C$_{1-2}$ alkyl-di(hetero)aryl, bicycloaryl, partially saturated bicycloaryl, bicyclohetoroaryl, partially saturated bicycloheteroaryl, C$_{4-6}$ heterocyclo-C$_{4-6}$ heterocyclyl, C$_{4-6}$ heterocyclo-aryl, aryl-C$_{4-6}$ heterocyclyl, C$_{4-6}$ heterocyclo-heteroaryl heteroaryl-C$_{4-6}$ heterocyclyl, or R$_{14}$ and R$_{15}$ are taken together with the nitrogen atom to which they are attached to form a heterocyclic ring of four to seven atoms, optionally containing any chemically stable combination of one to three O, C=O, NR$_5$, and S(O)$_x$;

R$_{16}$ and R'$_{16}$ are independently selected from H or C$_{1-6}$ alkyl;

R$_{17}$ and R$_{18}$ are independently the side chain of an naturally occurring amino acid, C$_{1-6}$ alkylidenyl-NR$_3$R$_4$, or an R$_{16}$ may be taken in conjunction either with R$_{17}$ or R$_{18}$ to form a proline, or 3-hydroxyproline residue;

x is 0, 1, or 2;

or a pharmaceutically acceptable salt, hydrate, or solvate thereof.

In some preferred embodiments, Ar$_1$ can be, but is not limited to,

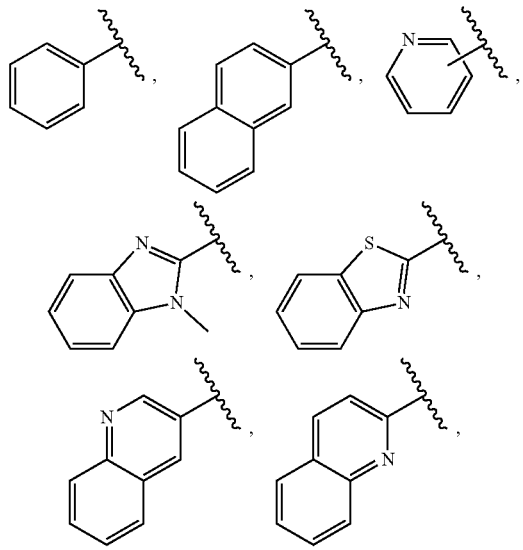

-continued
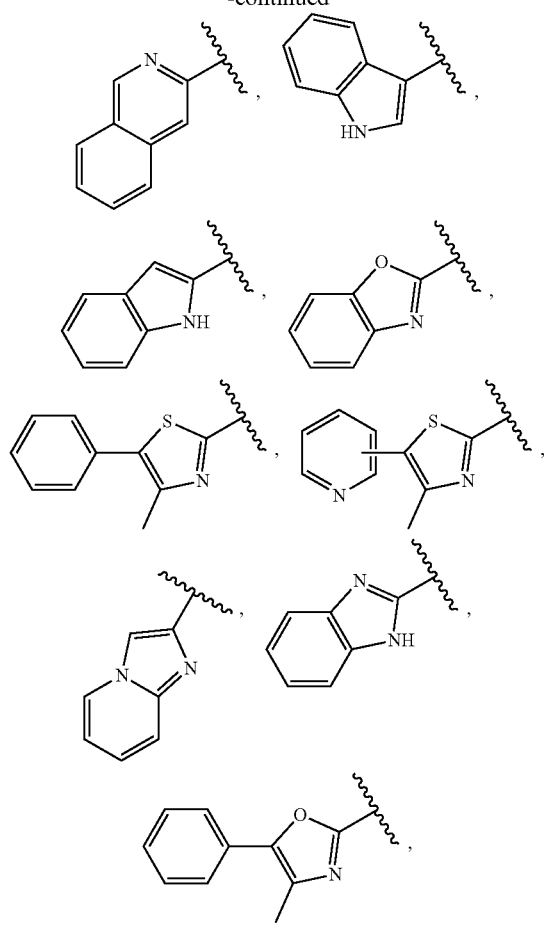
The above examples illustrate embodiments having a single $R_2$ substituent, it is understood that $Ar_1$ groups can be free of an $R_2$ substituent or contain one to four $R_2$ substituents.
In some embodiments, $R_1$ can be, but is not limited to,
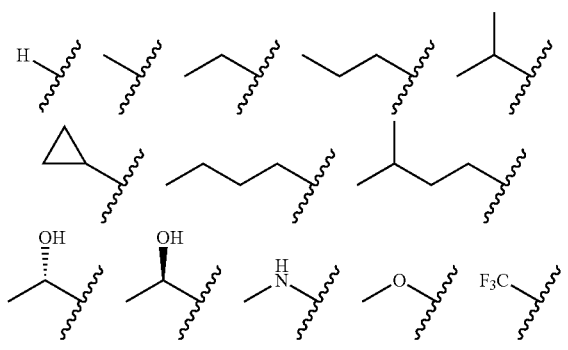
In some embodiments, $R_8$ can be, but is not limited to
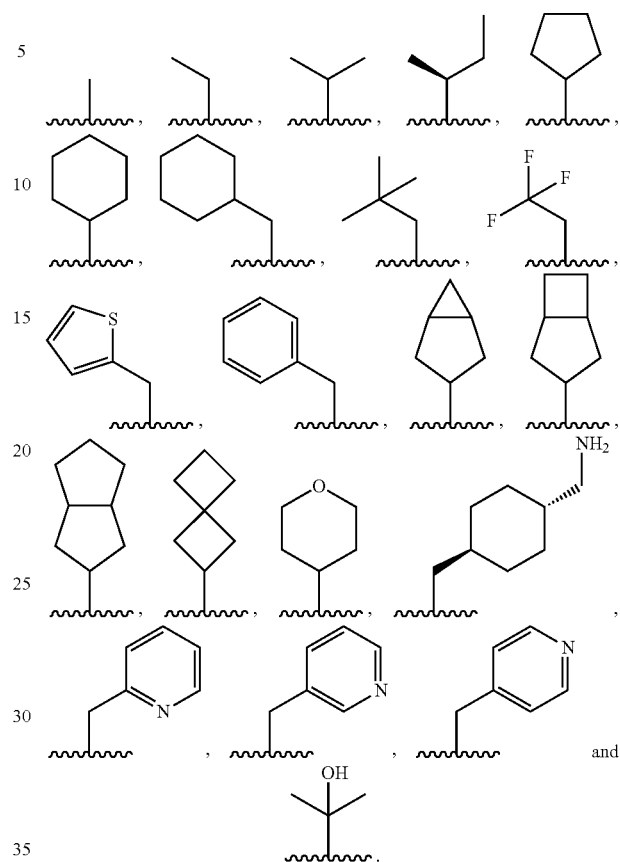
In some embodiments, $R_9$ can be, but is not limited to
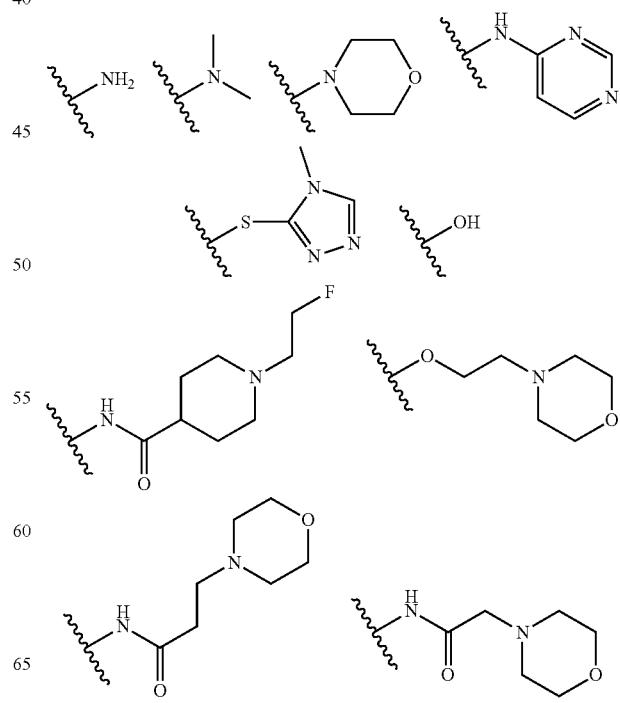

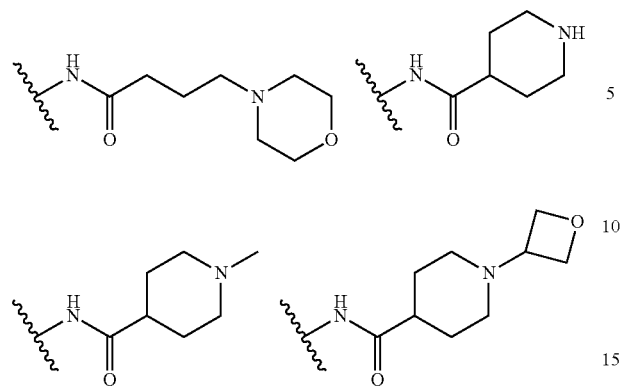
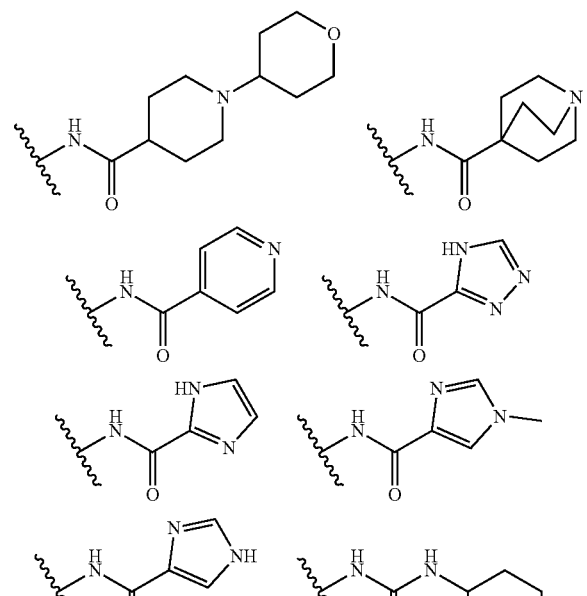
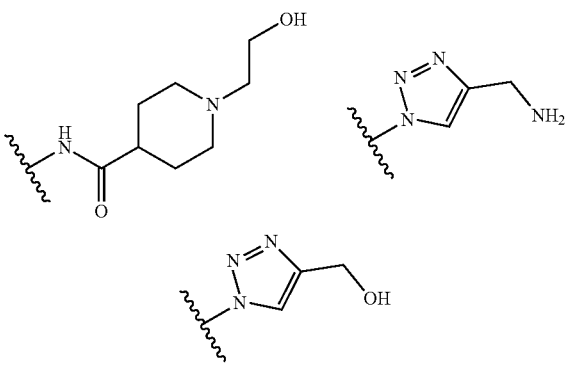
In some embodiments, $R_{14}$ or $R_{15}$ can be, but is not limited to,
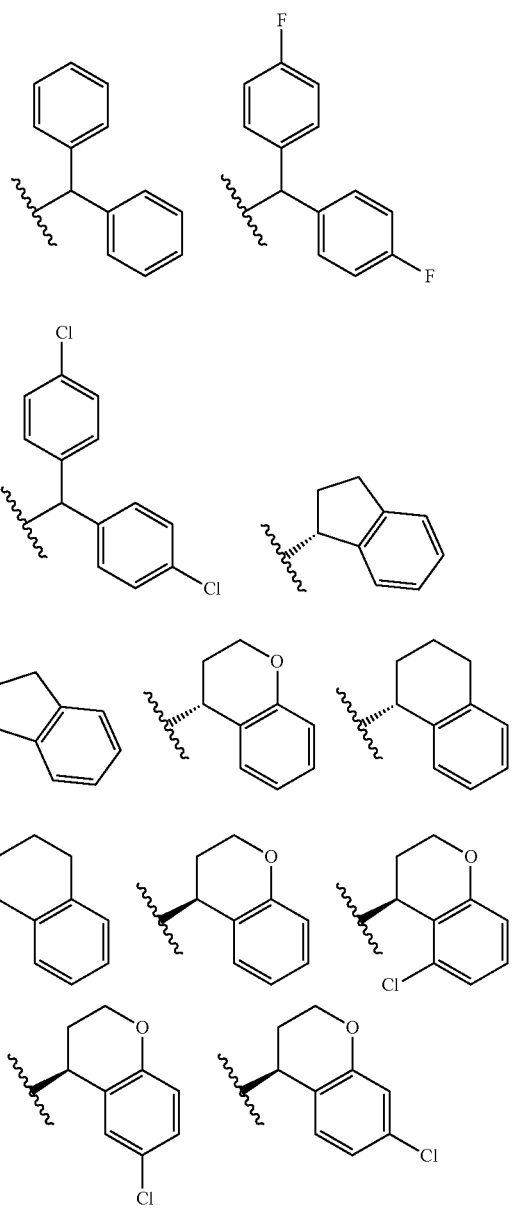

19
-continued

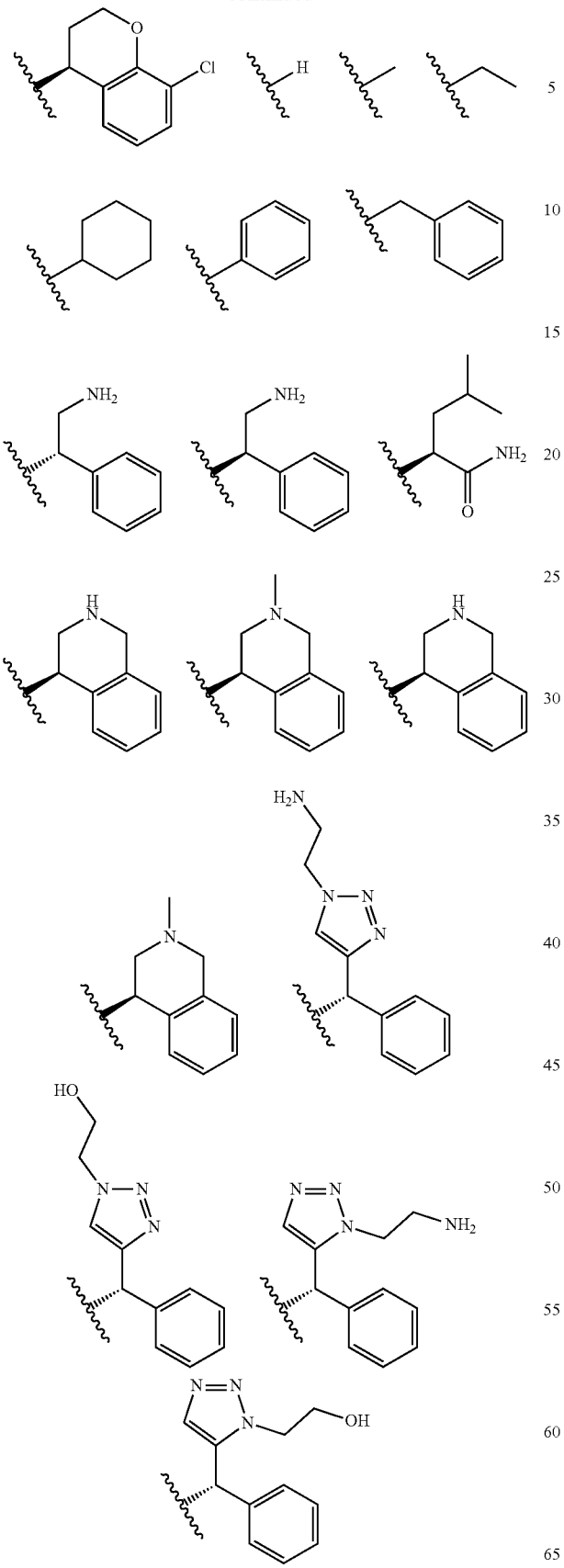

20
In some embodiments, $R_{16}$ can be, but is not limited to,

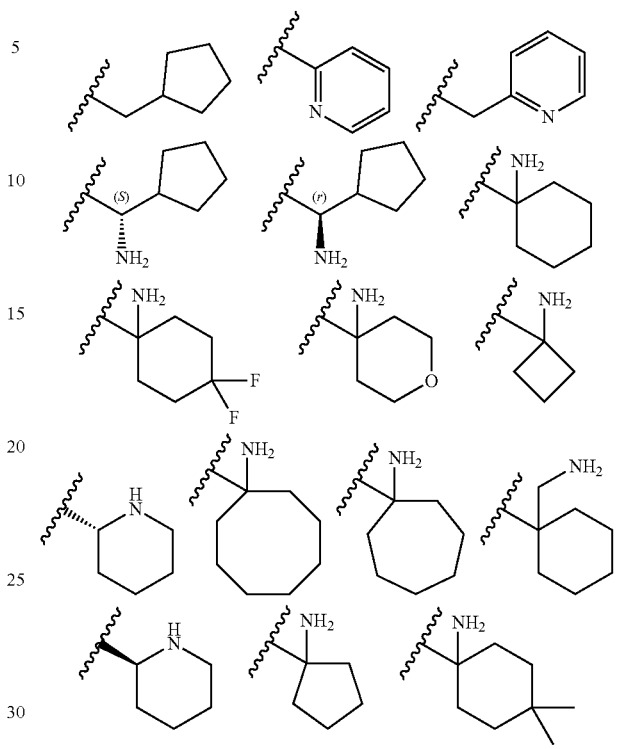

In preferred embodiments in a compound of Formula (1):
$Ar_1$ is selected from 2-benzothienyl, 2-naphthyl, 2-benzoxazolyl, 2-imidazo[1,2-a]pyridinyl or 4-methyl-5-(3-halophenyl)thiazol-2-yl, wherein there are one or $R_2$ substituents on the B-ring of the bicycle, selected from the group chloro, bromo. methyl, $CF_3$, methyl ethyl isopropyl and cyclopropyl.

$R_1$ is selected from H, methyl, ethyl, propyl, isopropyl, cyclopropyl, methylamino and methoxy.

$R_6$ and $R_7$ are jointly formed C(=O) or CH2.

$R_8$ is selected from [S]-butyl, cyclopentyl, cyclohexyl, 4-tetrahydropyranyl, benzyl, cyclohexylmethyl, 2-, 3-, and 4-pyridylmethylene, and trans-4-aminomethylcyclohexylmethylenyl.

For preferred compounds of Formula (Va) one of $R_{14}$ and $R_{15}$ is selected from H, and the other from tetrahydroisoquinolin-4-yl, 3,4-dihydrobenzopyran-4-yl, leucinamido, diphenylmethyl, tetralin-4-yl, 5- or 7-chlorotetrahydropyranyl.

In preferred embodiments wherein compounds are of Formula (II):
$Ar_1$ is benzothiazol-2-yl, imidazo[1,5-a]pyridine-2-yl, or 5-phenylthiazol-2-yl or 2-naphthyl.

$R_1$ is methyl, ethyl, isopropyl, cyclopropyl or methylamino.

Wherein there are one or $R_2$ substituents on the B-ring of the bicycle, selected from the group chloro, bromo. methyl, $CF_3$, methyl ethyl isopropyl and cyclopropyl.

$R_6$ and $R_7$ are taken together as =O or $CH_2$.

$R_8$ is cyclopentyl, cyclohexyl, 4-tetrahydropyranyl, [S]-2-butyl, benzyl, 3-tetrahydrofuranyl, cyclohexylmethyl.

$R_9$ is hydroxy, amino, methylamino, dimethylamino, 1-morpholino, 2-(1-morpholino)ethoxy, 2-(1-morpholino) acetamido, 3-(1-morpholino)propanamido, 4-(1-morpholino)butanamido, 3-(1-morpholino)-iso-butanamido, piperidin-4-ylcarboxamido, N-methylpiperidin-4-ylcarboxamido, N-(oxetan-3-yl)piperidin-4-ylcarboxamido, N-prop-2-ylpiperidin-4-ylcarboxamido, N-(2-hydroxyethyl)piperidin-4-ylcarboxamido, N-(2-aminoethyl)piperidin-4-ylcarboxamido, N-(2-fluoroethyl)piperidin-4-ylcarboxamido, piperidin-4-ylureido, N-methylpiperidin-4-ylureido, piperidin-4-ylsulfonamido, N-methylpiperidin-4-ylsulfonamido, azetindin-3-ylcarboxamido, (N-methylazetindin-3-yl)carboxamido, 1,2,4-triazol-3-ylcarboxamido, 5-hydroxymethyl-1,2,3-triazol-4-ylcarboxamido, 5-aminomethyl-1,2,3-triazol-4-ylcarboxamido, imadaz-4-ylcarboxamido, N-methylimadaz-4-ylcarboxamido, pyrid-4-ylcarboxamido, pyrimid-4-ylcarboxamido.

The compounds of formula (I) inhibit DCN1 and are useful in the treatment of a variety of diseases and conditions. In particular, the compounds of structural formula (I) are used in methods of treating a disease or condition wherein inhibition of DCN1 provides a benefit, for example, oxidative stress-related disease, including cancers, neurodegenerative diseases, cardiovascular diseases, acute lung injury, autoimmune diseases, chronic obstructive pulmonary disease, inflammation, and multiple sclerosis. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof, e.g., a chemotherapeutic agent and/or radiation known as useful in treating a particular cancer.

As used herein, the term "halo" is defined as encompassing fluoro, chloro, bromo, and iodo.

The term "hydroxy" is defined as —OH.

The term "alkoxy" is defined as —OR, wherein R is alkyl.

The term "amino" is defined as —NH₂, and the term "alkylamino" and "dialkylamino" are defined as —NR₂, wherein at least one R is alkyl and the second R is alkyl or hydrogen.

The term "nitro" is defined as —NO₂.

The term "cyano" is defined as —CN.

The term "trifluoromethyl" is defined as CF₃.

The term "trifluoromethoxy" is defined as OCF₃.

The term "azido" is defined as —N₃.

The term "carboxyl" is defined as —CO₂R, where R is H or alkyl.

The term "carbamoyl" is defined as —CON(R)₂, wherein R, independently, is H or alkyl.

The term "alkylthio" is defined as —SR, wherein R is alkyl.

The term "alkylsulfinyl" is defined as —S(O)R, wherein R is alkyl.

The term "alkylsulfonyl" is defined as —S(O₂)R, wherein R is alkyl.

The term "alkylsulfonamido" is defined as —S(O₂)NHR, wherein R is alkyl.

The term "alkylsulfamoyl" is defined as —NHS(O₂)R, wherein R is alkyl.

The term "allyl" is defined as CH₂=CHCH₂—.

The term "proparyl" is defined as CH≡CCH₂—.

As used herein, groups such as

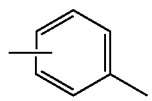

is an abbreviation for

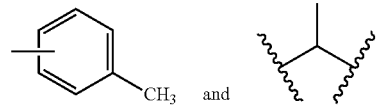

is an abbreviation for

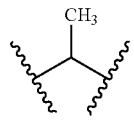

Lower alkyl is C₁₋₆alkyl, either straight chain or branched. Examples include methyl, ethyl, n-propyl i-propyl, n-butyl, [R]- or [S]-isobutyl, t-butyl, n-pentyl, [R]- or [S]-2-pentyl, 3 pentyl, [R]- or [S]-3-methylbut-2-yl, 1,1-dimethylpropyl, 2,2-dimethylpropyl, n-hexyl, [R]- or [S]-2-hexyl, [R]- or [S]-3-hexyl, [R]- or [S]-2-methylpent-1-yl, [R]- or [S]-2-methylpent-3-yl, [R]- or [S]-4-methylpent-2-yl, 2-methylpent-2-yl, [RR]-, [RS]-, [SR]- or [SS]-3-methylpent-2-yl, [R]- or [S]-3-methylpent-1-yl, 4-methylpent-1-yl, 2-methylpent-2-yl, 3-methylpent-3-yl, 2,2-dimethylbut-1-yl, 3,3-dimethylbut-1-yl, [R]- or [S]-3,3-dimethylbut-2-yl, or [R]- or [S]-2,3-dimethylbut-1-yl, 2,3-dimethylbut-2-yl.

Lower alkenyl is C₂₋₆alkenyl, either straight chain or branched. Examples include ethenyl, prop-1-en-1-yl, prop-1-en-2-yl, prop-2-en-1-yl, E- and Z-but-1-en-1-yl, E- or Z-but-2-en-1-yl, but-3-en-1-yl, [R]- or [S]-but-3-en-2-yl, E- or Z-but-2-en-2-yl, 2-methylprop-1-en-1-yl, 2-methylprop-2-en-1-yl, E- or Z-pent-1-en-1-yl, E- or Z-pent-2-en-1-yl, E- or Z-pent-2-en-2-yl, E- or Z-pent-2-en-3-yl, E- or Z-pent-3-en-1-yl, [R]- or [S]-E- or [R]- or [S]—Z-pent-3-en-2-yl, pent-4-en-1-yl, [R]- or [S]-pent-1-en-3-yl, [R]- or [S]-pent-4-en-2-yl, E- or Z-2-methylbut-1-en-1-yl, [R]- or [S}-2-methylbut-3-en-1-yl, 2-methylbut-3-en-2-yl, 3-methylbut-1-en-2-yl, [R]- or [S}-3-methylbut-1-en-2-yl, [R]- or [S}-2-methylbut-2-en-1-yl, 3-methylbut-2-en-1-yl, 3-methylbut-2-en-2-yl, [R]- or [S}-3-methylbut-3-en-2-yl, 3-methylbut-3-en-1-yl, 2-ethylprop-2-en-1-yl, E- or Z-hex-1-en-1-yl, hex-1-en-2-yl, [R]- or [S]-hex-1-en-3-yl, [R]- or [S]-hex-5-en-3-yl, [R]- or [S]-hex-5-en-2-yl, hex-5-en-1-yl, E- or Z-hex-2-en-1-yl, E- or Z-hex-2-en-2-yl, E- or Z-hex-2-en-3-yl, [R]- or [S]-E- or [R]- or [S]—Z-hex-4-en-3-yl, [R]- or [S]-E- or [R]- or [S]—Z-hex-4-en-2-yl, E- or Z-hex-4-en-1-yl, E- or Z-hex-3-en-1-yl, [R]- or [S]-E- or [R]- or [S]—Z-hex-3-en-2-yl, E- or Z-hex-3-en-3-yl, E- or Z-2-methylpent-1-en-1-yl, 2-propylprop-2-en-1-yl, [R]- or [S}-2-methylpent-1-en-3-yl, [R]- or [S}-4-methylpent-4-en-2-yl, 4-methylpent-4-en-1-yl, E- or Z-2-methylpent-2-en-1-yl, 2-methylpent-2-en-3-yl, [R]- or [S]-4-methylpent-3-en-2-yl, 4-methylpent-3-en-1-yl, [R]- or [S]-E- or [R]- or [S]—Z-2-methylpent-2-en-1-yl, E- or Z-2-methylpent-3-en-2-yl, E- or Z-2-methylpent-3-en-3-yl, E- or Z-4-methylpent-2-en-2-yl, E- or Z-4-methylpent-2-en-1-yl, [R]- or [S]-2-methylpent-4-en-1-yl, [R]- or [S]-4-methylpent-1-en-3-yl, E- or Z-4-methylpent-1-en-1-yl, 2-methylpent-4-en-2-yl, 4-methylpent-1-en-2-yl, E- or Z-3,3-dimethylbut-1-en-1-yl, 3,3-dimethylbut-1-en-2-yl, 2,2-dimethylbut-3-en-1-yl, E- or Z-2,3-dimethylbut-1-en-1-yl, 2,3-dimethylbut-3-en-2-yl, [R]- or [S]-2,3-dimethylbut-3-en-1-yl, 2-(1methylethyl)prop-2-en-1-yl, or 2,3-dimethylbut-2-en-1-yl.

Lower alkynyl is $C_{2-6}$alkynyl, either straight chain or branched. Examples include ethylnyl, prop-1-yn-1-yl, prop-2-yn-1-yl, but-1-yn-1-yl, but-2-yn-1-yl, but-3-yn-1-yl, [R]- or [S]-but-3-yn-2-yl, 3-methylbut-1-yn-1-yl, 2-methylbut-3-yn-3-yl, [R]- or [S]-2-methylbut-3-yn-1-yl, hex-1-yn-1-yl, [R]- or [S]-hex-1-yn-3-yl, [R]- or [S]-hex-5-yn-3-yl, [R]- or [S]-hex-5-yn-2-yl, hex-5-yn-1-yl, hex-2-yn-1-yl, [R]- or [S]-hex-4-yn-3-yl, [R]- or [S]-hex-4-yn-2-yl, hex-4-yn-1-yl, hex-3-yn-1-yl, [R]- or [S]-hex-3-yn-2-yl, 4-methylpent-1-yn-1-yl, [R]- or [S]-4-methylpent-1-yn-3-yl, 2-methylpent-4-yn-2-yl, [R]- or [S]-2-methylpent-4-yn-1-yl, [R]- or [S]-3-methylpent-1-yn-1-yl, [R]- or [S]-3-methylpent-1-yn-3-yl, [RR]-, [RS]-, [SR]- or [SS]-3-methylpent-4-yn-2-yl, [R]- or [S]-3-methylpent-4-yn-1-yl, [R]- or [S]-2-ethylbut-3-yn-1-yl, 3,3-dimethylbut-1-yn-1-yl, or 3,3-dimethylbut-3-yn-1-yl.

Lower cycloalkyl is $C_{3-8}$ cycloalkyl. Examples include cyclopropyl, cyclobutyl, cyclopentyl, cyclohexyl, cycloheptyl, and cyclooctyl.

Lower cycloalkenyl is $C_{4-8}$ cycloalkenyl. Examples include cyclobut-1-en-1-yl, [R]- or [S]-cyclobut-2-en-1-yl, cyclopent-1-en-1-yl, [R]- or [S]-cyclopent-2-en-1-yl, cyclopent-3-en-1-yl, cyclohex-1-en-1-yl, [R]- or [S]-cyclohex-2-en-1-yl, [R]- or [S]-cyclohex-3-en-1-yl, cyclohept-1-en-1-yl, [R]- or [S]-cyclohept-2-en-1-yl, [R]- or [S]-cyclohept-3-en-1-yl, cyclohept-4-en-1-yl, cyclooct-1-en-1-yl, [R]- or [S]-cyclooct-2-en-1-yl, [R]- or [S]-cyclooct-3-en-1-yl, and [R]- or [S]-cyclooct-4-en-1-yl, Heterocyclo defines rings of four to eight atoms which contain between one and three heteroatoms, chosen from O, $NR_5$ and $S(O)_x$, with the proviso that the species obey the valence laws, and be chemically stable. Rings may be linked at any position allowed by the valence laws, including N, $N^+$ and $S^{IV}$ or $S^{VI}$ heteroatoms. Representative examples include azetidine, oxetane, thietane, oxolane, pyrrolidine, thiolane, piperidine, oxane, thiane, azepane, oxapane, azocane, oxacane, thiacane, pyrazolidine, imidazolidine, 1,3-dioxolane, 1,2-dithiolane, 1,3-dithiolane, 1,2-diazinane, 1,3-diazinane, piperazine, 1,3-dioxane, 1,4-dioxane, 1,2-dithiane, 1,3-dithiane, 1,4-dithiane, 1,2-diazepane, 1,3-diazepane, 1,4-diazepane, 1,3-dioxepane, 1,4-dioxepane, 1,2-dithiepane, 1,3-dithiepane, 1,4-dithiepane, 1,2-diazocane, 1,3-diazocane, 1,4-diazocane, 1,5-diazocane, 1,3-dioxocane, 1,4-dioxocane, 1,5-dioxocane, 1,2-dithiocane, 1,3-dithiocane, 1,4-dithiocane, 1,5-dithiocane, 1,2-oxazolidine, 1,3-oxazolidine, 1,3-thiazolidine, 1,3-oxathialane, 1,2-oxazane, 1,3-oxazane, morpholine, 1,3-thiazane, thiomorpholine, 1,3-oxathiane, 1,4-oxathiane, 1,2-oxazepane, 1,3-oxazepane, 1,4-oxazepane, 1,3-oxathiepane, 1,4-oxathiepane, 1,3-thiazepane, 1,4-thiazepane, 1,2-oxazocane, 1,3-oxazocane, 1,4-oxazocane, 1,5-oxazocane, 1,3-oxathiocane, 1,4-oxathiocane, 1,5-oxathiocane, 1,3-thiazocane, 1,4-thiazocane, 1,5-thiazocane, 1,2,5-triazepane, 1,4,5-oxadiazepane, 1,2,5-oxadiazepane, 1,4,5-dioxazepane, 1,4,5-thiadiazepane, 1,2,5-triazocane, 1,4,5-oxadiazocane, 1,2,5-oxadiazocane, 1,2,6-oxadiazocane, 1,4,8-dioxazocane, 1,5,8-dioxazocane, 1,3,6-dioxazocane, 1,3,6-oxathiazocane, 1,4,5-oxathiazocane, 1,5,6-oxathiazocane, 1,4,5-oxadiazocane, 1,3,6-dioxathiocane, 1,3,7-dioxathiocane, 1,3,6-oxadithiocane, 1,4,7-oxadithiocane, 1,3,6-oxadithiocane, 1,3,6-trithiocane, 1,2-thiazolane-1,1,dioxide, 1,2,5-thiadiazolane-1,1,dioxide, 1,2-thiazinane-1,1,dioxide, 1,2,6-thiadiazinane-1,1,dioxide, 1,4-dithiane-1,1,dioxide, 1,4-dithiane-1,1,4,4-tetroxide, 1,4-oxathiane-1,1,dioxide, 1,4-thiazinane-1,1,dioxide, 1,4-oxathiepane-1,1,dioxide, 1,2-thiazepane-1,1,dioxide, 1,4-thiazepane1,1,dioxide, 1,4-dithiepane-1,1,dioxide, 1,4-dithiepane-1,1,4,4-tetroxide, 1,2,5-thiadiazepane-1,1-dioxide, 1,2,7-thiadiazepane-1,1-dioxide, 1,4,7-oxathiazepane-1,1-dioxide, 1,4,7-dithiazepane-1,1-dioxide, 1,4,7-dithiazepane-1,1,4,4-tetroxide, 1,4-dithiocane-1,1-dioxide, 1,5-dithiocane-1,1-dioxide, 1,4-dithiocane-1,1,4,4-tetroxide, 1,5-dithiocane-1,1,5,5-tetroxide, 1,4,8-oxathiazocane-1,1-dioxide, 1,5,8-oxathiazocane-1,1-dioxide, 1,4,5-oxathiazocane-1,1-dioxide, 1,5,6-oxathiazocane-1,1-dioxide, 1,4,8-thiadiazocane-1,1-dioxide, 1,5,8-thiadiazocane-1,1-dioxide, 1,4,5-thiadiazocane-1,1-dioxide, 1,2,8-thiadiazocane-1,1-dioxide, 1,3,6-oxadithiocane-1,1-dioxide, 1,3,6-oxadithiocane-1,1,3,3-tetroxide, 1,3,6-dithiazocane-1,1-dioxide, 1,3,6-dithiazocane-1,1,3,3-tetroxide, 1,3,8-dithiazocane-1,1-dioxide, 1,3,8-dithiazocane-1,1,3,3-tetroxide, 1,4,8-dithiazocane-1,1-dioxide, 1,4,8-dithiazocane-1,1,4,4-tetroxide, 1,5,2-dithiazocane-1,1-dioxide, 1,5,2-dithiazocane-1,1,5,5-tetroxide, 1,3,6-trithiocane-6,6-dioxide, 1,3,6-trithiocane-1,1-dioxide, 1,3,6-trithiocane-1,1,3,3-tetroxide, 1,3,6-trithiocane-1,1,6,6-tetroxide, and 1,3,6-trithiocane-1,1,3,3,6,6-hexoxide.

Bicycloalkyl is bicyclic structures of 5-12 carbon atoms, the two rings of which may be have fused, bridged, or spiro junctions. All chemically feasible diastereoisomers and enantiomers are included in the definition, as illustrated for bicyclo[2.1.0]pentyl below, where the point of attachment is marked by 1.

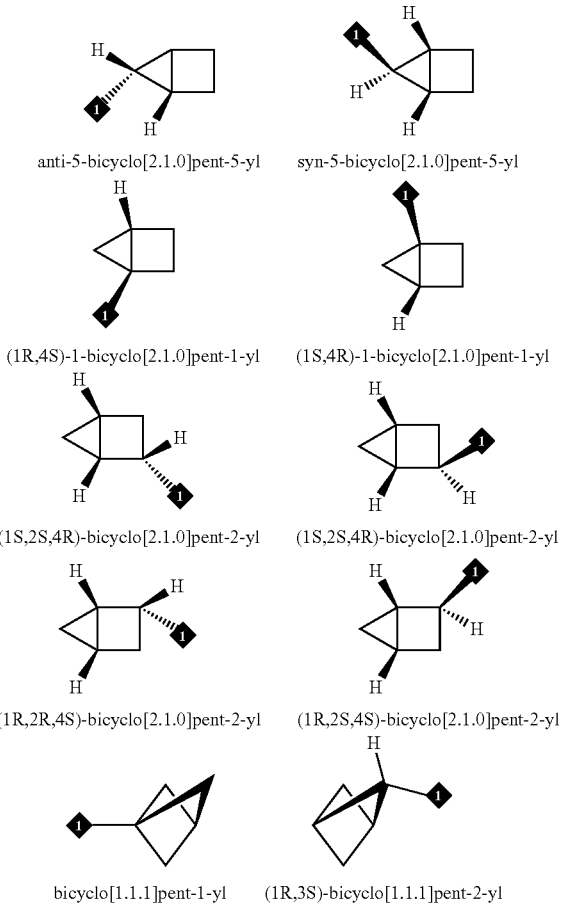

anti-5-bicyclo[2.1.0]pent-5-yl syn-5-bicyclo[2.1.0]pent-5-yl (1R,4S)-1-bicyclo[2.1.0]pent-1-yl (1S,4R)-1-bicyclo[2.1.0]pent-1-yl (1S,2S,4R)-bicyclo[2.1.0]pent-2-yl (1S,2S,4R)-bicyclo[2.1.0]pent-2-yl (1R,2R,4S)-bicyclo[2.1.0]pent-2-yl (1R,2S,4S)-bicyclo[2.1.0]pent-2-yl bicyclo[1.1.1]pent-1-yl (1R,3S)-bicyclo[1.1.1]pent-2-yl

 

(R)-spiro[2.2]pent-1-yl        (S)-spiro[2.2]pent-1-yl

Heterobicyclo includes the structures defined for bicycloalkyl, where between one and four carbon atoms have been replaced with heteroatoms, chosen from O, $NR_5$ and $S(O)_x$, with the proviso that the species obey the valence laws, and be chemically stable, and with the further proviso that no heteroatoms are placed in three membered rings, or more than one heteroatom is placed in a four membered ring, unless explicitly stated. Rings may be linked at any position allowed by the valence laws, including N, $N^+$ and $S^{IV}$ or $S^{VI}$ heteroatoms.

Aryl is phenyl, indenyl, indenyl, naphthyl, azulenyl, fluorenyl, anthracenyl, phenanthrenyl, all of which may be optionally substituted with up to four substituents independently chosen from, halogen, lower alkyl, lower alkenyl, lower alkynyl, OH, lower alkoxy, lower acyloxy, amino, lower acylamino, lower alkylamino, lower dialkylamino, lower $S(O)_x$alkyl, trifluoromethyl, carbaldehyde, carboxy, lower carboxyalkyl, carboxamido, lower carboxamidoalkyl, and lower carboxamidodialkyl, Heteroaryl is pyrrole, pyrazole, imidazole, 1,2,3-triazole, 1,2,4-triazole, tetrazole, furan, oxazole, isoxazole, thiophene, thiazole, isothiazole, 1,2,4-oxadiazole, 1,2,5-oxadiazole, 1,2,3-thiadiazole,1,2,4-thiadiazole, 1,2,5-thiadiazole, pyridine, pyridazine, pyrimidine, pyrazine, 1,2,3-triazine, 1,2,4-triazine, 1,3,5-triazine, or 1,2,4,5-tetrazine.

Polycycloheteroaryl is a fused bicyclic or tricyclic aromatic ring system of 8 to 12 atoms, at least one of which but not more than five (for bicycles), or seven (for tricycles) must O, N, NR, or S. Such polycyciic rings may include pyrrolo[2,3-b]pyrrole, pyrrolo[3,2-b]pyrrole, pyrrolo[2,3-c]pyrrole, pyrrolo[3,4-c]pyrrole, pyrrolo[2,3-b]furan, pyrrolo[3,2-b]furan, pyrrolo[3,4-b]furan, pyrrolo[2,3-c]furan, pyrrolo[3,4-c]furan, pyrrolo[2,3-b]thiophene, pyrrolo[3,4-b]thiophene, pyrrolo[3,2-b]thiophene, pyrrolo[2,3-c]thiophene, pyrrolo[3,4-c] thiophene, furano[2,3-b]furan, furano[3,2-b]furan, furano[2,3-c]furan, furano[3,4-c]furan, furano[2,3-b]thiophene, furano[3,4-b]thiophene, furano[3,2-b]thiophene, furano[2,3-c] thiophene, furano[3,4-c] thiophene, thieno[2,3-b]thiophene, thieno[3,2-b]thiophene, thieno[2,3-c]thiophene, thieno[3,4-c]thiophene, pyrrolo[2,3-c]pyrazole, pyrrolo[3,2-c]pyrazole, pyrrolo[3,4-c]pyrazole, furano[2,3-c]pyrazole, furano[3,2-c]pyrazole, furano[3,4-c]pyrazole,thieno[2,3-c]pyrazole, thieno[3,2-c]pyrazole, thieno[3,4-c]pyrazole, pyrrolo[2,3-d]imidazole, pyrrolo[3,4-d]imidazole, furano[2,3-d]imidazole, furano[3,4-d]imidazole, thieno[2,3-d]imidazole, thieno[3,4-d]imidazole, pyrrolo[2,3-d]-1,2,3-triazole, pyrrolo[3,4-d]-1,2,3-triazole, furano[2,3-d]-1,2,3-triazole, furano[3,4-d]-1,2,3-triazole, thieno[2,3-d]-1,2,3-triazole, thieno[3,4-d]-1,2,3-triazole, pyrrolo[3,2-d]isoxazole, pyrrolo[2,3-c]isoxazole, pyrrolo[3,4-d]isoxazole, pyrrolo[3,4-c]isoxazole, pyrrolo[2,3-d]isoxazole, pyrrolo[3,2-c]isoxazole, furano[3,2-d]isoxazole, furano[2,3-c]isoxazole, furano[3,4-d]isoxazole, furano[3,4-c]isoxazole, furano[2,3-d]isoxazole, furano[3,2-c]isoxazole, thieno[3,2-d]isoxazole, thieno[2,3-d]isoxazole, thieno[3,4-c]isoxazole, thieno[2,3-d]isoxazole, thieno[3,2-c]isoxazole, pyrrolo[3,2-d]oxazole, pyrrolo[2,3-d]oxazole, pyrrolo[3,4-d]oxazole, furano[3,2-d] oxazole, furano[2,3-d]oxazole, furano[3,4-d]oxazole, thieno[3,2-d]oxazole, thieno[2,3-d]oxazole, thieno[3,4-d]oxazole, pyrrolo[3,2-d]isothiazole, pyrrolo[2,3-c]isothiazole, pyrrolo[3,4-d]isothiazole, pyrrolo[3,4-c]isothiazole, pyrrolo[2,3-d]isothiazole, pyrrolo[3,2-c]isothiazole, furano[3,2-d]isothiazole, furano[2,3-c]isothiazole, furano[3,4-d]isothiazole, furano[3,4-c]isothiazole, furano[2,3-d]isothiazole, furano[3,2-c]isothiazole, thieno[3,2-d]isothiazole, thieno[2,3-c]isothiazole, thieno[3,4-d]isothiazole, thieno[3,4-c]isothiazole, thieno[2,3-d]isothiazole, thieno[3,2-c]isothiazole, pyrrolo[3,2-d]thiazole, pyrrolo[2,3-d]thiazole, pyrrolo[3,4-d]thiazole, furano[3,2-d]thiazole, furano[2,3-d]thiazole, furano[3,4-d]thiazole, thieno[3,2-d]thiazole, thieno[2,3-d]thiazole, thieno[3,4-d]thiazole, pyrrolo[3,2-d]-1,2,3-thiadiazole, pyrrolo[2,3-d]-1,2,3-thiadiazole, pyrrolo[3,4-d]-1,2,3-thiadiazole, furano[3,2-d]-1,2,3-thiadiazole, furano[2,3-d]-1,2,3-thiadiazole, furano[3,4-d]-1,2,3-thiadiazole, thieno[3,2-d]-1,2,3-thiadiazole, thieno[2,3-d]-1,2,3-thiadiazole, thieno[3,4-d]-1,2,3-thiadiazole, pyrrolo[2,3-c]-1,2,5-oxadiazole, pyrrolo[3,4-c]-1,2,5-oxadiazole, furano[2,3-c]-1,2,5-oxadiazole, furano[3,4-c]-1,2,5-oxadiazole, thieno[2,3-c]-1,2,5-oxadiazole, thieno[3,4-c]-1,2,5-oxadiazole, pyrrolo[2,3-c]-1,2,5-thiadiazole, pyrrolo[3,4-c]-1,2,5-thiadiazole, furano[2,3-c]-1,2,5-thiadiazole, furano[3,4-c]-1,2,5-thiadiazole, thieno[2,3-c]-1,2,5-thiadiazole, thieno[3,4-c]-1,2,5-thiadiazole, pyrazolo[3,4-c]pyrazole, pyrazolo[4,3-c]pyrazole, imidazo[4,5-c]pyrazole, ipyrazolo[4,3-d]triazole, imidazo[4,5-d]triazole, pyrazolo[3,4-c]isoxazole, pyrazolo[4,3-d]isoxazole, pyrazolo[4,3-c]isoxazole, pyrazolo[3,4-d]isoxazole, pyrazolo[4,3-d]oxazole, pyrazolo[3,4-d]oxazole, imidazo[4,5-c]isoxazole, imidazo[5,4-d]isoxazole, isoxazolo[3,4-d]triazole, oxazolo[4,5-d]triazole, pyrazolo[3,4-c]isothiazole, pyrazolo[4,3-d]isothiazole, pyrazolo[4,3-c]isothiazole, pyrazolo[3,4-d]isothiazole, pyrazolo[4,3-d]thiazole, pyrazolo[3,4-d]thiazole, imidazo[4,5-c]isothiazole, imidazo[5,4-d]isothiazole, isothiazolo[3,4-d]triazole, thiazolo[4,5-d]triazole, isoxazolo[3,4-c]isoxazole, isoxazolo[4,5-d]isoxazole, isoxazolo[5,4-c]isoxazole, isoxazolo[4,3-c]isoxazole, isoxazolo[4,5-c]isoxazole, isoxazolo[5,4-d]isoxazole, isoxazolo[3,4-d]oxazole, isoxazolo[4,3-d]oxazole, isoxazolo[4,5-d]oxazole, isoxazolo[5,4-d]oxazole, oxazolo[4,5-d]oxazole, oxazolo[5,4-d]oxazole, isoxazolo[3,4-c]isothiazole, isoxazolo[4,5-d]isothiazole, isoxazolo[5,4-c]isothiazole, isoxazolo[3,4-d]isothiazole, isoxazolo[4,3-c]isothiazole, isoxazolo[4,5-c]isothiazole, isoxazolo[5,4-d]isothiazole, isoxazolo[3,4-d]thiazole, oxazolo[5,4-d]isothiazole, isoxazolo[4,3-d]thiazole, oxazolo[4,5-d]isothiazole, isoxazolo[4,5-d]thiazole, oxazolo[5,4-c]isothiazole, isoxazolo[5,4-d]thiazole, oxazolo[4,5-c]isothiazole, oxazolo[4,5-d]thiazole, oxazolo[5,4-d]thiazole, isothiazolo[3,4-c]isothiazole, isothiazolo[4,5-d]isothiazole, isothiazolo[5,4-c]isothiazole, isothiazolo[4,3-c]isothiazole, isothiazolo[4,5-c]isothiazole, isothiazolo[5,4-d]isothiazole, isothiazolo[3,4-d]thiazole, isothiazolo[4,3-d]thiazole, isothiazolo[4,5-d]thiazole, isothiazolo[5,4-d]thiazole, thiazolo[4,5-d]thiazole, thiazolo[5,4-d]thiazole, pyrazolo[5,4-d]-1,2,3-thiadiazole, pyrazolo[3,4-d]-1,2,3-thiadiazole, imidazo[4,5-d]-1,2,3-thiadiazole, isoxazolo[4,3-d]-1,2,3-thiadiazole, isothiazolo[4,3-d]-1,2,3-thiadiazole, isoxazolo[4,5-d]-1,2,3-thiadiazole, isothiazolo[4,5-d]-1,2,3-thiadiazole, isoxazolo[3,4-d]-1,2,3-thiadiazole, isothiazolo[3,4-d]-1,2,3-thiadiazole,isoxazolo[5,4-d]-1,2,3-thiadiazole, isothiazolo[5,4-d]-1,2,3-thiadiazole, oxazolo[4,5-d]-1,2,3-thiadiazole, thiazolo[4,5-d]-1,2,3-thiadiazole, oxazolo[5,4-d]-1,2,3-thiadiazole, thiazolo[5,4-d]-1,2,3-thiadiazole, pyrazolo[4,3-d]-1,2,5-thiadiazole, pyrazolo[4,3-d]-1,2,5-oxadiazole, isoxazolo[4,3-d]-1,2,5- thiadiazole, isothiazolo[4,3-d]-1,2,5-thiadiazole, isoxazolo[4,3-d]-1,2,5-oxadiazole, isothiazolo[4,3-d]-1,2,5-oxadiazole, isoxazolo[4,5-d]-1,2,5-thiadiazole, isothiazolo[4,5-d]-1,2,5-thiadiazole, isoxazolo[4,5-d]-1,2,5-oxadiazole, isothiazolo[4,5-d]-1,2,5-oxadiazole, imidazo[4,5-d]-1,2,5-thiadiazole, imidazo[4,5-d]-1,2,5-oxadiazole, oxazolo[4,5-d]-1,2,5-thiadiazole, thiazolo[4,5-d]-1,2,5-thiadiazole, oxazolo[4,5-d]-1,2,5-oxadiazole, thiazolo[4,5-d]-1,2,5-oxadiazole, pyrrolo[1,2-b]thiazole, imidazo[1,2-b]pyrazole, imidazo[1,2-a]imidazole, imidazo[2,1-b]thiazole, imidazo[2,1-c]-1,2,4-triazole, thiazolo[2,3-c]-1,2,4-triazole, imidazo[1,2-b]-1,2,4-triazole, thiazolo[3,2-b]-1,2,4-triazole, oxazolo[3,2-b]-1,2,4-triazole, thiazolo[3,2-b]-1,2,4-triazole, triazolo[1,5-b]1,3,4-oxadiazole, triazolo[1,5-b] 1,3,4-thiadiazole, indole, isoindole, benzofuran, isobenzofuran, benzothiophene, isobenzothiophene, indolizine, indazole, benzimidazole, benzoxazole, benzoisooxazole, benzothiazole, benzoisothiazole, pyrazolo[1,5-a]pyridine, imidazo[1,5-a]pyridine, imidazo[1,2-a]pyridine, benzotriazole, benzo-1,2,5-oxadiazole benzo-1,2,3-thiadiazole, benzo-1,2,5-thiadiazole, pyrrolo[2,3-b]pyridine, pyrrolo[2,3-c]pyridine, pyrrolo[3,2-c]pyridine, pyrrolo[3,2-b]pyridine, furano[2,3-b]pyridine, furano [2,3-c]pyridine, furano [3,2-c]pyridine, furano [3,2-b]pyridine, thieno[2,3-b]pyridine, thieno [2,3-c]pyridine, thieno [3,2-c]pyridine, thieno [3,2-b]pyridine, pyrazolo[3,4-b]pyridine, pyrazolo [3,4-c]pyridine, pyrazolo [4,3-c]pyridine, pyrazolo [4,3-b]pyridine, isoxazolo[5,4-b]pyridine, isoxazolo[5,4-c]pyridine, isoxazolo[4,5-c]pyridine, isoxazolo[4,5-b]pyridine, isothiazolo[5,4-b]pyridine, isothiazolo[5,4-c]pyridine, isothiazolo[4,5-c]pyridine, isothiazolo[4,5-b]pyridine, imidazo[4,5-b]pyridine, imidazo[4,5-c]pyridine, oxazolo[5,4-b]pyridine, oxazolo[5,4-c]pyridine, oxazolo[4,5-c]pyridine, oxazolo[4,5-b]pyridine, thiazolo[5,4-b]pyridine, thiazolo[5,4-c]pyridine, thiazolo[4,5-c]pyridine, thiazolo[4,5-b]pyridine, 1,2,3-thiadiazolo[5,4-b]pyridine, 1,2,3-thiadiazolo[5,4-c]pyridine, 1,2,3-thiadiazolo[4,5-c]pyridine, 1,2,3-thiadiazolo[4,5-b]pyridine, 1,2,5-thiadiazolo[4,5-c]pyridine, 1,2,5-thiadiazolo[4,5-b]pyridine, 1,2,5-oxadiazolo[4,5-c]pyridine, 1,2,5-oxadiazolo[4,5-b]pyridine, pyrazolo[2,3-b]pyridazine, imidazo[3,4-b]pyridazine, imidazo[3,2-b]pyridazine, pyrazolo[2,3-c]pyrimidine, imidazo[3,4-c]pyrimidine, imidazo[1,2-c]pyrimidine, pyrazolo[5,1-c]pyrazine, imidazo[5,1-c]pyrazine, imidazo[1,2-c]pyrazine, pyrazolo[2,3-a]pyrimidine, imidazo[3,4-a]pyrimidine, imidazo[3,2-a]pyrimidine, pyrrolo[2,3-c]pyridazine, furano[2,3-c]pyridazine, thieno[2,3-c]pyridazine, pyrrolo[3,2-c]pyridazine, furano[3,2-c]pyridazine, thieno[3,2-c]pyridazine, pyrrolo[2,3-d]pyridazine, furano[2,3-d]pyridazine, thieno[2,3-dpyridazine, pyrrolo[2,3-d]pyrimidine, furano[2,3-d]pyrimidine, thieno[2,3-d]pyrimidine, pyrrolo[3,2-d]pyrimidine, furano[3,2-d]pyrimidine, thieno[3,2-d]pyrimidine, pyrrolo[2,3-b]pyrazine, furano[2,3-b]pyrazine, thieno[2,3-b]pyrazine, 1,2,3-triazolo[1,5-b]pyridazine, 1,2,4-triazolo[4,3-b]pyridazine, 1,2,4-triazolo[1,5-b]pyridazine, 1,2,3-triazolo[1,5-c]pyrimidine, 1,2,4-triazolo[4,3-c]pyrimidine, 1,2,4-triazolo[1,5-c]pyrimidine, 1,2,3-triazolo[1,5-a]pyrazine, 1,2,4-triazolo[4,3-a]pyrazine, 1,2,4-triazolo[1,5-a]pyrazine, 1,2,3-triazolo[1,5-a]pyrimidine, 1,2,4-triazolo[4,3-a]pyrimidine, 1,2,4-triazolo[1,5-a]pyrimidine, pyrazolo[3,4-c]pyridazine, isothiazolo[5,4-c]pyridazine, isoxazolo[5,4-c]pyridazine, imidazo[4,5-c]pyridazine, thiazolo[5,4-c]pyridazine, oxazolo[5,4-c]pyridazine, pyrazolo[3,4-d]pyrimidine, isothiazolo[5,4-d]pyrimidine, isoxazolo[5,4-d]pyrimidine, imidazo[4,5-d]pyrimidine, thiazolo[5,4-d]pyrimidine, oxazolo[5,4-d]pyrimidine, pyrazolo[4,3-d]pyrimidine, isothiazolo[4,5-d]pyrimidine, isoxazolo[4,5-d]pyrimidine, thiazolo[4,5-d]pyrimidine, oxazolo[4,5-d]pyrimidine, pyrazolo[3,4-b]pyrazine, isothiazolo[4,5-b]pyrazine, isoxazolo[4,5-b]pyrazine, imidazo[4,5-b]pyrazine, thiazolo[4,5-b]pyrazine, oxazolo[4,5-b]pyrazine, 1,2,3-triazolo[1,5-b]-1,2,4-triazine, 1,2,3-triazolo[5,1-f]-1,2,4-triazine, 1,2,3-triazolo[1,5-d]-1,2,4-triazine, 1,2,3-triazolo[5,1-c]-1,2,4-triazine, 1,2,4-triazolo[5,1-f]-1,2,4-triazine, 1,2,4-triazolo[3,4-f]-1,2,4-triazine, 1,2,4-triazolo[4,3-d]-1,2,4-triazine, 1,2,4-triazolo[1,5-d]-1,2,4-triazine, 1,2,3-triazolo[1,5-a]-1,3,5-triazine, 1,2,4-triazolo[1,5-a]-1,3,5-triazine, 1,2,4-triazolo[4,3-a]-1,3,5-triazine, 1,2,4-triazolo[3,4-c]-1,2,4-triazine, 1,2,4-triazolo[5,1-c]-1,2,4-triazine, 1,2,3-triazolo[4,5-c]pyridazine, 1,2,3-triazolo[4,5-d]pyrimidine, 1,2,3-triazolo[4,5-b]pyrazine, 1,2,3-triazolo[4,5-d]pyridazine, 1,2,3-thiadiazolo[4,5-d]pyridazine, 1,2,3-thiadiazolo[4,5-d]pyrimidine, 1,2,3-thiadiazolo[5,4-d]pyrimidine, 1,2,5-thiadiazolo[3,4-d]pyrimidine, 1,2,5-oxadiazolo[3,4-d]pyrimidine, 1,2,5-oxadiazolo[3,4-d]pyridazine, 1,2,5-thiadiazolo[3,4-d]pyridazine, 1,2,5-oxadiazolo[3,4-d]pyrazine, 1,2,5-thiadiazolo[3,4-d]pyrazine, pyrazolo[3,4-d]-1,2,3-triazine, pyrazolo[4,3-e]-1,2,4-triazine, pyrazolo[3,4-e]-1,2,4-triazine, pyrazolo[4,3-d]-1,2,3-triazine, imidazo[4,5-d]-1,2,3-triazine, imidazo[4,5-e]-1,2,4-triazine, oxazolo[4,5-e]-1,2,4-triazine, oxazolo[5,4-e]-1,2,4-triazine, oxazolo[4,5-d]-1,2,3-triazine, thiazolo[4,5-d]-1,2,3-triazine, thiazolo[5,4-d]-1,2,3-triazine, thiazolo[5,4-e]-1,2,4-triazine, thiazolo[4,5-e]-1,2,4-triazine, isothiazolo[4.5-d]-1,2,3-triazine, isoxazolo[4.5-d]-1,2,3-triazine, isoxazolo[5,4-d]-1,2,3-triazine, isoxazolo[4.5-e]-1,2,4-triazine, isoxazolo[4.3,d]-1,2,3-triazine, isothiazolo[4.3,d]-1,2,3-triazine, quinoline, isoquinoline, cinnoline, quinazoline, phthalazine, quinoxaline, 1,5-naphthyridine, 1,6-naphthyridine, 1,7-naphthyridine, 1,8-naphthyridine, 2,5-naphthyridine, 2,6-naphthyridine, 2,7-naphthyridine, pyrido[2,3-c]pyridazine, pyrido[3,4-c]pyridazine, pyrido[4,3-c]pyridazine, pyrido[3,2-c]pyridazine, pyrido[2,3-d]pyrimidine, pyrido[3,4-d]pyrimidine, pyrido[4,3-d]pyrimidine, pyrido[3,2-d]pyrimidine, pyrido[2,3-d]pyridazine, pyrido[3,4-d]pyridazine, pyrido[2,3-b]pyrazine, pyrido[3,4-b]pyrazine, pyridazo[3,4-c]pyridazine, pyridazo[4,5-c]pyridazine, pyridazo[4,5-c]pyridazine, pyrimido[5,4-c]pyridazine, pyrimido[4,5-c]pyridazine, pyrazino[2,3-c]pyridazine, pyrimido[4,5-d]pyridazine, pyrazino[2,3-d]pyridazine, pyrimido[4,5-d]-1,2,3-triazine, pyrimido[5,4-d]-1,2,3-triazine, pyrimido[4,5-e]-1,2,4-triazine, pyrimido[5,4-e]-1,2,4-triazine, and pyrazino[2,3-e]-1,2,4-triazine. Tricycles can be made by a 1,2-fusion of phenyl, or any of the earlier mentioned heteroaryl rings, to two adjacent, non-bridging atoms of any of the abovementioned bicycles, with the provisos that the valence rules be obeyed, the resultant tricycle be an aromatic entity, and that the fused tricycle contains no more than seven total heteroatoms.

All alkyl, alkenyl, alkynyl, cycloalkyl, cycloalkenyl, heterocyclyl, aryl, heteroaryl, and alkoxy groups can be optionally substituted with 1-3 groups independently selected from halo, hydroxy, alkoxy, oxo, lower acyloxy, amino, alkylamino, dialkylamino, alkylthio, alkylsulfonyl, heterocyclyl, aryl, heteroaryl, with the provisos that no carbon-linked substituent may iterate more than twice in total, and that the substituents produce chemically stable molecules.

All stereoisomers of compounds are claimed, except where a specific stereochemistry is delineated at a chiral center.

All analogues where hydrogen is replaced with deuterium are also claimed.

Additionally, salts of the compounds of structural formula (I) also are included in the present invention and can be used in the methods disclosed herein. The present invention further includes all possible stereoisomers and geometric isomers of the compounds of structural formula (I). The present invention includes both racemic compounds and optically active isomers. When a compound of structural formula (I) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I) are possible, the present invention is intended to include all tautomeric forms of the compounds.

Various compounds of the present invention can exist as salts. Pharmaceutically acceptable salts of compounds of structural formula (I) often are preferred in the methods of the invention. As used herein, the term "pharmaceutically acceptable salts" refers to salts or zwitterionic forms of the compounds of structural formula (I). Salts of compounds of formula (I) can be prepared during the final isolation and purification of the compounds or separately by reacting the compound with an acid or base having a suitable counterion. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I), as well as pharmaceutically acceptable salts, thereof.

Specific compounds of the present invention, and the bonding affinity to DCN1 protein, include, but are not limited to, compounds having a structure set forth below in Table 1.

TABLE 1

Chemical structures and binding affinities to DCN1 proteins

| ID | Number of Example | Chemical Structure | Binding affinity to DCN1 (IC50 (nM)) |
|---|---|---|---|
| DI-24 | 8 | 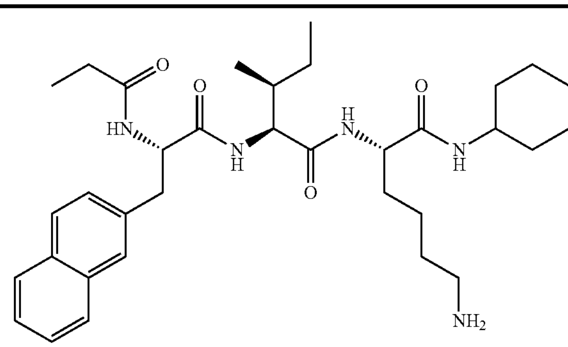 | >3 (µM) |
| DI-25 | 9 | 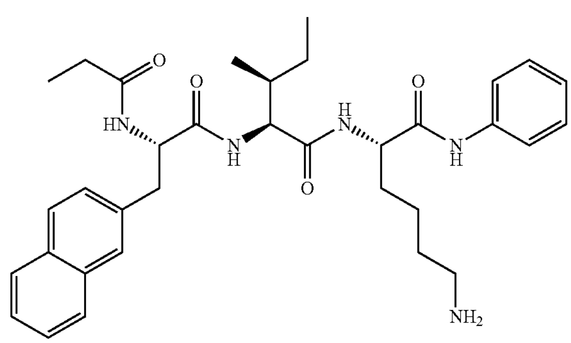 [SMILES: CCC(=O)N[C@@H](Cc1ccc2ccccc2c1)C(=O)N[C@H](C(=O)N[C@@H](CCCCN)C(=O)Nc1ccccc1)[C@@H](C)CC] | >10 (µM) |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-26 | 10 | 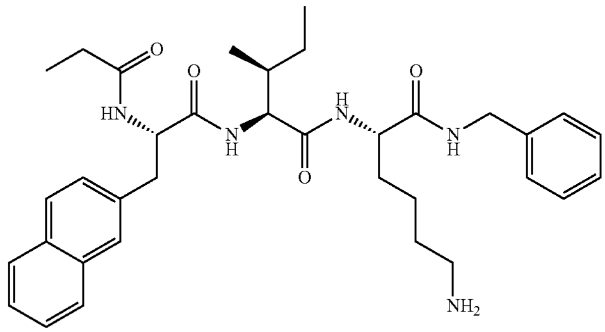 [SMILES: CCC(=O)N[C@@H](Cc1ccc2ccccc2c1)C(=O)N[C@H](C(=O)N[C@@H](CCCCN)C(=O)NCc1ccccc1)[C@@H](C)CC] | 3900 |
| DI-27 | 12 | 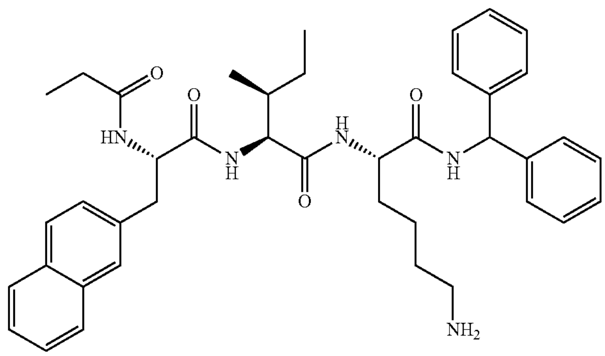 [SMILES: CCC(=O)N[C@@H](Cc1ccc2ccccc2c1)C(=O)N[C@H](C(=O)N[C@@H](CCCCN)C(=O)NC(c1ccccc1)c1ccccc1)[C@@H](C)CC] | 611 ± 193 |
| DI-28 | 128 | 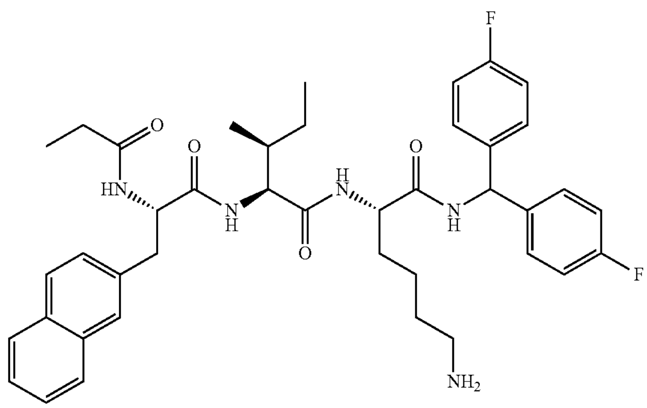 [SMILES: CCC(=O)N[C@@H](Cc1ccc2ccccc2c1)C(=O)N[C@H](C(=O)N[C@@H](CCCCN)C(=O)NC(c1ccc(F)cc1)c1ccc(F)cc1)[C@@H](C)CC] | 321 ± 32 |
| DI-29 | 129 | 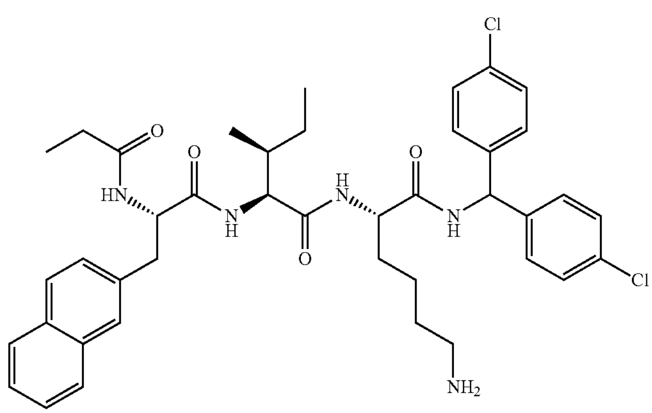 [SMILES: CCC(=O)N[C@@H](Cc1ccc2ccccc2c1)C(=O)N[C@H](C(=O)N[C@@H](CCCCN)C(=O)NC(c1ccc(Cl)cc1)c1ccc(Cl)cc1)[C@@H](C)CC] | 748 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-30 | 13 | 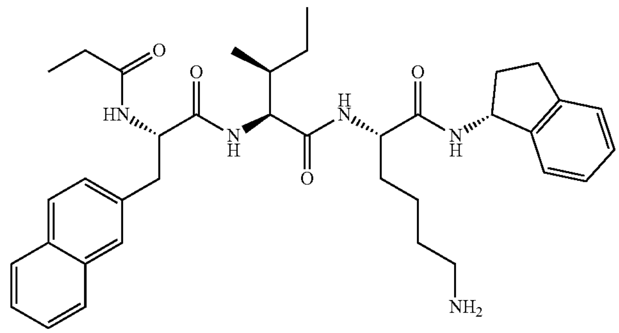 [SMILES: CCC(=O)N[C@@H](Cc1ccc2ccccc2c1)C(=O)N[C@H](C(=O)N[C@@H](CCCCN)C(=O)N[C@@H]1CCc2ccccc21)[C@@H](C)CC] | 913 |
| DI-31 | 14 | 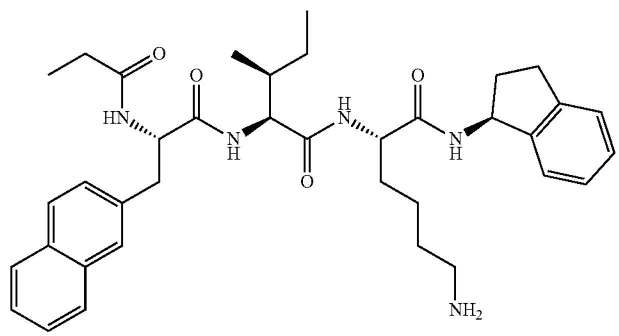 [SMILES: CCC(=O)N[C@@H](Cc1ccc2ccccc2c1)C(=O)N[C@H](C(=O)N[C@@H](CCCCN)C(=O)N[C@H]1CCc2ccccc21)[C@@H](C)CC] | 1926 |
| DI-32 | 15 | 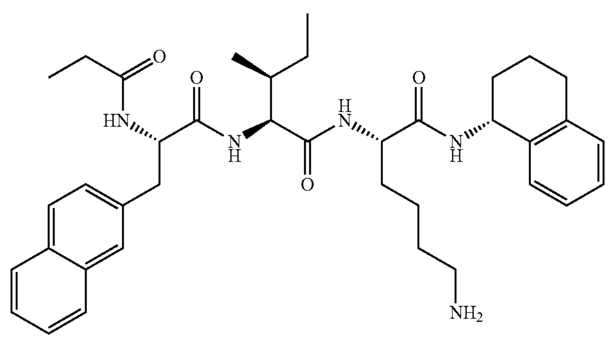 | 461 |
| DI-33 | 16 | 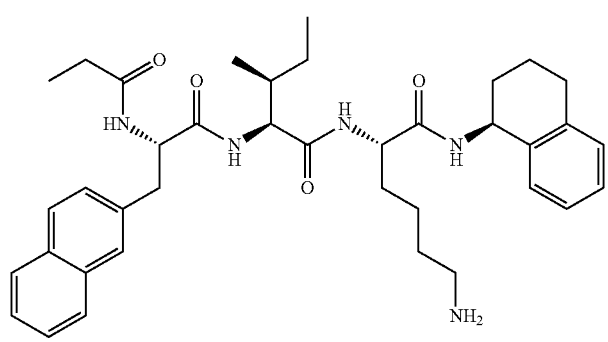 [SMILES: CCC(=O)N[C@@H](Cc1ccc2ccccc2c1)C(=O)N[C@H](C(=O)N[C@@H](CCCCN)C(=O)N[C@H]1CCCc2ccccc21)[C@@H](C)CC] | 795 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-34 | 17 | 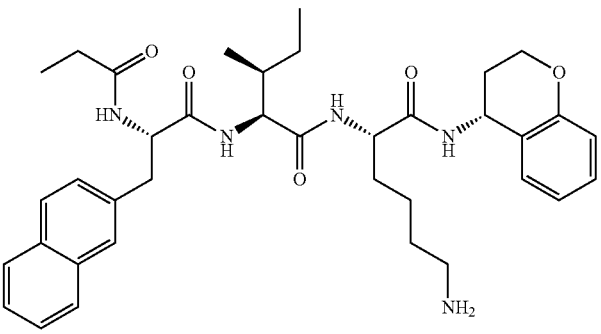 [SMILES: CCC(=O)N[C@@H](Cc1ccc2ccccc2c1)C(=O)N[C@H](C(=O)N[C@@H](CCCCN)C(=O)N[C@@H]1CCOc2ccccc21)[C@@H](C)CC] | 651 |
| DI-35 | 18 | 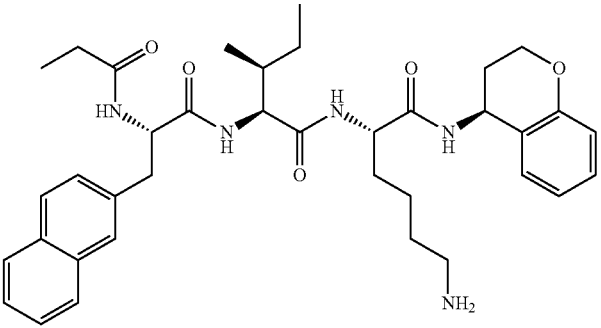 [SMILES: CCC(=O)N[C@@H](Cc1ccc2ccccc2c1)C(=O)N[C@H](C(=O)N[C@@H](CCCCN)C(=O)N[C@H]1CCOc2ccccc21)[C@@H](C)CC] | 3048 |
| DI-36 | 130 | 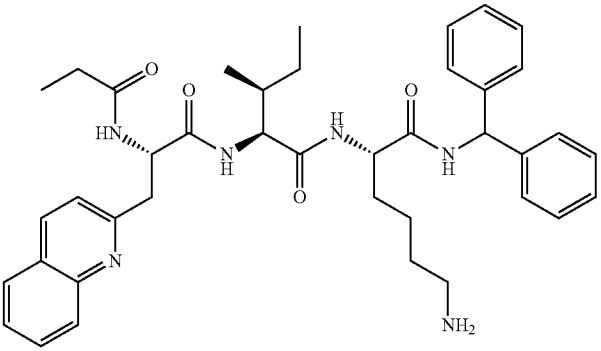 [SMILES: CCC(=O)N[C@@H](Cc1ccc2ccccc2n1)C(=O)N[C@H](C(=O)N[C@@H](CCCCN)C(=O)NC(c1ccccc1)c1ccccc1)[C@@H](C)CC] | 2365 |
| DI-37 | 131 | 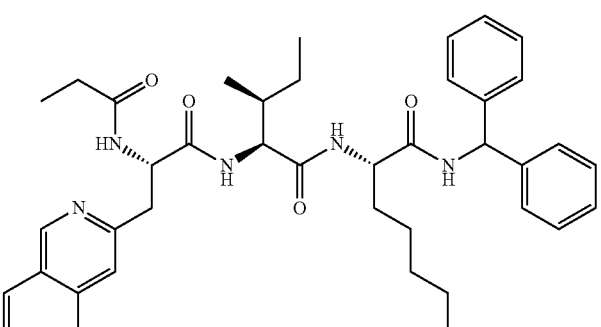 | 2614 |

TABLE 1-continued
Chemical structures and binding affinities to DCN1 proteins
| ID | Number of Example | Chemical Structure | Binding affinity to DCN1 (IC50 (nM)) |
|---|---|---|---|
| ZBB-01-161 | 132 | 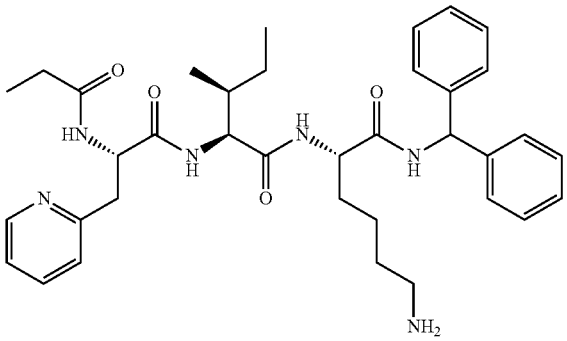 [SMILES: CCC(=O)N[C@@H](Cc1ccccn1)C(=O)N[C@H](C(=O)N[C@@H](CCCCN)C(=O)NC(c1ccccc1)c1ccccc1)[C@@H](C)CC] | >10 (μM) |
| ZBB-01-73 | 133 | 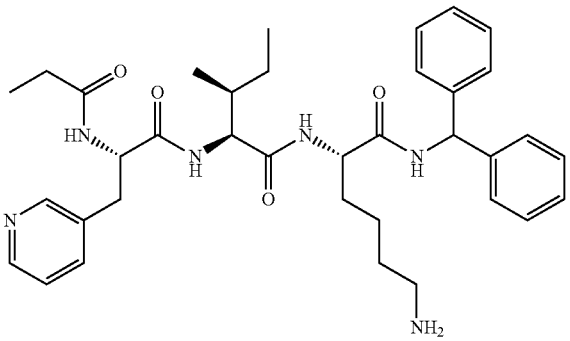 [SMILES: CCC(=O)N[C@@H](Cc1cccnc1)C(=O)N[C@H](C(=O)N[C@@H](CCCCN)C(=O)NC(c1ccccc1)c1ccccc1)[C@@H](C)CC] | >10 (μM) |
| ZBB-01-75 | 134 | 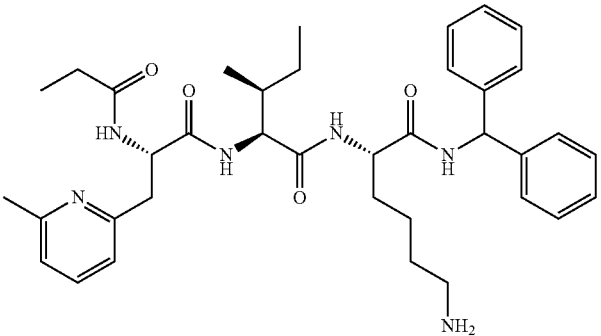 [SMILES: CCC(=O)N[C@@H](Cc1cccc(C)n1)C(=O)N[C@H](C(=O)N[C@@H](CCCCN)C(=O)NC(c1ccccc1)c1ccccc1)[C@@H](C)CC] | >10 (μM) |
| ZBB-01-111 | 135 | 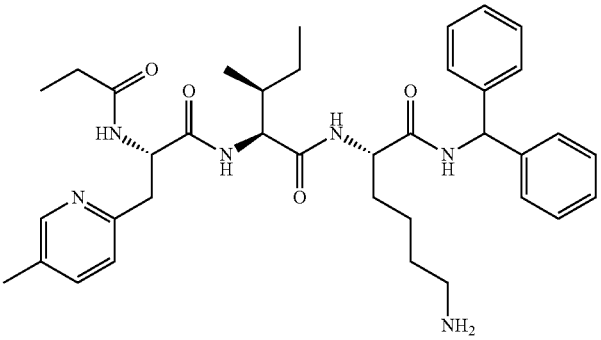 [SMILES: CCC(=O)N[C@@H](Cc1ccc(C)cn1)C(=O)N[C@H](C(=O)N[C@@H](CCCCN)C(=O)NC(c1ccccc1)c1ccccc1)[C@@H](C)CC] | >10 (μM) |

TABLE 1-continued
Chemical structures and binding affinities to DCN1 proteins
| ID | Number of Example | Chemical Structure | Binding affinity to DCN1 (IC50 (nM)) |
|---|---|---|---|
| ZBB-01-98 | 136 | 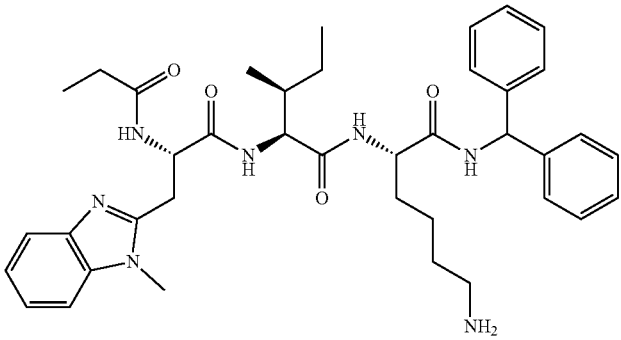 [SMILES: CCC(=O)N[C@@H](Cc1nc2ccccc2n1C)C(=O)N[C@H](C(=O)N[C@@H](CCCCN)C(=O)NC(c1ccccc1)c1ccccc1)[C@@H](C)CC] | >5 (µM) |
| DI-38 | 20 | 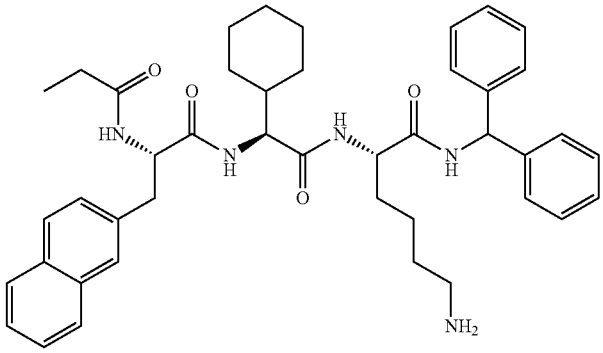 [SMILES: CCC(=O)N[C@@H](Cc1ccc2ccccc2c1)C(=O)N[C@H](C(=O)N[C@@H](CCCCN)C(=O)NC(c1ccccc1)c1ccccc1)C1CCCCC1] | 341 |
| DI-39 | 19 | 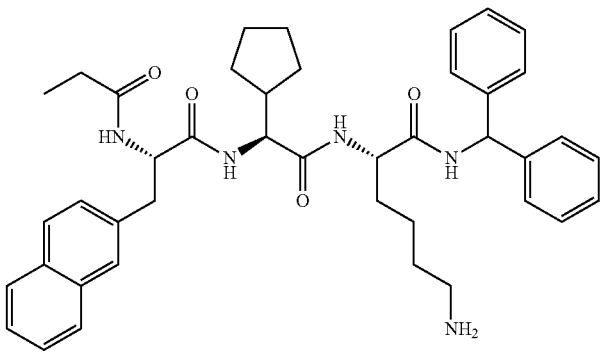 [SMILES: CCC(=O)N[C@@H](Cc1ccc2ccccc2c1)C(=O)N[C@H](C(=O)N[C@@H](CCCCN)C(=O)NC(c1ccccc1)c1ccccc1)C1CCCC1] | 270 |
| DI-40 | 22 | 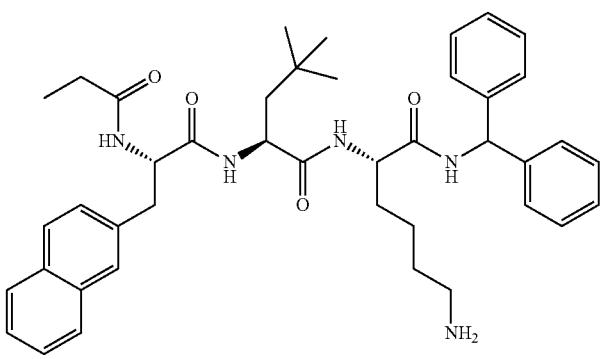 [SMILES: CCC(=O)N[C@@H](Cc1ccc2ccccc2c1)C(=O)N[C@@H](CC(C)(C)C)C(=O)N[C@@H](CCCCN)C(=O)NC(c1ccccc1)c1ccccc1] | 361 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-41 | 23 | 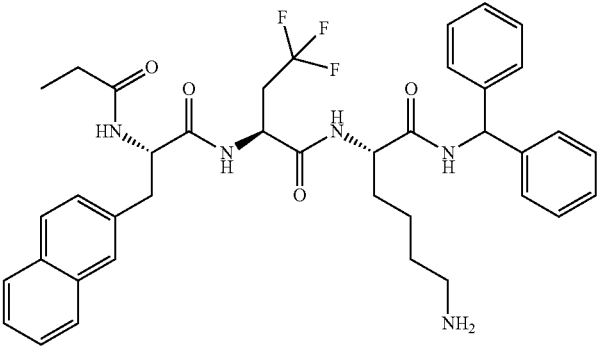 [SMILES: CCC(=O)N[C@@H](Cc1ccc2ccccc2c1)C(=O)N[C@@H](CC(F)(F)F)C(=O)N[C@@H](CCCCN)C(=O)NC(c1ccccc1)c1ccccc1] | >1 (µM) |
| DI-42 | 24 | 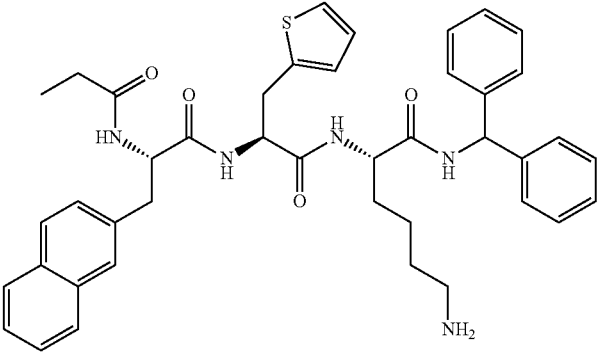 [SMILES: CCC(=O)N[C@@H](Cc1ccc2ccccc2c1)C(=O)N[C@@H](Cc1cccs1)C(=O)N[C@@H](CCCCN)C(=O)NC(c1ccccc1)c1ccccc1] | 967 |
| DI-43 | 21 | 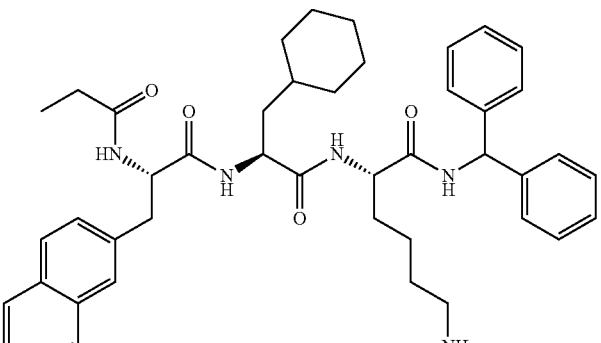 | 290 |
| DI-47 | 137 | 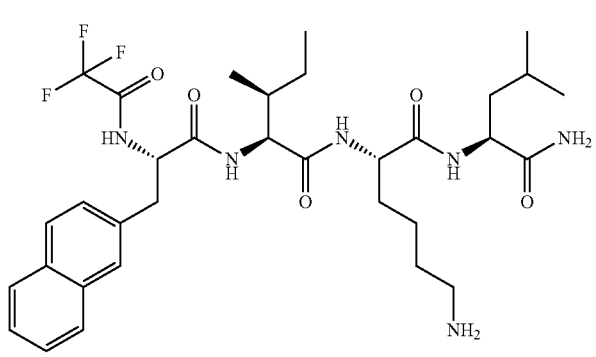 [SMILES: CC[C@H](C)[C@H](NC(=O)[C@H](Cc1ccc2ccccc2c1)NC(=O)C(F)(F)F)C(=O)N[C@@H](CCCCN)C(=O)N[C@@H](CC(C)C)C(N)=O] | precipitation |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-49 | 138 | 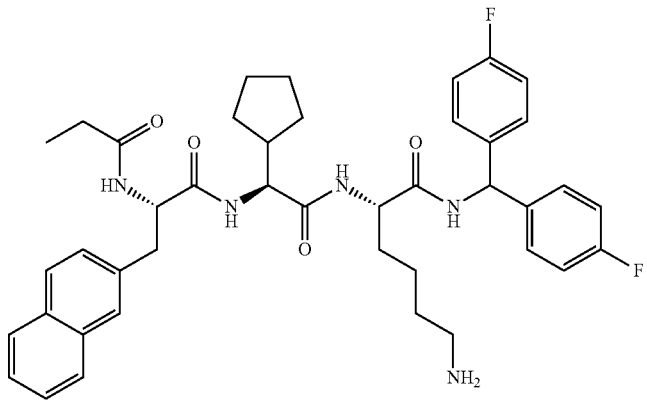 [SMILES: CCC(=O)N[C@@H](Cc1ccc2ccccc2c1)C(=O)N[C@H](C(=O)N[C@@H](CCCCN)C(=O)NC(c1ccc(F)cc1)c1ccc(F)cc1)C1CCCC1] | 1750 |
| DI-50 | 139 | 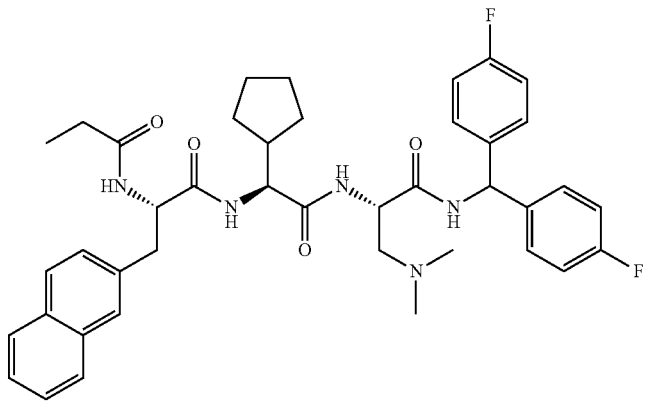 [SMILES: CCC(=O)N[C@@H](Cc1ccc2ccccc2c1)C(=O)N[C@H](C(=O)N[C@@H](CN(C)C)C(=O)NC(c1ccc(F)cc1)c1ccc(F)cc1)C1CCCC1] | >10 (μM) |
| DI-51 | 140 | 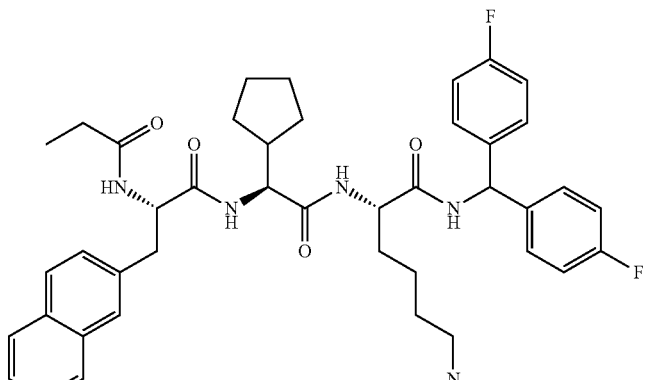 | 483 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-52 | 141 | 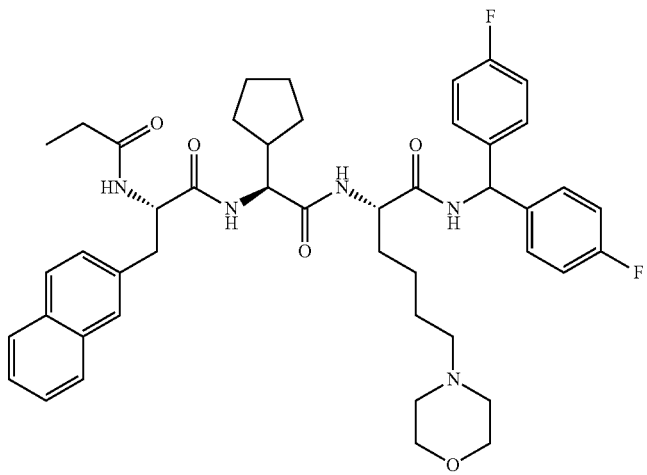 [SMILES: CCC(=O)N[C@@H](Cc1ccc2ccccc2c1)C(=O)N[C@H](C(=O)N[C@@H](CCCCN1CCOCC1)C(=O)NC(c1ccc(F)cc1)c1ccc(F)cc1)C1CCCC1] | 871 |
| DI-53 | 142 | 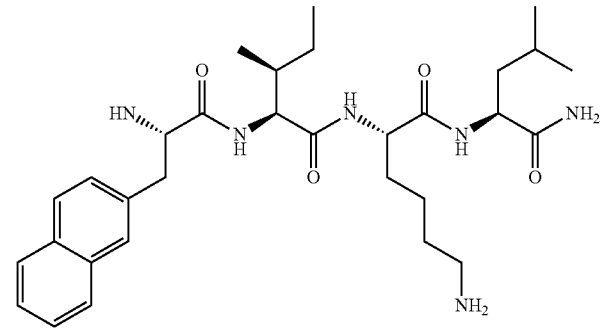 [SMILES: CC[C@H](C)[C@H](NC(=O)[C@@H](N)Cc1ccc2ccccc2c1)C(=O)N[C@@H](CCCCN)C(=O)N[C@@H](CC(C)C)C(N)=O] | >10 (μM) |
| DI-54 | 143 | 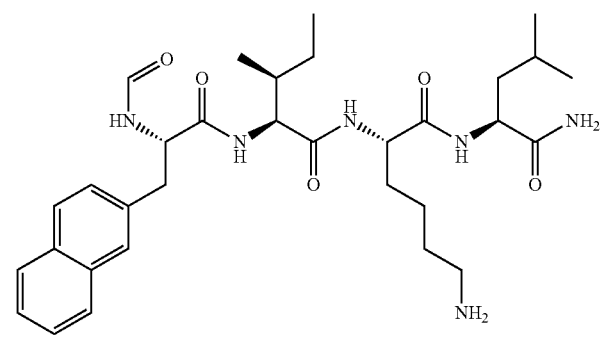 [SMILES: CC[C@H](C)[C@H](NC(=O)[C@H](Cc1ccc2ccccc2c1)NC=O)C(=O)N[C@@H](CCCCN)C(=O)N[C@@H](CC(C)C)C(N)=O] | >10 (μM) |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-55 | 144 | 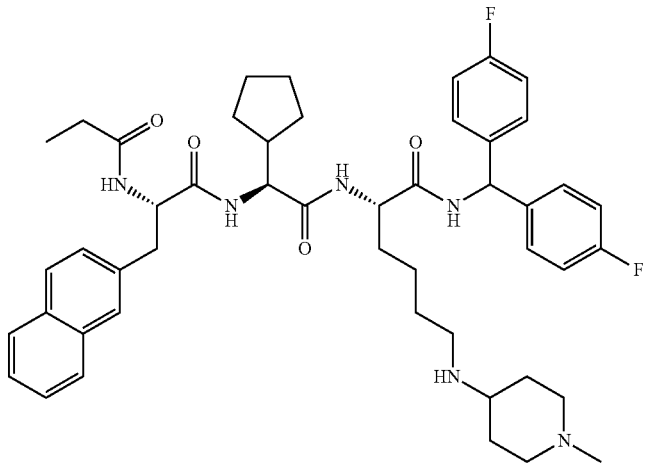 [SMILES: CCC(=O)N[C@@H](Cc1ccc2ccccc2c1)C(=O)N[C@H](C(=O)N[C@@H](CCCCNC1CCN(C)CC1)C(=O)NC(c1ccc(F)cc1)c1ccc(F)cc1)C1CCCC1] | 273 |
| DI-56 | 145 | 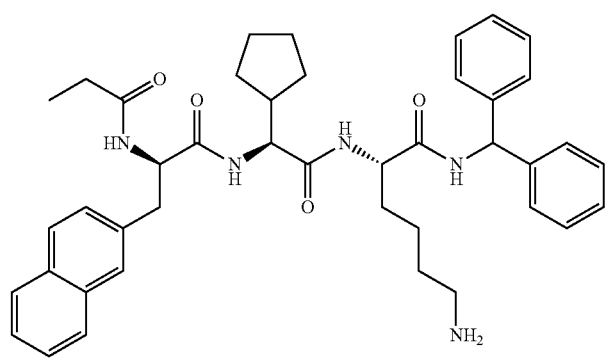 [SMILES: CCC(=O)N[C@H](Cc1ccc2ccccc2c1)C(=O)N[C@H](C(=O)N[C@@H](CCCCN)C(=O)NC(c1ccccc1)c1ccccc1)C1CCCC1] | >10 μM |
| DI-57 | 146 | 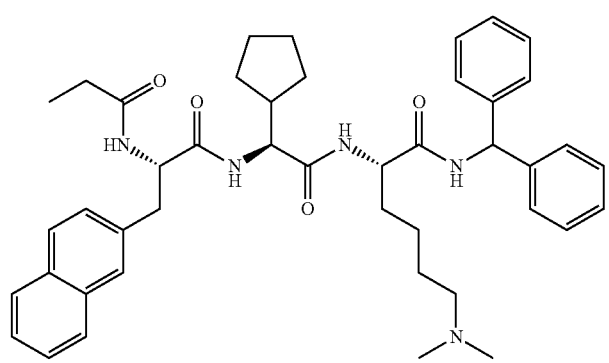 [SMILES: CCC(=O)N[C@@H](Cc1ccc2ccccc2c1)C(=O)N[C@H](C(=O)N[C@@H](CCCCN(C)C)C(=O)NC(c1ccccc1)c1ccccc1)C1CCCC1] | 464 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-58 | 147 | 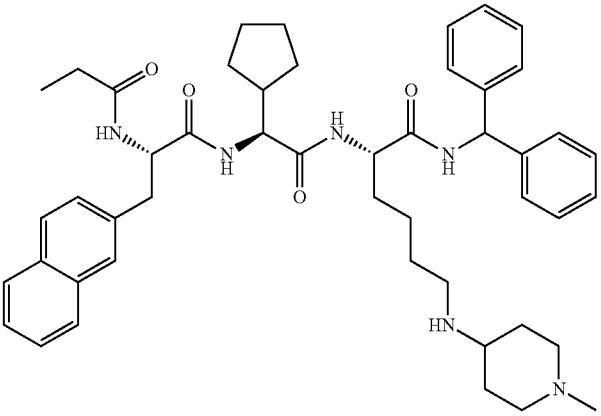 [SMILES: CCC(=O)N[C@@H](Cc1ccc2ccccc2c1)C(=O)N[C@H](C(=O)N[C@@H](CCCCNC1CCN(C)CC1)C(=O)NC(c1ccccc1)c1ccccc1)C1CCCC1] | 354 |
| DI-59 | 148 | 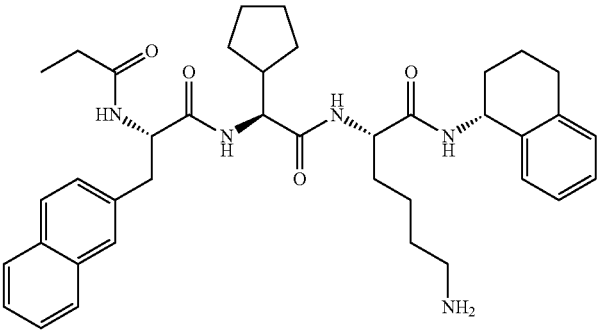 | 402 |
| DI-60 | 149 | 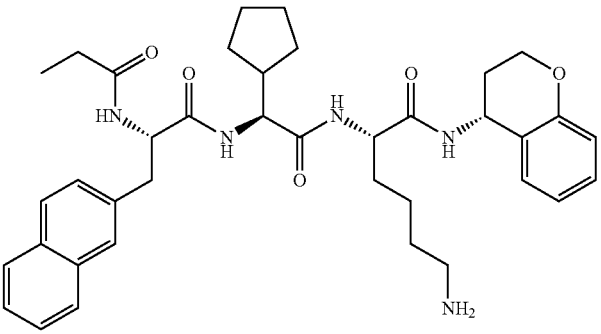 [SMILES: CCC(=O)N[C@@H](Cc1ccc2ccccc2c1)C(=O)N[C@H](C(=O)N[C@@H](CCCCN)C(=O)N[C@@H]1CCCc2ccccc21)C1CCCC1] | 378 |
| DI-61 | 150 | 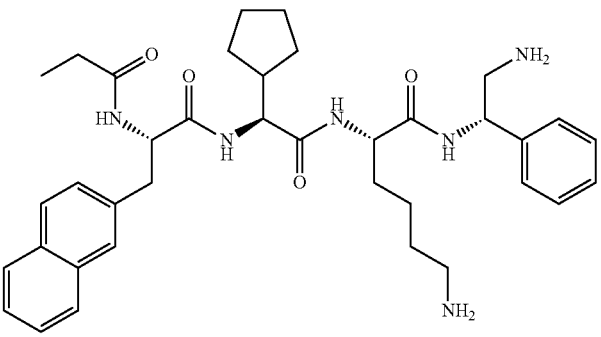 [SMILES: CCC(=O)N[C@@H](Cc1ccc2ccccc2c1)C(=O)N[C@H](C(=O)N[C@@H](CCCCN)C(=O)N[C@H](CN)c1ccccc1)C1CCCC1] | 1998 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-62 | 151 | 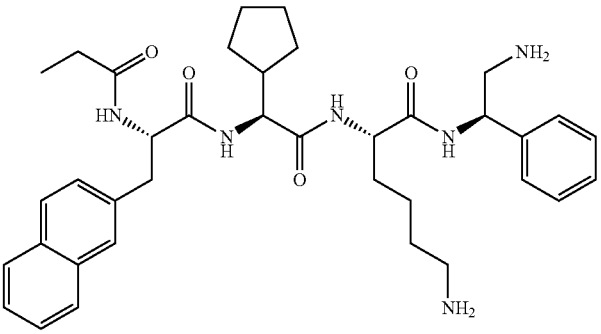 [SMILES: CCC(=O)N[C@@H](Cc1ccc2ccccc2c1)C(=O)N[C@H](C(=O)N[C@@H](CCCCN)C(=O)N[C@@H](CN)c1ccccc1)C1CCCC1] | >10 (μM) |
| DI-63 | 27 | 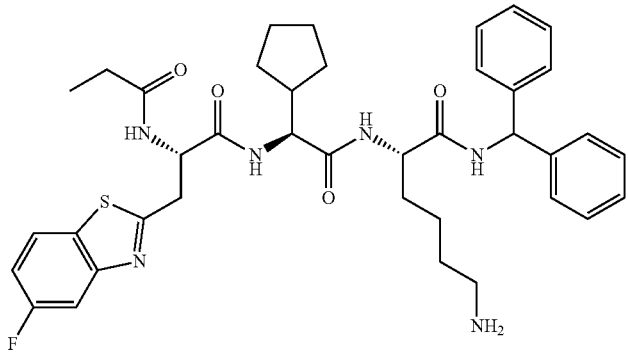 [SMILES: CCC(=O)N[C@@H](Cc1nc2cc(F)ccc2s1)C(=O)N[C@H](C(=O)N[C@@H](CCCCN)C(=O)NC(c1ccccc1)c1ccccc1)C1CCCC1] | 1197 |
| DI-64 | 30 | 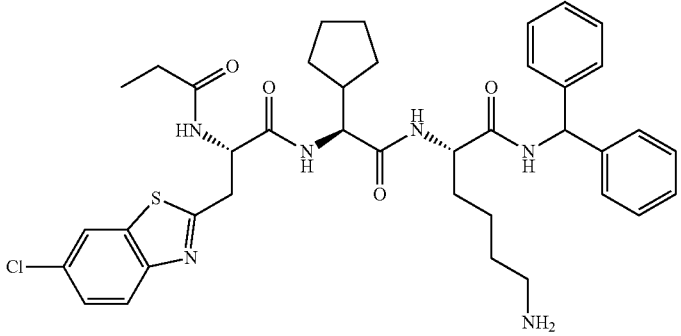 [SMILES: CCC(=O)N[C@@H](Cc1nc2ccc(Cl)cc2s1)C(=O)N[C@H](C(=O)N[C@@H](CCCCN)C(=O)NC(c1ccccc1)c1ccccc1)C1CCCC1] | 193 |
| ZBB-01-74-1 | 152 | 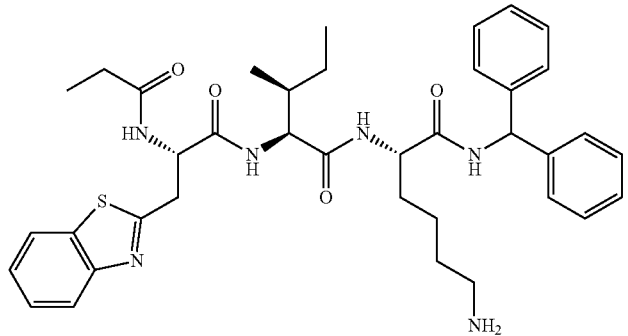 [SMILES: CCC(=O)N[C@@H](Cc1nc2ccccc2o1)C(=O)N[C@H](C(=O)N[C@@H](CCCCN)C(=O)NC(c1ccccc1)c1ccccc1)[C@@H](C)CC] | 376 |

TABLE 1-continued

Chemical structures and binding affinities to DCN1 proteins

| ID | Number of Example | Chemical Structure | Binding affinity to DCN1 (IC50 (nM)) |
|---|---|---|---|
| ZBB-01-160 | 153 | 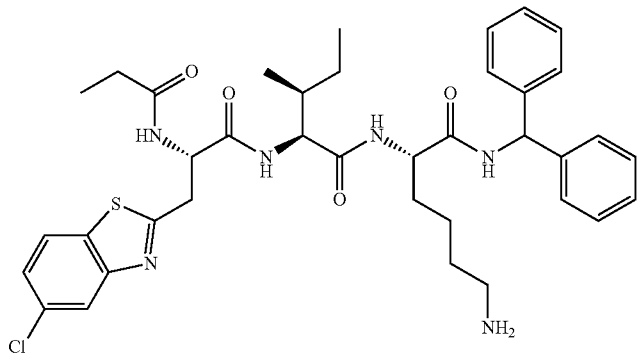 [SMILES: CCC(=O)N[C@@H](Cc1nc2cc(Cl)ccc2o1)C(=O)N[C@H](C(=O)N[C@@H](CCCCN)C(=O)NC(c1ccccc1)c1ccccc1)[C@@H](C)CC] | 1898 |
| ZBB-01-220 | 154 | 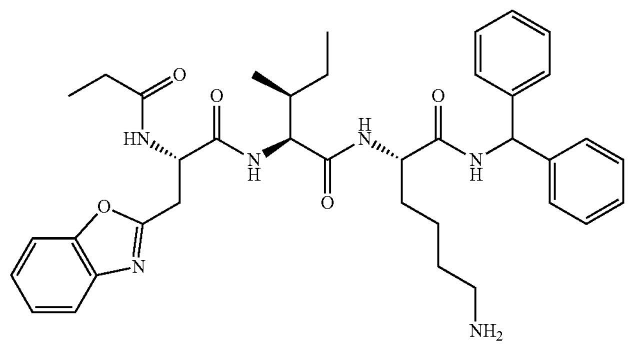 | 981 |
| ZBB-01-221 | 155 | 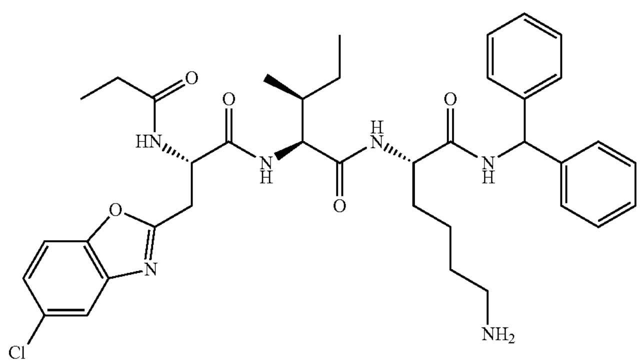 | 1196 |
| ZBB-01-222 | 156 | 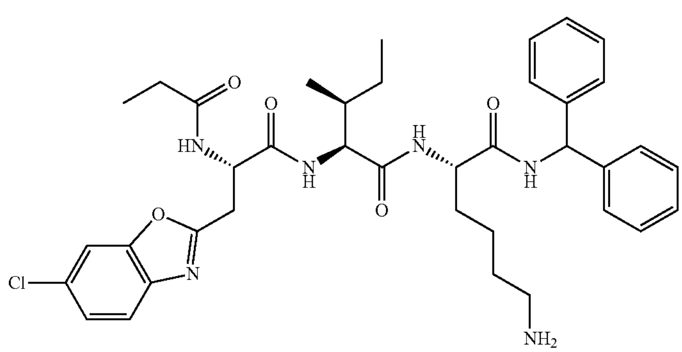 [SMILES: CCC(=O)N[C@@H](Cc1nc2ccc(Cl)cc2o1)C(=O)N[C@H](C(=O)N[C@@H](CCCCN)C(=O)NC(c1ccccc1)c1ccccc1)[C@@H](C)CC] | 194 |

TABLE 1-continued
Chemical structures and binding affinities to DCN1 proteins
| ID | Number of Example | Chemical Structure | Binding affinity to DCN1 (IC50 (nM)) |
|---|---|---|---|
| ZBB-01-258 | 157 | 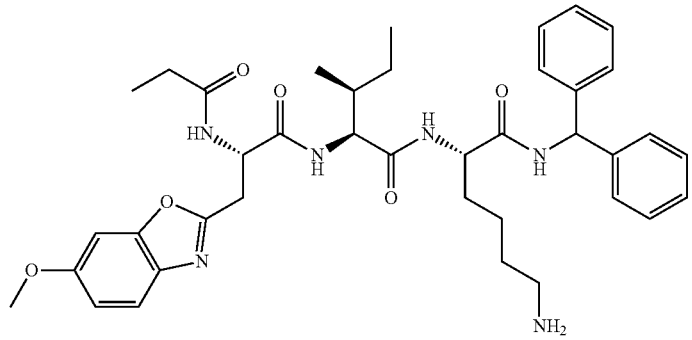 [SMILES: CCC(=O)N[C@@H](Cc1nc2ccc(OC)cc2o1)C(=O)N[C@H](C(=O)N[C@@H](CCCCN)C(=O)NC(c1ccccc1)c1ccccc1)[C@@H](C)CC] | 265 |
| DI-65 | 29 | 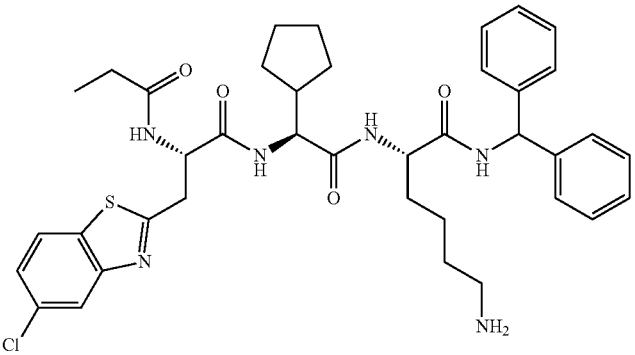 [SMILES: CCC(=O)N[C@@H](Cc1nc2cc(Cl)ccc2s1)C(=O)N[C@H](C(=O)N[C@@H](CCCCN)C(=O)NC(c1ccccc1)c1ccccc1)C1CCCC1] | 572 |
| DI-66 | 26 | 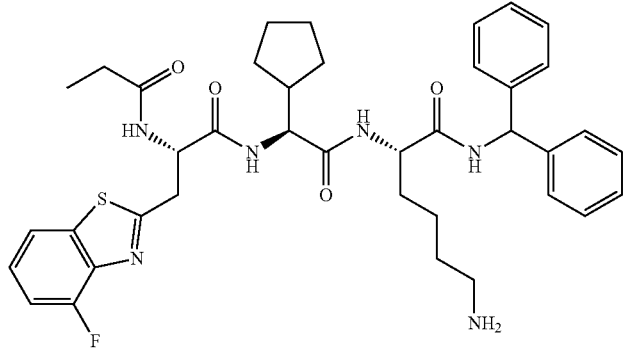 [SMILES: CCC(=O)N[C@@H](Cc1nc2c(F)cccc2s1)C(=O)N[C@H](C(=O)N[C@@H](CCCCN)C(=O)NC(c1ccccc1)c1ccccc1)C1CCCC1] | >3 (μM) |
| DI-67 | 28 | 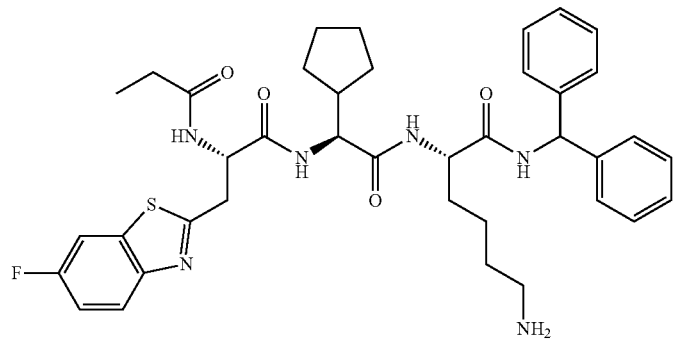 [SMILES: CCC(=O)N[C@@H](Cc1nc2ccc(F)cc2s1)C(=O)N[C@H](C(=O)N[C@@H](CCCCN)C(=O)NC(c1ccccc1)c1ccccc1)C1CCCC1] | 413 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-68 | 25 | 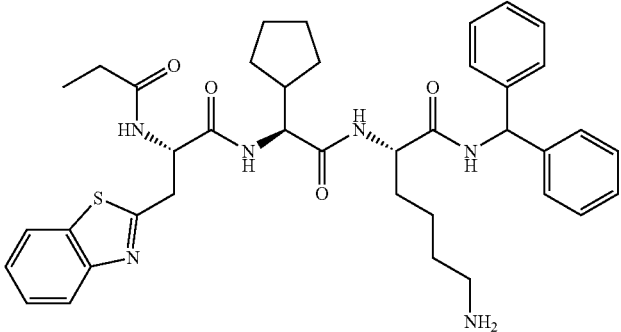 [SMILES: CCC(=O)N[C@@H](Cc1nc2ccccc2s1)C(=O)N[C@H](C(=O)N[C@@H](CCCCN)C(=O)NC(c1ccccc1)c1ccccc1)C1CCCC1] | 397 |
| DI-69 | 158 | 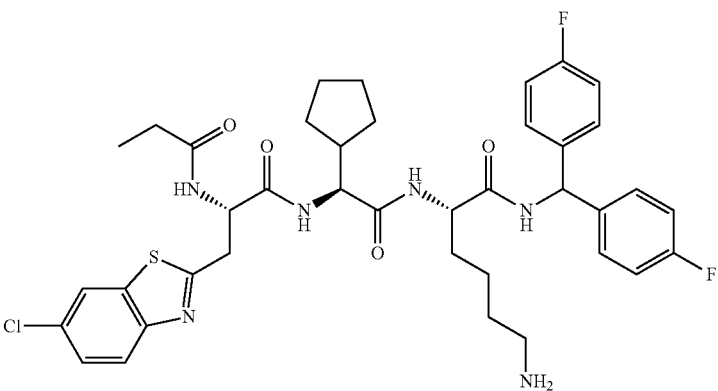 [SMILES: CCC(=O)N[C@@H](Cc1nc2ccc(Cl)cc2s1)C(=O)N[C@H](C(=O)N[C@@H](CCCCN)C(=O)NC(c1ccc(F)cc1)c1ccc(F)cc1)C1CCCC1] | 307 |
| DI-70 | 33 | 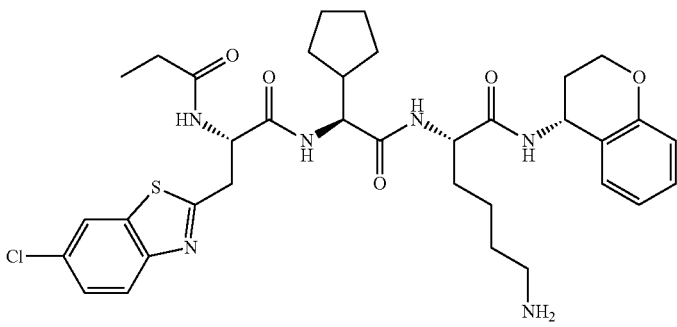 | 103 |
| DI-71 | 32 | 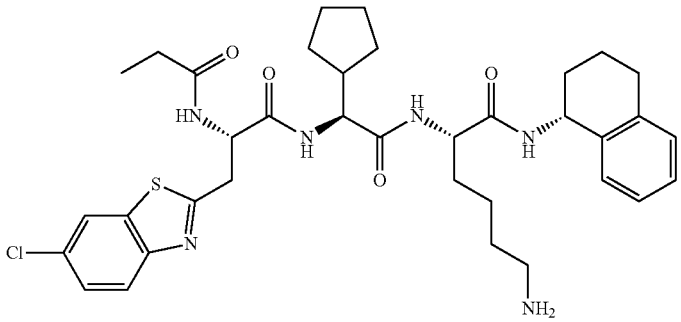 [SMILES: CCC(=O)N[C@@H](Cc1nc2ccc(Cl)cc2s1)C(=O)N[C@H](C(=O)N[C@@H](CCCCN)C(=O)N[C@@H]1CCOc2ccccc21)C1CCCC1] | 157 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-72-1 | 159 | 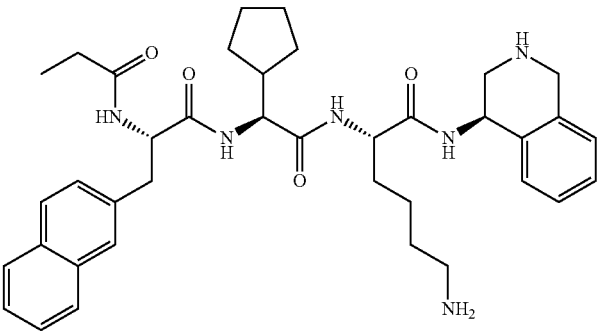 [SMILES: CCC(=O)N[C@@H](Cc1ccc2ccccc2c1)C(=O)N[C@H](C(=O)N[C@@H](CCCCN)C(=O)N[C@H]1CNCc2ccccc21)C1CCCC1] | >3 (µM) |
| DI-72-2 | 160 | 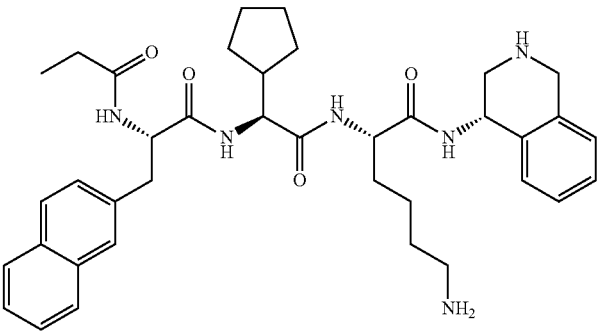 [SMILES: CCC(=O)N[C@@H](Cc1ccc2ccccc2c1)C(=O)N[C@H](C(=O)N[C@@H](CCCCN)C(=O)N[C@@H]1CNCc2ccccc21)C1CCCC1] | 457 |
| DI-73-2 | 161 | 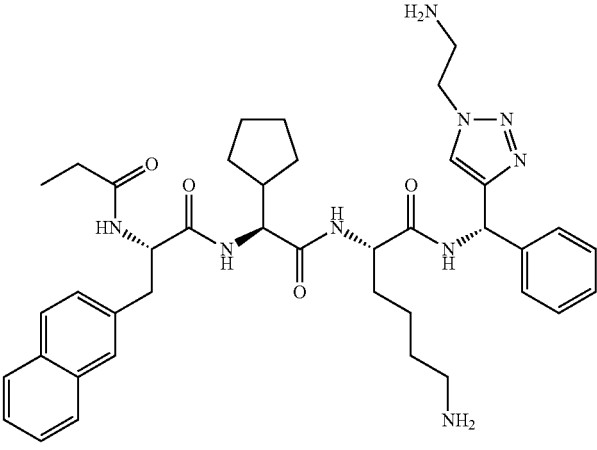 [SMILES: CCC(=O)N[C@@H](Cc1ccc2ccccc2c1)C(=O)N[C@H](C(=O)N[C@@H](CCCCN)C(=O)N[C@@H](c1ccccc1)c1cn(CCN)nn1)C1CCCC1] | 943 |
| DI-75-1 | 39 | 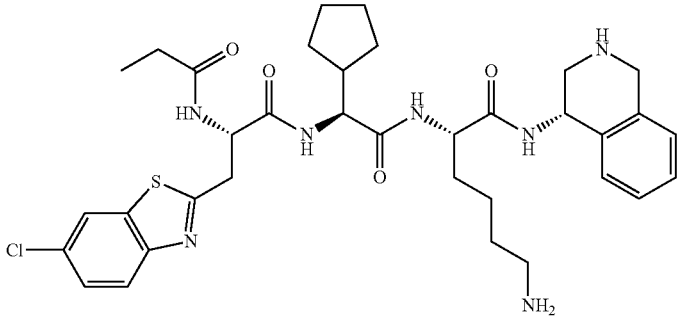 [SMILES: CCC(=O)N[C@@H](Cc1nc2ccc(Cl)cc2s1)C(=O)N[C@H](C(=O)N[C@@H](CCCCN)C(=O)N[C@@H]1CNCc2ccccc21)C1CCCC1] | 173 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-75-2 | 162 | 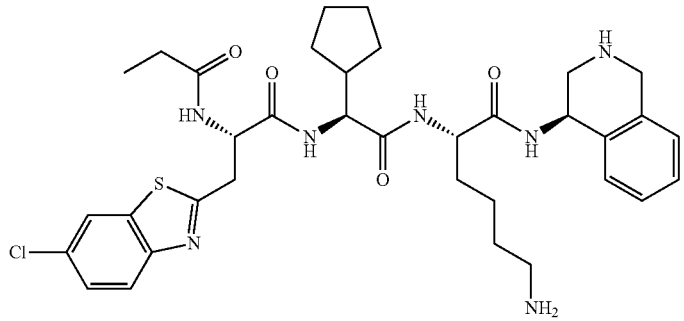 [SMILES: CCC(=O)N[C@@H](Cc1nc2ccc(Cl)cc2s1)C(=O)N[C@H](C(=O)N[C@@H](CCCCN)C(=O)N[C@H]1CNCc2ccccc21)C1CCCC1] | 797 |
| DI-76 | 40 | 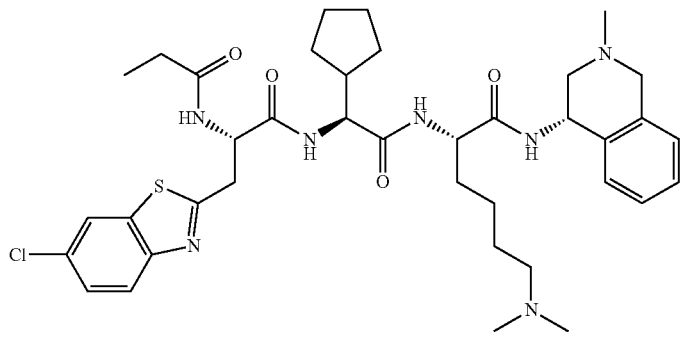 [SMILES: CCC(=O)N[C@@H](Cc1nc2ccc(Cl)cc2s1)C(=O)N[C@H](C(=O)N[C@@H](CCCCN(C)C)C(=O)N[C@@H]1CN(C)Cc2ccccc21)C1CCCC1] | 163 |
| DI-77 | 163 | 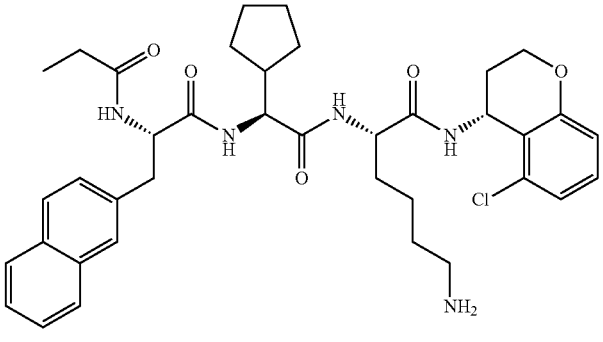 [SMILES: CCC(=O)N[C@@H](Cc1ccc2ccccc2c1)C(=O)N[C@H](C(=O)N[C@@H](CCCCN)C(=O)N[C@@H]1CCOc2cccc(Cl)c21)C1CCCC1] | 103 |
| DI-78 | 164 | 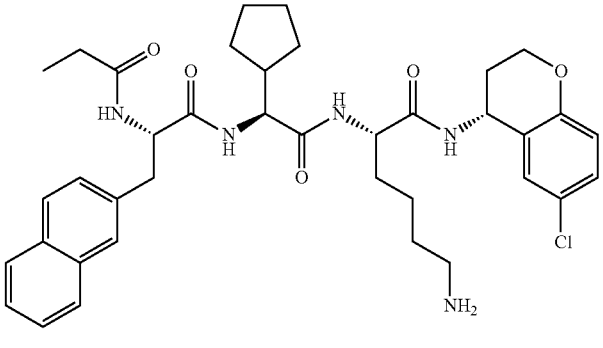 [SMILES: CCC(=O)N[C@@H](Cc1ccc2ccccc2c1)C(=O)N[C@H](C(=O)N[C@@H](CCCCN)C(=O)N[C@@H]1CCOc2ccc(Cl)cc21)C1CCCC1] | 394 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-79 | 165 | 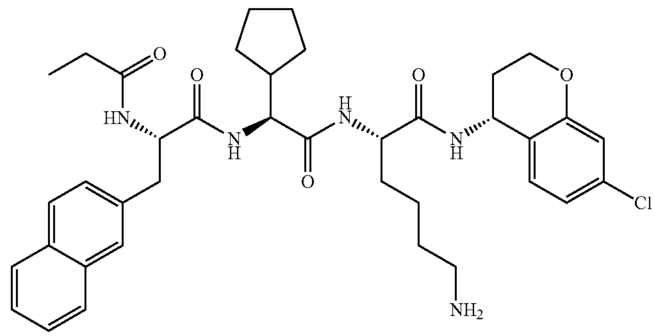 [SMILES: CCC(=O)N[C@@H](Cc1ccc2ccccc2c1)C(=O)N[C@H](C(=O)N[C@@H](CCCCN)C(=O)N[C@@H]1CCOc2cc(Cl)ccc21)C1CCCC1] | 122 |
| DI-80 | 166 | 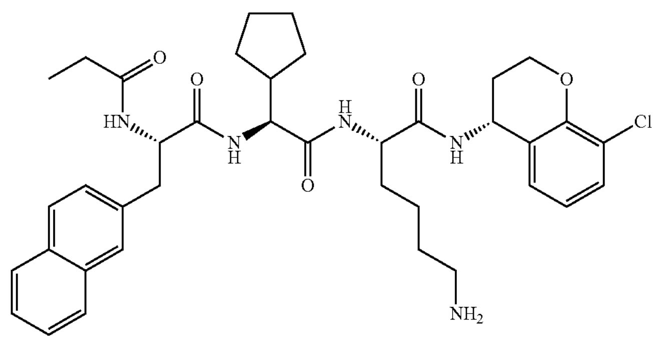 [SMILES: CCC(=O)N[C@@H](Cc1ccc2ccccc2c1)C(=O)N[C@H](C(=O)N[C@@H](CCCCN)C(=O)N[C@@H]1CCOc2c(Cl)cccc21)C1CCCC1] | 193 |
| DI-81 | 167 | 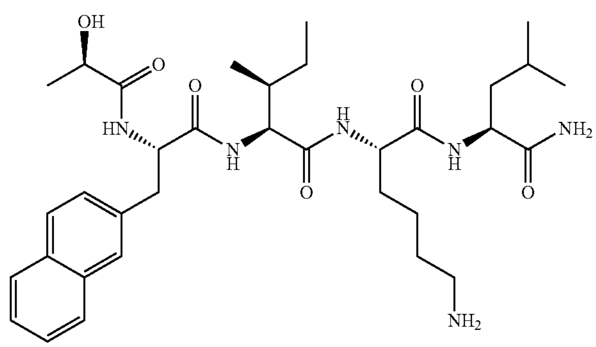 [SMILES: CC[C@H](C)[C@H](NC(=O)[C@H](Cc1ccc2ccccc2c1)NC(=O)[C@@H](C)O)C(=O)N[C@@H](CCCCN)C(=O)N[C@@H](CC(C)C)C(N)=O] | >10 μM |
| DI-82 | 168 | 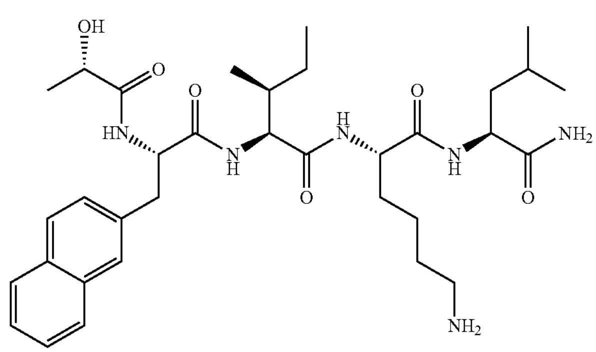 [SMILES: CC[C@H](C)[C@H](NC(=O)[C@H](Cc1ccc2ccccc2c1)NC(=O)[C@H](C)O)C(=O)N[C@@H](CCCCN)C(=O)N[C@@H](CC(C)C)C(N)=O] | >10 μM |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-83 | 169 | 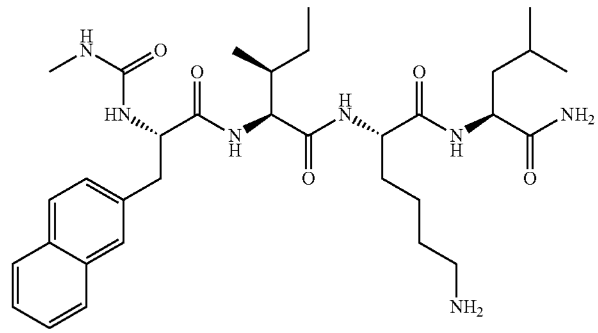 [SMILES: CC[C@H](C)[C@H](NC(=O)[C@H](Cc1ccc2ccccc2c1)NC(=O)NC)C(=O)N[C@@H](CCCCN)C(=O)N[C@@H](CC(C)C)C(N)=O] | >10 (µM) |
| DI-84 | 170 | 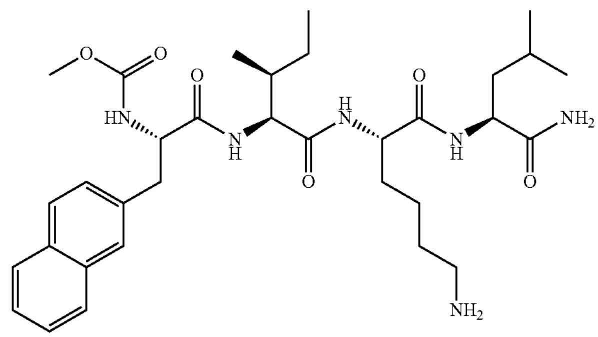 [SMILES: CC[C@H](C)[C@H](NC(=O)[C@H](Cc1ccc2ccccc2c1)NC(=O)OC)C(=O)N[C@@H](CCCCN)C(=O)N[C@@H](CC(C)C)C(N)=O] | >10 µM |
| DI-85 | 171 | | 168 |
| DI-85 | 172 | | 121 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-87 | 173 | 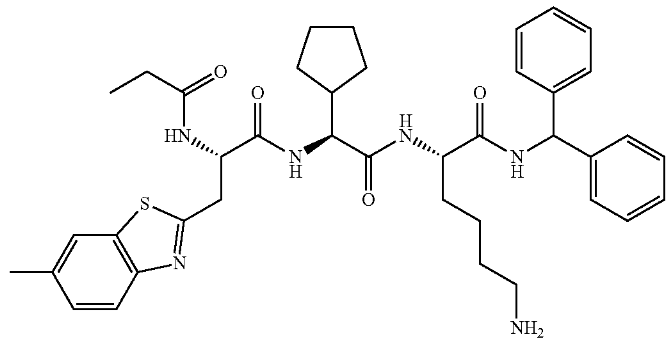 [SMILES: CCC(=O)N[C@@H](Cc1nc2ccc(C)cc2s1)C(=O)N[C@H](C(=O)N[C@@H](CCCCN)C(=O)NC(c1ccccc1)c1ccccc1)C1CCCC1] | 58.1 |
| DI-88 | 174 | 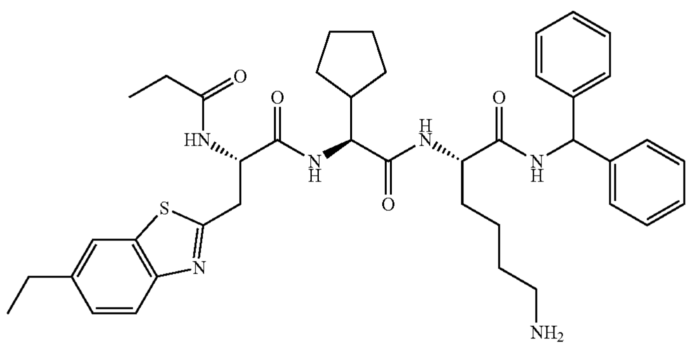 [SMILES: CCC(=O)N[C@@H](Cc1nc2ccc(CC)cc2s1)C(=O)N[C@H](C(=O)N[C@@H](CCCCN)C(=O)NC(c1ccccc1)c1ccccc1)C1CCCC1] | 77.5 |
| DI-90 | 31 | 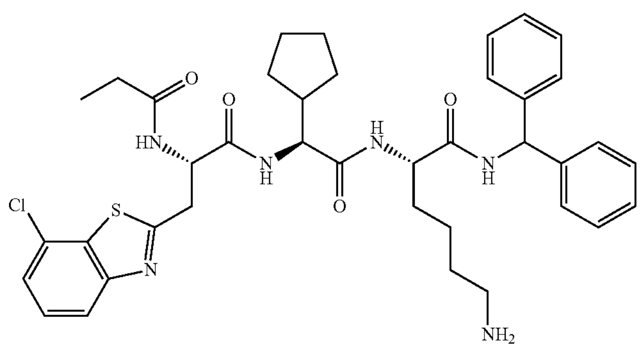 [SMILES: CCC(=O)N[C@@H](Cc1nc2cccc(Cl)c2s1)C(=O)N[C@H](C(=O)N[C@@H](CCCCN)C(=O)NC(c1ccccc1)c1ccccc1)C1CCCC1] | 137 |
| DI-91 | 175 | 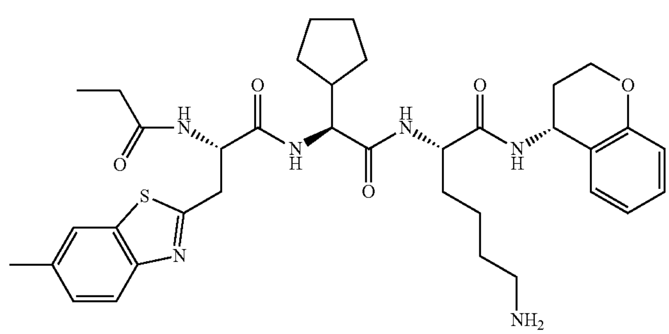 [SMILES: CCC(=O)N[C@@H](Cc1nc2ccc(C)cc2s1)C(=O)N[C@H](C(=O)N[C@@H](CCCCN)C(=O)N[C@@H]1CCOc2ccccc21)C1CCCC1] | 90.6 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-92 | 176 | 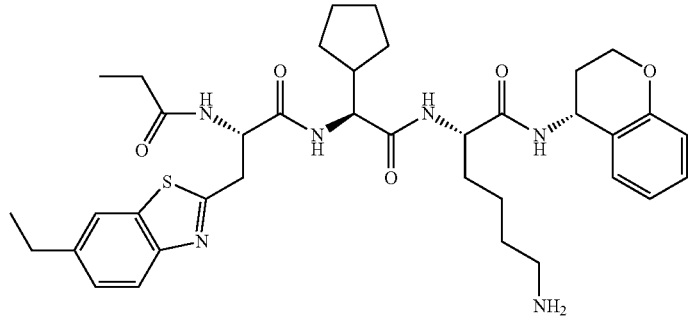 [SMILES: CCC(=O)N[C@@H](Cc1nc2ccc(CC)cc2s1)C(=O)N[C@H](C(=O)N[C@@H](CCCCN)C(=O)N[C@@H]1CCOc2ccccc21)C1CCCC1] | 79.0 |
| DI-93 | 11 | 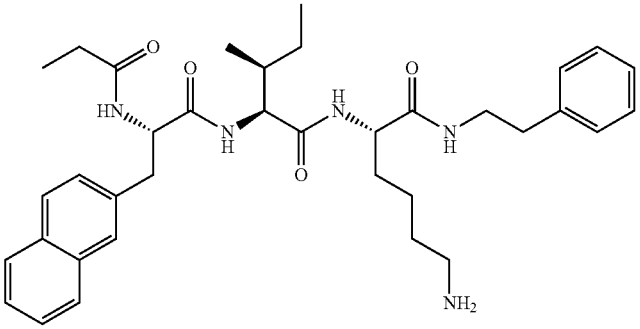 [SMILES: CCC(=O)N[C@@H](Cc1ccc2ccccc2c1)C(=O)N[C@H](C(=O)N[C@@H](CCCCN)C(=O)NCCc1ccccc1)[C@@H](C)CC] | >10 (µM) |
| DI-94 | 177 | 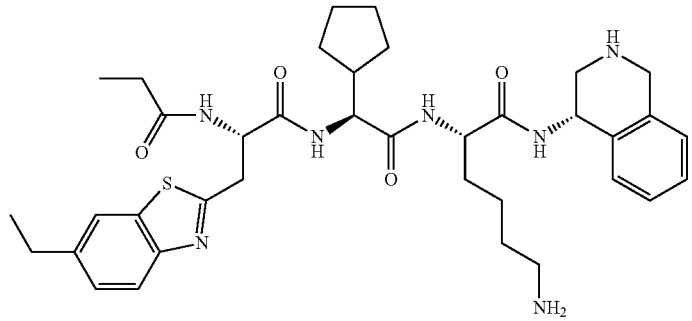 [SMILES: CCC(=O)N[C@@H](Cc1nc2ccc(CC)cc2s1)C(=O)N[C@H](C(=O)N[C@@H](CCCCN)C(=O)N[C@@H]1CNCc2ccccc21)C1CCCC1] | 79.0 |
| DI-96 | 178 | 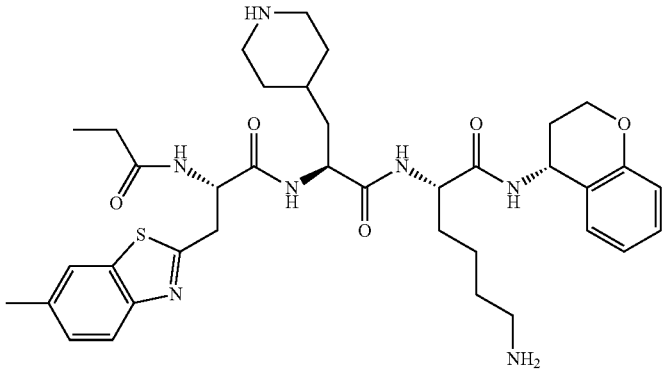 [SMILES: CCC(=O)N[C@@H](Cc1nc2ccc(C)cc2s1)C(=O)N[C@@H](CC1CCNCC1)C(=O)N[C@@H](CCCCN)C(=O)N[C@@H]1CCOc2ccccc21] | 596 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-97 | 179 | 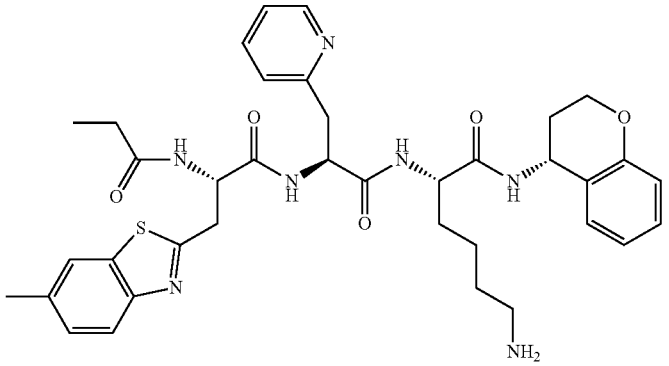 [SMILES: CCC(=O)N[C@@H](Cc1nc2ccc(C)cc2s1)C(=O)N[C@@H](Cc1ccccn1)C(=O)N[C@@H](CCCCN)C(=O)N[C@@H]1CCOc2ccccc21] | 133 |
| DI-98 | 180 | 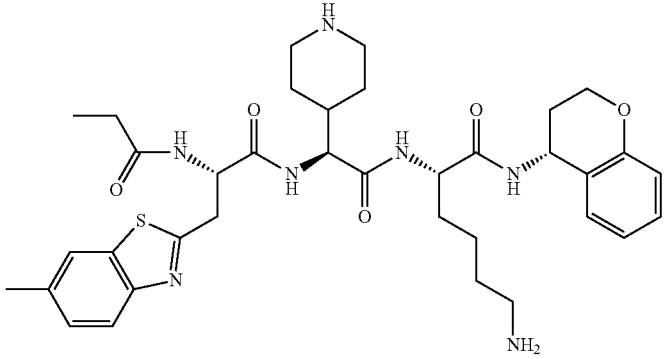 [SMILES: CCC(=O)N[C@@H](Cc1nc2ccc(C)cc2s1)C(=O)N[C@H](C(=O)N[C@@H](CCCCN)C(=O)N[C@@H]1CCOc2ccccc21)C1CCNCC1] | >1 (μM) |
| DI-99 | 181 | 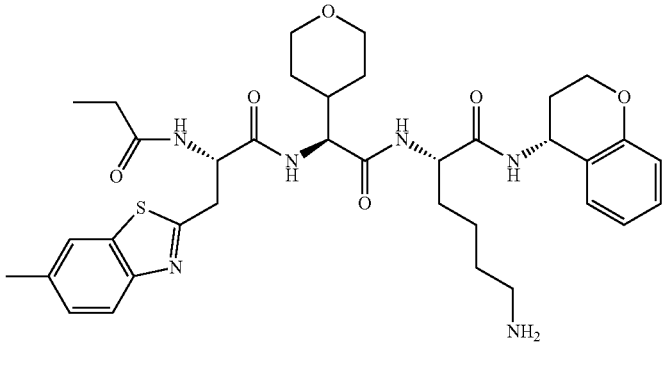 | 176 |
| DI-100 | 182 | 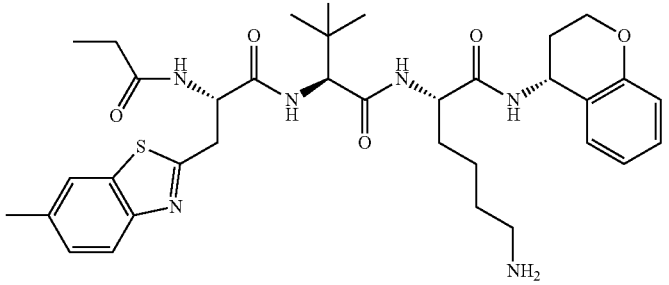 | 375 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-401 | 183 | 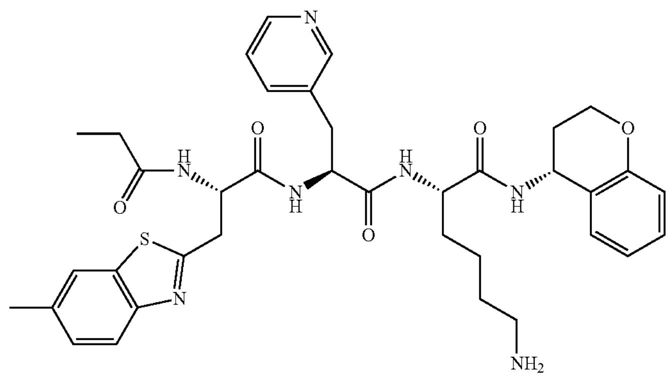 [SMILES: CCC(=O)N[C@@H](Cc1nc2ccc(C)cc2s1)C(=O)N[C@@H](Cc1cccnc1)C(=O)N[C@@H](CCCCN)C(=O)N[C@@H]1CCOc2ccccc21] | 165 |
| DI-402 | 184 | 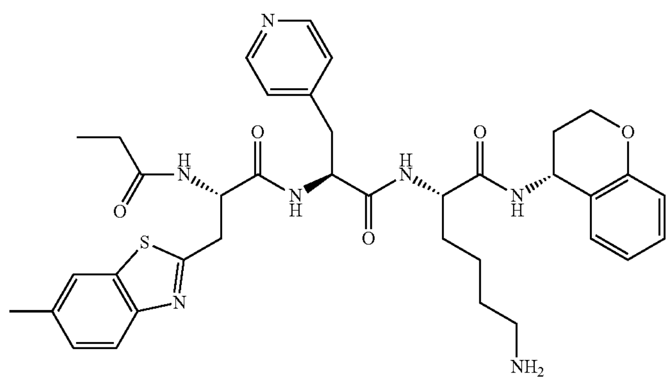 [SMILES: CCC(=O)N[C@@H](Cc1nc2ccc(C)cc2s1)C(=O)N[C@@H](Cc1ccncc1)C(=O)N[C@@H](CCCCN)C(=O)N[C@@H]1CCOc2ccccc21] | 149 |
| DI-403 | 185 | 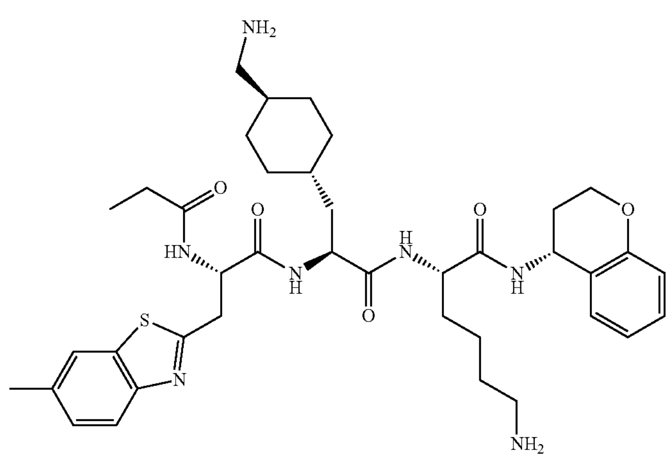 [SMILES: CCC(=O)N[C@@H](Cc1nc2ccc(C)cc2s1)C(=O)N[C@@H](C[C@H]1CC[C@H](CN)CC1)C(=O)N[C@@H](CCCCN)C(=O)N[C@@H]1CCOc2ccccc21] | 111 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-404 | 37 | 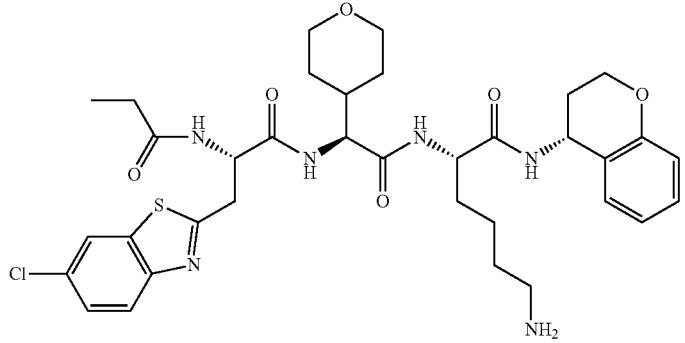 | 49.0 |
| DI-405 | 186 | 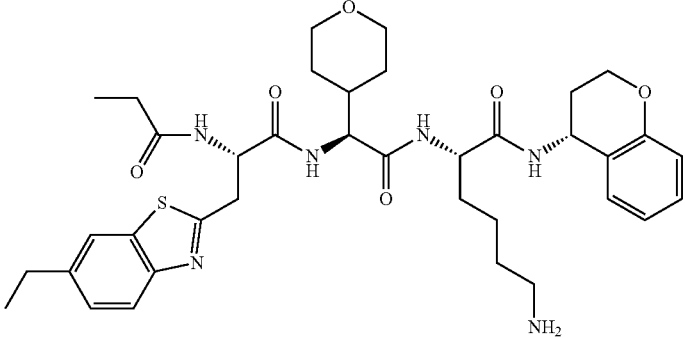 [SMILES: CCC(=O)N[C@@H](Cc1nc2ccc(CC)cc2s1)C(=O)N[C@H](C(=O)N[C@@H](CCCCN)C(=O)N[C@@H]1CCOc2ccccc21)C1CCOCC1] | 169 |
| Di-406 | 187 | 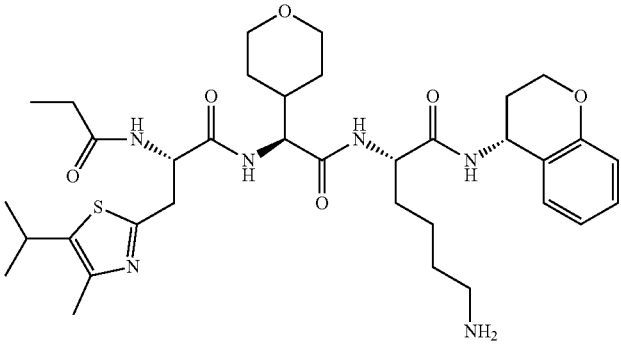 [SMILES: CCC(=O)N[C@@H](Cc1nc(C)c(C(C)C)s1)C(=O)N[C@H](C(=O)N[C@@H](CCCCN)C(=O)N[C@@H]1CCOc2ccccc21)C1CCOCC1] | 886 |
| DI-407 | 188 | 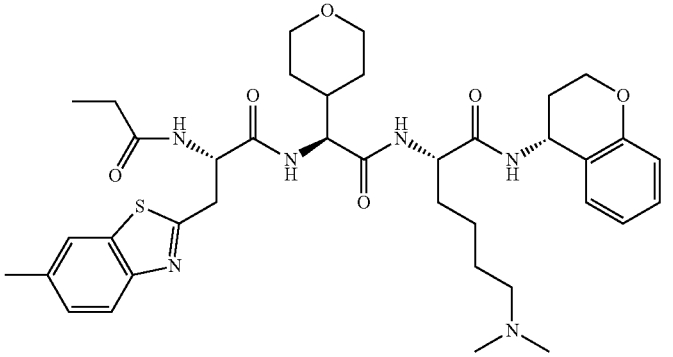 [SMILES: CCC(=O)N[C@@H](Cc1nc2ccc(C)cc2s1)C(=O)N[C@H](C(=O)N[C@@H](CCCCN(C)C)C(=O)N[C@@H]1CCOc2ccccc21)C1CCOCC1] | 156 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-408 | 189 | 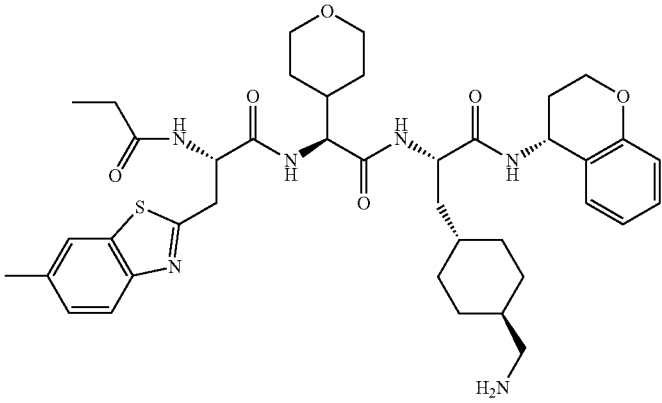 [SMILES: CCC(=O)N[C@@H](Cc1nc2ccc(C)cc2s1)C(=O)N[C@H](C(=O)N[C@@H](C[C@H]1CC[C@H](CN)CC1)C(=O)N[C@@H]1CCOc2ccccc21)C1CCOCC1] | 230 |
| DI-409 | 190 | 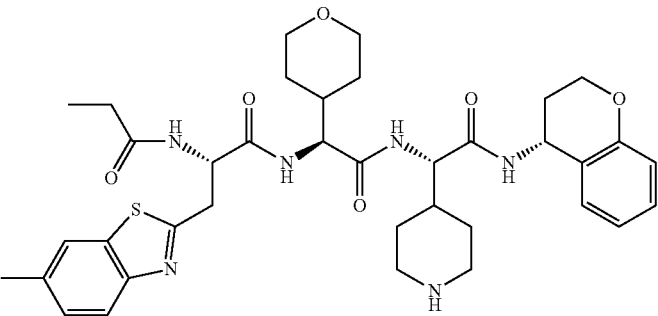 [SMILES: CCC(=O)N[C@@H](Cc1nc2ccc(C)cc2s1)C(=O)N[C@H](C(=O)N[C@H](C(=O)N[C@@H]1CCOc2ccccc21)C1CCNCC1)C1CCOCC1] | 412 |
| DI-410 | 191 | 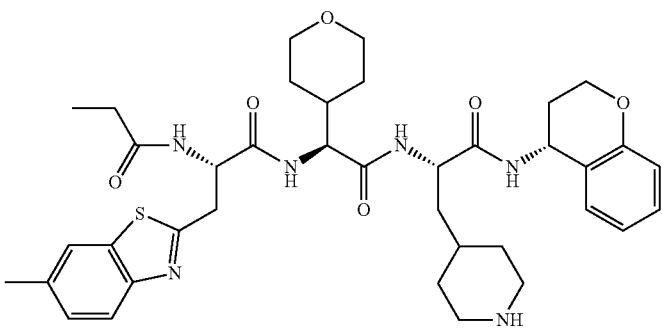 [SMILES: CCC(=O)N[C@@H](Cc1nc2ccc(C)cc2s1)C(=O)N[C@H](C(=O)N[C@@H](CC1CCNCC1)C(=O)N[C@@H]1CCOc2ccccc21)C1CCOCC1] | 187 |
| DI-411 | 38 | 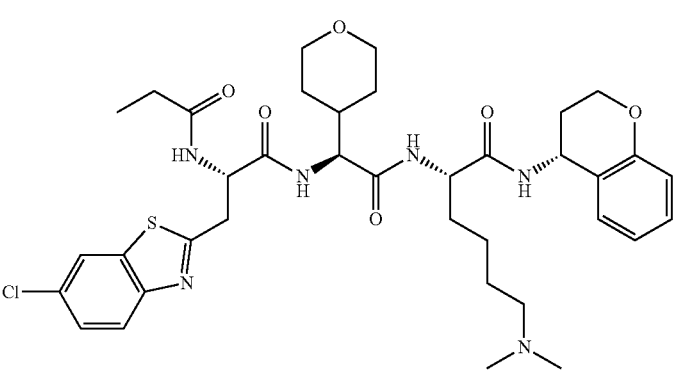 [SMILES: CCC(=O)N[C@@H](Cc1nc2ccc(Cl)cc2s1)C(=O)N[C@H](C(=O)N[C@@H](CCCCN(C)C)C(=O)N[C@@H]1CCOc2ccccc21)C1CCOCC1] | 123 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-412 | 192 | 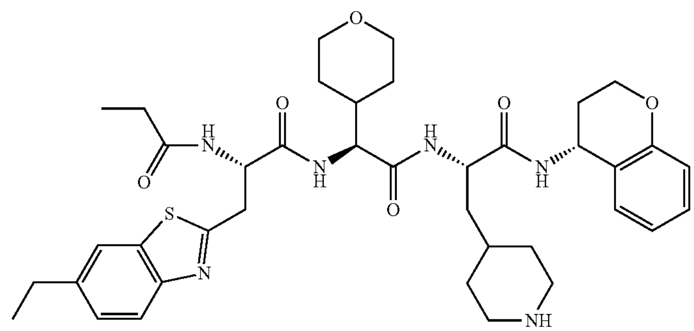 [SMILES: CCC(=O)N[C@@H](Cc1nc2ccc(CC)cc2s1)C(=O)N[C@H](C(=O)N[C@@H](CC1CCNCC1)C(=O)N[C@@H]1CCOc2ccccc21)C1CCOCC1] | 171 |
| DI-413 | 41 | 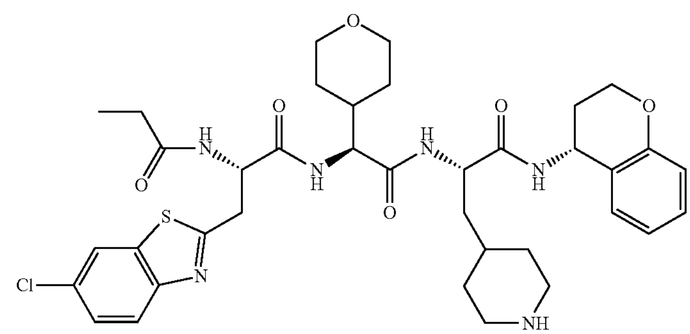 [SMILES: CCC(=O)N[C@@H](Cc1nc2ccc(Cl)cc2s1)C(=O)N[C@H](C(=O)N[C@@H](CC1CCNCC1)C(=O)N[C@@H]1CCOc2ccccc21)C1CCOCC1] | 222 |
| DI-414 | 193 | 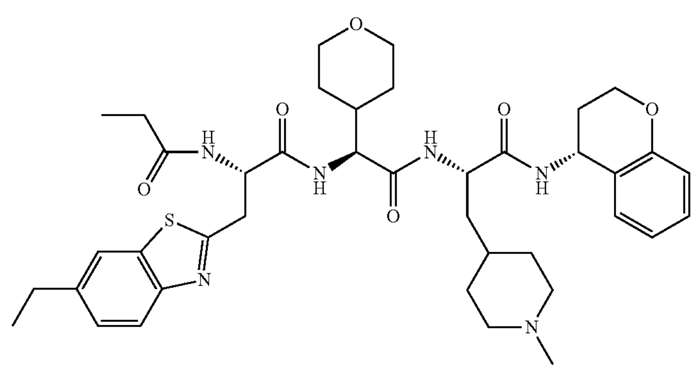 [SMILES: CCC(=O)N[C@@H](Cc1nc2ccc(CC)cc2s1)C(=O)N[C@H](C(=O)N[C@@H](CC1CCN(C)CC1)C(=O)N[C@@H]1CCOc2ccccc21)C1CCOCC1] | 171 |
| DI-415 | 42 | 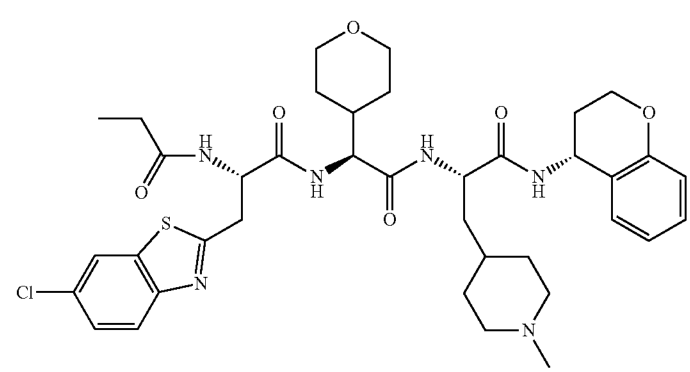 [SMILES: CCC(=O)N[C@@H](Cc1nc2ccc(Cl)cc2s1)C(=O)N[C@H](C(=O)N[C@@H](CC1CCN(C)CC1)C(=O)N[C@@H]1CCOc2ccccc21)C1CCOCC1] | 299 |

TABLE 1-continued

Chemical structures and binding affinities to DCN1 proteins

| ID | Number of Example | Chemical Structure | Binding affinity to DCN1 (IC50 (nM)) |
|---|---|---|---|
| ZBB-02-103 | 194 | 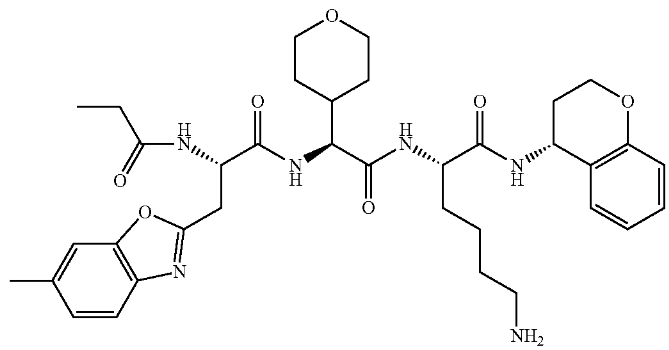 [SMILES: CCC(=O)N[C@@H](Cc1nc2ccc(C)cc2o1)C(=O)N[C@H](C(=O)N[C@@H](CCCCN)C(=O)N[C@@H]1CCOc2ccccc21)C1CCOCC1] | 93.8 |
| ZBB-02-104 | 195 | 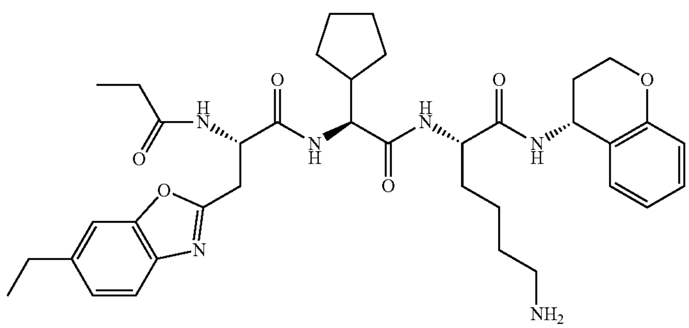 [SMILES: CCC(=O)N[C@@H](Cc1nc2ccc(CC)cc2o1)C(=O)N[C@H](C(=O)N[C@@H](CCCCN)C(=O)N[C@@H]1CCOc2ccccc21)C1CCCC1] | 120 |
| ZBB-02-113 | 196 | | 71.1 |
| ZBB-02-113 | 197 | | 102 |

TABLE 1-continued

Chemical structures and binding affinities to DCN1 proteins

| ID | Number of Example | Chemical Structure | Binding affinity to DCN1 (IC50 (nM)) |
|---|---|---|---|
| ZBB-02-135 | 198 | 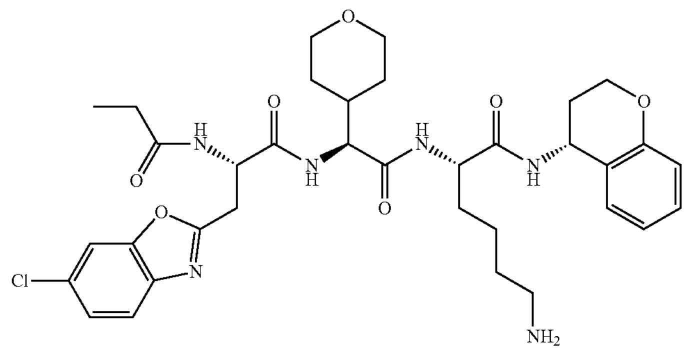 [SMILES: CCC(=O)N[C@@H](Cc1nc2ccc(Cl)cc2o1)C(=O)N[C@H](C(=O)N[C@@H](CCCCN)C(=O)N[C@@H]1CCOc2ccccc21)C1CCOCC1] | 120 |
| DI-416 | 199 | 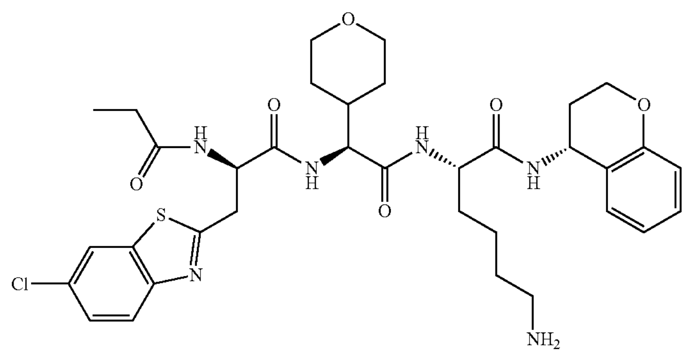 [SMILES: CCC(=O)N[C@H](Cc1nc2ccc(Cl)cc2s1)C(=O)N[C@H](C(=O)N[C@@H](CCCCN)C(=O)N[C@@H]1CCOc2ccccc21)C1CCOCC1] | >10 (μM) |
| DI-417 | 35 | 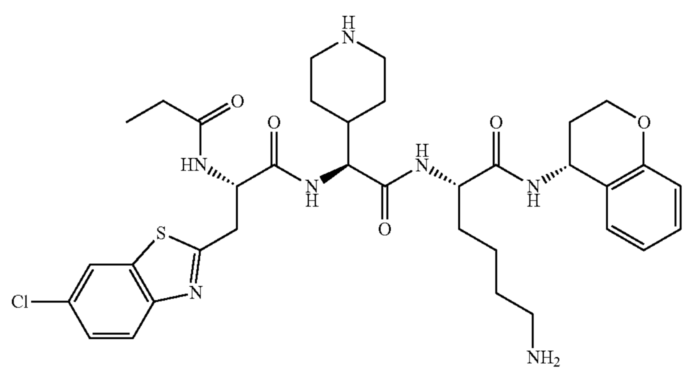 [SMILES: CCC(=O)N[C@@H](Cc1nc2ccc(Cl)cc2s1)C(=O)N[C@H](C(=O)N[C@@H](CCCCN)C(=O)N[C@@H]1CCOc2ccccc21)C1CCNCC1] | >5 (μM) |
| DI-418 | 200 | 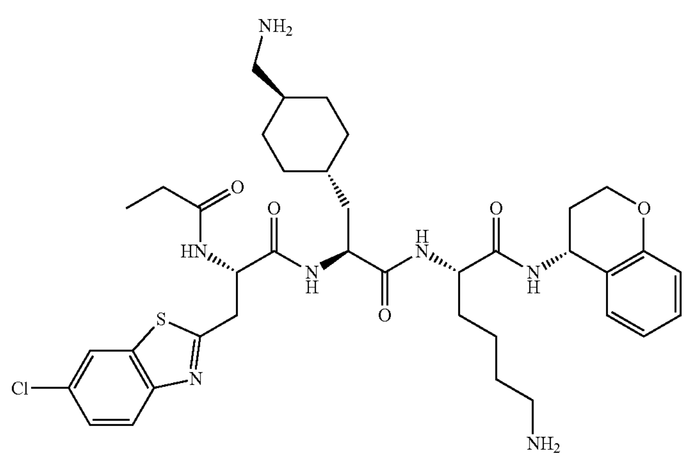 [SMILES: CCC(=O)N[C@@H](Cc1nc2ccc(Cl)cc2s1)C(=O)N[C@@H](C[C@H]1CC[C@H](CN)CC1)C(=O)N[C@@H](CCCCN)C(=O)N[C@@H]1CCOc2ccccc21] | 203 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-419 | 201 | 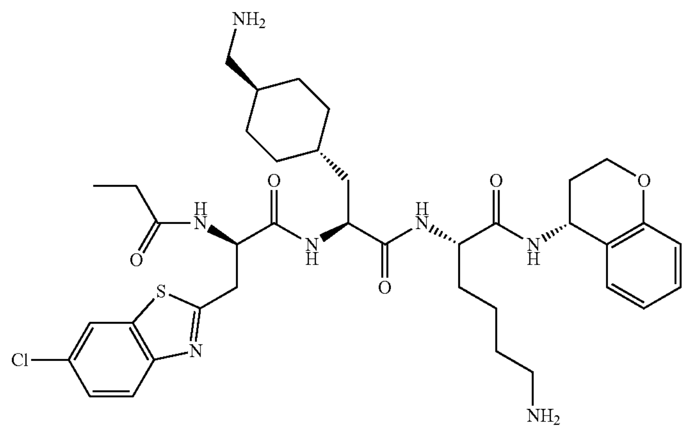 [SMILES: CCC(=O)N[C@H](Cc1nc2ccc(Cl)cc2s1)C(=O)N[C@@H](C[C@H]1CC[C@H](CN)CC1)C(=O)N[C@@H](CCCCN)C(=O)N[C@@H]1CCOc2ccccc21] | >10 (µM) |
| DI-420 | 202 | 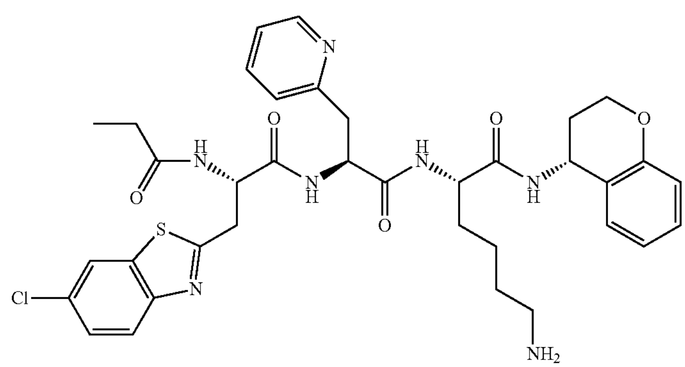 [SMILES: CCC(=O)N[C@@H](Cc1nc2ccc(Cl)cc2s1)C(=O)N[C@@H](Cc1ccccn1)C(=O)N[C@@H](CCCCN)C(=O)N[C@@H]1CCOc2ccccc21] | 251 |
| DI-421 | 203 | 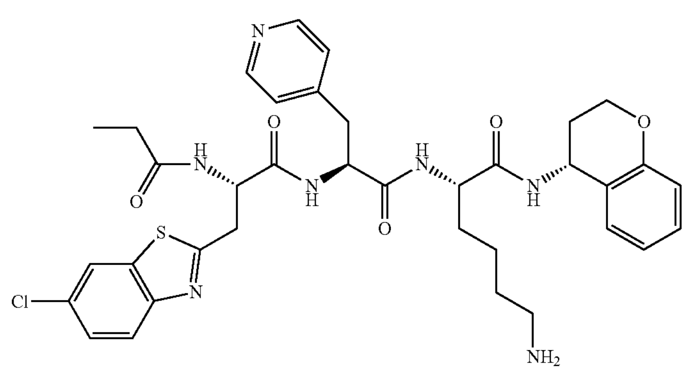 [SMILES: CCC(=O)N[C@@H](Cc1nc2ccc(Cl)cc2s1)C(=O)N[C@@H](Cc1ccncc1)C(=O)N[C@@H](CCCCN)C(=O)N[C@@H]1CCOc2ccccc21] | 282 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-422 | 204 | 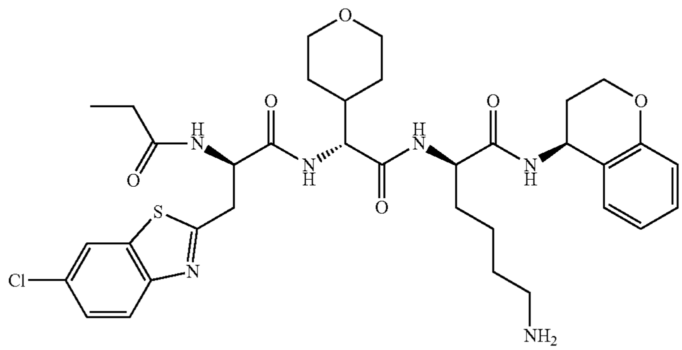 [SMILES: CCC(=O)N[C@H](Cc1nc2ccc(Cl)cc2s1)C(=O)N[C@@H](C(=O)N[C@H](CCCCN)C(=O)N[C@H]1CCOc2ccccc21)C1CCOCC1] | >10 (µM) |
| DI-427 | 45 | 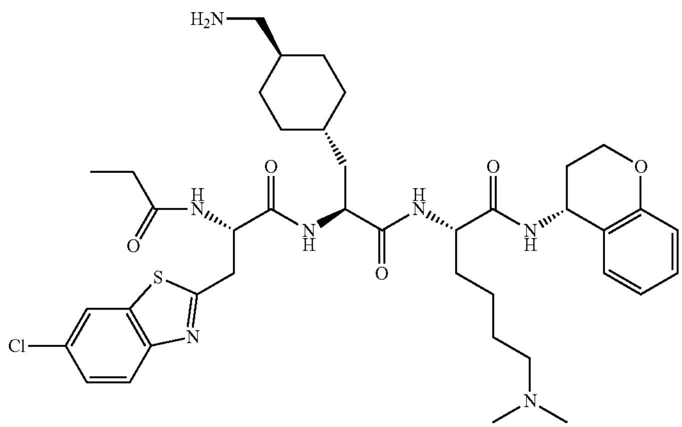 [SMILES: CCC(=O)N[C@@H](Cc1nc2ccc(Cl)cc2s1)C(=O)N[C@@H](C[C@H]1CC[C@H](CN)CC1)C(=O)N[C@@H](CCCCN(C)C)C(=O)N[C@@H]1CCOc2ccccc21] | 116 |
| DI-427biotin | | 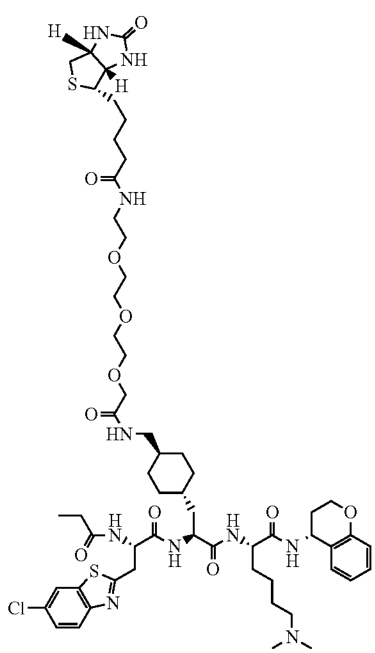 [SMILES: CCC(=O)N[C@@H](Cc1nc2ccc(Cl)cc2s1)C(=O)N[C@@H](C[C@H]1CC[C@H](CNC(=O)COCCOCCOCCNC(=O)CCCC[C@@H]2SC[C@@H]3NC(=O)N[C@@H]32)CC1)C(=O)N[C@@H](CCCCN(C)C)C(=O)N[C@@H]1CCOc2ccccc21] | 189 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-427biotin (NC) | | 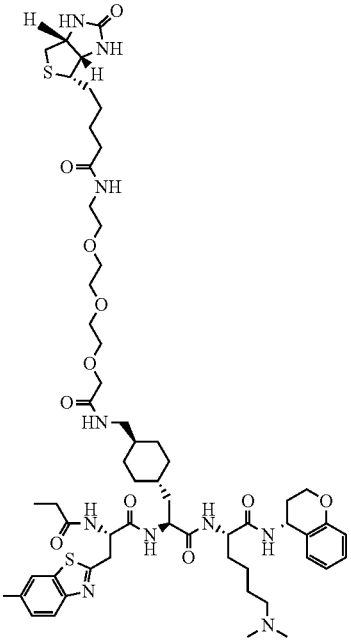 | >10 (μM) |
| DI-429 | 43 | 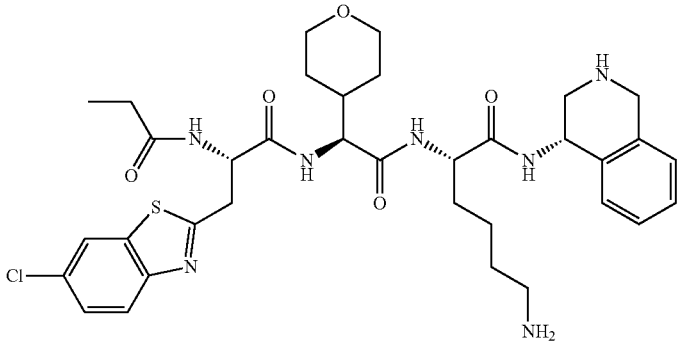 [SMILES: CCC(=O)N[C@@H](Cc1nc2ccc(Cl)cc2s1)C(=O)N[C@H](C(=O)N[C@@H](CCCCN)C(=O)N[C@@H]1CNCc2ccccc21)C1CCOCC1] | 84.3 |
| DI-430 | 44 | 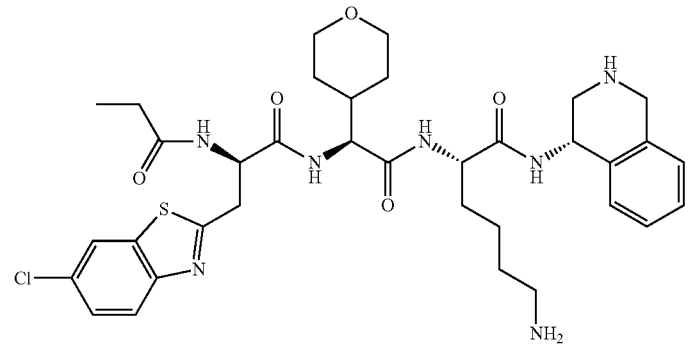 [SMILES: CCC(=O)N[C@H](Cc1nc2ccc(Cl)cc2s1)C(=O)N[C@H](C(=O)N[C@@H](CCCCN)C(=O)N[C@@H]1CNCc2ccccc21)C1CCOCC1] | >1 (μM) |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-431 | 34 | 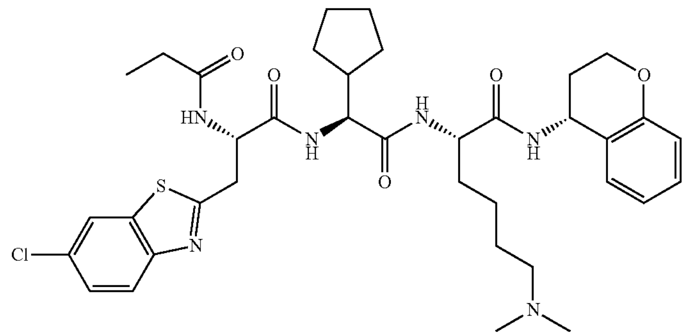 [SMILES: CCC(=O)N[C@@H](Cc1nc2ccc(Cl)cc2s1)C(=O)N[C@H](C(=O)N[C@@H](CCCCN(C)C)C(=O)N[C@@H]1CCOc2ccccc21)C1CCCC1] | 17.9 |
| DI-431NC | 205 | 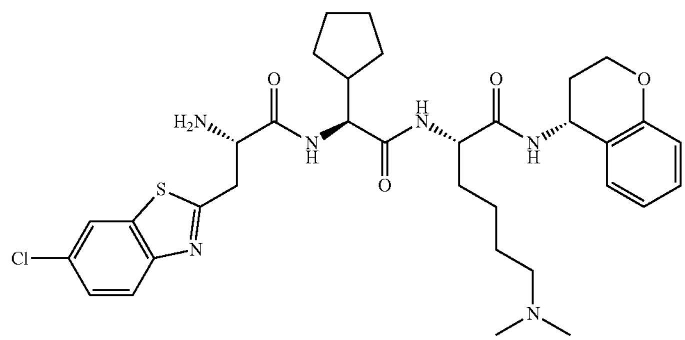 [SMILES: CN(C)CCCC[C@H](NC(=O)[C@@H](NC(=O)[C@@H](N)Cc1nc2ccc(Cl)cc2s1)C1CCCC1)C(=O)N[C@@H]1CCOc2ccccc21] | >10 (μM) |
| DI-477 | 206 | 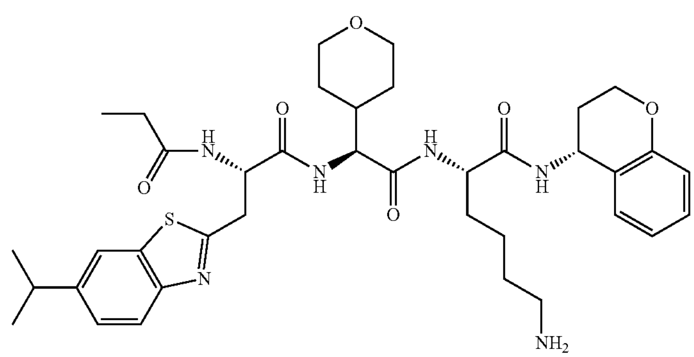 [SMILES: CCC(=O)N[C@@H](Cc1nc2ccc(C(C)C)cc2s1)C(=O)N[C@H](C(=O)N[C@@H](CCCCN)C(=O)N[C@@H]1CCOc2ccccc21)C1CCOCC1] | 42.9 |
| DI-478 | 207 | 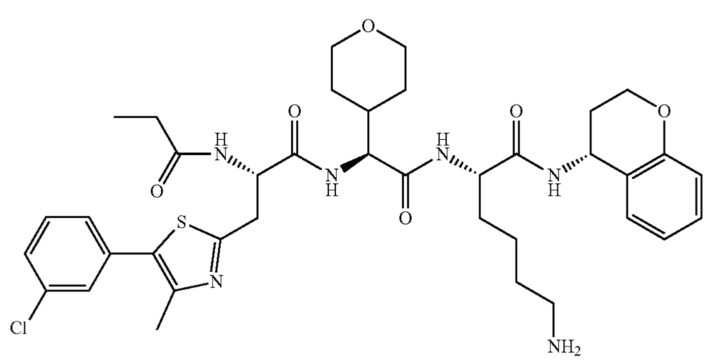 [SMILES: CCC(=O)N[C@@H](Cc1nc(C)c(-c2cccc(Cl)c2)s1)C(=O)N[C@H](C(=O)N[C@@H](CCCCN)C(=O)N[C@@H]1CCOc2ccccc21)C1CCOCC1] | 139 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-479 | 208 | 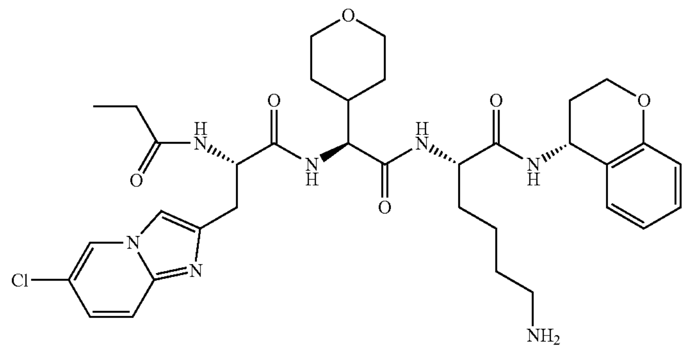 [SMILES: CCC(=O)N[C@@H](Cc1cn2cc(Cl)ccc2n1)C(=O)N[C@H](C(=O)N[C@@H](CCCCN)C(=O)N[C@@H]1CCOc2ccccc21)C1CCOCC1] | 157 |
| DI-480 | 209 | 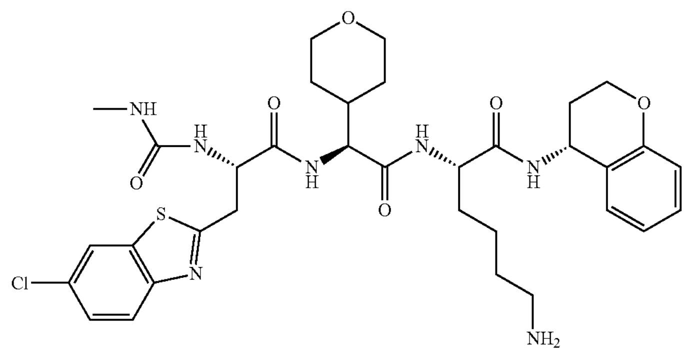 [SMILES: CNC(=O)N[C@@H](Cc1nc2ccc(Cl)cc2s1)C(=O)N[C@H](C(=O)N[C@@H](CCCCN)C(=O)N[C@@H]1CCOc2ccccc21)C1CCOCC1] | 278 |
| DI-481 | 210 & 211 | 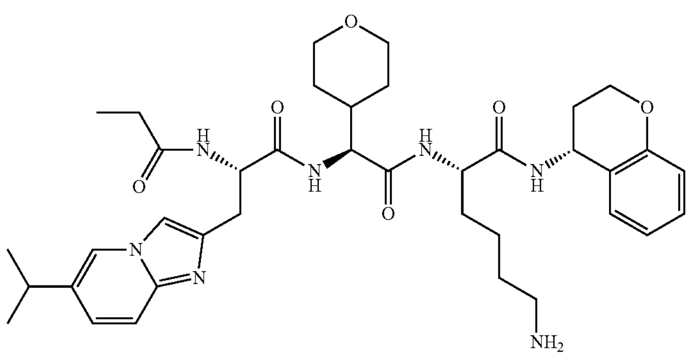 [SMILES: CCC(=O)N[C@@H](Cc1cn2cc(C(C)C)ccc2n1)C(=O)N[C@H](C(=O)N[C@@H](CCCCN)C(=O)N[C@@H]1CCOc2ccccc21)C1CCOCC1] | 81.2 |
| DI-482 | 212 | 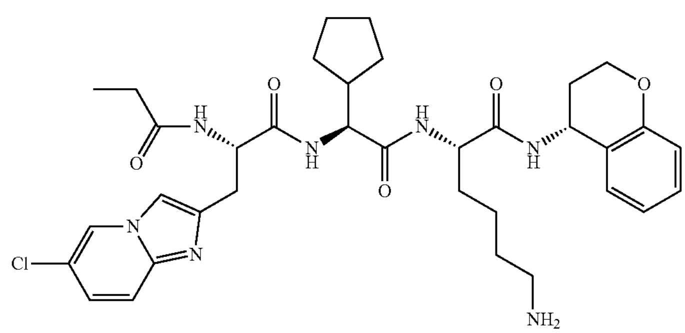 [SMILES: CCC(=O)N[C@@H](Cc1cn2cc(Cl)ccc2n1)C(=O)N[C@H](C(=O)N[C@@H](CCCCN)C(=O)N[C@@H]1CCOc2ccccc21)C1CCCC1] | 55.6 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-501 | 213 | 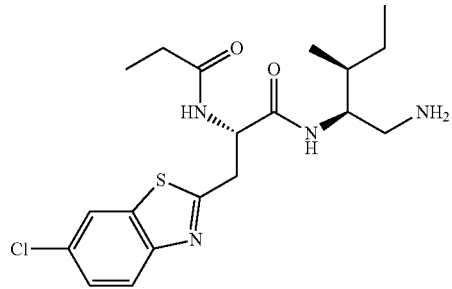 [SMILES: CCC(=O)N[C@@H](Cc1nc2ccc(Cl)cc2s1)C(=O)N[C@H](CN)[C@@H](C)CC] | 746 ± 72 |
| DI-505 | 214 | 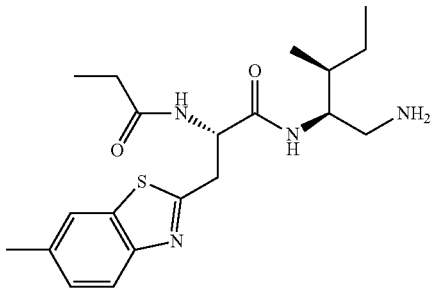 [SMILES: CCC(=O)N[C@@H](Cc1nc2ccc(C)cc2s1)C(=O)N[C@H](CN)[C@@H](C)CC] | 491 |
| DI-506 | 215 | 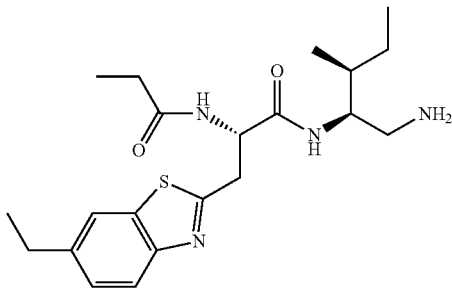 [SMILES: CCC(=O)N[C@@H](Cc1nc2ccc(CC)cc2s1)C(=O)N[C@H](CN)[C@@H](C)CC] | 230 |
| DI-507 | 216 | 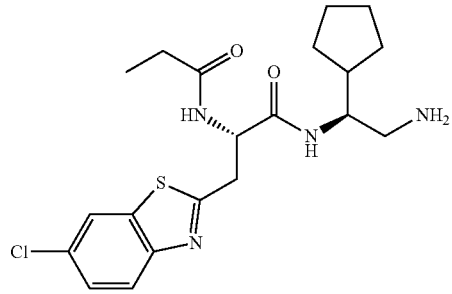 [SMILES: CCC(=O)N[C@@H](Cc1nc2ccc(Cl)cc2s1)C(=O)N[C@H](CN)C1CCCC1] | 559 |
| DI-508 | 86 | 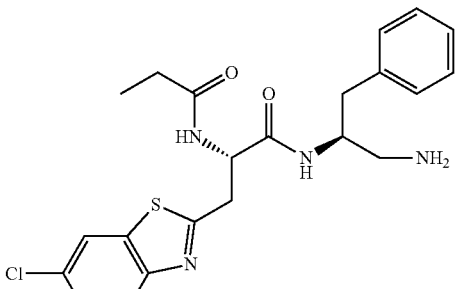 | 491 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-508DL | 87 | 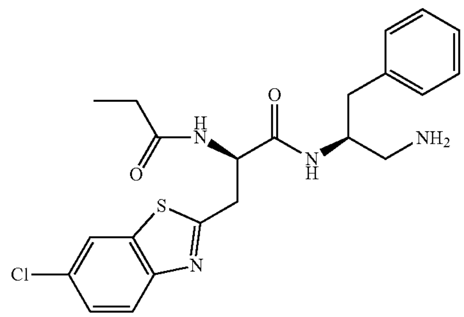 [SMILES: CCC(=O)N[C@H](Cc1nc2ccc(Cl)cc2s1)C(=O)N[C@H](CN)Cc1ccccc1] | >10 (μM) |
| DI-508DD | 88 | 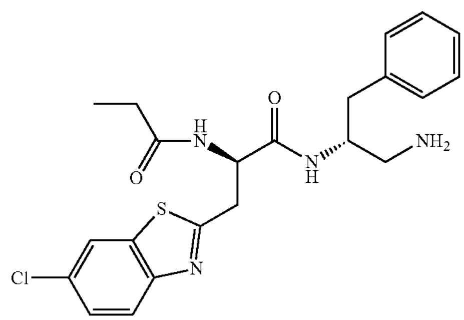 [SMILES: CCC(=O)N[C@H](Cc1nc2ccc(Cl)cc2s1)C(=O)N[C@@H](CN)Cc1ccccc1] | >10 (μM) |
| DI-510 | 217 | 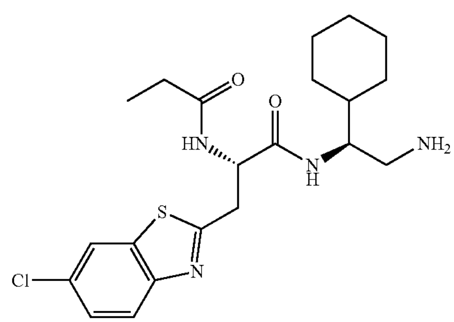 [SMILES: CCC(=O)N[C@@H](Cc1nc2ccc(Cl)cc2s1)C(=O)N[C@H](CN)C1CCCCC1] | 346 |
| DI-511 | 218 | 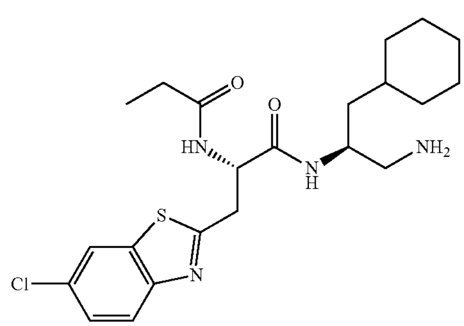 [SMILES: CCC(=O)N[C@@H](Cc1nc2ccc(Cl)cc2s1)C(=O)N[C@H](CN)CC1CCCCC1] | 316 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-512 | 219 | 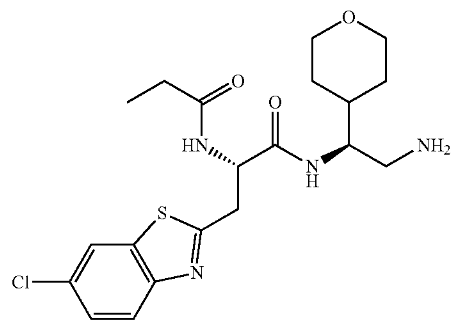 [SMILES: CCC(=O)N[C@@H](Cc1nc2ccc(Cl)cc2s1)C(=O)N[C@H](CN)C1CCOCC1] | 1559 |
| DI-515 | 220 | 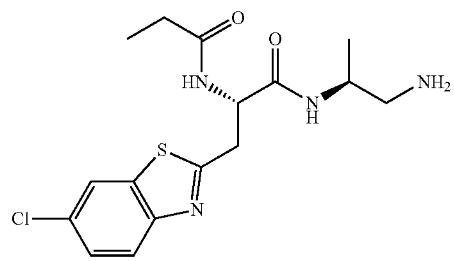 [SMILES: CCC(=O)N[C@@H](Cc1nc2ccc(Cl)cc2s1)C(=O)N[C@@H](C)CN] | >10 (µM) |
| DI-516 | 221 | 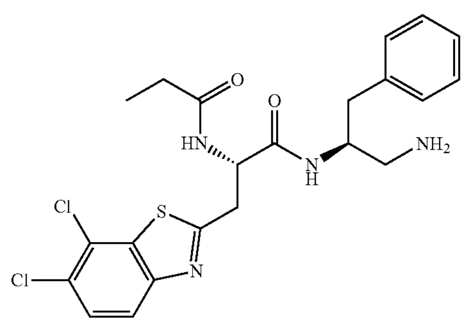 [SMILES: CCC(=O)N[C@@H](Cc1nc2ccc(Cl)c(Cl)c2s1)C(=O)N[C@H](CN)Cc1ccccc1] | 294 |
| DI-517 | 55 | 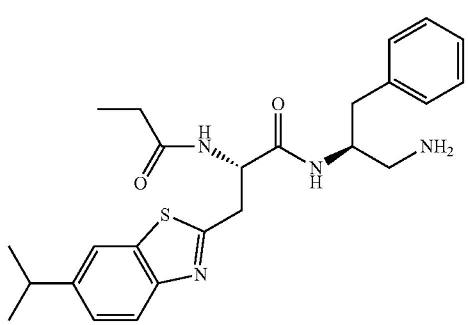 [SMILES: CCC(=O)N[C@@H](Cc1nc2ccc(C(C)C)cc2s1)C(=O)N[C@H](CN)Cc1ccccc1] | 179 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-517DL | 89 | 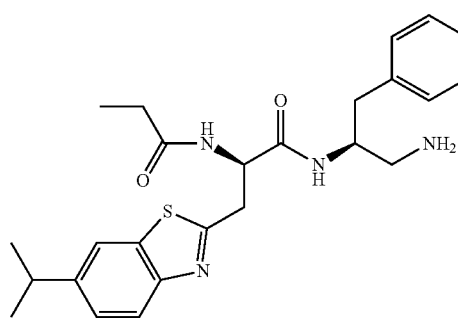 | >10 (μM) |
| DI-517LD | 90 | 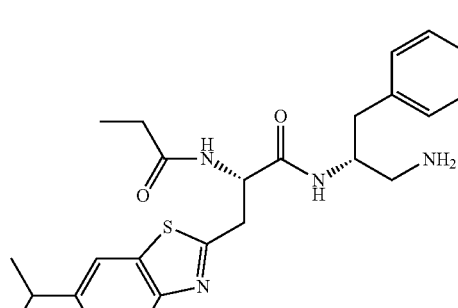 | >5 (μM) |
| DI-517DD | 91 | 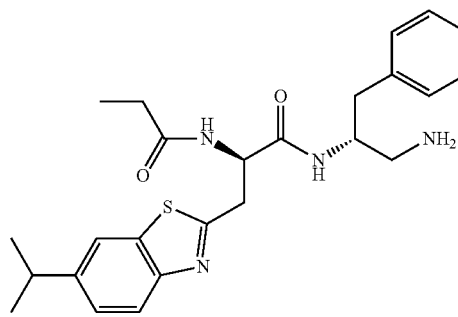 | >10 (μM) |
| DI-518 | 222 | 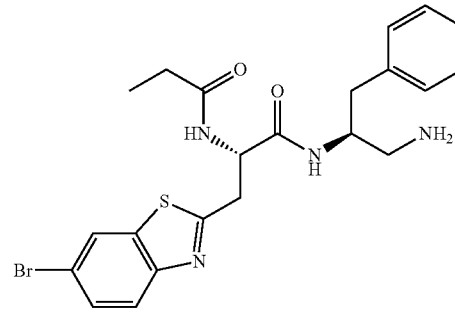 | 858 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-520 | 223 | 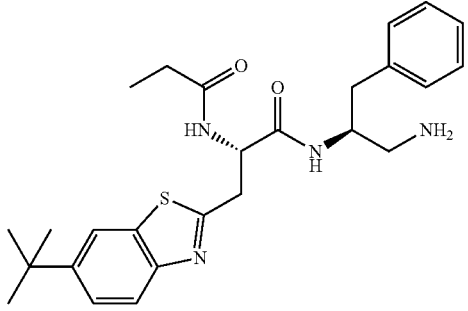 [SMILES: CCC(=O)N[C@@H](Cc1nc2ccc(C(C)(C)C)cc2s1)C(=O)N[C@H](CN)Cc1ccccc1] | 949 |
| DI-522 | 224 | 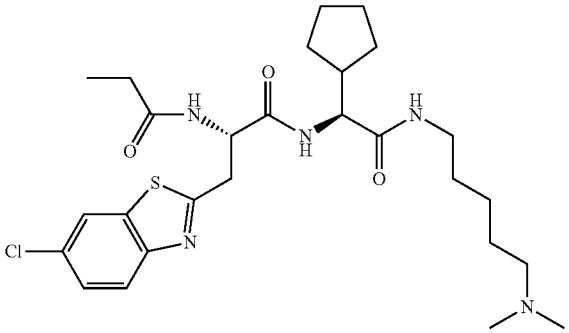 [SMILES: CCC(=O)N[C@@H](Cc1nc2ccc(Cl)cc2s1)C(=O)N[C@H](C(=O)NCCCCCN(C)C)C1CCCC1] | 575 |
| DI-526 | 99 | 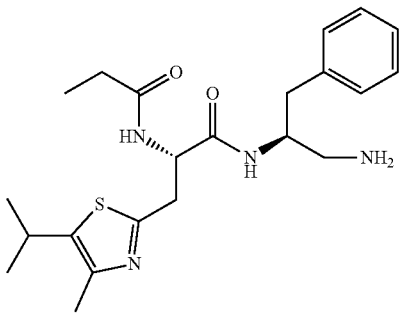 [SMILES: CCC(=O)N[C@@H](Cc1nc(C)c(C(C)C)s1)C(=O)N[C@H](CN)Cc1ccccc1] | >10 (µM) |
| DI-531 | 100 | 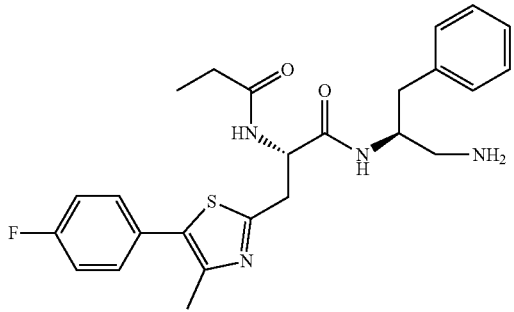 [SMILES: CCC(=O)N[C@@H](Cc1nc(C)c(-c2ccc(F)cc2)s1)C(=O)N[C@H](CN)Cc1ccccc1] | 2220 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-532 | | 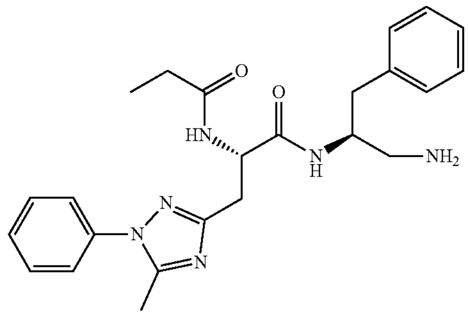 [SMILES: CCC(=O)N[C@@H](Cc1nc(C)n(-c2ccccc2)n1)C(=O)N[C@H](CN)Cc1ccccc1] | >10 (µM) |
| DI-533 | | 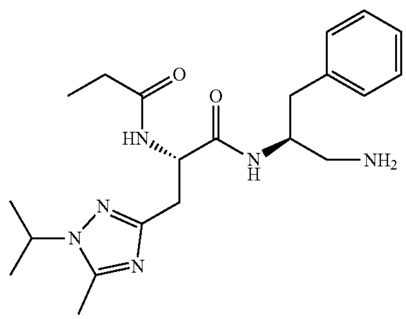 [SMILES: CCC(=O)N[C@@H](Cc1nc(C)n(C(C)C)n1)C(=O)N[C@H](CN)Cc1ccccc1] | >10 (µM) |
| DI-534 | | 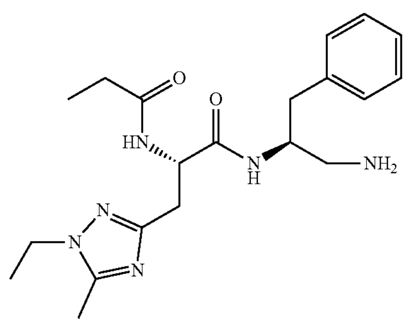 [SMILES: CCC(=O)N[C@@H](Cc1nc(C)n(CC)n1)C(=O)N[C@H](CN)Cc1ccccc1] | NT |
| DI-538 | 101 | 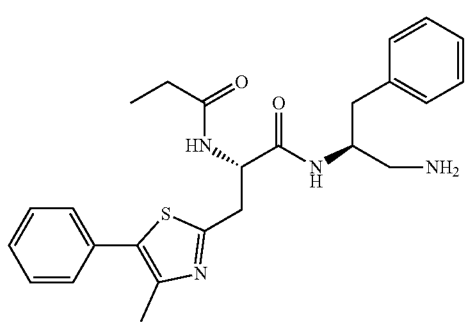 [SMILES: CCC(=O)N[C@@H](Cc1nc(C)c(-c2ccccc2)s1)C(=O)N[C@H](CN)Cc1ccccc1] | 1737 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-539 | 102 | 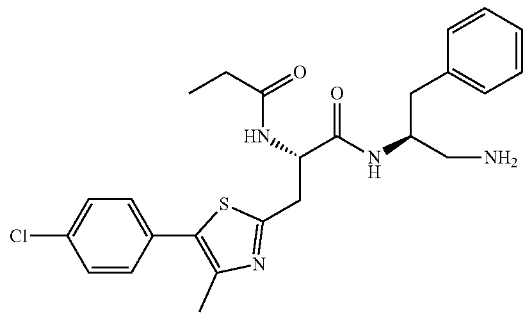 [SMILES: CCC(=O)N[C@@H](Cc1nc(C)c(-c2ccc(Cl)cc2)s1)C(=O)N[C@H](CN)Cc1ccccc1] | 1279 |
| DI-540 | 225 | 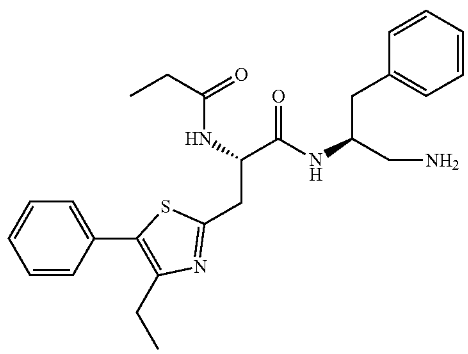 [SMILES: CCC(=O)N[C@@H](Cc1nc(CC)c(-c2ccccc2)s1)C(=O)N[C@H](CN)Cc1ccccc1] | >3 (μM) |
| DI-546-1 | 226 | 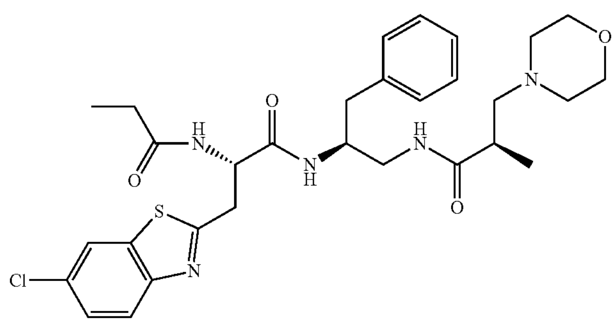 [SMILES: CCC(=O)N[C@@H](Cc1nc2ccc(Cl)cc2s1)C(=O)N[C@H](CNC(=O)[C@H](C)CN1CCOCC1)Cc1ccccc1] | 611 |
| DI-546-2 | 227 | 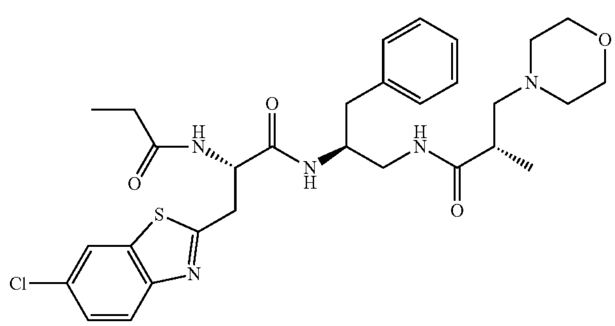 [SMILES: CCC(=O)N[C@@H](Cc1nc2ccc(Cl)cc2s1)C(=O)N[C@H](CNC(=O)[C@@H](C)CN1CCOCC1)Cc1ccccc1] | 471 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI547 | 92 | 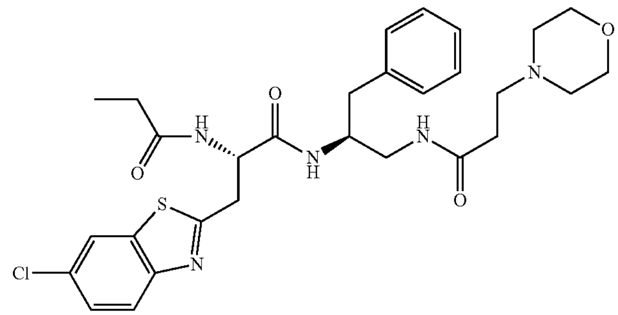 [SMILES: CCC(=O)N[C@@H](Cc1nc2ccc(Cl)cc2s1)C(=O)N[C@H](CNC(=O)CCN1CCOCC1)Cc1ccccc1] | 244 |
| DI-550 | 103 | 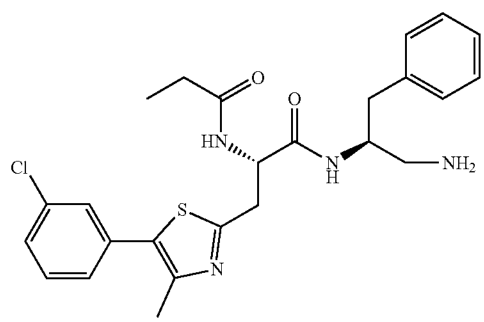 [SMILES: CCC(=O)N[C@@H](Cc1nc(C)c(-c2cccc(Cl)c2)s1)C(=O)N[C@H](CN)Cc1ccccc1] | 264 |
| DI-551 | 104 | 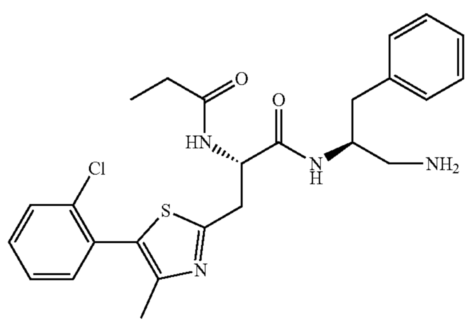 [SMILES: CCC(=O)N[C@@H](Cc1nc(C)c(-c2ccccc2Cl)s1)C(=O)N[C@H](CN)Cc1ccccc1] | >10 (μM) |
| DI-552 | 105 | 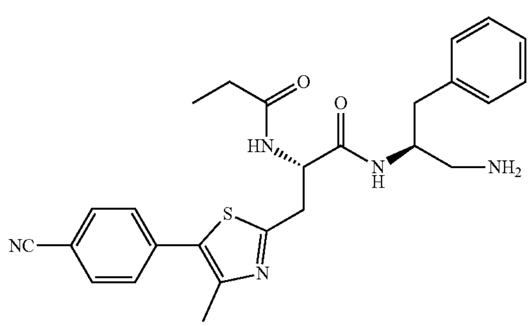 [SMILES: CCC(=O)N[C@@H](Cc1nc(C)c(-c2ccc(C#N)cc2)s1)C(=O)N[C@H](CN)Cc1ccccc1] | >10 (μM) |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-553 | 106 | 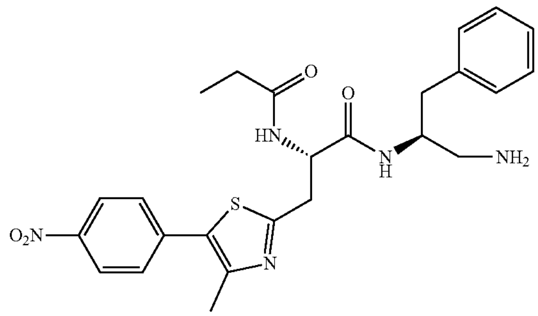 [SMILES: CCC(=O)N[C@@H](Cc1nc(C)c(-c2ccc([N+](=O)[O-])cc2)s1)C(=O)N[C@H](CN)Cc1ccccc1] | >10 (μM) |
| DI-554 | 228 | 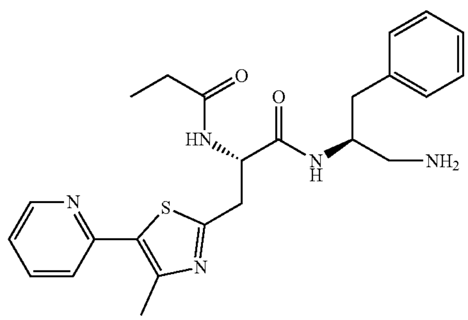 [SMILES: CCC(=O)N[C@@H](Cc1nc(C)c(-c2ccccn2)s1)C(=O)N[C@H](CN)Cc1ccccc1] | >10 (μM) |
| DI-555 | 229 | 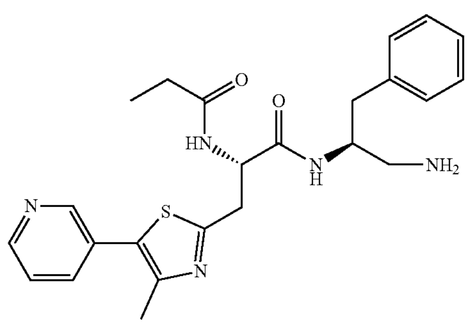 [SMILES: CCC(=O)N[C@@H](Cc1nc(C)c(-c2cccnc2)s1)C(=O)N[C@H](CN)Cc1ccccc1] | >10 (μM) |
| DI-556 | 230 | 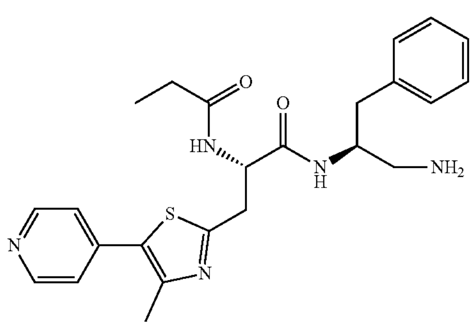 [SMILES: CCC(=O)N[C@@H](Cc1nc(C)c(-c2ccncc2)s1)C(=O)N[C@H](CN)Cc1ccccc1] | >10 (μM) |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-557 | 231 | 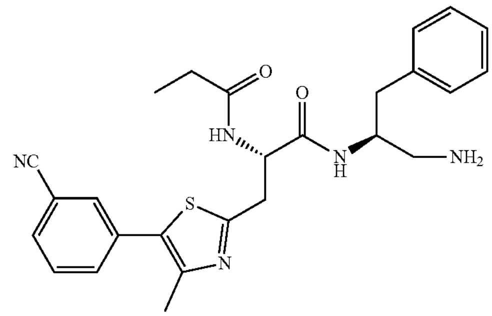 [SMILES: CCC(=O)N[C@@H](Cc1nc(C)c(-c2cccc(C#N)c2)s1)C(=O)N[C@H](CN)Cc1ccccc1] | >10 (μM) |
| DI-558 | 232 | 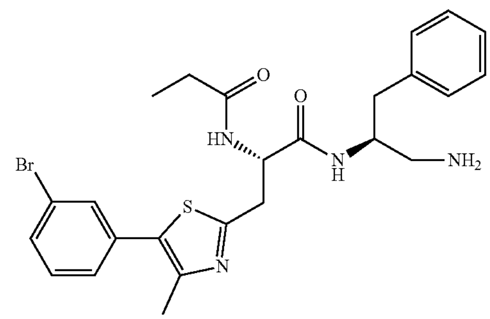 [SMILES: CCC(=O)N[C@@H](Cc1nc(C)c(-c2cccc(Br)c2)s1)C(=O)N[C@H](CN)Cc1ccccc1] | 984 |
| DI-559 | 233 | 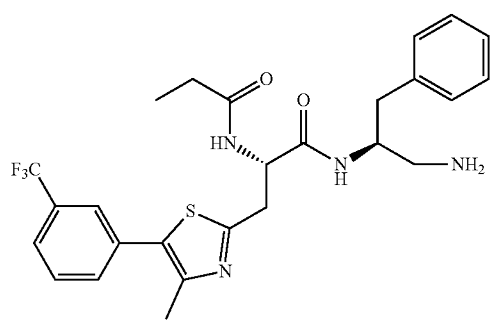 [SMILES: CCC(=O)N[C@@H](Cc1nc(C)c(-c2cccc(C(F)(F)F)c2)s1)C(=O)N[C@H](CN)Cc1ccccc1] | >10 (μM) |
| DI-560 | 234 | 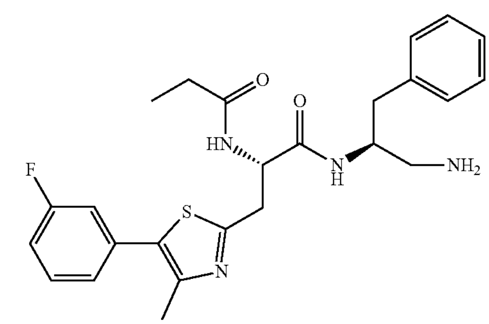 [SMILES: CCC(=O)N[C@@H](Cc1nc(C)c(-c2cccc(F)c2)s1)C(=O)N[C@H](CN)Cc1ccccc1] | 1276 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-561 | 235 | 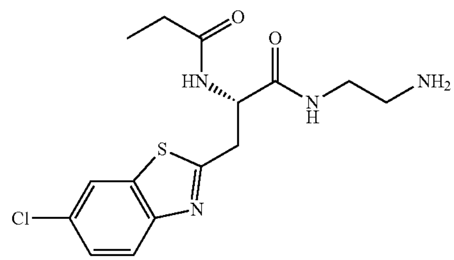 [SMILES: CCC(=O)N[C@@H](Cc1nc2ccc(Cl)cc2s1)C(=O)NCCN] | >10 (μM) |
| DI-562 | 236 | 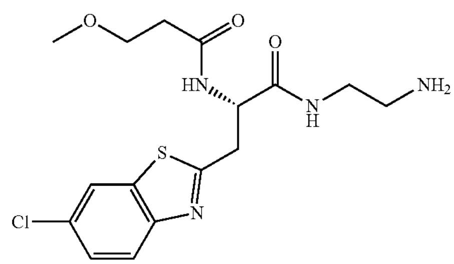 [SMILES: COCCC(=O)N[C@@H](Cc1nc2ccc(Cl)cc2s1)C(=O)NCCN] | >10 (μM) |
| DI-563 | 237 | 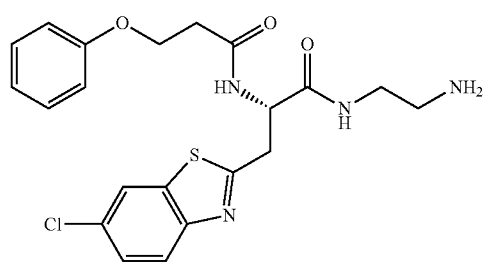 [SMILES: NCCNC(=O)[C@H](Cc1nc2ccc(Cl)cc2s1)NC(=O)CCOc1ccccc1] | >10 (μM) |
| DI-564 | 238 | 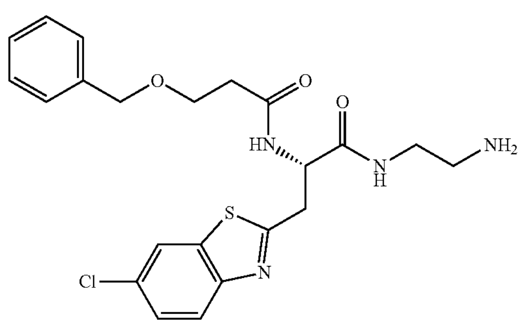 [SMILES: NCCNC(=O)[C@H](Cc1nc2ccc(Cl)cc2s1)NC(=O)CCOCc1ccccc1] | >10 (μM) |
| DI-565 | 239 | 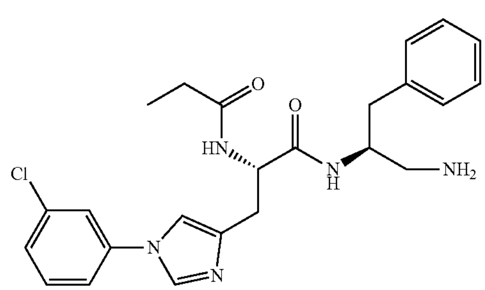 [SMILES: CCC(=O)N[C@@H](Cc1cn(-c2cccc(Cl)c2)cn1)C(=O)N[C@H](CN)Cc1ccccc1] | >10 (μM) |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-566 | 240 | 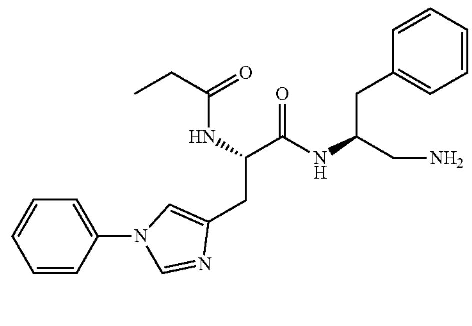 [SMILES: CCC(=O)N[C@@H](Cc1cn(-c2ccccc2)cn1)C(=O)N[C@H](CN)Cc1ccccc1] | |
| DI-572 | 93 | | 89.9 |
| DI-572 | 94 | | >10 (μM) |
| DI-581 | 241 | 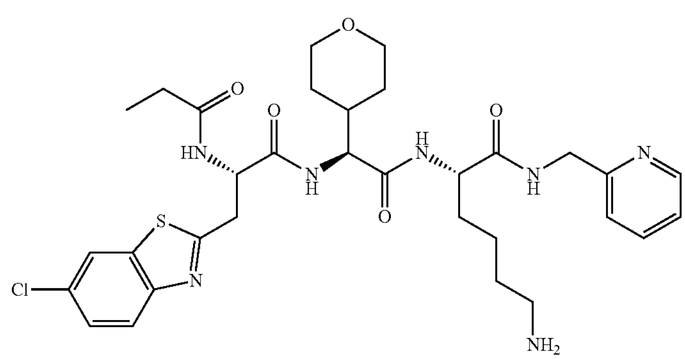 [SMILES: CCC(=O)N[C@@H](Cc1nc2ccc(Cl)cc2s1)C(=O)N[C@H](C(=O)N[C@@H](CCCCN)C(=O)NCc1ccccn1)C1CCOCC1] | 913 |

TABLE 1-continued

Chemical structures and binding affinities to DCN1 proteins

| ID | Number of Example | Chemical Structure | Binding affinity to DCN1 (IC50 (nM)) |
| --- | --- | --- | --- |
| DI-582 | 242 | 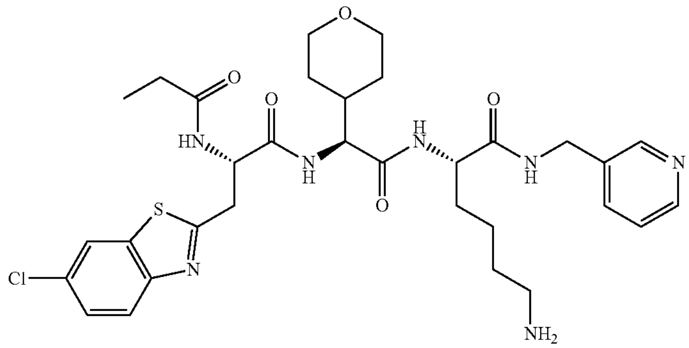 | 1195 |
| DI-583 | 243 | 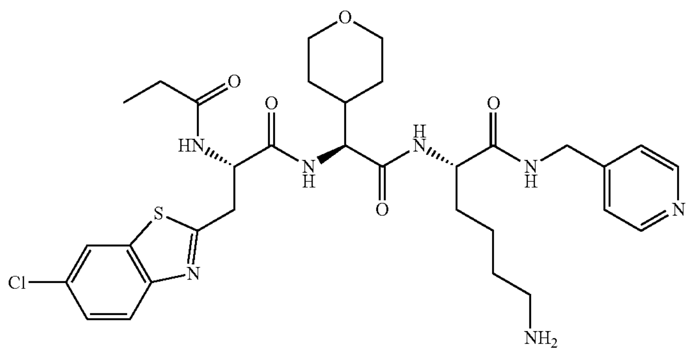 [SMILES: CCC(=O)N[C@@H](Cc1nc2ccc(Cl)cc2s1)C(=O)N[C@H](C(=O)N[C@@H](CCCCN)C(=O)NCc1ccncc1)C1CCOCC1] | 1514 |
| DI-584 | 244 & 245 | 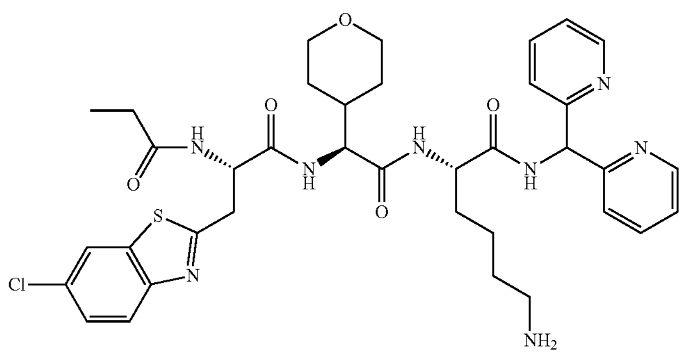 [SMILES: CCC(=O)N[C@@H](Cc1nc2ccc(Cl)cc2s1)C(=O)N[C@H](C(=O)N[C@@H](CCCCN)C(=O)NC(c1ccccn1)c1ccccn1)C1CCOCC1] | 297 |
| DI-585 | 246 | 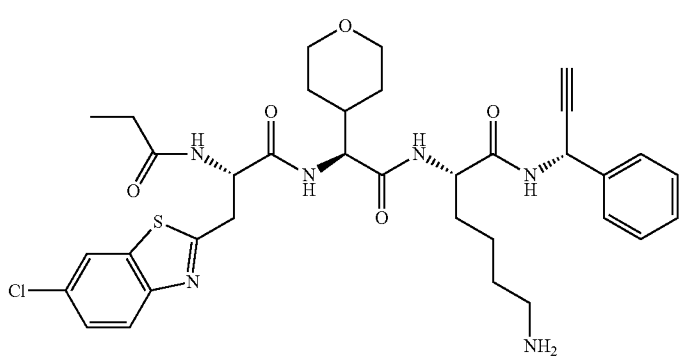 [SMILES: C#C[C@@H](NC(=O)[C@H](CCCCN)NC(=O)[C@@H](NC(=O)[C@H](Cc1nc2ccc(Cl)cc2s1)NC(=O)CC)C1CCOCC1)c1ccccc1] | |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-586 | 247 & 248 | 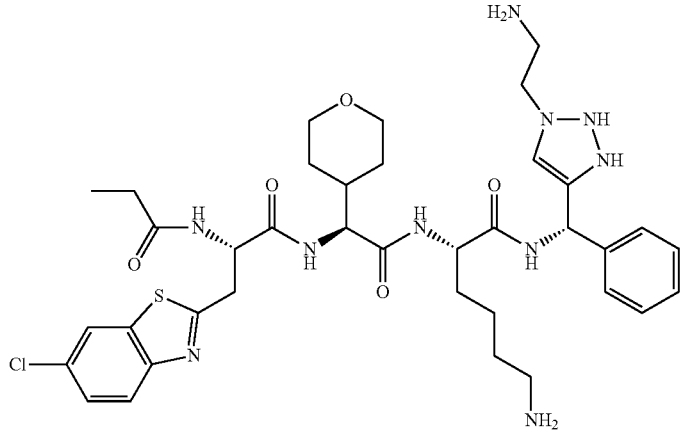 [SMILES: CCC(=O)N[C@@H](Cc1nc2ccc(Cl)cc2s1)C(=O)N[C@H](C(=O)N[C@@H](CCCCN)C(=O)N[C@H](C1=CN(CCN)NN1)c1ccccc1)C1CCOCC1] | 171 |
| DI-587 | 249 & 250 | 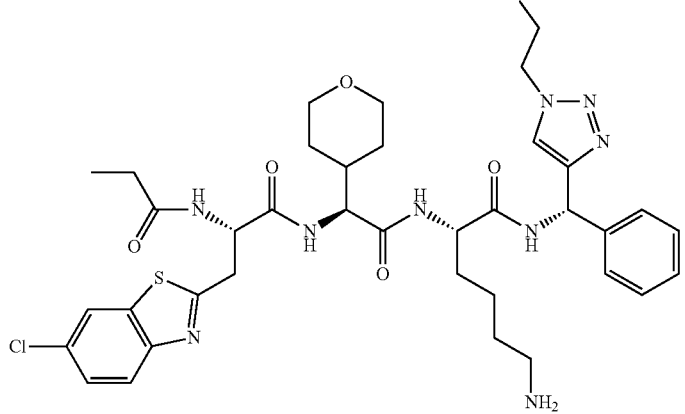 | 120 |
| DI-589 | 108 | 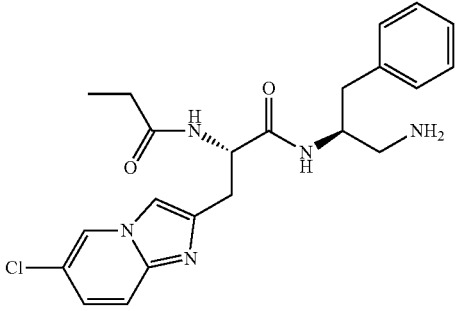 [SMILES: CCC(=O)N[C@@H](Cc1cn2cc(Cl)ccc2n1)C(=O)N[C@H](CN)Cc1ccccc1] | 4171 |
| DI-590 | 56 | 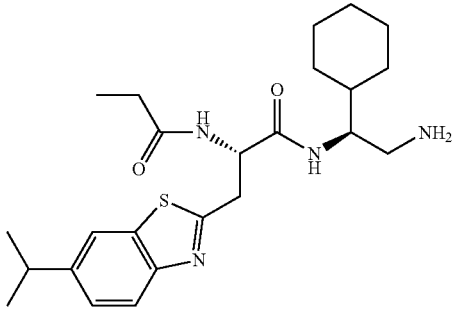 [SMILES: CCC(=O)N[C@@H](Cc1nc2ccc(C(C)C)cc2s1)C(=O)N[C@H](CN)C1CCCCC1] | 79.6 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-590DD | 122 | 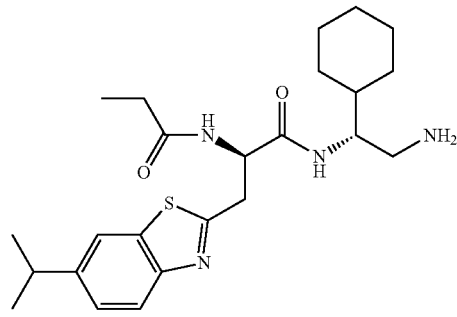 [SMILES: CCC(=O)N[C@H](Cc1nc2ccc(C(C)C)cc2s1)C(=O)N[C@@H](CN)C1CCCCC1] | >10 (μM) |
| DI-591 | 58 | 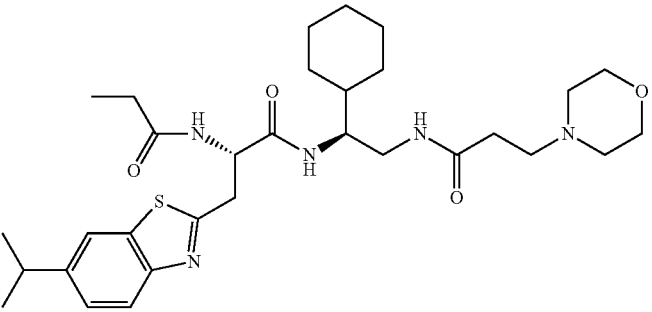 [SMILES: CCC(=O)N[C@@H](Cc1nc2ccc(C(C)C)cc2s1)C(=O)N[C@H](CNC(=O)CCN1CCOCC1)C1CCCCC1] | 90.7 |
| DI-591DD | 123 | 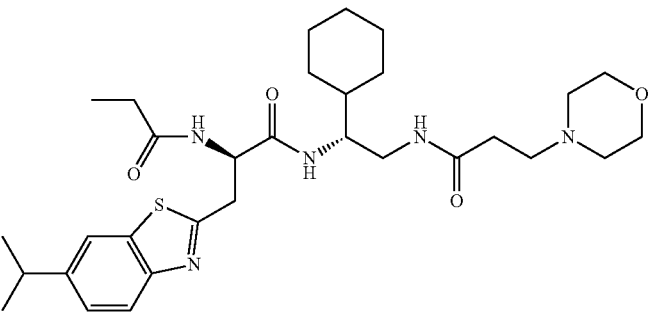 [SMILES: CCC(=O)N[C@H](Cc1nc2ccc(C(C)C)cc2s1)C(=O)N[C@@H](CNC(=O)CCN1CCOCC1)C1CCCCC1] | >10 (μM) |
| DI-708 | 251 | 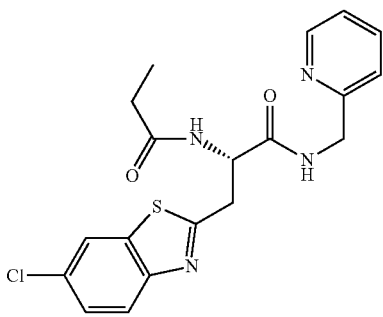 [SMILES: CCC(=O)N[C@@H](Cc1nc2ccc(Cl)cc2s1)C(=O)NCc1ccccn1] | >5 (μM) |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-713 | 252 | 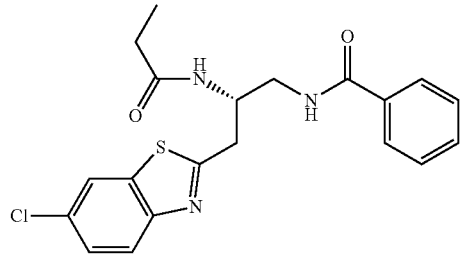 [SMILES: CCC(=O)N[C@H](CNC(=O)c1ccccc1)Cc1nc2ccc(Cl)cc2s1] | 1835 |
| DI-714 | 253 | 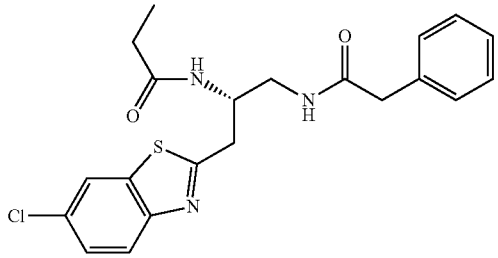 [SMILES: CCC(=O)N[C@H](CNC(=O)Cc1ccccc1)Cc1nc2ccc(Cl)cc2s1] | 1195 |
| DI-715 | 254 | 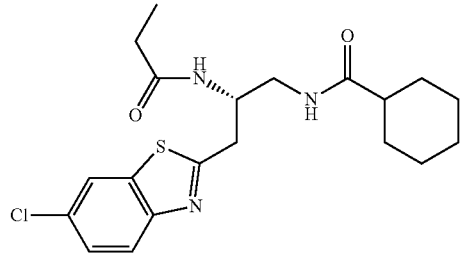 [SMILES: CCC(=O)N[C@H](CNC(=O)C1CCCCC1)Cc1nc2ccc(Cl)cc2s1] | 1345 |
| DI-716 | 255 | 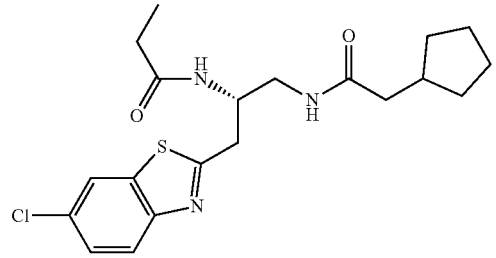 [SMILES: CCC(=O)N[C@H](CNC(=O)CC1CCCC1)Cc1nc2ccc(Cl)cc2s1] | 802 |
| DI-717 | 256 | 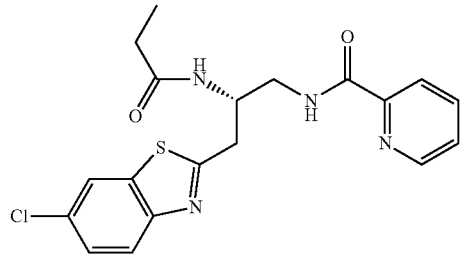 | 2135 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-718 | 257 | 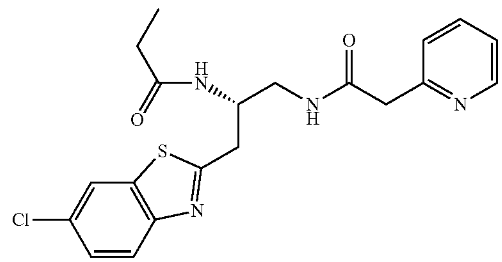 [SMILES: CCC(=O)N[C@H](CNC(=O)Cc1ccccn1)Cc1nc2ccc(Cl)cc2s1] | 3451 |
| DI-722 | 258 | 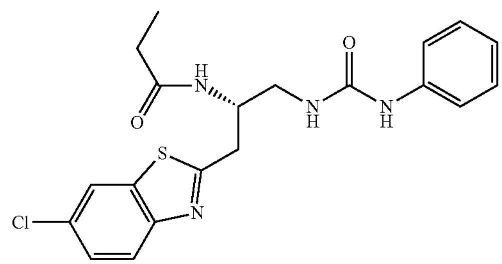 [SMILES: CCC(=O)N[C@H](CNC(=O)Nc1ccccc1)Cc1nc2ccc(Cl)cc2s1] | 3915 |
| DI-723 | 259 | 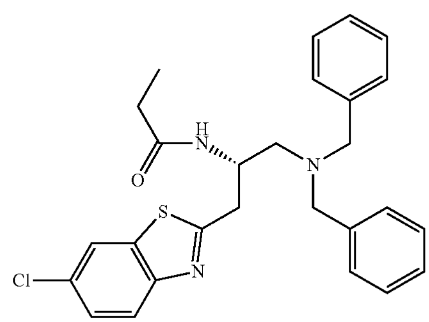 [SMILES: CCC(=O)N[C@@H](Cc1nc2ccc(Cl)cc2s1)CN(Cc1ccccc1)Cc1ccccc1] | >10 (μM) |
| DI-724 | 260 | 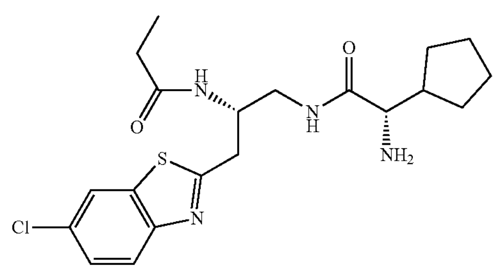 [SMILES: CCC(=O)N[C@H](CNC(=O)[C@@H](N)C1CCCC1)Cc1nc2ccc(Cl)cc2s1] | 1195 |
| DI-725 | 261 | 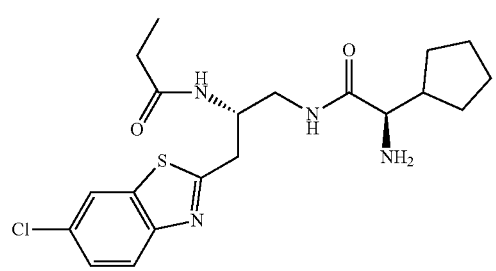 [SMILES: CCC(=O)N[C@H](CNC(=O)[C@H](N)C1CCCC1)Cc1nc2ccc(Cl)cc2s1] | >5 (μM) |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-726 | 119 | 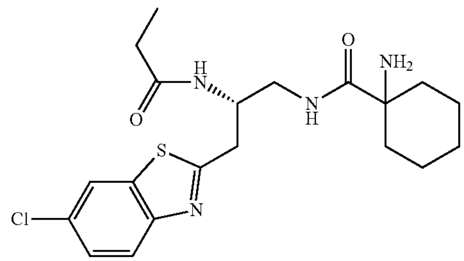 [SMILES: CCC(=O)N[C@H](CNC(=O)C1(N)CCCCC1)Cc1nc2ccc(Cl)cc2s1] | 477 |
| DI-727 | 80 | 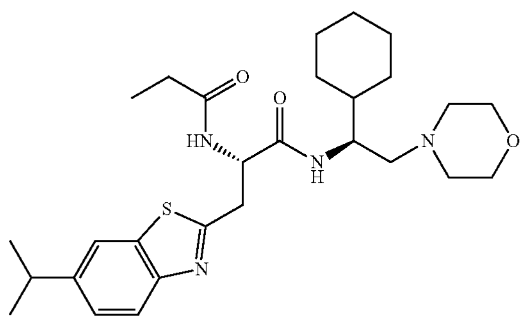 [SMILES: CCC(=O)N[C@@H](Cc1nc2ccc(C(C)C)cc2s1)C(=O)N[C@H](CN1CCOCC1)C1CCCCC1] | 157 |
| DI-728 | 81 | 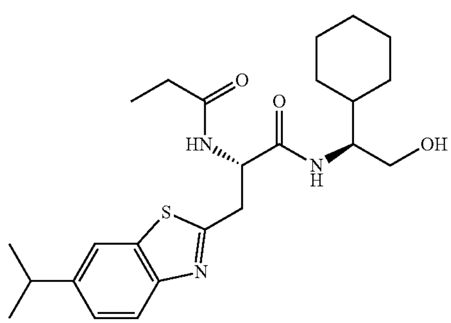 [SMILES: CCC(=O)N[C@@H](Cc1nc2ccc(C(C)C)cc2s1)C(=O)N[C@H](CO)C1CCCCC1] | 127 |
| DI-729 | 79 | 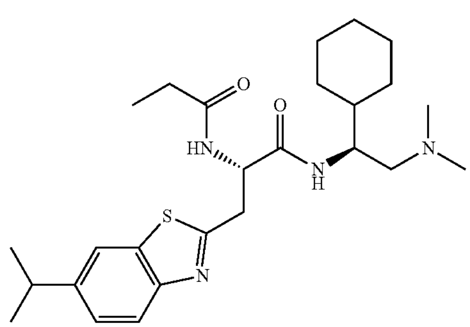 [SMILES: CCC(=O)N[C@@H](Cc1nc2ccc(C(C)C)cc2s1)C(=O)N[C@H](CN(C)C)C1CCCCC1] | 93.6 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-730 | 57 | 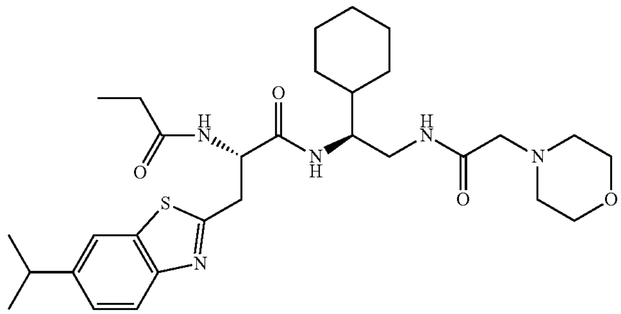 [SMILES: CCC(=O)N[C@@H](Cc1nc2ccc(C(C)C)cc2s1)C(=O)N[C@H](CNC(=O)CN1CCOCC1)C1CCCCC1] | 70.4 |
| DI-731 | 59 | 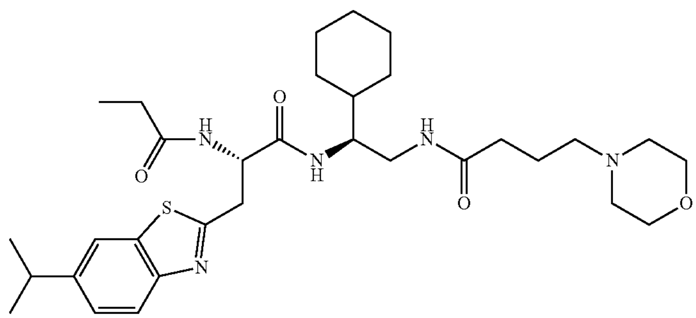 [SMILES: CCC(=O)N[C@@H](Cc1nc2ccc(C(C)C)cc2s1)C(=O)N[C@H](CNC(=O)CCCN1CCOCC1)C1CCCCC1] | 63.1 |
| DI-732 | 60 | 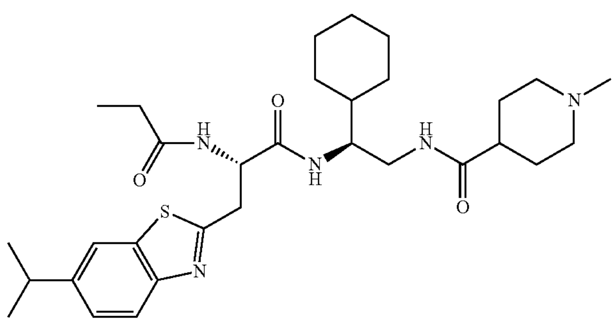 [SMILES: CCC(=O)N[C@@H](Cc1nc2ccc(C(C)C)cc2s1)C(=O)N[C@H](CNC(=O)C1CCN(C)CC1)C1CCCCC1] | 71.1 |
| DI-732DD | 124 | 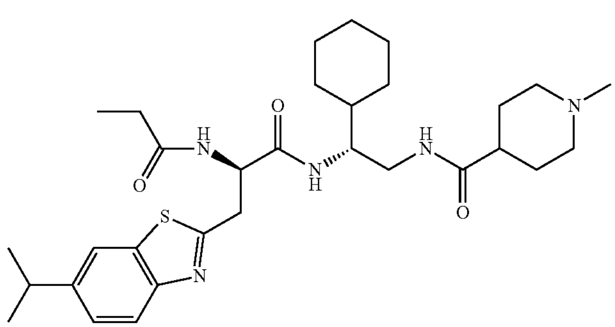 [SMILES: CCC(=O)N[C@H](Cc1nc2ccc(C(C)C)cc2s1)C(=O)N[C@@H](CNC(=O)C1CCN(C)CC1)C1CCCCC1] | >10 (μM) |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-733 | 61 | 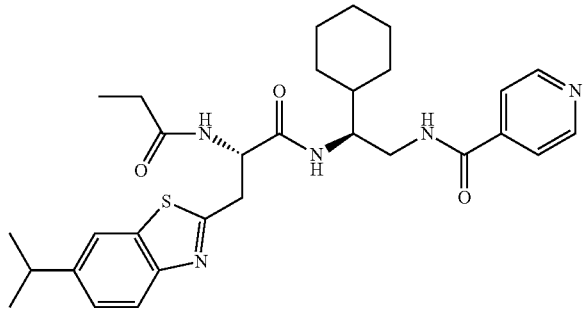 [SMILES: CCC(=O)N[C@@H](Cc1nc2ccc(C(C)C)cc2s1)C(=O)N[C@H](CNC(=O)c1ccncc1)C1CCCCC1] | 128 |
| DI-734 | 78 | 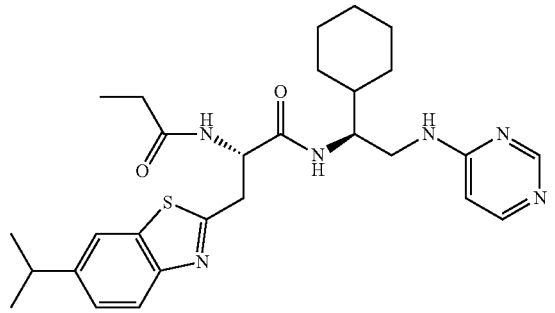 [SMILES: CCC(=O)N[C@@H](Cc1nc2ccc(C(C)C)cc2s1)C(=O)N[C@H](CNc1ccncn1)C1CCCCC1] | 189 |
| DI-735 | 85 | 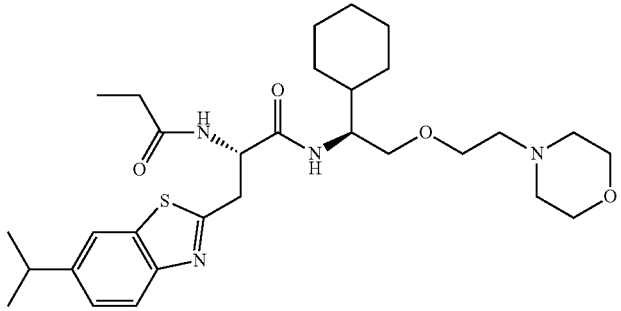 [SMILES: CCC(=O)N[C@@H](Cc1nc2ccc(C(C)C)cc2s1)C(=O)N[C@H](COCCN1CCOCC1)C1CCCCC1] | 138 |
| DI-736 | 262 | 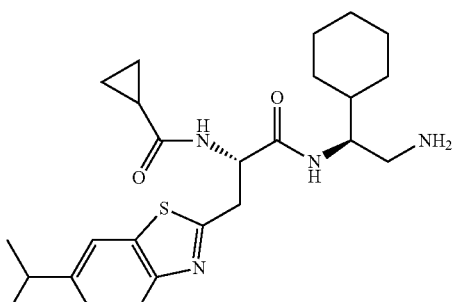 | 155 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-737 | 263 | 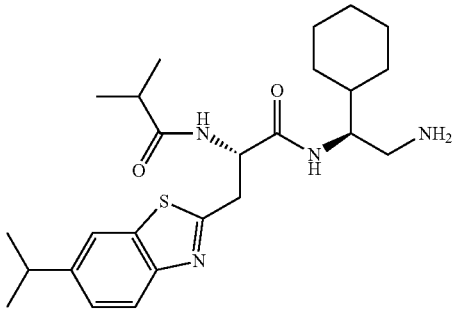 [SMILES: CC(C)C(=O)N[C@@H](Cc1nc2ccc(C(C)C)cc2s1)C(=O)N[C@H](CN)C1CCCCC1] DI-737 | 139 |
| DI-738 | 107 | 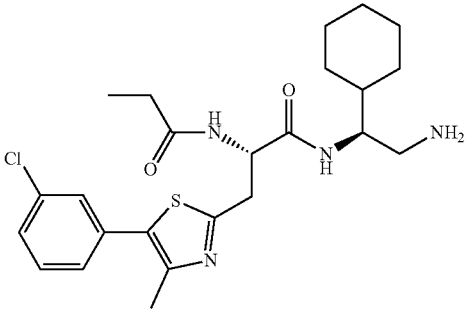 [SMILES: CCC(=O)N[C@@H](Cc1nc(C)c(-c2cccc(Cl)c2)s1)C(=O)N[C@H](CN)C1CCCCC1] | 704 |
| DI-739 | 53 | 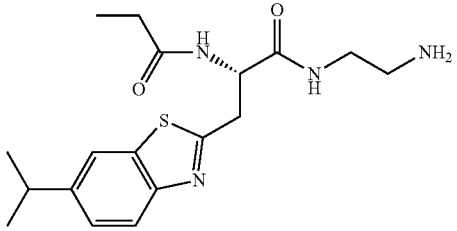 [SMILES: CCC(=O)N[C@@H](Cc1nc2ccc(C(C)C)cc2s1)C(=O)NCCN] | >10 μM |
| DI-740 | 95 | 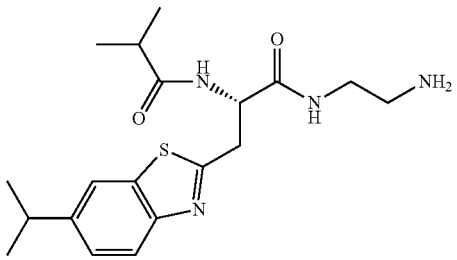 [SMILES: CC(C)C(=O)N[C@@H](Cc1nc2ccc(C(C)C)cc2s1)C(=O)NCCN] | >10 μM |
| DI-741 | 96 | 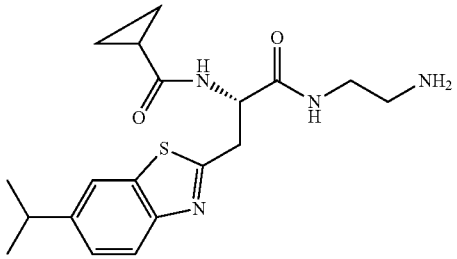 [SMILES: CC(C)c1ccc2nc(C[C@H](NC(=O)C3CC3)C(=O)NCCN)sc2c1] | >10 μM |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-742 | 97 & 98 | 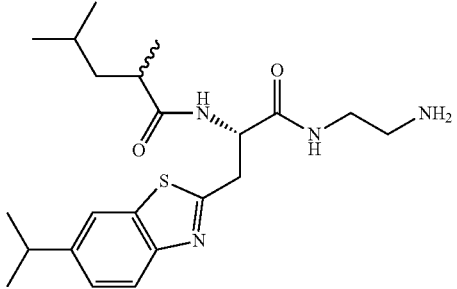 [SMILES: CC(C)CC(C)C(=O)N[C@@H](Cc1nc2ccc(C(C)C)cc2s1)C(=O)NCCN] | >10 μM |
| DI-743 | 264 | 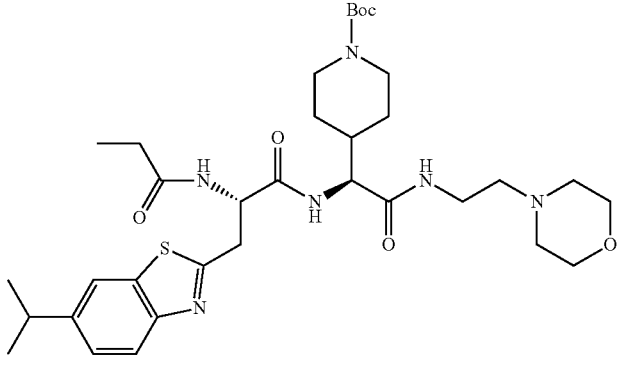 [SMILES: CCC(=O)N[C@@H](Cc1nc2ccc(C(C)C)cc2s1)C(=O)N[C@H](C(=O)NCCN1CCOCC1)C1CCN(C(=O)OC(C)(C)C)CC1] | 1502 |
| DI-745 | 265 | 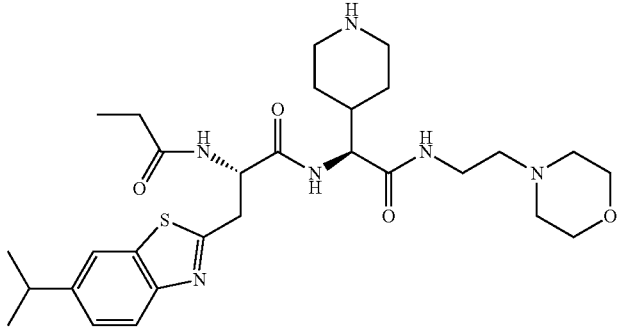 [SMILES: CCC(=O)N[C@@H](Cc1nc2ccc(C(C)C)cc2s1)C(=O)N[C@H](C(=O)NCCN1CCOCC1)C1CCNCC1] | >10 μM |
| DI-746 | 266 | 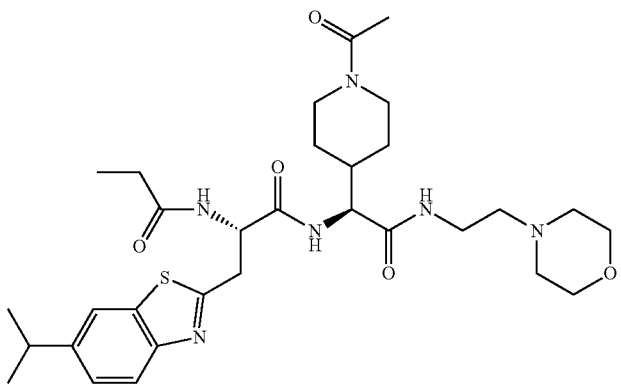 [SMILES: CCC(=O)N[C@@H](Cc1nc2ccc(C(C)C)cc2s1)C(=O)N[C@H](C(=O)NCCN1CCOCC1)C1CCN(C(C)=O)CC1] | |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-747 | 267 | 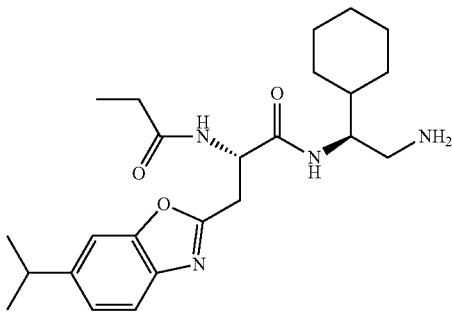 DI-747 | |
| DI-748 | 62 | 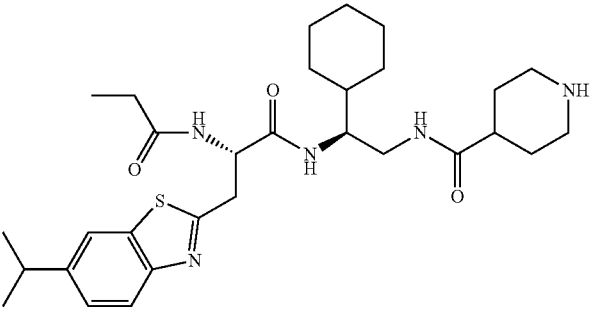 [SMILES: CCC(=O)N[C@@H](Cc1nc2ccc(C(C)C)cc2s1)C(=O)N[C@H](CNC(=O)C1CCNCC1)C1CCCCC1] | 25.9 |
| DI-749 | 77 | 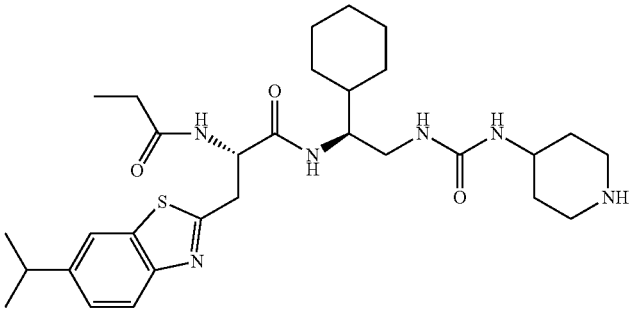 [SMILES: CCC(=O)N[C@@H](Cc1nc2ccc(C(C)C)cc2s1)C(=O)N[C@H](CNC(=O)NC1CCNCC1)C1CCCCC1] | 52.9 |
| DI-750 | 63 | 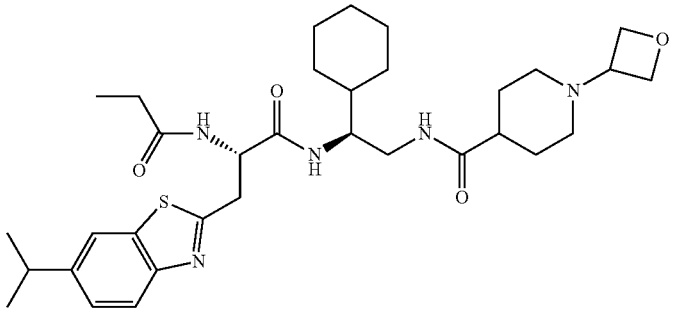 [SMILES: CCC(=O)N[C@@H](Cc1nc2ccc(C(C)C)cc2s1)C(=O)N[C@H](CNC(=O)C1CCN(C2COC2)CC1)C1CCCCC1] | 67.3 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-761 | 36 | DI-761 | |
| DI-762 | 84 | DI-762 | 241.9 |
| DI-763 | 64 | DI-763 | 36.0 |
| DI-764 | 65 | DI-764 | 118.6 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-765 | 268 | 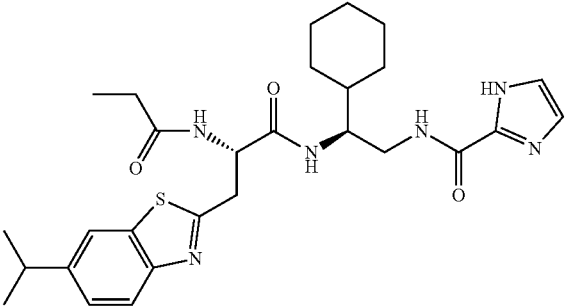 [SMILES: CCC(=O)N[C@@H](Cc1nc2ccc(C(C)C)cc2s1)C(=O)N[C@H](CNC(=O)c1ncc[nH]1)C1CCCCC1] DI-765 | 1208 |
| DI-766 | 66 | 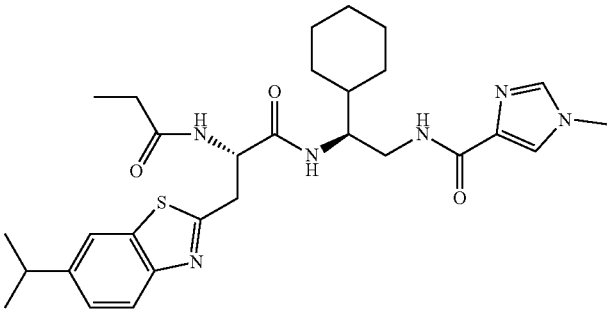 [SMILES: CCC(=O)N[C@@H](Cc1nc2ccc(C(C)C)cc2s1)C(=O)N[C@H](CNC(=O)c1cn(C)cn1)C1CCCCC1] DI-766 | 298.6 |
| DI-767 | 67 | 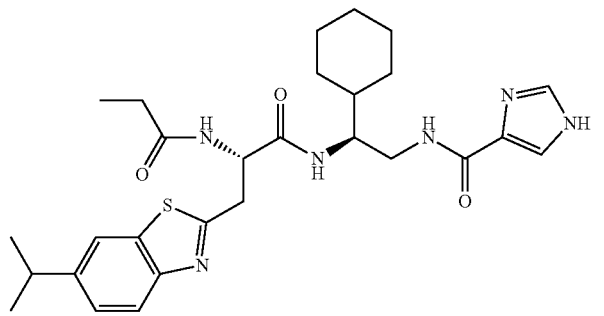 [SMILES: CCC(=O)N[C@@H](Cc1nc2ccc(C(C)C)cc2s1)C(=O)N[C@H](CNC(=O)c1c[nH]cn1)C1CCCCC1] DI-767 | 257.0 |
| DI-769 | 68 | 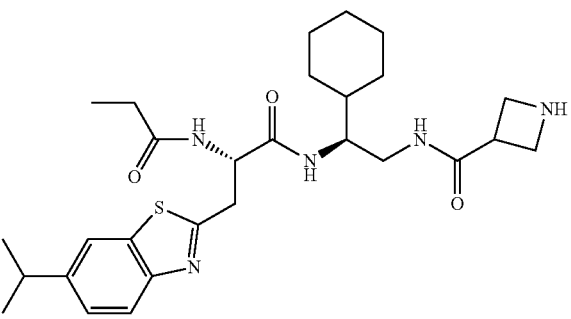 [SMILES: CCC(=O)N[C@@H](Cc1nc2ccc(C(C)C)cc2s1)C(=O)N[C@H](CNC(=O)C1CNC1)C1CCCCC1] DI-769 | 66.6 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-770 | 69 | DI-769 | 71.6 |
| DI-772 | 70 | 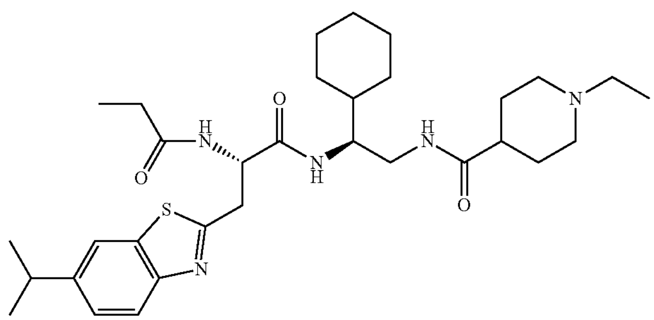 [SMILES: CCC(=O)N[C@@H](Cc1nc2ccc(C(C)C)cc2s1)C(=O)N[C@H](CNC(=O)C1CCN(CC)CC1)C1CCCCC1] | 45.1 |
| DI-773 | 71 | 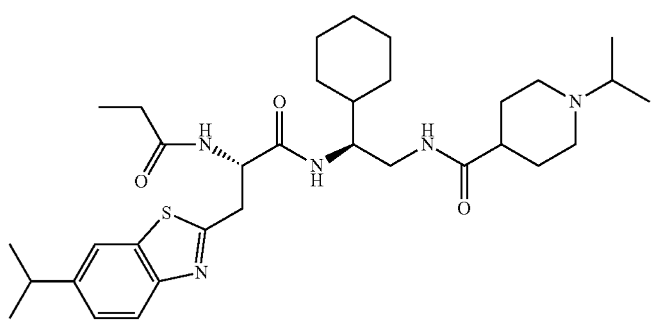 [SMILES: CCC(=O)N[C@@H](Cc1nc2ccc(C(C)C)cc2s1)C(=O)N[C@H](CNC(=O)C1CCN(C(C)C)CC1)C1CCCCC1] | 110 |
| DI-774 | 72 | 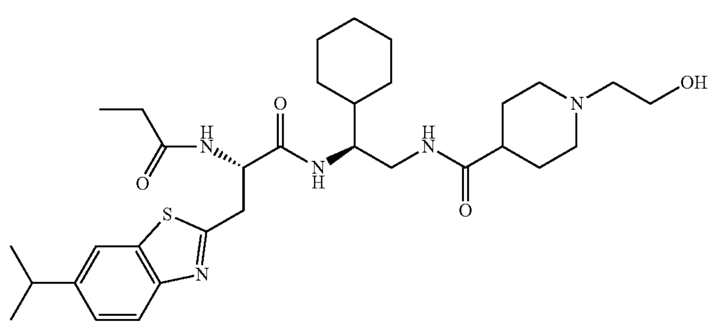 [SMILES: CCC(=O)N[C@@H](Cc1nc2ccc(C(C)C)cc2s1)C(=O)N[C@H](CNC(=O)C1CCN(CCO)CC1)C1CCCCC1] | 65.9 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-775 | 82 | DI-775 | 242.9 |
| DI-776 | 83 | DI-776 | 656.2 |
| DI-777 | 77 | DI-777 | 55.3 |
| DI-778 | 74 | DI-778 | 112.3 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-781 | 126 | 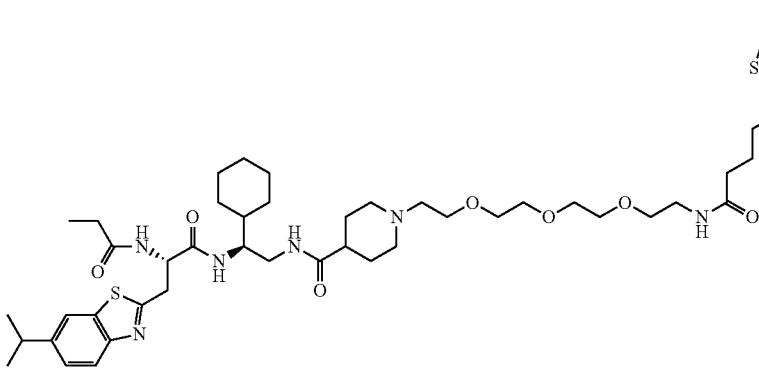<br>DI-781 | 29.6 |
| DI-782 | 127 | 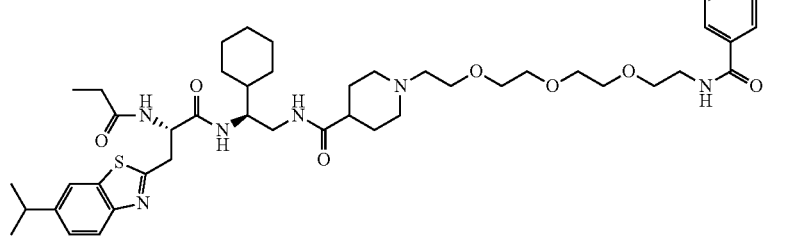<br>DI-782-fluorescein | Kd = 21.9 |
| DI-783 | 75 | 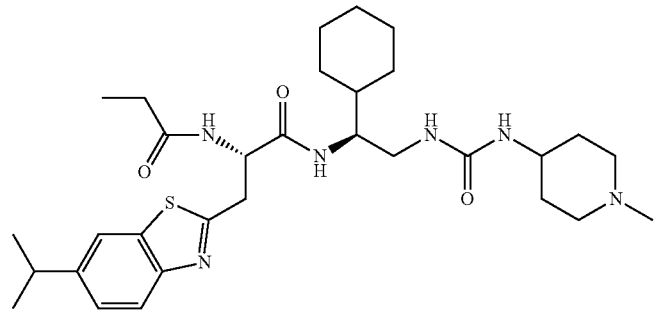 [SMILES: CCC(=O)N[C@@H](Cc1nc2ccc(C(C)C)cc2s1)C(=O)N[C@H](CNC(=O)NC1CCN(C)CC1)C1CCCCC1]<br>DI-783 | 75.6 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-784 | 76 | 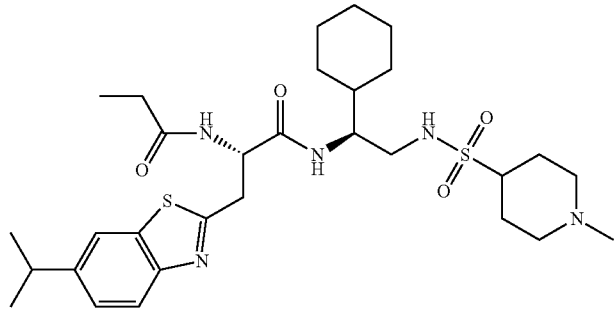 [SMILES: CCC(=O)N[C@@H](Cc1nc2ccc(C(C)C)cc2s1)C(=O)N[C@H](CNS(=O)(=O)C1CCN(C)CC1)C1CCCCC1] DI-784 | 65.7 |
| DI-789 | 109 | 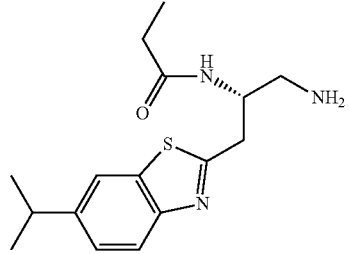 [SMILES: CCC(=O)N[C@H](CN)Cc1nc2ccc(C(C)C)cc2s1] DI-789 | >10 μM |
| DI-790 | 110 | 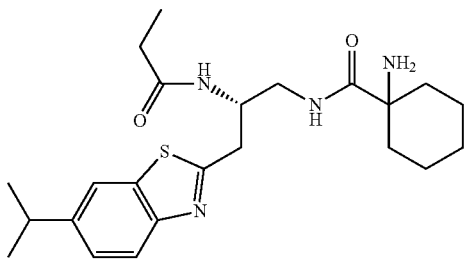 [SMILES: CCC(=O)N[C@H](CNC(=O)C1(N)CCCCC1)Cc1nc2ccc(C(C)C)cc2s1] DI-790 | 1905 |
| DI-791 | 269 | 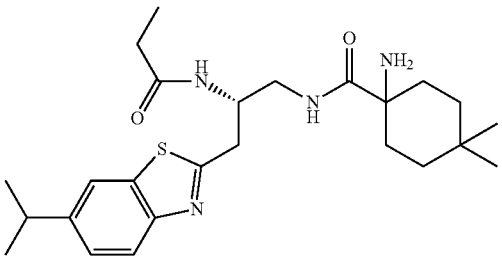 [SMILES: CCC(=O)N[C@H](CNC(=O)C1(N)CCC(C)(C)CC1)Cc1nc2ccc(C(C)C)cc2s1] DI-791 | >10 μM |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-792 | 111 | DI-792 | >5 µM |
| DI-793 | 112 | DI-793 | 5064 |
| DI-794 | 113 | DI-794 | 4110 |
| DI-795 | 114 | DI-795 | 1555 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-796 | 115 | 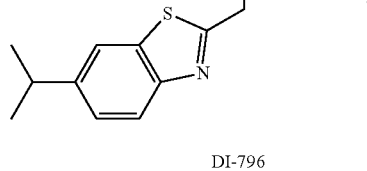<br>DI-796 | 2393 |
| DI-797 | 116 | 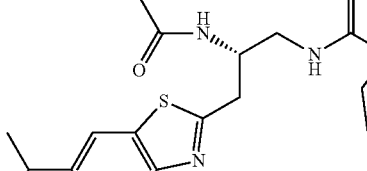<br>DI-797 | 2201 |
| DI-798 | 117 | 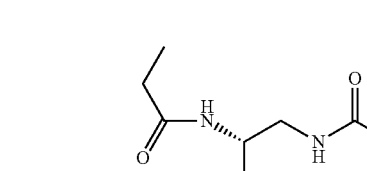<br>DI-798 | 875 |
| DI-799 | 118 | 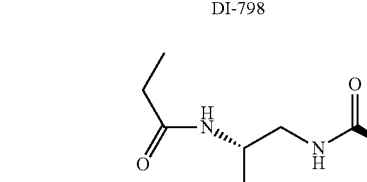<br>DI-799 | 3106 |

TABLE 1-continued
Chemical structures and binding affinities to DCN1 proteins
| ID | Number of Example | Chemical Structure | Binding affinity to DCN1 (IC50 (nM)) |
|---|---|---|---|
| DI-800 | 270 | 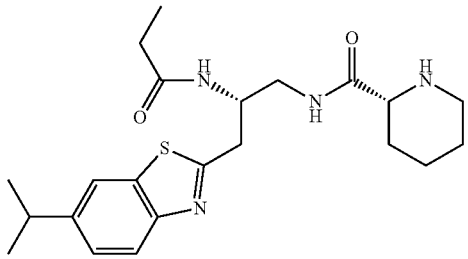 [SMILES: CCC(=O)N[C@H](CNC(=O)[C@H]1CCCCN1)Cc1nc2ccc(C(C)C)cc2s1] DI-800 | >10 μM |
| DI-801 | 2 | 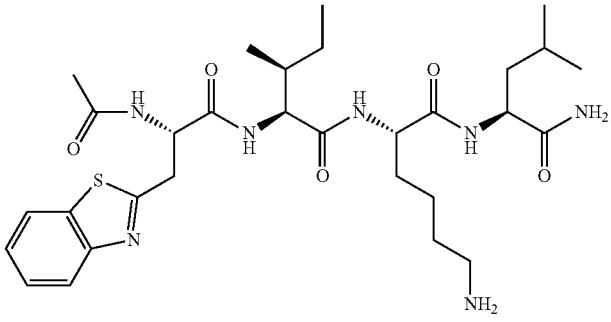 [SMILES: CC[C@H](C)[C@H](NC(=O)[C@H](Cc1nc2ccccc2s1)NC(C)=O)C(=O)N[C@@H](CCCCN)C(=O)N[C@@H](CC(C)C)C(N)=O] | 322 |
| DI-802 | 4 | 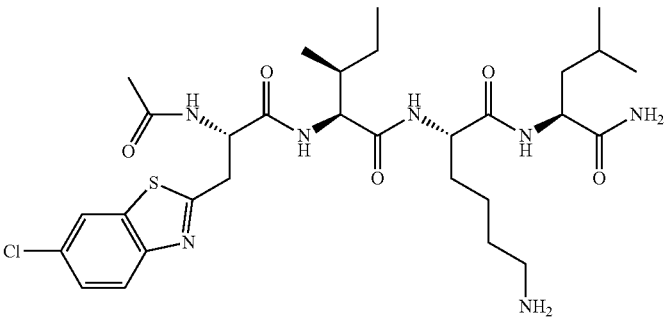 [SMILES: CC[C@H](C)[C@H](NC(=O)[C@H](Cc1nc2ccc(Cl)cc2s1)NC(C)=O)C(=O)N[C@@H](CCCCN)C(=O)N[C@@H](CC(C)C)C(N)=O] | 116 |
| DI-803 | 5 | 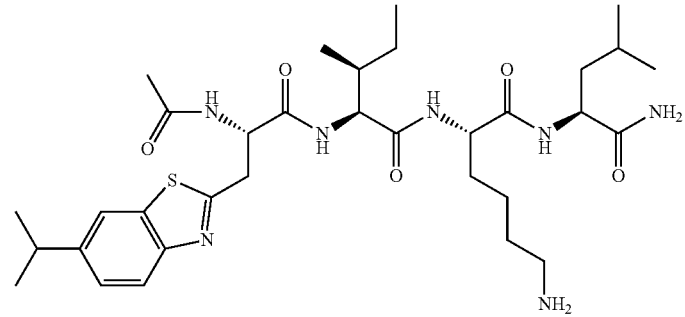 [SMILES: CC[C@H](C)[C@H](NC(=O)[C@H](Cc1nc2ccc(C(C)C)cc2s1)NC(C)=O)C(=O)N[C@@H](CCCCN)C(=O)N[C@@H](CC(C)C)C(N)=O] | 40.1 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-804 | 271 | 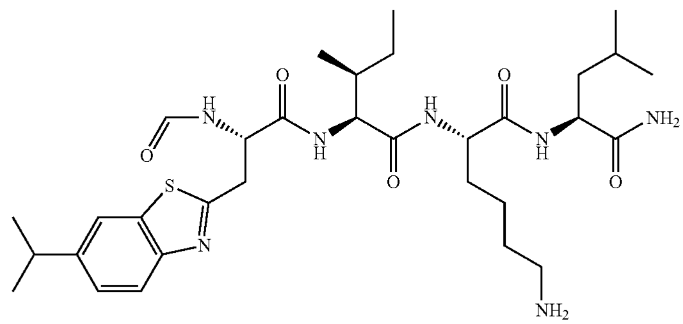 [SMILES: CC[C@H](C)[C@H](NC(=O)[C@H](Cc1nc2ccc(C(C)C)cc2s1)NC=O)C(=O)N[C@@H](CCCCN)C(=O)N[C@@H](CC(C)C)C(N)=O] | 122 |
| DI-805 | 272 | 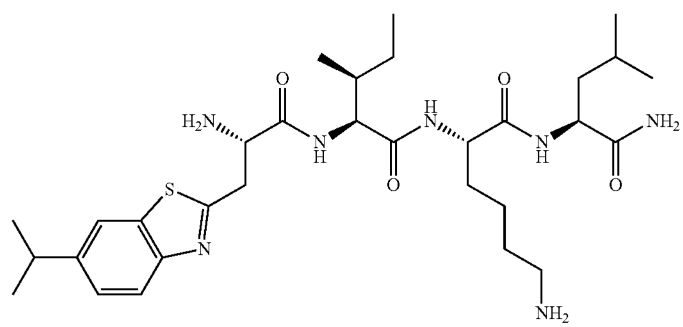 [SMILES: CC[C@H](C)[C@H](NC(=O)[C@@H](N)Cc1nc2ccc(C(C)C)cc2s1)C(=O)N[C@@H](CCCCN)C(=O)N[C@@H](CC(C)C)C(N)=O] | >10 μM |
| DI-806 | 273 | 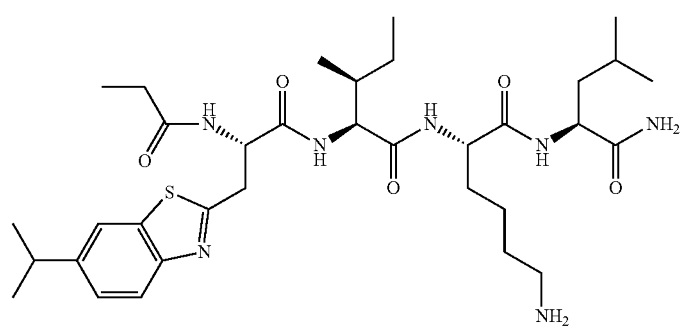 [SMILES: CCC(=O)N[C@@H](Cc1nc2ccc(C(C)C)cc2s1)C(=O)N[C@H](C(=O)N[C@@H](CCCCN)C(=O)N[C@@H](CC(C)C)C(N)=O)[C@@H](C)CC] | 51.0 |
| DI-807 | 274 | 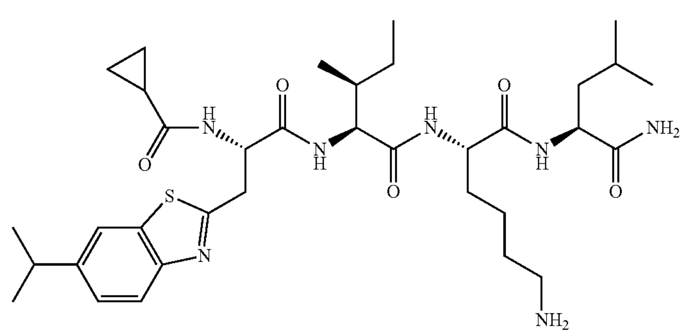 [SMILES: CC[C@H](C)[C@H](NC(=O)[C@H](Cc1nc2ccc(C(C)C)cc2s1)NC(=O)C1CC1)C(=O)N[C@@H](CCCCN)C(=O)N[C@@H](CC(C)C)C(N)=O] | 82.5 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-808 | 275 | 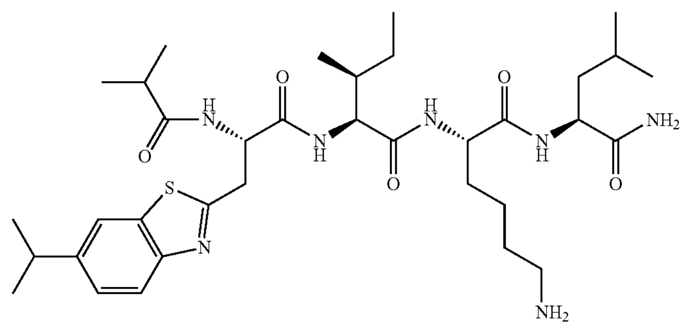 [SMILES: CC[C@H](C)[C@H](NC(=O)[C@H](Cc1nc2ccc(C(C)C)cc2s1)NC(=O)C(C)C)C(=O)N[C@@H](CCCCN)C(=O)N[C@@H](CC(C)C)C(N)=O] | 77.8 |
| DI-809 | 276 | 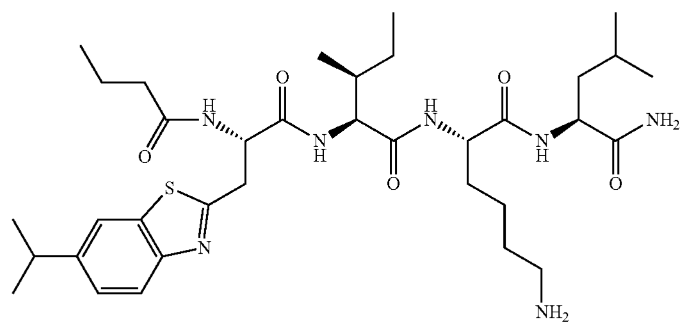 [SMILES: CCCC(=O)N[C@@H](Cc1nc2ccc(C(C)C)cc2s1)C(=O)N[C@H](C(=O)N[C@@H](CCCCN)C(=O)N[C@@H](CC(C)C)C(N)=O)[C@@H](C)CC] | 109 |
| DI-810 | 277 | 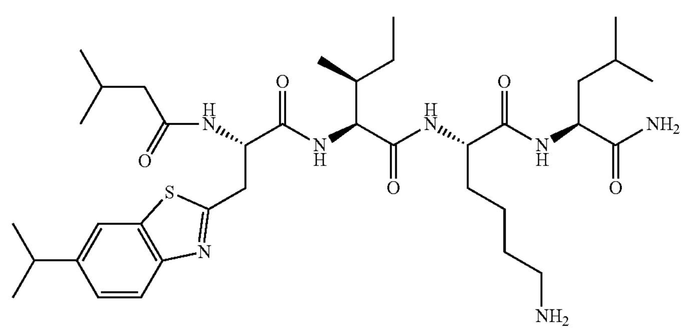 [SMILES: CC[C@H](C)[C@H](NC(=O)[C@H](Cc1nc2ccc(C(C)C)cc2s1)NC(=O)CC(C)C)C(=O)N[C@@H](CCCCN)C(=O)N[C@@H](CC(C)C)C(N)=O] | 517 |
| DI-811 | 278 | 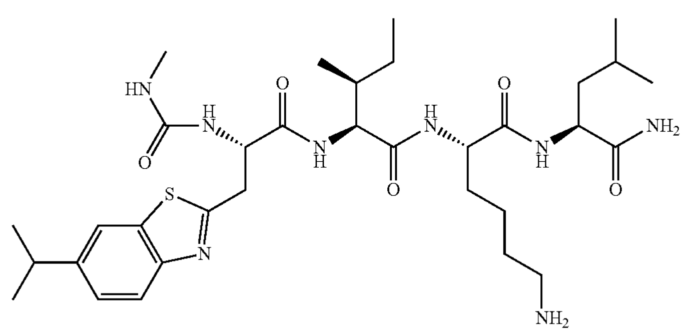 [SMILES: CC[C@H](C)[C@H](NC(=O)[C@H](Cc1nc2ccc(C(C)C)cc2s1)NC(=O)NC)C(=O)N[C@@H](CCCCN)C(=O)N[C@@H](CC(C)C)C(N)=O] | 68.2 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-812 | 279 | 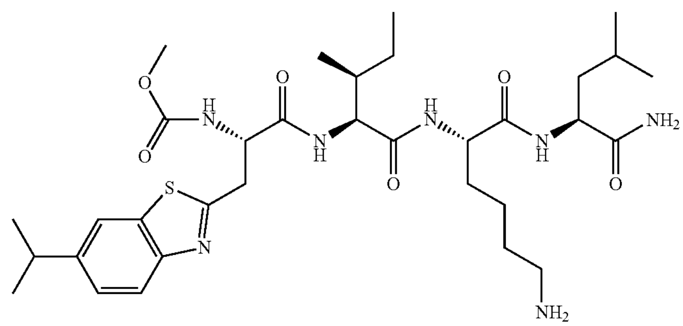 [SMILES: CC[C@H](C)[C@H](NC(=O)[C@H](Cc1nc2ccc(C(C)C)cc2s1)NC(=O)OC)C(=O)N[C@@H](CCCCN)C(=O)N[C@@H](CC(C)C)C(N)=O] | 217 |
| DI-813 | 280 | 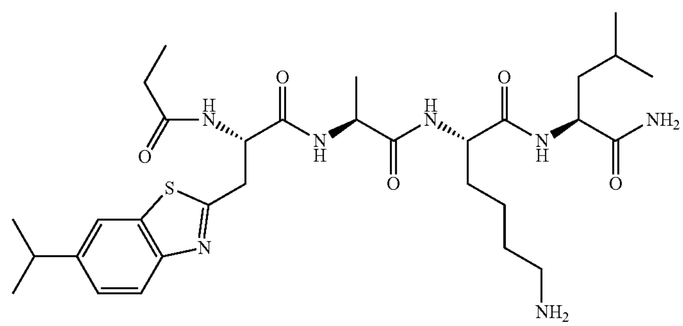 [SMILES: CCC(=O)N[C@@H](Cc1nc2ccc(C(C)C)cc2s1)C(=O)N[C@@H](C)C(=O)N[C@@H](CCCCN)C(=O)N[C@@H](CC(C)C)C(N)=O] | 69.4 |
| DI-814 | 281 | 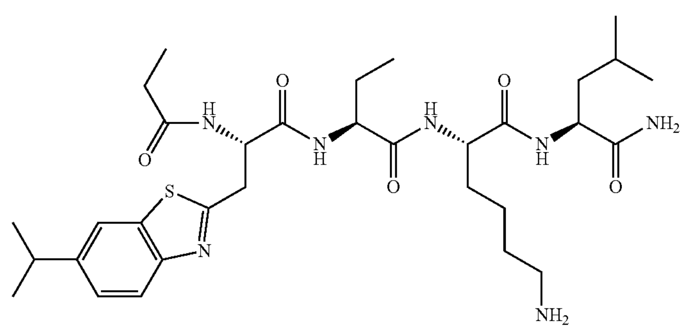 [SMILES: CCC(=O)N[C@@H](Cc1nc2ccc(C(C)C)cc2s1)C(=O)N[C@@H](CC)C(=O)N[C@@H](CCCCN)C(=O)N[C@@H](CC(C)C)C(N)=O] | 37.4 |
| DI-815 | 282 | 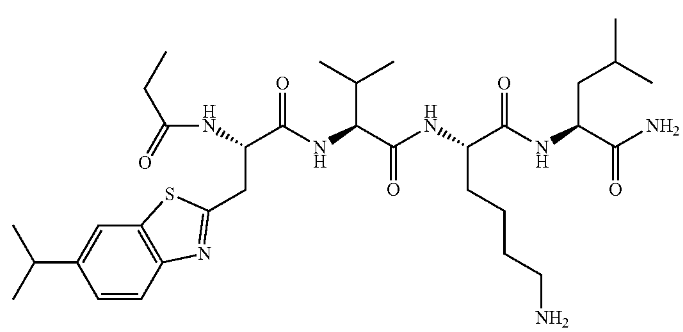 [SMILES: CCC(=O)N[C@@H](Cc1nc2ccc(C(C)C)cc2s1)C(=O)N[C@H](C(=O)N[C@@H](CCCCN)C(=O)N[C@@H](CC(C)C)C(N)=O)C(C)C] | 72.0 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-816 | 283 | 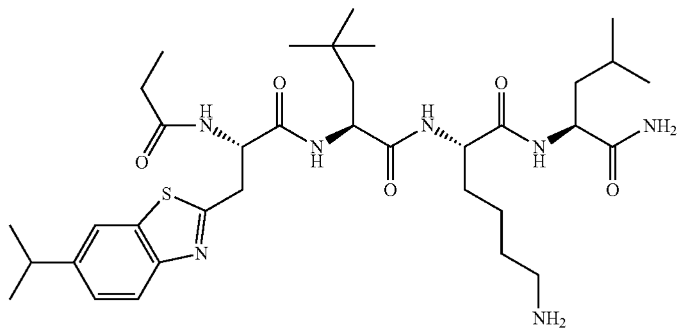 [SMILES: CCC(=O)N[C@@H](Cc1nc2ccc(C(C)C)cc2s1)C(=O)N[C@@H](CC(C)(C)C)C(=O)N[C@@H](CCCCN)C(=O)N[C@@H](CC(C)C)C(N)=O] | 83.0 |
| DI-817 | 284 | 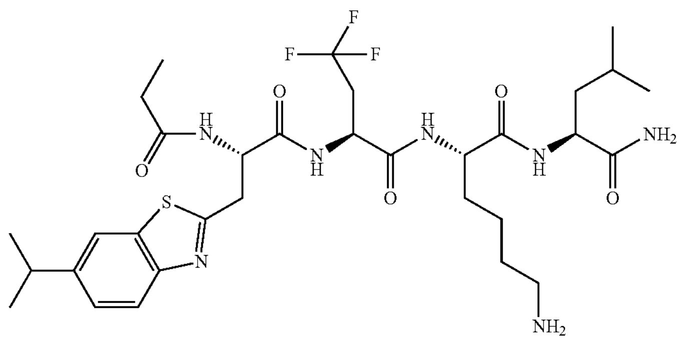 [SMILES: CCC(=O)N[C@@H](Cc1nc2ccc(C(C)C)cc2s1)C(=O)N[C@@H](CC(F)(F)F)C(=O)N[C@@H](CCCCN)C(=O)N[C@@H](CC(C)C)C(N)=O] | 153.8 |
| DI-818 | 285 | 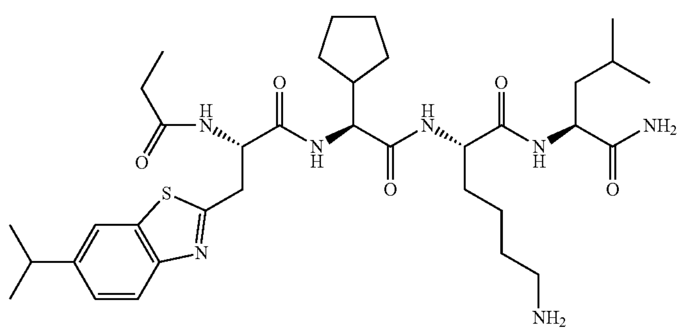 [SMILES: CCC(=O)N[C@@H](Cc1nc2ccc(C(C)C)cc2s1)C(=O)N[C@H](C(=O)N[C@@H](CCCCN)C(=O)N[C@@H](CC(C)C)C(N)=O)C1CCCC1] | <100 |
| DI-819 | 286 | 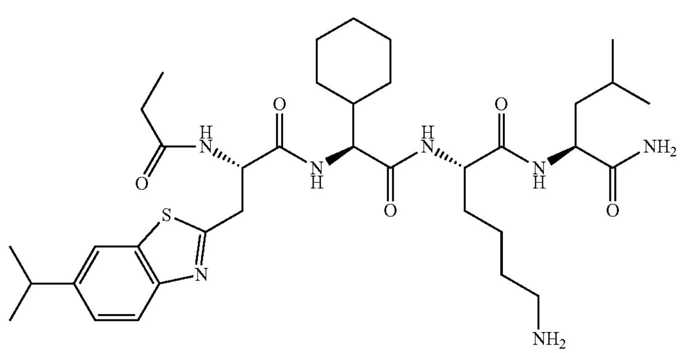 [SMILES: CCC(=O)N[C@@H](Cc1nc2ccc(C(C)C)cc2s1)C(=O)N[C@H](C(=O)N[C@@H](CCCCN)C(=O)N[C@@H](CC(C)C)C(N)=O)C1CCCCC1] | 58.3 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-820 | 2287 | 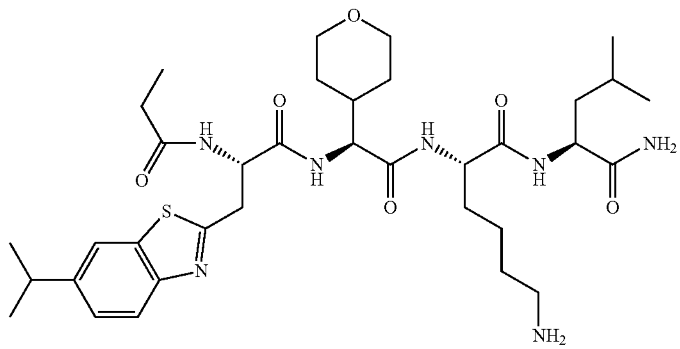 [SMILES: CCC(=O)N[C@@H](Cc1nc2ccc(C(C)C)cc2s1)C(=O)N[C@H](C(=O)N[C@@H](CCCCN)C(=O)N[C@@H](CC(C)C)C(N)=O)C1CCOCC1] | 279.9 |
| DI-821 | 288 | 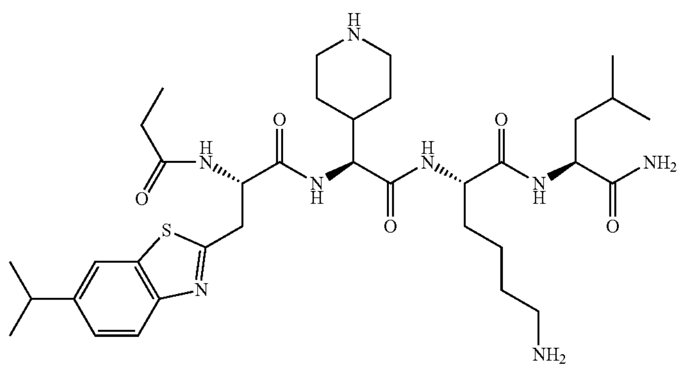 [SMILES: CCC(=O)N[C@@H](Cc1nc2ccc(C(C)C)cc2s1)C(=O)N[C@H](C(=O)N[C@@H](CCCCN)C(=O)N[C@@H](CC(C)C)C(N)=O)C1CCNCC1] | >10 μM |
| DI-822 | 289 | 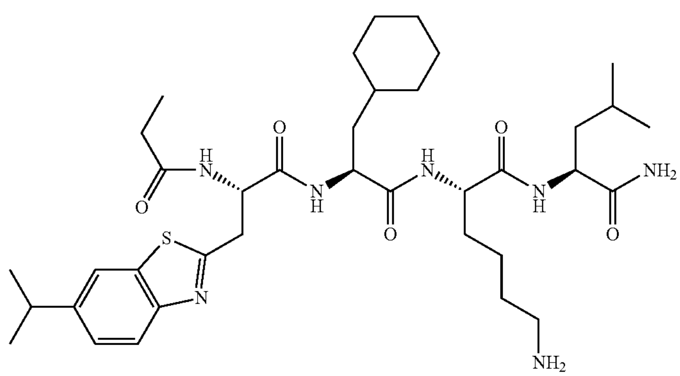 [SMILES: CCC(=O)N[C@@H](Cc1nc2ccc(C(C)C)cc2s1)C(=O)N[C@@H](CC1CCCCC1)C(=O)N[C@@H](CCCCN)C(=O)N[C@@H](CC(C)C)C(N)=O] | 137.9 |
| DI-823 | 290 | 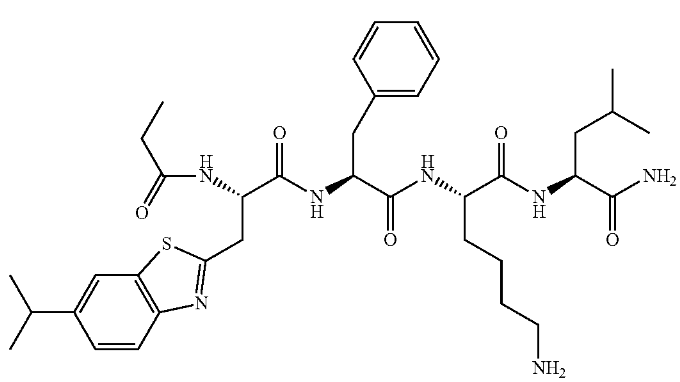 [SMILES: CCC(=O)N[C@@H](Cc1nc2ccc(C(C)C)cc2s1)C(=O)N[C@@H](Cc1ccccc1)C(=O)N[C@@H](CCCCN)C(=O)N[C@@H](CC(C)C)C(N)=O] | 55.6 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-824 | 291 | 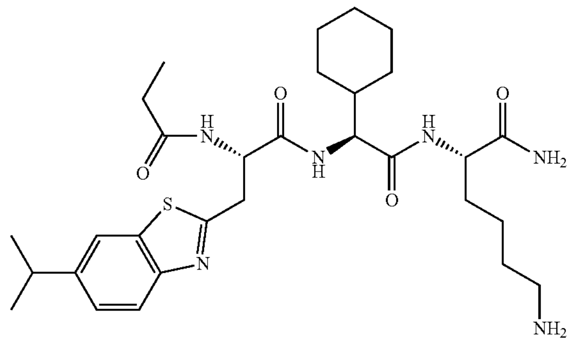 [SMILES: CCC(=O)N[C@@H](Cc1nc2ccc(C(C)C)cc2s1)C(=O)N[C@H](C(=O)N[C@@H](CCCCN)C(N)=O)C1CCCCC1] | 116 |
| DI-825 | 120 | 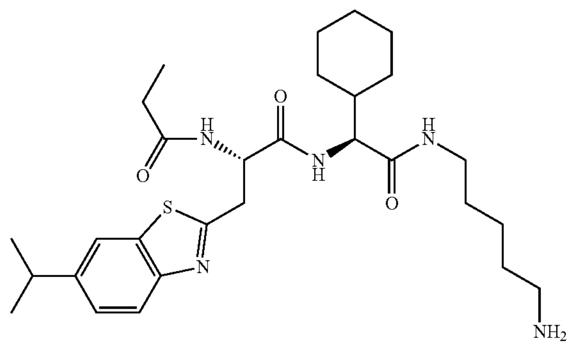 [SMILES: CCC(=O)N[C@@H](Cc1nc2ccc(C(C)C)cc2s1)C(=O)N[C@H](C(=O)NCCCCCN)C1CCCCC1] | |
| DI-826 | 121 | 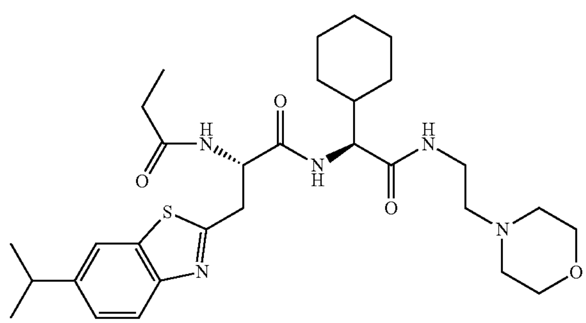 [SMILES: CCC(=O)N[C@@H](Cc1nc2ccc(C(C)C)cc2s1)C(=O)N[C@H](C(=O)NCCN1CCOCC1)C1CCCCC1] | |
| DI-827 | 6 | 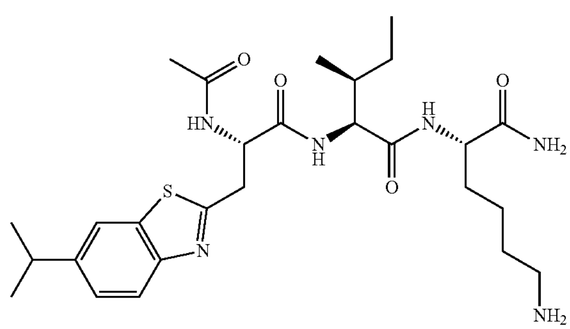 [SMILES: CC[C@H](C)[C@H](NC(=O)[C@H](Cc1nc2ccc(C(C)C)cc2s1)NC(C)=O)C(=O)N[C@@H](CCCCN)C(N)=O] | 632 ± 29 |

DI-827

TABLE 1-continued

Chemical structures and binding affinities to DCN1 proteins

| ID | Number of Example | Chemical Structure | Binding affinity to DCN1 (IC50 (nM)) |
|---|---|---|---|
| DI-828 | 7 | (structure DI-828) | 1036 ± 128 |
| DI-829 | 46 | (structure DI-829) | 281 ± 29 |
| DI-830 | 47 | (structure DI-830) | 95.0 ± 15.8 |
| DI-831 | 3 | (structure DI-831) | 9.2 ± 1.4 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-832 | 54 | 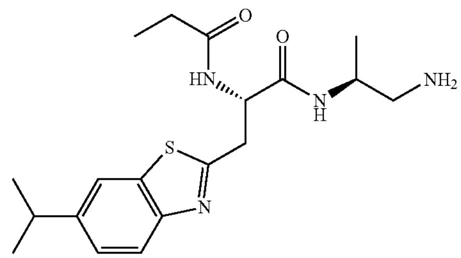 [SMILES: CCC(=O)N[C@@H](Cc1nc2ccc(C(C)C)cc2s1)C(=O)N[C@@H](C)CN] | >10 μM |
| DI-833 | 48 | 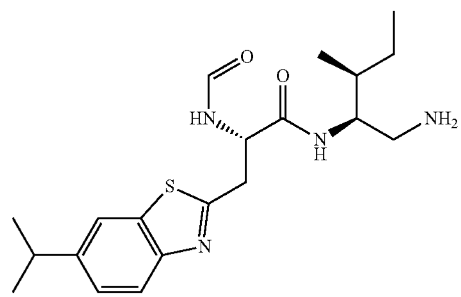 [SMILES: CC[C@H](C)[C@@H](CN)NC(=O)[C@H](Cc1nc2ccc(C(C)C)cc2s1)NC=O] | >5 μM |
| DI-834 | 49 | 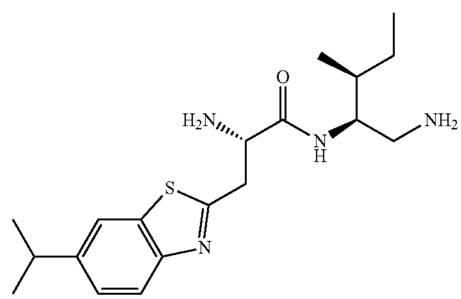 [SMILES: CC[C@H](C)[C@@H](CN)NC(=O)[C@@H](N)Cc1nc2ccc(C(C)C)cc2s1] | >10 μM |
| DI-835 | 50 | 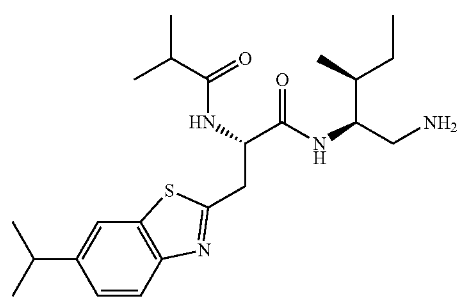 [SMILES: CC[C@H](C)[C@@H](CN)NC(=O)[C@H](Cc1nc2ccc(C(C)C)cc2s1)NC(=O)C(C)C] | 255 ± 29 |
| DI-836 | 51 | 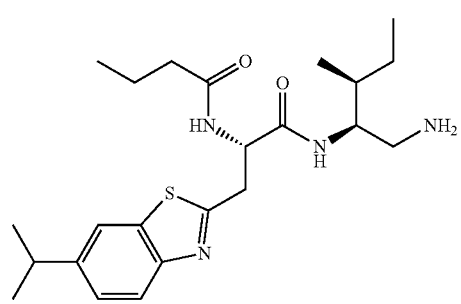 [SMILES: CCCC(=O)N[C@@H](Cc1nc2ccc(C(C)C)cc2s1)C(=O)N[C@H](CN)[C@@H](C)CC] | 944 ± 176 |

TABLE 1-continued

Chemical structures and binding affinities to DCN1 proteins

| ID | Number of Example | Chemical Structure | Binding affinity to DCN1 (IC50 (nM)) |
|---|---|---|---|
| DI-837 | 52 | 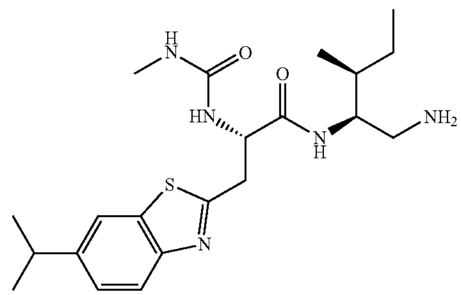 [SMILES: CC[C@H](C)[C@@H](CN)NC(=O)[C@H](Cc1nc2ccc(C(C)C)cc2s1)NC(=O)NC] | 558 ± 125 |
| DI-751 | 125 | Exact Mass: 753.3747<br>Molecular Weight: 753.9232 | 31.5 |
| DI06 | 1 | DI-06 | >10 μM |

The present invention provides DCN1 inhibitors of structural formula (I) for the treatment of a variety of diseases and conditions wherein inhibition of DCN1 provides a beneficial effect. In one embodiment, the present invention relates to a method of treating an individual suffering from a disease or condition wherein inhibition of the DCN1 provides a benefit comprising administering a therapeutically effective amount of a compound of structural formula (I) to an individual in need thereof.

The method of the present invention can be accomplished by administering a compound of structural formula (I) as the neat compound or as a pharmaceutical composition. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of DCN1 provides a benefit, packaged separately or together, and an insert having instructions for using these active agents.

In many embodiments, a compound of structural formula (I) is administered in conjunction with a second therapeutic agent useful in the treatment of a disease or condition wherein inhibition of DCN1 provides a benefit. The second therapeutic agent is different from the compound of structural formula (I). A compound of structural formula (I) and the second therapeutic agent can be administered simultaneously or sequentially to achieve the desired effect. In addition, the compound of structural formula (I) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered. The compounds of structural formula (I) therefore can be used in conjunction with one or more second therapeutic agents, for example, but not limited to, anticancer agents. It is envisioned that one or more dose of a DCN1 inhibitor of structural formula (I) and/or one or more dose of a second therapeutic agent can be administered.

A present DCN1 inhibitor can be used in the treatment of a variety of diseases and conditions, including for example, metabolic disorders, oxidative stress-related diseases, cardiovascular diseases, neurodegenerative diseases, viral infections, inflammation, acute lung injury, chronic obstructive pulmonary diseases, metabolic disorders, multiple sclerosis, inflammation, cancer, and autoimmune disease.

In the present method, a therapeutically effective amount of a compound of structural formula (I), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects.

Toxicity and therapeutic efficacy of the compounds of structural formula (I) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the DCN1 inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present DCN1 inhibitor can be administered at a frequency of: one dose per day for 2 days with rest for 5 days for 2 weeks; one dose per day for 3 days with rest for 4 days for 3 weeks; weekly dosing for 2 weeks; weekly dosing for 4 weeks; or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a DCN1 inhibitor of structural formula (I) or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 g/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

The chemotherapeutic agent can be any pharmacological agent or compound that induces apoptosis. The pharmacological agent or compound can be, for example, a small organic molecule, peptide, polypeptide, nucleic acid, or antibody Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a DCN1 inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the DCN1 inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

In addition to its use in therapeutic medicine, compounds of structural formula (I), and pharmaceutically acceptable salts thereof, also are useful as pharmacological tools in the development and standardization of in vitro and in vivo test systems for the evaluation of the effects of inhibitors of DCN1 in laboratory animals, such as cats, dogs, rabbits, monkeys, rats, and mice, as part of the search for new therapeutic agents.

In accordance with an important feature of the present invention, compounds of structural formula (I) were synthesized and evaluated as inhibitors for DCN1. For example, compounds of the present invention typically have a binding affinity ($IC_{50}$) to DCN1 of less than 500 nM.

Compounds of structural formula (I) were prepared using the following synthetic procedures.

Synthesis of intermediates amino acids:

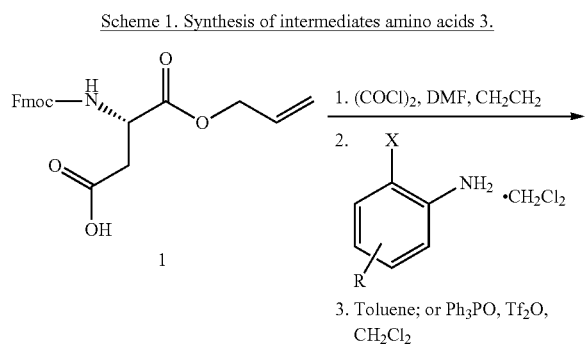

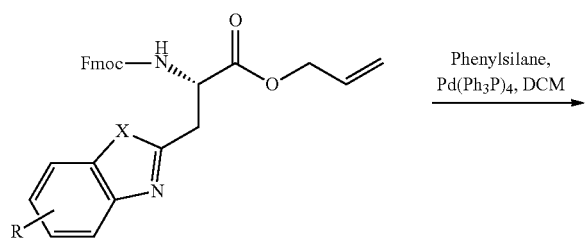

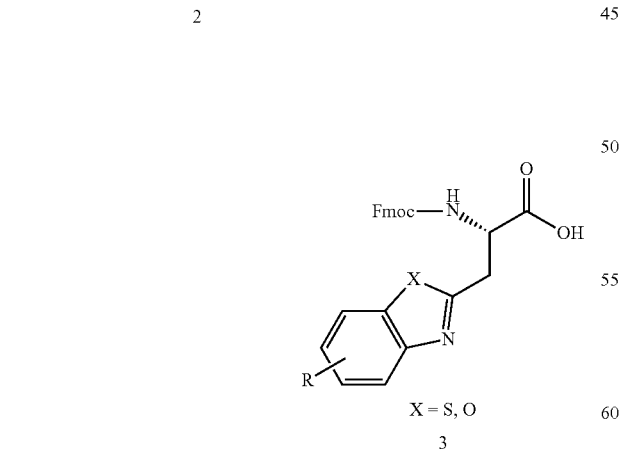

As shown in scheme 1, compounds 3 were afforded by transforming the carboxylic acid of compound 1 to benzothiazoles. A reported method[1] was employed for form the benzothiazole ring.

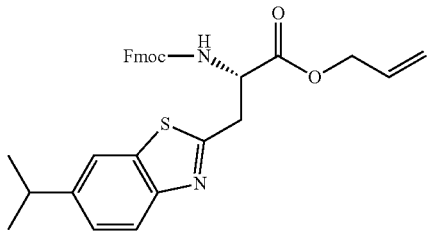

Allyl (S)-2-((((9H-fluoren-9-yl)methoxy)carbonyl) amino)-3-(6-isopropylbenzo[d]thiazol-2-yl)propanoate (2a)

To a solution of (S)-3-((((9H-fluoren-9-yl)methoxy)carbonyl)amino)-4-(allyloxy)-4-oxobutanoic acid (1, 5 g, 12.6 mmol) in $CH_2Cl_2$ (300 mL) was added oxalyl chloride (3.3 mL, 38.0 mmol) and catalytic amount of DMF at 0° C. The reaction mixture was concentrated after being stirred for 0.5 h. The residue was suspended in toluene (250 mL) and treated with 2-amino-5-isopropylbenzenethiol (2.1 g, 12.6 mmol). The resultant mixture was stirred overnight at room temperature. The solution was diluted with EtOAc and washed with saturated sodium bicarbonate, 1.0 M HCl, brine and dried over sodium sulfate. The solvent was evaporated and the crude product was purified by flash chromatography on silica gel to afford intermediate 2a (3.5 g, 53%). $^1$H NMR (400 MHz, $CDCl_3$) δ 7.98 (d, J=8.4 Hz, 1H), 7.86-7.75 (m, 2H), 7.72 (s, 1H), 7.65 (t, J=7.1 Hz, 2H), 7.49-7.36 (m, 3H), 7.33-7.27 (m, 2H), 6.46 (d, J=8.5 Hz, 1H), 5.98-5.88 (m, 1H), 5.36 (d, J=17.2 Hz, 1H), 5.25 (dd, J=10.4, 0.8 Hz, 1H), 5.02 (dt, J=8.5, 5.3 Hz, 1H), 4.72 (d, J=4.9 Hz, 2H), 4.46 (d, J=7.3 Hz, 2H), 4.30 (t, J=7.3 Hz, 1H), 3.75 (qd, J=15.7, 5.3 Hz, 2H), 3.08 (dt, J=13.7, 6.9 Hz, 1H), 1.37 (d, J=6.9 Hz, 6H). $^{13}$C NMR (101 MHz, $CDCl_3$) δ 170.46, 165.13, 156.11, 151.53, 146.40, 143.98, 143.89, 141.35, 135.55, 131.60, 127.75, 127.14, 125.38, 125.30, 122.69, 120.04, 118.86, 118.74, 67.36, 66.42, 53.35, 47.19, 35.76, 34.30, 24.30. UPLC-MS (ESI-MS) m/z: calculated for $C_{31}H_{31}N_2O_4S^+$ 527.20, found 527.26 $[M+H]^+$.

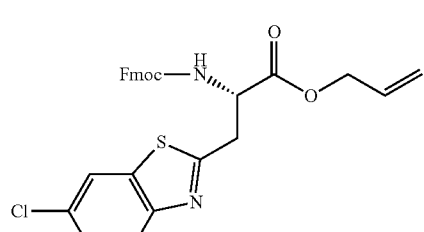

Allyl (S)-2-((((9H-fluoren-9-yl)methoxy)carbonyl) amino)-3-(6-chlorobenzo[d]thiazol-2-yl)propanoate (2b)

Intermediate 2b was prepared in 46% yield by a similar procedure as that for 2a. $^1$H NMR (300 MHz, $CDCl_3$) δ 7.91 (d, J=8.7 Hz, 1H), 7.84 (d, J=1.4 Hz, 1H), 7.78 (d, J=7.3 Hz, 2H), 7.67-7.54 (m, 2H), 7.52-7.37 (m, 3H), 7.36-7.22 (m, 2H), 6.12 (d, J=8.1 Hz, 1H), 5.95-5.82 (m, 1H), 5.32 (d, J=17.3 Hz, 1H), 5.23 (d, J=10.3 Hz, 1H), 5.03-4.85 (m, 1H), 4.68 (d, J=5.1 Hz, 2H), 4.43 (d, J=7.1 Hz, 2H), 4.27 (t, J=7.0 Hz, 1H), 3.71 (qd, J=15.8, 4.9 Hz, 2H). $^{13}$C NMR (75 MHz, CDCl$_3$) δ 170.16, 166.49, 155.90, 151.56, 143.72, 141.31, 136.40, 131.32, 131.20, 127.74, 127.07, 126.97, 125.15, 123.70, 121.17, 120.02, 119.05, 67.30, 66.52, 52.98, 47.11, 35.79.

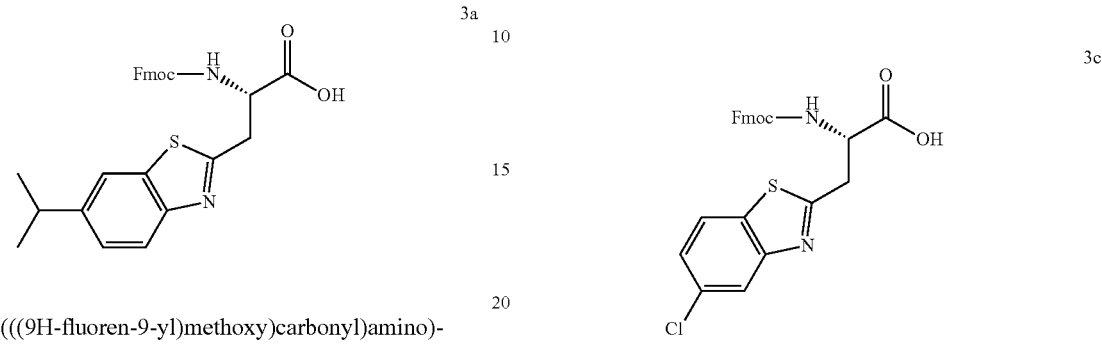

(S)-2-((((9H-fluoren-9-yl)methoxy)carbonyl)amino)-3-(6-isopropylbenzo[d]thiazol-2-yl)propanoic acid (3a)

Phenylsilane (1.9 g, 17.1 mmol) was added to a solution of 2a (3.0 g, 5.7 mmol) and Tetrakis(triphenylphosphine)palladium(0) (658 mg, 0.57 mmol) in DCM. The resultant solution was stirred 1 h before being concentrated. The residue was purified by flash chromatography on silica gel to afford 3a (2.24 g, 81%). H NMR (400 MHz, DMSO) δ 8.01-7.82 (m, 5H), 7.64 (dd, J=11.7, 7.6 Hz, 2H), 7.41-7.37 (m, 3H), 7.29-7.25 (m, 1H), 7.23-7.13 (m, 1H), 4.57-4.51 (m, 1H), 4.30-4.16 (m, 3H), 3.60 (dd, J=15.1, 4.6 Hz, 1H), 3.44 (dd, J=15.0, 9.9 Hz, 1H), 3.03 (dt, J=13.7, 6.8 Hz, 1H), 1.26 (d, J=6.9 Hz, 6H). $^{13}$C NMR (101 MHz, DMSO) δ 172.71, 167.25, 156.39, 151.46, 146.13, 144.23, 144.14, 141.15, 135.65, 128.06, 127.49, 125.71, 125.65, 125.51, 122.45, 120.55, 119.48, 66.18, 54.10, 47.04, 35.53, 33.97, 24.55, 24.54. UPLC-MS (ESI-MS) m/z: calculated for $C_{28}H_{27}N_2O_4S^+$ 487.17, found 487.19 [M+H]$^+$.

(S)-2-((((9H-fluoren-9-yl)methoxy)carbonyl)amino)-3-(6-chlorobenzo[d]thiazol-2-yl)propanoic acid (3b)

Intermediate 3b was prepared from 2b in 79% yield by a similar procedure as that for 3a. $^1$H NMR (300 MHz, CD$_3$OD:CCl$_3$D=1:10) δ 7.84 (d, J=8.7 Hz, 1H), 7.78 (d, J=2.0 Hz, 1H), 7.72 (d, J=7.5 Hz, 2H), 7.57-7.54 (m, 2H), 7.43-7.30 (m, 3H), 7.24 (t, J=7.4 Hz, 2H), 4.95-4.66 (m, 1H), 4.45-4.25 (m, 2H), 4.19 (t, J=7.0 Hz, 1H), 3.67-3.64 (m, 2H). $^{13}$C NMR (75 MHz, CD$_3$OD:CCl$_3$D=1:10) δ 172.19, 167.48, 156.13, 151.13, 143.66, 141.24, 136.32, 131.19, 127.68, 127.02, 126.96, 125.06, 123.37, 121.15, 119.93, 67.15, 52.92, 47.03, 35.67. UPLC-MS (ESI-MS) m/z: calculated for $C_{25}H_{20}ClN_2O_4S^+$ 479.08, found 479.19 [M+H]$^+$.

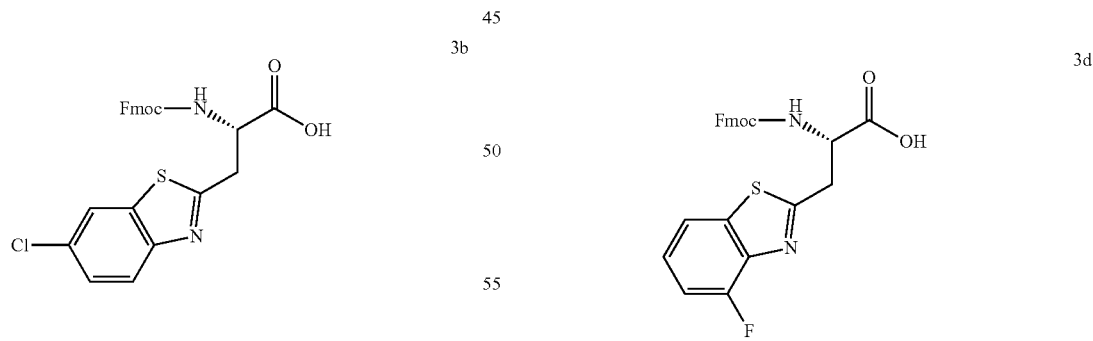

(S)-2-((((9H-fluoren-9-yl)methoxy)carbonyl)amino)-3-(5-chlorobenzo[d]thiazol-2-yl)propanoic acid (3c)

Intermediate 3c was prepared from 1 in 41% yield in two steps using a similar procedure as that for 3a. $^1$H NMR (400 MHz, DMSO) δ 13.04 (br, 1H), 8.11 (d, J=8.6 Hz, 1H), 8.02 (d, J=1.9 Hz, 1H), 7.93 (d, J=8.6 Hz, 1H), 7.88 (d, J=7.5 Hz, 2H), 7.67-7.94 (m, 2H), 7.48 (dd, J=8.6, 2.0 Hz, 1H), 7.41-7.38 (m, 2H), 7.30-7.22 (m, 2H), 4.54 (td, J=9.5, 4.6 Hz, 1H), 4.29-4.27 (m, 2H), 4.20 (t, J=6.8 Hz, 1H), 3.63 (dd, J=15.2, 4.5 Hz, 1H), 3.47 (dd, J=15.1, 9.9 Hz, 1H). $^{13}$C NMR (101 MHz, DMSO) δ 172.59, 170.94, 156.41, 153.89, 144.21, 144.15, 141.17, 134.25, 131.33, 128.07, 127.48, 125.64, 125.57, 124.05, 122.28, 120.57, 66.15, 53.92, 47.05, 35.62. UPLC-MS (ESI-MS) m/z: calculated for $C_{25}H_{20}ClN_2O_4S^+$ 479.08, found 479.22 [M+H]$^+$.

Intermediate 3d was prepared from 1 in 36% yield in two steps using a similar procedure as that for 3a. $^1$H NMR (400 MHz, DMSO), δ 13.0 (br. 1H), 7.97-7.87 (m, 4H), 7.66-7.64 (m, 2H), 7.87 (d, J=7.5, 2H), 7.48-7.22 (m, 6H), 4.54 (dt, J=4.0, 8.8, 1H), 4.28 (d, J=6.3, 2H), 4.20 (t, J=6.8, 1H), 3.65 (dd, J=4.6, 15.1, 1H), 3.49 (dd, J=9.9, 15.1, 1H); $^{13}$C NMR (75 MHz, CD3OD).

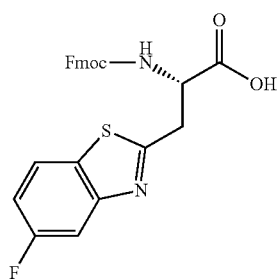
3e

Intermediate 3e was prepared from 1 in 39% yield in two steps using a similar procedure as that for 3a.: $^1$H NMR (400 MHz, DMSO), δ 13.0 (br. 1H), 8.12-8.09 (m, 1H), 7.94 (d, J=8.6, 1H), 7.87 (d, J=7.5, 2H), 7.79 (dd, J=2.5, 9.9, 1H), 7.67-7.64 (m, 2H), 7.41-7.23 (m, 5H), 4.55 (dt, J=4.0, 9.4, 1H), 4.29 (d, J=6.7, 2H), 4.20 (t, J=6.8, 1H), 3.63 (dd, J=4.5, 15.1, 1H), 3.47 (dd, J=9.8, 15.1, 1H); $^{13}$C NMR (75 MHz, CD3OD).

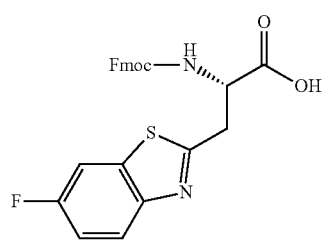
3f

Intermediate 3f was prepared from 1 in 32% yield in two steps using a similar procedure as that for 3a.: $^1$H NMR (400 MHz, DMSO), δ 13.0 (br. 1H), 7.99-7.92 (m, 3H), 7.88 (d, J=7.5, 2H), 7.67-7.64 (m, 2H), 7.42-7.34 (m, 3H), 7.30-7.23 (m, 2H), 4.54 (dt, J=4.4, 8.6, 1H), 4.28 (d, J=7.0, 2H), 4.20 (t, J=6.8, 1H), 3.60 (dd, J=4.3, 15.1, 1H), 3.45 (dd, J=9.8, 15.1, 1H); $^{13}$C NMR (75 MHz, CD3OD).

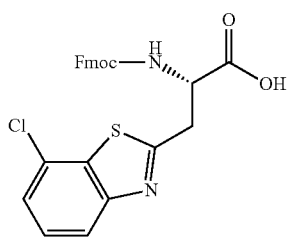
3g

Intermediate 3g was prepared from 1 in 35% yield in two steps using a similar procedure as that for 3a. ESI-MS m/z: calculated for $C_{25}H_{20}ClN_2O_4S^+$ 479.1, found 479.4 [M+H]$^+$.

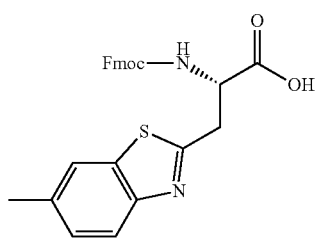
3h

Intermediate 3h was prepared from 1 in two steps using a similar procedure as that for 3a. ESI-MS m/z: calculated for $C_{26}H_{23}N_2O_4S+$ 459.1, found 459.8 [M+H]$^+$.

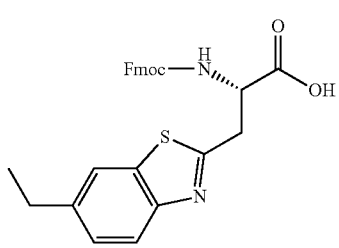
3i

Intermediate 3i was prepared from 1 in two steps using a similar procedure as that for 3a. ESI-MS m/z: calculated for $C_{27}H_{25}N_2O_4S+$ 473.2, found 473.5[M+H]$^+$.

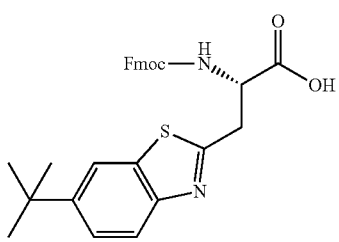
3j

Intermediate 3j was prepared from 1 in two steps using a similar procedure as that for 3a. ESI-MS m/z: calculated for $C_{29}H_{29}N_2O_4S+$ 501.2, found 501.9 [M+H]$^+$.

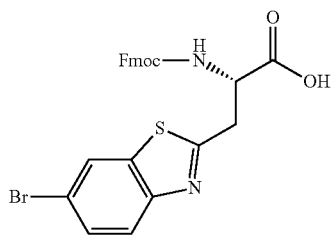
3k

Intermediate 3k was prepared from 1 in two steps using a similar procedure as that for 3a. ESI-MS m/z: calculated for $C_{25}H_{20}BrN_2O_4S^+$ 523.0, found 523.6 [M+H]$^+$.

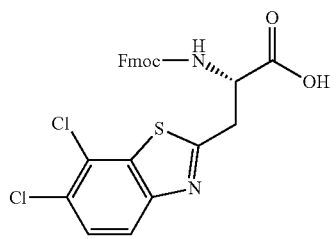
3s

Intermediate 3s was prepared from 1 in two steps using a similar procedure as that for 3a. ESI-MS m/z: calculated for $C_{25}H_{18}Cl_2N_2O_4S^+$ 512.0, found 512.5 [M+H]$^+$.

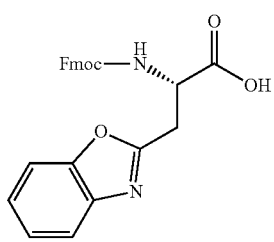
31

31: To a solution of (S)-3-((((9H-fluoren-9-yl)methoxy)carbonyl)amino)-4-(allyloxy)-4-oxobutanoic acid (1, 5 g, 12.6 mmol) in CH$_2$Cl$_2$ (300 mL) was added oxalyl chloride (3.3 mL, 38.0 mmol) and catalytic amount of DMF at 0° C. The reaction mixture was concentrated after being stirred for 0.5 h. The residue was suspended in CH$_2$Cl$_2$ (250 mL) and treated with 2-amino-5-isopropylbenzenethiol (2.1 g, 12.6 mmol) and N,N-Diisopropylethylamine (5 mL). The resulting mixture was stirred for 3 h and treated with water. The separated organic phase was dried over Na$_2$SO$_4$ and concentrated to get 31-1. Trifluoromethanesulfonic anhydride (3.2 ml, 18.9 mmol) was added slowly to a solution of triphenylphosphane oxide (10.5 g, 37.8 mmol) in dry CH$_2$Cl$_2$ (250 mL) at 0° C. After the mixture was stirred at 0° C. for 10 min, 31-1 was then added at the same temperature. The reaction was allowed to warm to room temperature and stirred for 5 h. The reaction mixture was quenched with 10% aqueous NaHCO$_3$ solution. The aqueous layer was extracted with CH$_2$Cl$_2$, and the combined organic layers were dried over Na$_2$SO$_4$, filtered, and concentrated. The crude product The crude product was purified by flash chromatography on silica gel to afford 31. ESI-MS m/z: calculated for $C_{25}H_{21}N_2O_5^+$ 429.1, found 429.6.

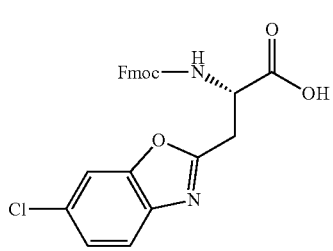
3m

Intermediate 3m was prepared from 1 in two steps using a similar procedure as that for 31. ESI-MS m/z: calculated for $C_{25}H_{20}ClN_2O_5^+$ 463.1, found 463.0 [M+H]$^+$.

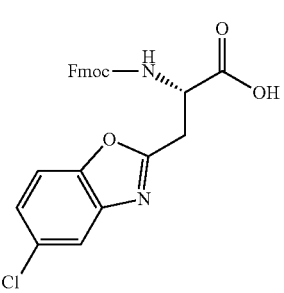
3n

Intermediate 3n was prepared from 1 in two steps using a similar procedure as that for 31. ESI-MS m/z: calculated for $C_{25}H_{20}ClN_2O_5^+$ 463.1, found 463.2 [M+H]$^+$.

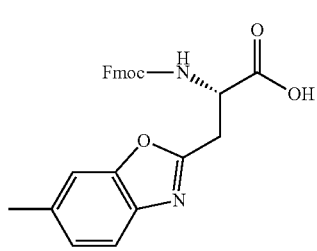
3o

Intermediate 3o was prepared from 1 in two steps using a similar procedure as that for 31. ESI-MS m/z: calculated for $C_{26}H_{23}N_2O_5^+$ 443.1, found 443.2 [M+H]$^+$.

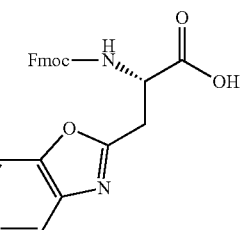
3p

Intermediate 3p was prepared from 1 in two steps using a similar procedure as that for 31. ESI-MS m/z: calculated for $C_{27}H_{25}N_2O_5^+$ 457.2, found 457.4 [M+H]$^+$.

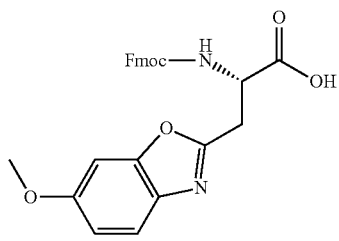
3q

Intermediate 3q was prepared from 1 in two steps using a similar procedure as that for 31. ESI-MS m/z: calculated for $C_{26}H_{23}N_2O_6^+$ 459.2, found 459.2 [M+H]$^+$.

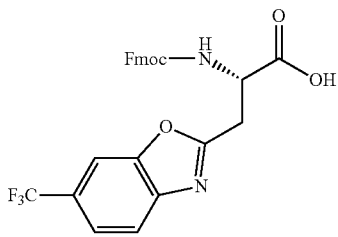

Intermediate 3r was prepared from 1 in two steps using a similar procedure as that for 31. ESI-MS m/z: calculated for $C_{26}H_{20}F_3N_2O_5^+$ 497.2, found 497.8 [M+H]$^+$.

Solid-Phase Synthesis of Peptides

General method: The longer peptides were synthesized on an ABI 433 Peptide Synthesizer using Fmoc chemistry. Rink amide resin was used as the solid support and the coupling reagents were HBTU (O-(Benzotriazol-1-yl)-N,N,N,N'-tetramethyluronium hexafluorophosphate) and HOBt (1-Hydroxybenzotriazole hydrate). The crude peptides were cleaved from the resin by cleavage cocktail (TFA:TES:H$_2$O, 18 mL:0.5 mL:1 mL), which also led to removal of the protecting groups. The cleavage solution was evaporated and purified by RP-HPLC to give peptides. Shorter peptides were generally made by using standard solution phase chemistry, coupling Fmoc amino acids using HATA/HOBT in DMF, using methods well known to those of skill in the art.

Example 1

DI-06

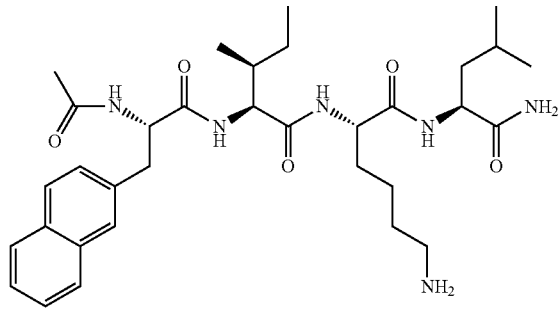 [SMILES: CC[C@H](C)[C@H](NC(=O)[C@H](Cc1ccc2ccccc2c1)NC(C)=O)C(=O)N[C@@H](CCCCN)C(=O)N[C@@H](CC(C)C)C(N)=O]

HRMS (ESI-MS) m/z: calculated for $C_{33}H_{51}N_6O_5^+$ 611.3915, found 611.3914 [M+H]$^+$.

Example 2

DI-801

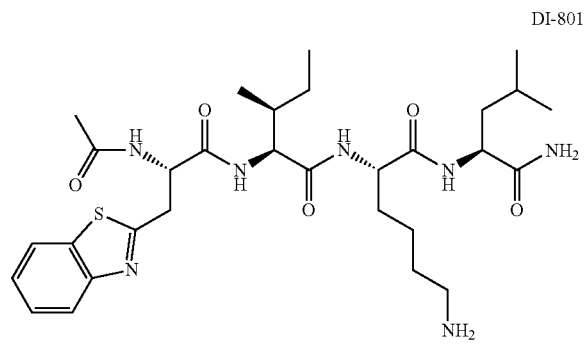 [SMILES: CC[C@H](C)[C@H](NC(=O)[C@H](Cc1nc2ccccc2s1)NC(C)=O)C(=O)N[C@@H](CCCCN)C(=O)N[C@@H](CC(C)C)C(N)=O]

(S)-2-((2S,3 S)-2-((S)-2-acetamido-3-(benzo[d]thiazol-2-yl)propanamido)-3-methylpentanamido)-6-amino-N—((S)-1-amino-4-methyl-1-oxopentan-2-yl)hexanamide: H NMR (400 MHz, MeOD) δ 7.97 (d, J=9.0 Hz, 2H), 7.60-7.48 (m, 1H), 7.48-7.38 (m, 1H), 4.98 (dd, J=8.5, 5.2 Hz, 1H), 4.39 (ddd, J=12.5, 9.2, 5.6 Hz, 2H), 4.22 (d, J=7.6 Hz, 1H), 3.65 (dd, J=15.4, 5.2 Hz, 1H), 3.50 (dd, J=15.4, 8.5 Hz, 1H), 2.92 (t, J=7.4 Hz, 2H), 2.01 (s, 3H), 1.91-1.77 (m, 2H), 1.76-1.38 (m, 9H), 1.21-1.15 (m, 1H), 1.01-0.83 (m, 12H). $^{13}$C NMR (101 MHz, MeOD) δ 176.01, 172.18, 172.03, 171.35, 167.73, 152.61, 135.10, 126.01, 125.09, 122.04, 121.47, 58.17, 53.04, 52.78, 51.40, 40.76, 39.11, 36.63, 34.97, 30.76, 26.52, 24.62, 24.48, 22.15, 22.11, 21.14, 20.37, 14.51, 9.97. UPLC-MS (ESI-MS) m/z: calculated for $C_{30}H_{48}N_7O_5S^+$ 618.34, found 618.29 [M+H]$^+$.

Example 3

DI-831

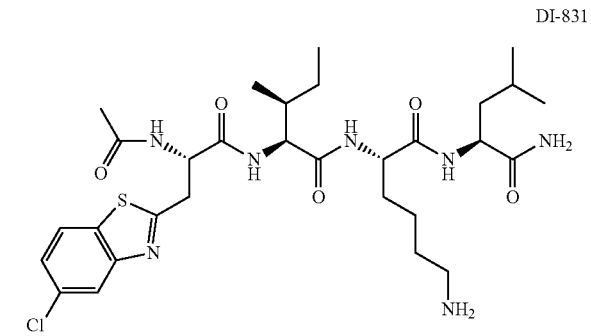 [SMILES: CC[C@H](C)[C@H](NC(=O)[C@H](Cc1nc2cc(Cl)ccc2s1)NC(C)=O)C(=O)N[C@@H](CCCCN)C(=O)N[C@@H](CC(C)C)C(N)=O]

(S)-2-((2S,3 S)-2-((S)-2-acetamido-3-(5-chlorobenzo[d]thiazol-2-yl)propanamido)-3-methylpentanamido)-6-amino-N—((S)-1-amino-4-methyl-1-oxopentan-2-yl)hexanamide: $^1$H NMR (400 MHz, MeOD) δ 8.54 (d, J=7.7 Hz, 1H), 8.23 (d, J=7.7 Hz, 1H), 8.06 (d, J=7.0 Hz, 2H), 7.98-7.95 (m, 2H), 7.45 (dd, J=8.6, 2.1 Hz, 1H), 5.00-4.95 (m, 1H), 4.48-4.32 (m, 2H), 4.20 (t, J=7.7 Hz, 1H), 3.65 (dd, J=15.5, 5.3 Hz, 1H), 3.50 (dd, J=15.5, 8.4 Hz, 1H), 2.93 (t, J=7.4 Hz, 2H), 2.01 (s, 3H), 1.91-1.77 (m, 2H), 1.74-1.39 (m, 9H), 1.20-1.12 (m, 1H), 1.00-0.82 (m, 12H). $^{13}$C NMR (101 MHz, MeOD) δ 176.00, 172.21, 172.12, 171.97, 171.21, 170.07, 153.57, 133.71, 131.95, 125.36, 122.63, 121.78, 58.10, 52.88, 52.71, 51.36, 40.80, 39.13, 36.65, 35.00, 30.79, 26.55, 24.58, 24.48, 22.14, 22.10, 21.13, 20.37, 14.49, 9.95. UPLC-MS (ESI-MS) m/z: calculated for $C_{30}H_{47}ClN_7O_5S^+$ 652.30, found 652.25 [M+H]$^+$.

Example 4

DI-802

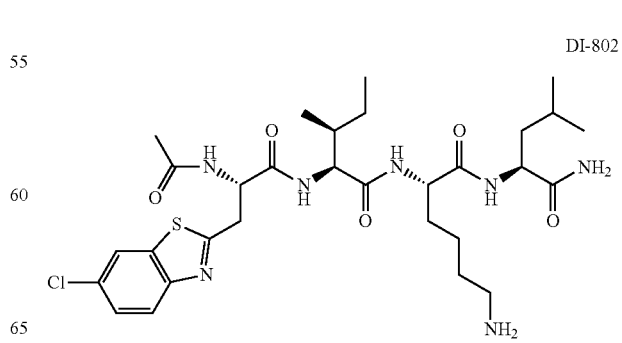

(S)-2-((2S,3 S)-2-((S)-2-acetamido-3-(6-chlorobenzo[d]thiazol-2-yl)propanamido)-3-methylpentanamido)-6-amino-N—((S)-1-amino-4-methyl-1-oxopentan-2-yl)hexanamide: ¹H NMR (400 MHz, MeOD) δ 8.53 (d, J=7.6 Hz, 1H), 8.23 (d, J=7.5 Hz, 1H), 8.08-8.06 (m, 2H), 8.03 (d, J=2.0 Hz, 1H), 7.92 (d, J=8.7 Hz, 1H), 7.52 (dd, J=8.7, 2.1 Hz, 1H), 5.00-4.93 (m, 1H), 4.50-4.30 (m, 2H), 4.20 (t, J=7.7 Hz, 1H), 3.64 (dd, J=15.5, 5.2 Hz, 1H), 3.48 (dd, J=15.5, 8.4 Hz, 1H), 2.93 (t, J=7.4 Hz, 2H), 2.01 (s, 3H), 1.90-1.78 (m, 2H), 1.75-1.34 (m, 9H), 1.23-1.09 (m, 1H), 1.06-0.73 (m, 12H). ¹³C NMR (101 MHz, MeOD) δ 176.00, 172.18, 172.13, 171.96, 171.22, 168.56, 151.37, 136.58, 130.86, 126.64, 123.07, 121.14, 58.10, 52.90, 52.73, 51.36, 40.79, 39.13, 36.63, 34.92, 30.77, 26.55, 24.58, 24.47, 22.14, 22.10, 21.12, 20.36, 14.49, 9.95. UPLC-MS (ESI-MS) m/z: calculated for $C_{30}H_{47}ClN_7O_5S^+$ 652.30, found 652.28 [M+H]⁺.

Example 5

DI-803

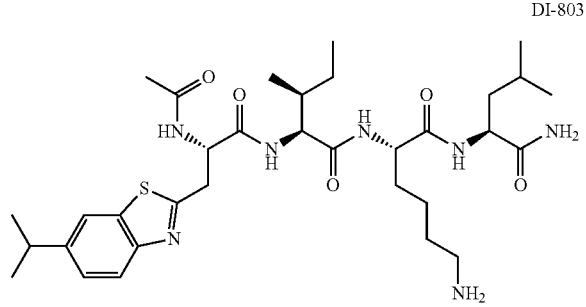 [SMILES: CC[C@H](C)[C@H](NC(=O)[C@H](Cc1nc2ccc(C(C)C)cc2s1)NC(C)=O)C(=O)N[C@@H](CCCCN)C(=O)N[C@@H](CC(C)C)C(N)=O]

(S)-2-((2S,3 S)-2-((S)-2-acetamido-3-(6-isopropylbenzo[d]thiazol-2-yl)propanamido)-3-methylpentanamido)-6-amino-N—((S)-1-amino-4-methyl-1-oxopentan-2-yl)hexanamide: ¹H NMR (400 MHz, MeOD) δ 7.87 (d, J=8.5 Hz, 1H), 7.82 (d, J=1.7 Hz, 1H), 7.42 (dd, J=8.5, 1.7 Hz, 1H), 4.94 (dd, J=8.6, 5.0 Hz, 1H), 4.43-4.36 (m, 2H), 4.20 (d, J=7.6 Hz, 1H), 3.62 (dd, J=15.4, 5.0 Hz, 1H), 3.47 (dd, J=15.4, 8.7 Hz, 1H), 3.08 (dt, J=13.8, 6.9 Hz, 1H), 2.93 (t, J=7.4 Hz, 2H), 2.01 (s, 3H), 1.90-1.79 (m, 2H), 1.77-1.39 (m, 9H), 1.33 (d, J=6.9 Hz, 6H), 1.19-1.12 (m, 1H), 0.98-0.85 (m, 12H). ¹³C NMR (101 MHz, MeOD) δ 176.00, 172.19, 172.15, 172.05, 171.39, 166.88, 150.96, 146.66, 135.29, 125.15, 121.69, 118.56, 58.20, 53.11, 52.73, 51.36, 40.79, 39.13, 36.56, 34.88, 34.09, 30.74, 26.51, 24.60, 24.48, 23.16, 22.15, 22.09, 21.13, 20.36, 14.50, 9.95. UPLC-MS (ESI-MS) m/z: calculated for $C_{33}H_{54}N_7O_5S^+$ 660.39, found 661.01 [M+H]⁺.

Example 6

DI-827

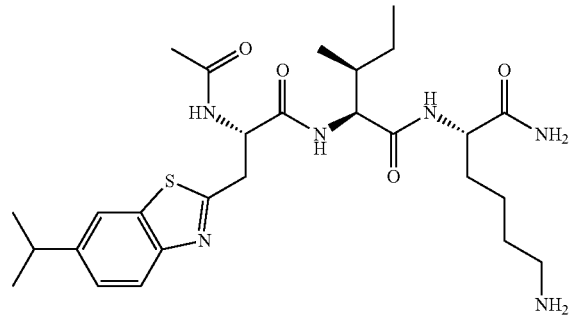

(S)-2-((2S,3 S)-2-((S)-2-acetamido-3-(6-isopropylbenzo[d]thiazol-2-yl)propanamido)-3-methylpentanamido)-6-aminohexanamide: ¹H NMR (400 MHz, MeOD) δ 8.53 (d, J=7.7 Hz, 1H), 8.21 (d, J=8.0 Hz, 1H), 8.08 (d, J=7.7 Hz, 1H), 7.87 (d, J=8.5 Hz, 1H), 7.82 (d, J=1.7 Hz, 1H), 7.42 (dd, J=8.5, 1.7 Hz, 1H), 4.94 (dd, J=8.6, 5.1 Hz, 1H), 4.44-4.30 (m, 1H), 4.19 (t, J=7.7 Hz, 1H), 3.63 (dd, J=15.4, 5.1 Hz, 1H), 3.46 (dd, J=15.4, 8.6 Hz, 1H), 3.08 (dt, J=13.8, 6.9 Hz, 1H), 2.93 (t, J=7.5 Hz, 2H), 2.01 (s, 3H), 1.94-1.80 (m, 2H), 1.76-1.60 (m, 3H), 1.56-1.38 (m, 3H), 1.33 (d, J=6.9 Hz, 6H), 1.20-1.13 (m, 1H), 0.95 (d, J=6.8 Hz, 3H), 0.88 (t, J=7.4 Hz, 3H). ¹³C NMR (101 MHz, MeOD) δ 174.86, 172.20, 172.10, 171.48, 166.94, 150.94, 146.68, 135.28, 125.16, 121.67, 118.57, 58.35, 53.07, 52.35, 39.16, 36.38, 34.85, 34.09, 30.97, 26.53, 24.59, 23.16, 22.25, 21.14, 14.51, 9.89. UPLC-MS (ESI-MS) m/z: calculated for $C_{27}H_{43}N_6O_4S^+$ 547.31, found 547.22 [M+H]⁺.

Example 7

DI-828

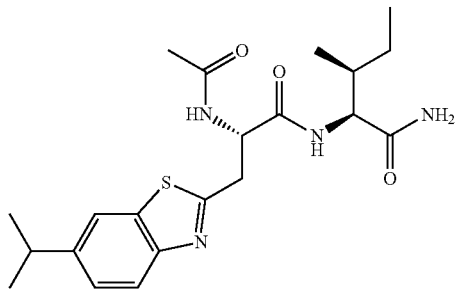

(2S,3S)-2-((S)-2-acetamido-3-(6-isopropylbenzo[d]thiazol-2-yl)propanamido)-3-methylpentanamide ¹H NMR (400 MHz, MeOD) δ 7.86 (d, J=8.5 Hz, 1H), 7.81 (d, J=1.7 Hz, 1H), 7.41 (dd, J=8.5, 1.7 Hz, 1H), 5.01-4.95 (m, 1H), 4.32-4.22 (m, 1H), 3.64 (dd, J=15.3, 5.7 Hz, 1H), 3.46 (dd, J=15.3, 8.0 Hz, 1H), 3.07 (dt, J=13.8, 6.9 Hz, 1H), 1.99 (s, 3H), 1.93-1.80 (m, 1H), 1.56-1.50 (m, 1H), 1.33 (d, J=6.9 Hz, 6H), 1.22-1.14 (m, 1H), 0.95 (d, J=6.8 Hz, 3H), 0.91 (t, J=7.4 Hz, 3H). ¹³C NMR (101 MHz, MeOD) δ 174.65, 172.01, 171.07, 167.02, 150.89, 146.59, 135.26, 125.14, 121.58, 118.52, 57.81, 52.73, 36.70, 34.95, 34.08, 24.26, 23.15, 21.06, 14.58, 10.27. UPLC-MS (ESI-MS) m/z: calculated for $C_{21}H_{31}N_4O_3S^+$ 419.21, found 419.27 [M+H]$^+$.

1. Synthesis of Examples 8-18.

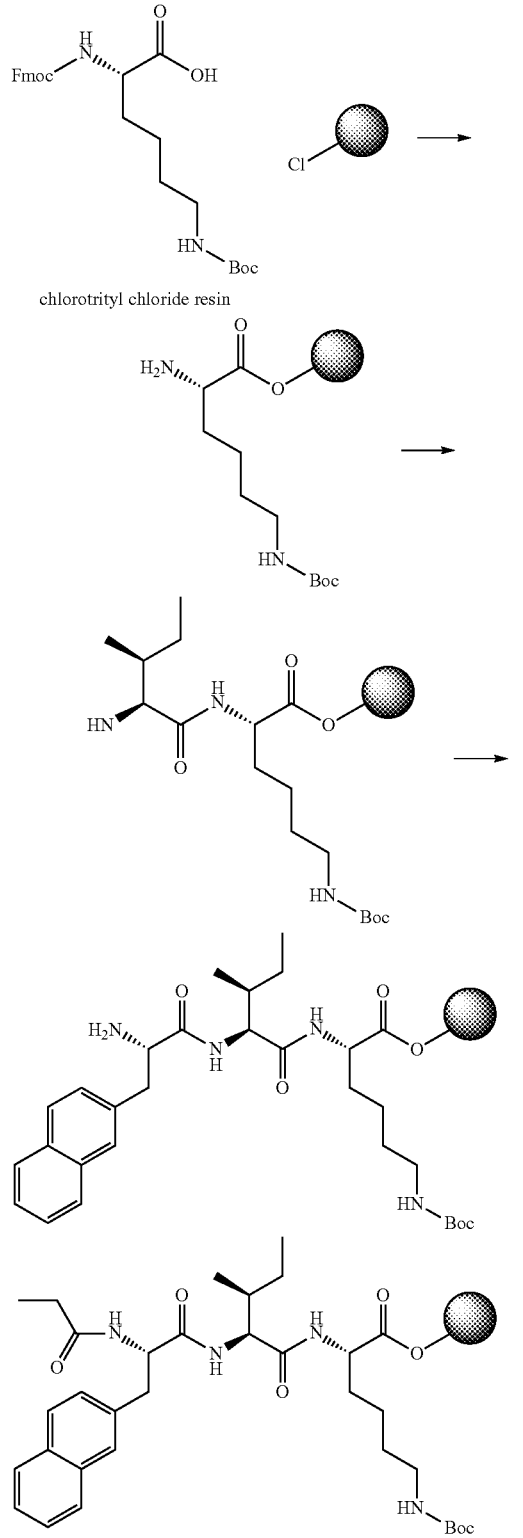

Scheme 2. Synthesis of Examples 8-18.

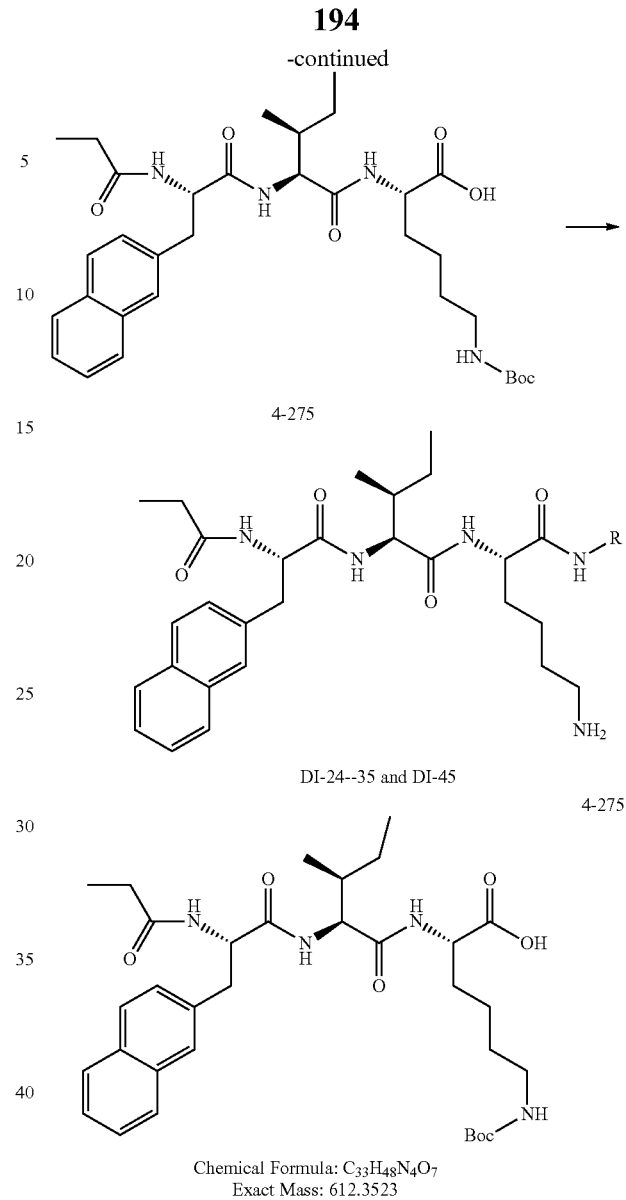

The common intermediate 4-275 was synthesized manually using 2-chlorotrityl chloride resin as the solid support. The Fmoc-Lys(Boc)-OH was loaded to 2-chlorotrityl chloride resin by shaking a mixture of 2-chlorotrityl chloride resin (1 equiv.), Fmoc-Lys(Boc)-OH (1 equiv.) and DIPEA (3 equiv.) in DCM in a reaction vessel overnight. Next, Fmoc chemistry was used to carry out the chain elongation. The crude carboxylic acid 4-275 was cleaved from the resin with 0.5% TFA in $CH_2Cl_2$. The cleavage solution was evaporated and purified by HPLC to yield common intermediate 4-275. 4-275: $^1$H NMR (300 MHz, CDCl$_3$:CD3OD=5:1), δ 7.78-7.75 (m, 3H), 7.64 (s, 1H), 7.45-7.44 (m, 2H), 7.34-7.30 (m, 2H), 4.82-4.80 (m, 1H), 4.51-4.40 (m, 1H), 4.21-3.98 (m, 1H), 3.25-2.80 (m, 4H), 2.18-2.15 (m, 2H), 1.82-1.26 (m, 18H), 1.04 (t, J=7.6, 3H), 0.90-0.84 (m, 6H); $^{13}$C NMR (75 MHz, CDCl$_3$), δ 175.1, 174.2, 172.1, 171.7, 156.7, 134.2, 133.5, 132.4, 128.1, 128.0, 127.6, 127.4, 126.1, 125.7, 79.3, 58.0, 57.8, 54.1, 52.3, 40.1, 38.0, 37.0, 31.4, 29.3, 28.4, 24.8, 22.7, 15.2, 10.9, 9.7.

General Procedure for the Synthesis of Examples 8-18:

A solution of acid 4-275 (0.05 mmol, 1 equiv.), the corresponding amine (0.10 mmol, 2 equiv.), HBTU (38 mg, 0.10 mmol, 2 equiv.), HOBt (14 mg, 0.10 mmol, 2 equiv.) and DIEA (27 μL, 0.15 mmol, 3 equiv.) in THF (5 mL) was stirred at room temperature for 2 h before being concentrated. The residue was then redissolved in EtOAc, washed with saturated sodium bicarbonate, 1.0 M HCl, brine and dried over sodium sulfate. After removal of the solvent under vacuum, the residue was treated with 3 mL trifluoroacetic acid in DCM (10 ML) at room temperature for 3 h. The reaction mixture was evaporated and the crude product was purified by RP-HPLC to provide the compounds Examples 8-18 in in 70% to 85% yields.

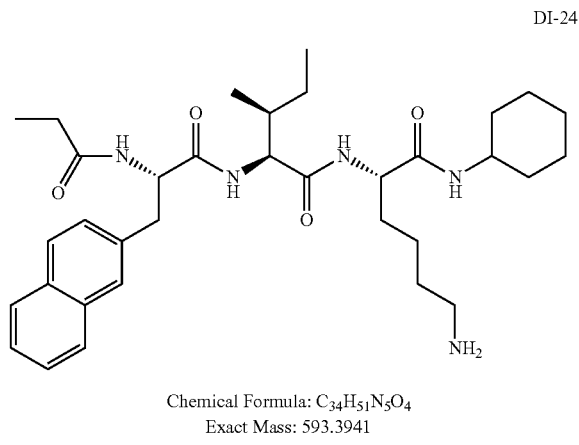 [SMILES: CCC(=O)N[C@@H](Cc1ccc2ccccc2c1)C(=O)N[C@H](C(=O)N[C@@H](CCCCN)C(=O)NC1CCCCC1)[C@@H](C)CC]

DI-24

Chemical Formula: $C_{34}H_{51}N_5O_4$
Exact Mass: 593.3941

Example 8

$^1$H NMR (300 MHz, CD$_3$OD), δ 8.17-8.12 (m, 2H), 7.95 (d, J=7.8, 1H), 7.83-7.71 (m, 4H), 7.48-7.38 (m, 3H), 4.80-4.72 (m, 1H), 4.32-4.25 (m, 1H), 4.20-4.15 (m, 1H), 3.63-3.60 (m, 1H), 3.10-3.02 (m, 1H), 2.87 (t, J=7.5, 2H), 2.21-2.13 (m, 2H), 1.85-1.54 (m, 10H), 1.42-1.17 (m, 8H), 1.01-0.88 (m, 8H); $^{13}$C NMR (75 MHz, CD3OD), δ 177.2, 174.0, 173.4, 172.5, 136.0, 134.9, 133.9, 129.1, 128.9, 128.6, 128.4, 127.1, 126.7, 59.4, 56.1, 54.2, 40.6, 38.6, 38.0, 33.7, 32.4, 29.9, 28.0, 26.6, 26.1, 23.7, 15.9, 11.3, 10.3.

DI-25

Chemical Formula: $C_{34}H_{45}N_5O_4$
Exact Mass: 587.3472

Example 9

$^1$HNMR (300 MHz, CD$_3$OD), δ 9.74 (s, 1H), 8.32 (d, J=7.7, 1H), 8.04 (d, J=7.7, 1H), 7.83-7.77 (m, 3H), 7.70 (s, 1H), 7.57-7.54 (m, 2H), 7.45-7.38 (m, 3H), 7.33-7.27 (m, 2H), 7.12-7.08 (m, 1H), 4.81-4.76 (m, 1H), 4.50-4.45 (m, 1H), 4.24 (t, J=7.8, 1H), 3.54-3.36 (m, 1H), 3.10-3.02 (m, 1H), 2.88 (t, J=7.5, 2H), 2.21-2.14 (m, 2H), 1.87-1.29 (m, 8H), 1.23-1.16 (m, 1H), 1.01-0.88 (m, 9H); $^{13}$C NMR (75 MHz, CD3OD), δ 177.2, 174.0, 173.6, 171.9, 139.4, 136.0, 134.9, 133.9, 129.9, 129.1, 128.9, 128.6, 128.4, 127.1, 126.7, 125.5, 121.3, 59.4, 56.1, 54.9, 40.6, 38.6, 38.1, 32.3, 29.9, 28.1, 26.0, 23.8, 15.9, 11.3, 10.3.

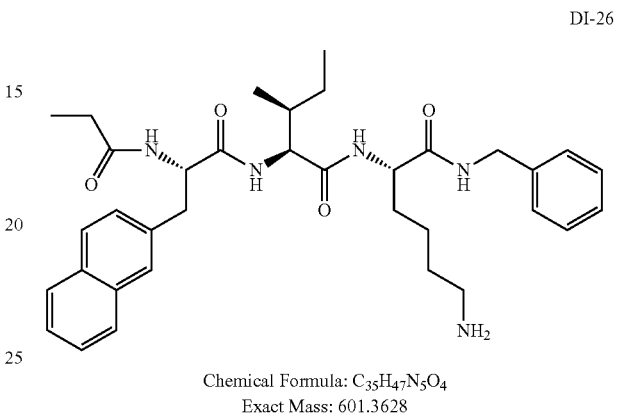

DI-26

Chemical Formula: $C_{35}H_{47}N_5O_4$
Exact Mass: 601.3628

Example 10

$^1$H NMR (300 MHz, CD$_3$OD), δ 8.36 (t, J=5.8, 1H), 8.21 (d, J=7.9, 1H), 8.12 (d, J=7.7, 1H), 7.96 (d, J=7.8, 1H), 7.82-7.77 (m, 3H), 7.69 (s, 1H), 7.48-7.36 (m, 3H), 7.33-7.23 (m, 5H), 4.80-4.69 (m, 1H), 4.44-4.31 (m, 3H), 4.20-4.15 (m, 1H), 3.33-3.26 (m, 1H), 3.08-3.00 (m, 1H), 2.85 (t, J=7.7, 2H), 2.19-2.12 (m, 2H), 1.84-1.29 (m, 8H), 1.22-1.12 (m, 1H), 0.97 (t, J=7.7, 3H), 0.90-0.85 (m, 6H); $^{13}$C NMR (75 MHz, CD3OD), δ 177.2, 174.1, 173.6, 173.5, 139.7, 136.0, 134.9, 133.9, 129.6, 129.1, 128.8, 128.6, 128.4, 128.3, 127.1, 126.7, 59.4, 56.1, 54.3, 44.1, 40.5, 38.5, 38.0, 32.3, 29.9, 28.0, 26.0, 23.7, 15.9, 11.3, 10.3.

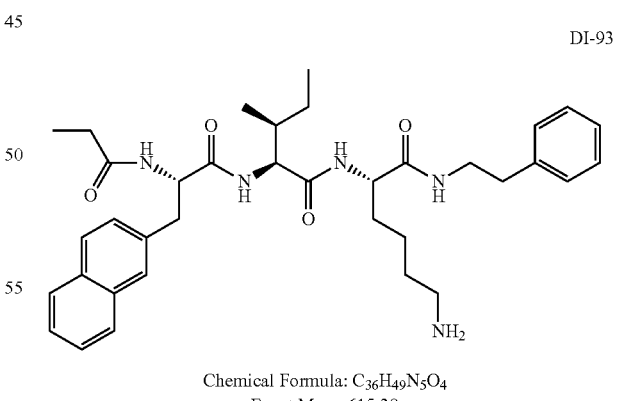

DI-93

Chemical Formula: $C_{36}H_{49}N_5O_4$
Exact Mass: 615.38

Example 11

$^1$H NMR (300 MHz, CD$_3$OD), δ 8.16-8.13 (m, 2H), 8.01-7.98 (m, 1H), 7.78-7.76 (m, 3H), 7.69 (s, 1H), 7.44-7.37 (m, 3H), 7.28-7.18 (m, 5H), 4.78-4.74 (m, 1H), 4.25-

4.15 (m, 2H), 3.46-3.33 (m, 3H), 3.08-3.01 (m, 1H), 2.85-2.79 (m, 4H), 2.17-2.12 (m, 2H), 1.82-1.55 (m, 6H), 1.30-1.15 (m, 3H), 0.99-0.86 (m, 9H); $^{13}$C NMR (75 MHz, CD3OD), δ 177.2, 174.1, 173.6, 173.4, 140.3, 136.0, 134.9133.9, 129.9, 129.5, 129.1, 128.9, 128.8, 128.6, 128.3, 127.4, 127.1, 126.7, 59.4, 56.1, 54.2, 41.9, 40.5, 38.6, 38.0, 36.4, 32.4, 29.9, 28.0, 26.0, 23.7, 15.9, 11.3, 10.3.

7.11 (m, 4H), 5.35 (dd, J=7.7, 15.4, 1H), 4.73-4.68 (m, 1H), 4.37-4.33 (m, 1H), 4.21-4.16 (m, 1H), 3.28-3.21 (m, 1H), 3.04-2.96 (m, 2H), 2.89-2.80 (m, 3H), 2.52-2.42 (m, 1H), 2.17-2.10 (m, 2H), 1.90-1.80 (m, 3H), 1.72-1.37 (m, 6H), 1.28-1.14 (m, 1H), 0.98-0.87 (m, 9H); $^{13}$C NMR (75 MHz, CD3OD), δ 177.2, 174.1, 173.52, 173.48, 144.5, 144.2, 136.0, 134.9, 133.9, 129.1, 129.0, 128.8, 128.6, 128.4, 127.6, 127.1, 126.7, 125.7, 125.2, 59.5, 56.1, 55.9, 54.3, 40.6, 38.5, 38.0, 34.2, 32.3, 31.1, 29.8, 28.0, 26.1, 23.8, 16.0, 11.4, 10.3.

DI-27

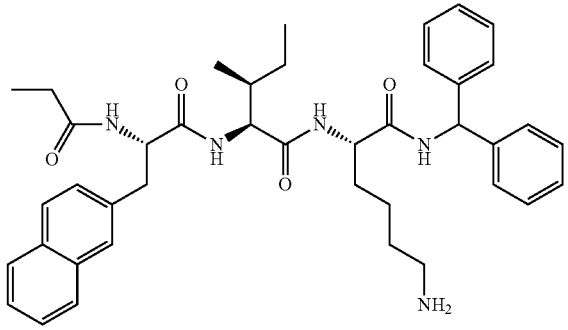

Chemical Formula: $C_{41}H_{51}N_5O_4$
Exact Mass: 677.3941

Example 12

$^1$H NMR (300 MHz, CD$_3$OD), δ 8.71 (d, J=8.3, 1H), 8.11 (d, J=7.7, 1H), 7.95 (d, J=7.9, 1H), 7.82-7.76 (m, 3H), 7.68 (s, 1H), 7.46-7.23 (m, 13H), 6.17-6.14 (m, 1H), 4.74-4.69 (m, 1H), 4.47-4.42 (m, 1H), 4.20-4.15 (m, 1H), 3.27-3.21 (m, 1H), 3.07-2.99 (m, 1H), 2.82 (t, J=7.7, 2H), 2.19-2.12 (m, 2H), 1.83-1.73 (m, 2H), 1.70-1.48 (m, 4H), 1.38-1.34 (m, 2H), 1.20-1.10 (m, 1H), 0.97 (t, J=7.6, 3H), 0.88-0.83 (m, 6H); $^{13}$C NMR (75 MHz, CD3OD), δ 177.2, 174.0, 173.6, 172.8, 142.9, 142.7, 136.0, 134.9, 133.9, 129.6, 129.5, 129.1, 128.84, 128.77, 128.6, 128.5, 128.41, 128.37, 127.1, 126.7, 59.4, 58.3, 56.1, 54.2, 40.5, 38.5, 38.0, 32.3, 29.9, 28.0, 26.1, 23.7, 15.9, 11.3, 10.3.

DI-35

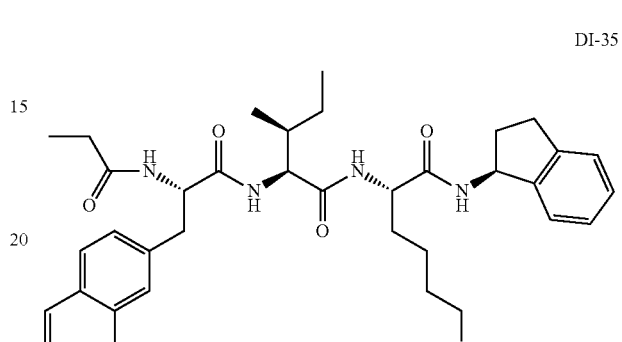

Chemical Formula: $C_{37}H_{49}N_5O_4$
Exact Mass: 627.3785

Example 14

$^1$H NMR (300 MHz, CD$_3$OD), δ 8.25-8.18 (m, 2H), 8.11 (d, J=7.6, 1H), 7.97 (d, J=7.9, 1H), 7.82-7.76 (m, 3H), 7.69 (s, 1H), 7.45-7.37 (m, 3H), 7.23-7.17 (m, 4H), 5.34 (dd, J=7.5, 15.2, 1H), 4.77-4.72 (m, 1H), 4.38-4.33 (m, 1H), 4.21-4.16 (m, 1H), 3.34-3.27 (m, 1H), 3.07-2.95 (m, 2H), 2.89-2.79 (m, 3H), 2.50-2.43 (m, 1H), 2.19-2.11 (m, 2H), 1.92-1.83 (m, 3H), 1.72-1.38 (m, 6H), 1.22-1.12 (m, 1H), 0.98-0.85 (m, 9H); $^{13}$C NMR (75 MHz, CD3OD), δ 177.2, 174.0, 173.5, 173.4, 144.6, 144.2, 136.0, 134.9, 133.9, 129.1, 129.0, 128.8, 128.6, 128.4, 127.7, 127.1, 126.7, 125.8, 125.0, 59.3, 56.1, 55.9, 54.2, 40.6, 38.6, 38.0, 34.2, 32.6, 31.1, 29.9, 28.0, 26.0, 23.8, 15.9, 11.3, 10.3.

DI-30

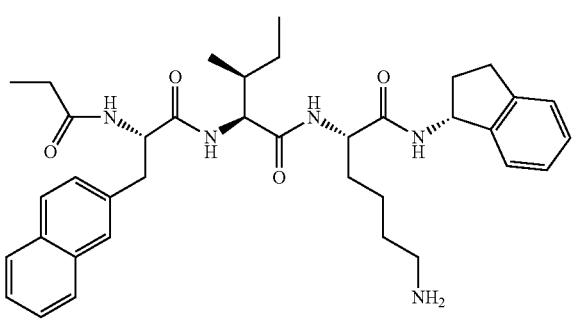

Chemical Formula: $C_{37}H_{49}N_5O_4$
Exact Mass: 627.3785

Example 13

$^1$H NMR (300 MHz, CD$_3$OD), δ 8.25 (d, J=7.8, 1H), 8.19 (d, J=8.2, 1H), 8.10 (d, J=7.5, 1H), 7.97 (d, J=7.6, 1H), 7.81-7.75 (m, 3H), 7.66 (s, 1H), 7.46-7.34 (m, 3H), 7.23-

DI-32

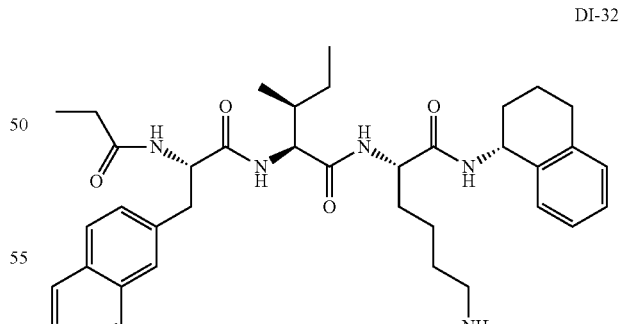

Chemical Formula: $C_{38}H_{51}N_5O_4$
Exact Mass: 641.3941

Example 15

$^1$H NMR (300 MHz, CD3OD), δ 8.27-8.19 (m, 2H), 8.09 (d, J=7.5, 1H), 7.97 (d, J=7.6, 1H), 7.81-7.75 (m, 3H), 7.67

(s, 1H), 7.45-7.35 (m, 3H), 7.18-7.07 (m, 4H), 5.07-5.05 (m, 1H), 4.71-4.68 (m, 1H), 4.35-4.33 (m, 1H), 4.23-4.17 (m, 1H), 3.28-3.21 (m, 1H), 3.04-2.80 (m, 5H), 2.18-2.11 (m, 2H), 2.03-1.28 (m, 12H), 1.25-1.15 (m, 1H), 0.98-0.88 (m, 9H); $^{13}$C NMR (75 MHz, CD3OD), δ 177.2, 174.0, 173.5, 173.0, 138.7, 137.4, 136.0, 134.9, 133.9, 130.1, 129.5, 129.0, 128.8, 128.6, 128.4, 128.3, 127.1, 126.7, 59.4, 56.0, 54.3, 40.5, 38.5, 38.0, 32.4, 31.2, 30.2, 29.8, 28.0, 26.1, 23.8, 21.4, 16.0, 11.4, 10.3

DI-33

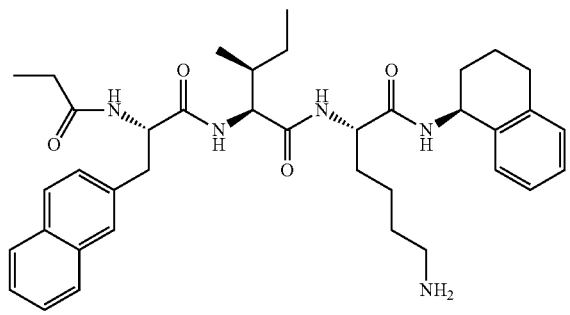

Chemical Formula: $C_{38}H_{51}N_5O_4$
Exact Mass: 641.3941

Example 16

$^1$H NMR (300 MHz, CD$_3$OD), δ 8.26-8.18 (m, 2H), 8.11 (d, J=7.7, 1H), 7.97 (d, J=8.0, 1H), 7.82-7.77 (m, 3H), 7.70 (s, 1H), 7.45-7.37 (m, 3H), 7.13-7.08 (m, 4H), 5.04-5.03 (m, 1H), 4.78-4.73 (m, 1H), 4.38-4.33 (m, 1H), 4.22-4.17 (m, 1H), 3.27-3.21 (m, 1H), 3.08-3.00 (m, 1H), 2.89-2.79 (m, 4H), 2.18-2.09 (m, 2H), 1.96-1.29 (m, 12H), 1.22-1.12 (m, 1H), 1.02-0.86 (m, 9H); $^{13}$C NMR (75 MHz, CD3OD), δ 177.1, 174.0, 173.5, 172.8, 138.8, 137.4, 136.0, 134.9, 133.9, 130.2, 129.5, 129.1, 128.8, 128.6, 128.4, 128.3, 127.1, 126.7, 59.3, 56.0, 54.3, 40.5, 38.6, 38.0, 32.5, 31.1, 30.2, 29.9, 28.0, 26.0, 23.7, 21.1, 15.9, 11.3, 10.3.

DI-34

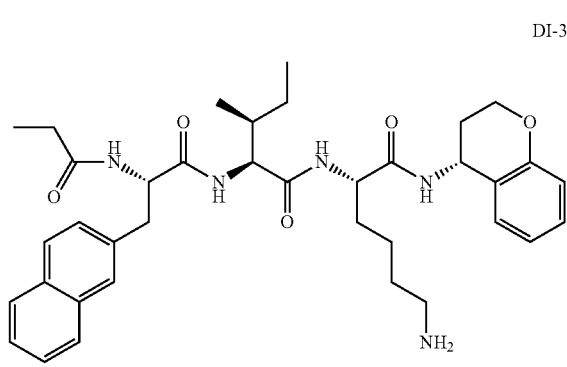

Chemical Formula: $C_{37}H_{49}N_5O_5$
Exact Mass: 643.3734

Example 17

$^1$H NMR (300 MHz, CD$_3$OD), δ 8.31 (d, J=8.0, 1H), 8.25 (d, J=7.9, 1H), 8.08 (d, J=7.5, 1H), 7.94 (d, J=7.5, 1H), 7.82-7.76 (m, 3H), 7.68 (s, 1H), 7.48-7.35 (m, 3H), 7.16-7.10 (m, 2H), 6.86-6.76 (m, 2H), 5.10-5.04 (m, 1H), 4.69-4.64 (m, 1H), 4.35-4.32 (m, 1H), 4.24-4.15 (m, 3H), 3.27-3.21 (m, 1H), 3.03-2.96 (m, 1H), 2.90-2.85 (m, 2H), 2.21-2.11 (m, 3H), 2.02-1.37 (m, 9H), 1.25-1.15 (m, 1H), 0.99-0.88 (m, 9H); $^{13}$C NMR (75 MHz, CD3OD), δ 177.2, 174.1, 173.6, 173.1, 156.5, 136.0, 134.9, 133.9, 130.5, 130.1, 129.1, 128.8, 128.63, 128.61, 128.4, 127.1, 126.7, 123.3, 121.6, 118.0, 64.4, 59.5, 56.1, 54.3, 44.8, 40.6, 38.4, 38.0, 32.3, 30.2, 29.8, 28.0, 26.1, 23.8, 16.0, 11.4, 10.3.

DI-35

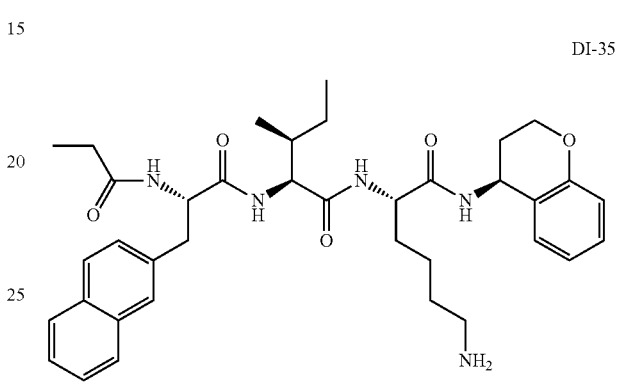

Chemical Formula: $C_{37}H_{49}N_5O_5$
Exact Mass: 643.3734

Example 18

$^1$H NMR (300 MHz, CD$_3$OD), δ not very pure. Should estimate purity by HPLC. Then at least quote MH+ Where are DI-28&29? If they are to be included, number them at end. In fact any missing numbers need to be just added to end of list. Otherwise it becomes too complex to construct Example # List 2. Synthesis of Examples 19-24.

Scheme 3. Synthesis of Examples 19-24.

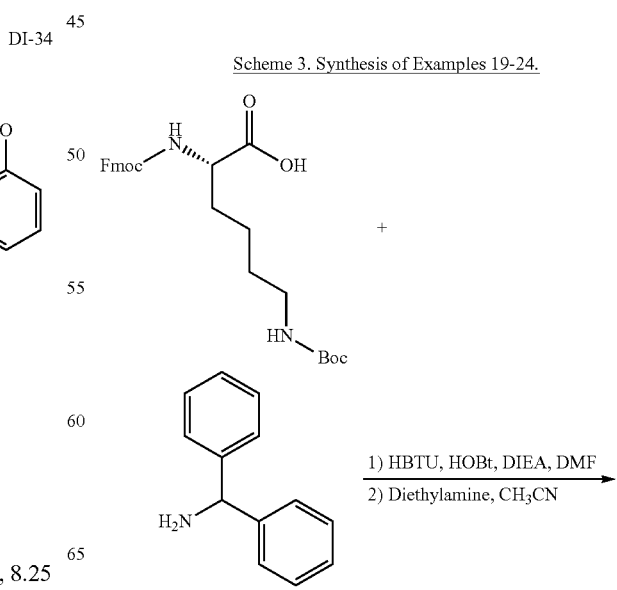

-continued

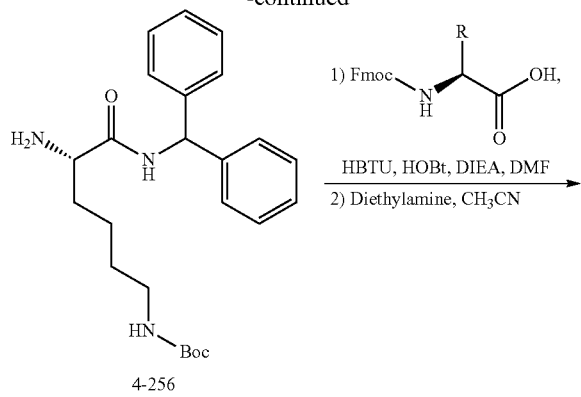

4-256

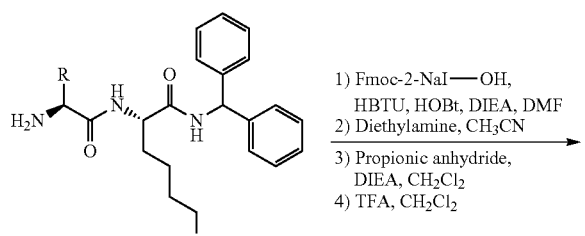

DI-xx-intermediate

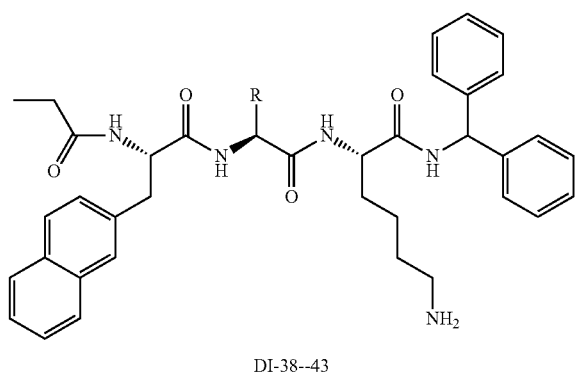

DI-38--43

4-256

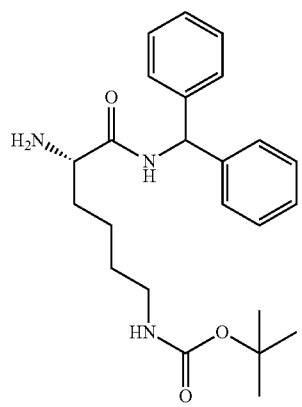

Chemical Formula: $C_{24}H_{33}N_3O_3$
Exact Mass: 411.2522

4-256:

To a solution of Fmoc-Lys(Boc)-OH (4.7 g, 10 mmol, 1 equiv.), HBTU (7.6 g, 20 mmol, 2 equiv.), HOBt (2.7 g, 20 mmol, 2 equiv.) and DIEA (5.2 mL, 30 mmol, 3 equiv.) in DMF (50 mL) was added benzhydrylamine (1.53 g, 10 mmol, 1 equiv.) and the resultant mixture was stirred at room temperature for 2 h. The solution was diluted with EtOAc and washed with saturated sodium bicarbonate, 1.0 M HCl, brine and dried over sodium sulfate. After removal of the solvent under vacuum, the residue was treated with 10 mL diethylamine in Acetonitrile (90 mL) for 1 h. The reaction mixture was evaporated and the crude product was purified by flash chromatography on silica gel to afford 4-256 (3.1 g, 76% over three steps). 4-256: $^1$HNMR (300 MHz, CDCl$_3$), δ 8.25 (d, J=8.6, 1H), 7.30-7.18 (m, 10H), 6.19 (d, J=8.6, 1H), 5.05 (brd. 1H), 3.33-3.29 (m, 1H), 3.02-3.00 (m, 2H), 1.87-1.76 (m, 3H), 1.57-1.30 (m, 14H); $^{13}$C NMR (75 MHz, CDCl$_3$), δ 174.4, 156.2, 141.8, 128.58, 128.56, 127.4, 127.3, 78.8, 56.3, 54.9, 40.1, 34.6, 29.7, 28.5, 22.8.

General Procedures for the Synthesis of Examples 19-24:

To a solution of the corresponding Fmoc protected amino acid (0.3 mmol, 1 equiv.), HBTU (228 g, 0.6 mmol, 2 equiv.), HOBt (81 mg, 0.6 mmol, 2 equiv.) and DIEA (157 µL, 0.9 mmol, 3 equiv.) in DMF (10 mL) was added 4-256 (123 mg, 0.3 mmol, 1 equiv.) and the resultant mixture was stirred at room temperature for 1 h. The solution was diluted with EtOAc and washed with saturated sodium bicarbonate, 1.0 M HCl, brine and dried over sodium sulfate. After removal of the solvent under vacuum, the residue was treated with 1 mL diethylamine in Acetonitrile (9 mL) for 1 h. The reaction mixture was evaporated and the crude product was purified by flash chromatography on silica gel to afford the appropriate intermediate in 60% to 75% yields over two steps.

To a solution of Fmoc-2-Nal-OH (44 mg, 0.1 mmol, 1 equiv.), HBTU (76 g, 0.2 mmol, 2 equiv.), HOBt (27 mg, 0.2 mmol, 2 equiv.) and DIEA (52 µL, 0.3 mmol, 3 equiv.) in DMF (5 mL) was added the corresponding amine (0.1 mmol, 1 equiv.) and the resulting mixture was stirred at room temperature for 1 h. The solution was diluted with EtOAc and washed with saturated sodium bicarbonate, 1.0 M HCl, brine and dried over sodium sulfate. After removal of the solvent under vacuum, the residue was treated with 1 mL diethylamine in Acetonitrile (9 mL) for 1 h. The reaction mixture was evaporated and the residue was redissolved in DCM (5 mL) and was treated with Propionic anhydride (39 mg, 0.3 mmoL, 3 equiv.) and DIEA (87 µL, 0.5 mmol, 5 equiv.) for half an hour. The reaction mixture was evaporated and treated with 3 mL trifluoroacetic acid in DCM (10 ML) at room temperature for 3 h. This reaction mixture was concentrated and purified by RP-HPLC to provide the compounds in Table 5.

4-272

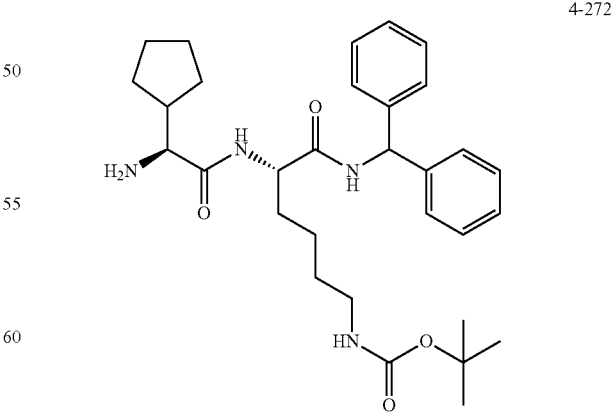

Chemical Formula: $C_{31}H_{44}N_4O_4$
Exact Mass: 536.3363

4-272:

¹HNMR (300 MHz, CDCl₃), δ 8.16 (d, J=8.4, 1H), 7.76 (d, J=8.5, 1H), 7.35-7.16 (m, 10H), 6.23 (d, J=8.4, 1H), 4.81 (brd. 1H), 4.74-4.67 (m, 1H), 3.04-2.98 (m, 3H), 2.09-2.04 (m, 1H), 1.89-1.78 (m, 1H), 1.73-1.43 (m, 20H), 1.36-1.18 (m, 4H); ¹³C NMR (75 MHz, CDCl₃), δ 175.4, 171.0, 156.1, 141.7, 141.4, 128.6, 128.5, 127.6, 127.43, 127.38, 127.2, 79.0, 58.4, 56.7, 52.5, 43.7, 40.2, 32.4, 29.5, 29.3, 28.5, 27.6, 25.6, 25.4, 22.7.

Example 19

¹H NMR (300 MHz, CD₃OD), δ 8.66 (d, J=8.3, 1H), 8.30 (d, J=8.0, 1H), 8.07 (d, J=7.3, 1H), 7.82-7.76 (m, 3H), 7.68 (s, 1H), 7.46-7.24 (m, 13H), 6.15 (d, J=8.2, 1H), 4.76-4.70 (m, 1H), 4.49-4.42 (m, 1H), 4.17-4.12 (m, 1H), 3.27-3.25 (m, 1H), 3.06-2.98 (m, 1H), 2.82 (t, J=7.5, 2H), 2.23-2.11 (m, 3H), 1.86-1.24 (m, 14H), 0.96 (t, J=7.6, 3H); ¹³C NMR (75 MHz, CD3OD), δ 177.1, 173.94, 173.87, 172.8, 142.9, 142.7, 136.0, 134.9, 133.9, 129.7, 129.5, 129.0, 128.9, 128.8, 128.61, 128.58, 128.4, 127.1, 126.7, 59.0, 58.4, 56.0, 54.2, 43.4, 40.5, 38.6, 32.2, 30.5, 30.3, 29.9, 27.9, 26.2, 25.9, 23.7, 10.2.

DI-38-intermediate

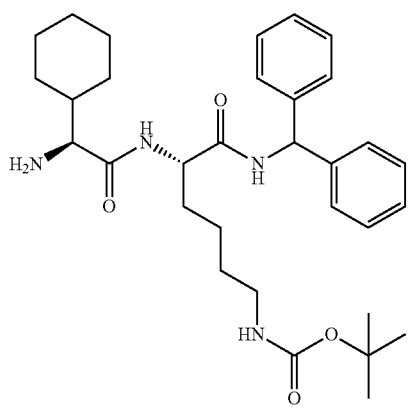

Chemical Formula: C₃₂H₄₆N₄O₄
Exact Mass: 550.3519

Example 20 Intermediate

¹H NMR (300 MHz, CDCl₃), δ 7.80 (d, J=8.2, 1H), 7.72 (d, J=8.3, 1H), 7.35-7.18 (m, 10H), 6.21 (d, J=8.3, 1H), 4.65 (brd. 1H), 4.59-4.51 (m, 1H), 3.06-2.95 (m, 3H), 1.95-1.58 (m, 8H), 1.45-1.42 (m, 11H), 1.36-1.00 (m, 9H); ¹³C NMR (75 MHz, CDCl₃), δ 175.0, 170.9, 156.1, 141.6, 141.4, 128.64, 128.56, 127.5, 127.3, 79.1, 59.9, 56.9, 52.7, 41.0, 40.2, 31.6, 30.2, 29.5, 28.4, 26.7, 26.3, 26.14, 26.07, 22.8.

Example 20

¹H NMR (300 MHz, CD₃OD), δ 8.69 (d, J=8.3, 1H), 8.28 (d, J=7.9, 1H), 8.10 (d, J=7.6, 1H), 7.93 (d, J=7.9, 1H), 7.82-7.77 (m, 3H), 7.69 (s, 1H), 7.46-7.24 (m, 13H), 6.15 (d, J=8.2, 1H), 4.75-4.70 (m, 1H), 4.46-4.41 (m, 1H), 4.14 (t, J=7.7, 1H), 3.27-3.26 (m, 1H), 3.07-3.00 (m, 1H), 2.82 (t, J=7.5, 2H), 2.20-2.12 (m, 2H), 1.82-1.55 (m, 9H), 1.40-1.12 (m, 6H), 1.00-0.95 (m, 5H); ¹³C NMR (75 MHz, CD3OD), δ 177.2, 173.9, 173.4, 172.8, 142.9, 142.7, 136.0, 134.9, 133.9, 129.7, 129.6, 129.1, 128.9, 128.8, 128.6, 128.5, 128.4, 127.1, 126.7, 59.8, 58.4, 56.0, 54.2, 41.3, 40.5, 38.6, 32.3, 30.7, 30.1, 29.9, 27.9, 27.2, 27.1, 27.0, 23.7, 10.3.

DI-43-intermediate

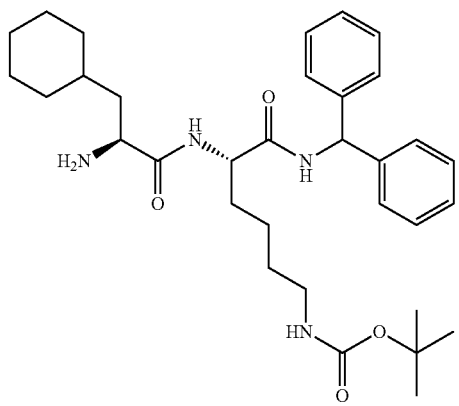

Chemical Formula: C₃₃H₄₈N₄O₄
Exact Mass: 564.3676

32.0, 29.6, 28.5, 26.4, 26.3, 26.1, 22.7.

Example 21 Intermediate

¹H NMR (300 MHz, CDCl₃), δ 8.02 (d, J=8.5, 1H), 7.85 (d, J=8.5, 1H), 7.35-7.15 (m, 10H), 6.22 (d, J=8.3, 1H), 4.72 (t, J=5.8, 1H), 4.67-4.59 (m, 1H), 3.17-3.13 (m, 1H), 3.04-2.93 (m, 2H), 1.90-1.79 (m, 1H), 1.66-1.58 (m, 9H), 1.49-1.42 (m, 11H), 1.35-1.08 (m, 7H), 0.98-0.77 (m, 2H); ¹³C NMR (75 MHz, CDCl₃), δ 176.3, 171.0, 156.0, 141.6, 141.5, 128.6, 128.5, 127.6, 127.4, 127.2, 78.9, 56.7, 52.63, 52.56, 42.5, 40.2, 34.2, 34.1, 32.2, 32.0, 29.6, 28.5, 26.4, 26.3, 26.1, 22.7.

Example 21

¹H NMR (300 MHz, CD₃OD), δ 8.67 (d, J=8.3, 1H), 8.20-8.08 (m, 2H), 7.83-7.77 (m, 3H), 7.69 (s, 1H), 7.46-7.24 (m, 13H), 6.17 (d, J=8.3, 1H), 4.70-4.65 (m, 1H), 4.45-4.36 (m, 2H), 3.27-3.25 (m, 1H), 3.08-3.00 (m, 1H), 2.83 (t, J=7.4, 2H), 2.16 (q, J=7.7, 2H), 1.82-1.55 (m, 11H), 1.39-1.14 (m, 6H), 0.99-0.88 (m, 5H); ¹³C NMR (75 MHz, CD3OD), δ 177.2, 174.8, 174.1, 172.9, 142.9, 142.7, 135.9, 134.9, 133.9, 129.63, 129.56, 129.1, 128.9, 128.7, 128.6, 128.5, 128.44, 128.40, 127.1, 126.7, 58.3, 56.0, 54.3, 52.8, 40.5, 40.3, 38.6, 35.2, 34.8, 33.3, 32.2, 29.9, 27.9, 27.5, 27.3, 27.1, 23.7, 10.2.

DI-40-intermediate

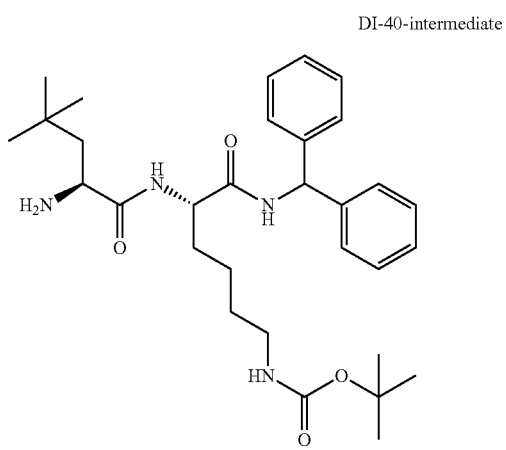

Chemical Formula: C$_{31}$H$_{46}$N$_4$O$_4$
Exact Mass: 538.3519

Example 22 Intermediate $^1$H NMR (300 MHz, CDCl$_3$), S 7.91 (d, J=8.4, 1H), 7.83 (d, J=8.4, 1H), 7.32-7.16 (m, 10H), 6.22 (d, J=8.3, 1H), 4.68 (brd., 1H), 4.61-4.53 (m, 1H), 3.15-3.02 (m, 3H), 1.94-1.79 (m, 2H), 1.69-1.42 (m, 13H), 1.32-1.09 (m, 4H), 0.93 (s, 9H); $^{13}$C NMR (75 MHz, CDCl$_3$), δ 1768, 170.9, 156.0, 141.6, 141.5, 128.6, 128.5, 127.5, 127.4, 127.2, 79.0, 56.7, 52.9, 52.7, 49.2, 40.1, 31.9, 30.7, 30.0, 29.6, 28.5, 22.8.

Example 22

$^1$H NMR (300 MHz, CD$_3$OD), δ 8.66 (d, J=8.3, 1H), 8.16-8.10 (m, 2H); 7.79-7.74 (m, 3H), 7.66 (s, 1H), 7.43-7.22 (m, 13H), 6.16-6.13 (m, 1H), 4.67-4.62 (m, 1H), 4.42-4.39 (m, 1H), 3.27-3.22 (m, 1H), 3.03-2.96 (m, 1H), 2.80 (t, J=7.4, 2H), 2.15-2.08 (m, 2H), 1.81-1.54 (m, 5H), 1.36-1.27 (m, 3H), 0.95-0.89 (m, 12H); $^{13}$C NMR (75 MHz, CD3OD), δ 177.2, 174.9, 173.6, 172.9, 142.9, 142.7, 136.0, 134.9, 133.9, 129.6, 129.5, 129.1, 128.8, 128.7, 128.64, 128.62, 128.5, 128.41, 128.38, 127.1, 126.7, 58.3, 56.1, 54.3, 52.7, 46.0, 40.5, 38.4, 32.3, 31.4, 30.1, 29.8, 27.9, 23.7, 10.2.

DI-41-intermediate

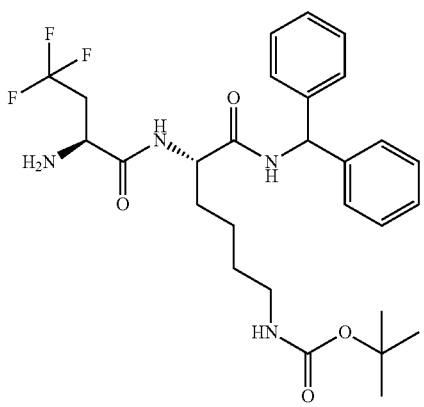

Chemical Formula: C$_{28}$H$_{37}$F$_3$N$_4$O$_4$
Exact Mass: 550.2767

Example 23 Intermediate $^1$H NMR (300 MHz, CDCl$_3$), δ 8.12 (d, J=8.5, 1H), 7.80 (d, J=8.3, 1H), 7.36-7.14 (m, 10H), 6.20 (d, J=8.3, 1H), 4.74 (d, J=5.9, 1H), 4.63-4.56 (m, 1H), 3.42-3.25 (m, 2H), 3.04-2.95 (m, 2H), 2.78-2.60 (m, 1H), 1.91-1.61 (m, 4H), 1.47-1.42 (m, 11H), 1.35-1.23 (m, 2H); $^{13}$C NMR (75 MHz, CDCl$_3$), δ.

Example 23

$^1$H NMR (300 MHz, CD$_3$OD), δ 8.72 (d, J=8.2, 1H), 8.18 (d, J=6.9, 1H), 7.82-7.77 (m, 3H), 7.68 (s, 1H), 7.47-7.23 (m, 13H), 6.17 (d, J=8.3, 1H), 4.61-4.54 (m, 2H), 4.43-4.39 (m, 1H), 3.29-3.27 (m, 1H), 3.10-3.01 (m, 1H), 2.86-2.59 (m, 4H), 2.15 (q, d=7.6, 2H), 1.84-1.56 (m, 4H), 1.37-1.29 (m, 2H), 0.94 (t, J=7.6, 3H); $^{13}$C NMR (75 MHz, CD3OD), δ

DI-42-intermediate

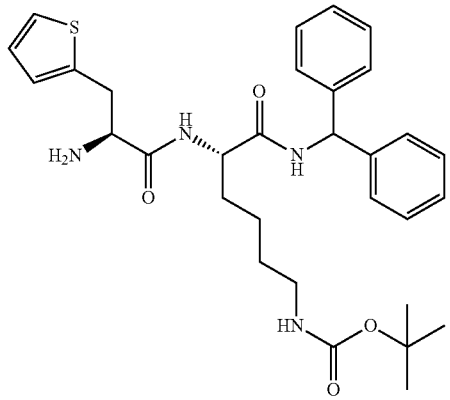

Chemical Formula: C$_{31}$H$_{40}$N$_4$O$_4$S
Exact Mass: 564.2770

Example 24 Intermediate $^1$H NMR (300 MHz, CDCl$_3$), δ 8.07 (d, J=8.2, 1H), 7.95 (d, J=8.4, 1H), 7.34-7.15 (m, 11H), 6.93-6.90 (m, 1H), 6.78-6.77 (m, 1H), 6.22 (d, J=8.4, 1H), 4.76-4.64 (m, 2H), 3.36-2.94 (m, 5H), 1.84-1.63 (m, 3H), 1.45-1.42 (m, 11H), 1.24-1.08 (m, 3H); $^{13}$C NMR (75 MHz, CDCl$_3$), δ 174.0, 170.8, 156.1, 141.6, 141.4, 139.2, 128.64, 128.56, 127.54, 127.46, 127.3, 127.0, 126.7, 124.7, 79.0, 56.7, 55.9, 52.6, 40.3, 35.0, 32.3, 29.5, 28.5, 22.6.

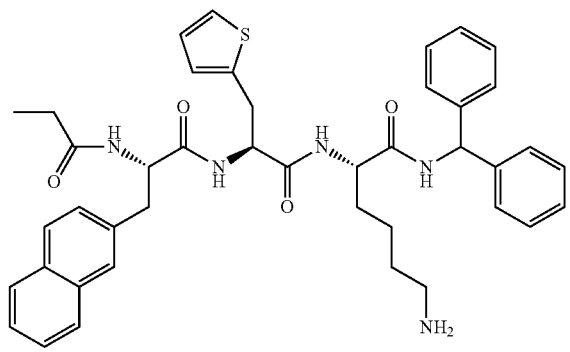

DI-42

Chemical Formula: C$_{42}$H$_{47}$N$_5$O$_4$S
Exact Mass: 717.3349

Example 24

$^1$H NMR (300 MHz, CD$_3$OD), δ 8.70 (d, J=8.4, 1H), 8.14 (d, J=7.6, 1H), 8.07 (d, J=7.0, 1H), 7.82-7.76 (m, 3H), 7.65 (s, 1H), 7.46-7.43 (m, 2H), 7.33-7.27 (m, 11H), 7.17-7.15 (m, 1H), 6.84-6.82 (m, 2H), 6.18 (d, J=8.3, 1H), 4.61-4.53 (m, 2H), 4.47-4.40 (m, 1H), 3.28-3.22 (m, 3H), 3.05-2.98 (m, 1H), 2.83 (t, J=7.4, 2H), 2.14 (q, J=7.6, 2H), 1.80-1.58 (m, 4H), 1.37-1.32 (m, 2H), 0.94 (t, J=7.6, 3H); $^{13}$C NMR (75 MHz, CD3OD), δ 177.4, 174.0, 172.81, 172.78, 142.9, 142.7, 139.6, 135.9, 134.9, 133.9, 129.62, 129.57, 129.1, 128.8, 128.6, 128.5, 128.3, 128.0, 127.8, 127.1, 126.7, 125.6, 58.3, 56.4, 56.2, 54.4, 40.5, 38.7, 32.44, 32.38, 29.8, 27.9, 23.6, 10.2.

3. Synthesis of Examples 25-31.
Scheme 4.
Synthesis of compounds Examples 25-31.

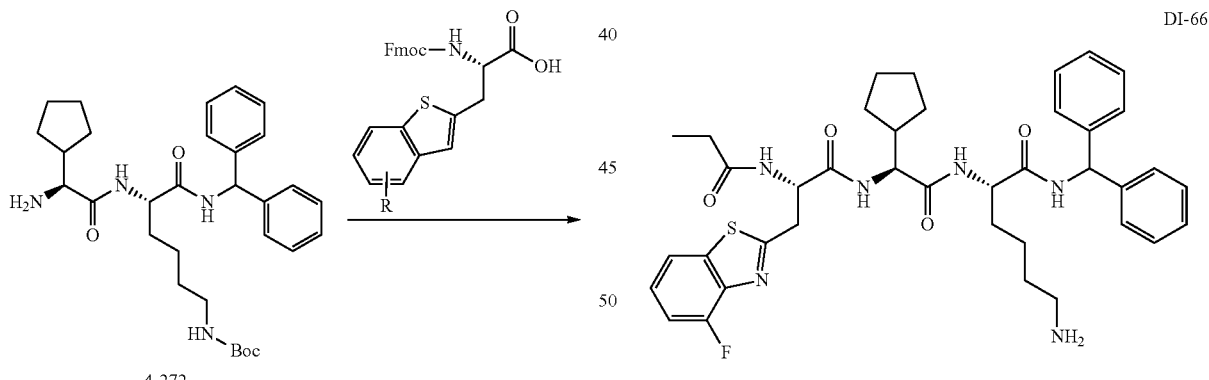

4-272

The following compounds were prepared from 4-272 using a similar procedure as that for Example 19. compounds Example 25.

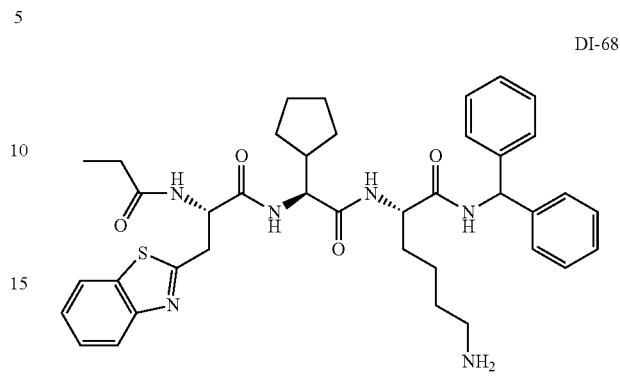

DI-68

Chemical Formula: C$_{39}$H$_{48}$N$_6$O$_4$S
Exact Mass: 696.3458

Example 25

$^1$H NMR (300 MHz, CD3OD), δ 8.63 (d, J=7.6, 1H), 8.31 (t, J=8.2, 1H), 8.10 (d, J=6.7, 1H), 7.93 (d, J=7.9, 2H), 7.52-7.38 (m, 2H), 7.32-7.23 (m, 10H), 6.14 (d, J=7.8, 1H), 4.95-4.91 (m, 1H), 4.46-4.43 (m, 1H), 4.14-4.09 (m, 1H), 3.61-3.34 (m, 2H), 2.84 (t, J=7.0, 2H), 2.27-2.17 (m, 3H), 2.02-1.24 (m, 14H), 1.05 (t, J=7.4, 3H); $^{13}$C NMR (75 MHz, CD3OD), δ177.2, 173.9, 172.8, 172.7, 169.2, 154.0, 142.8, 142.7, 136.5, 129.6, 129.5, 128.8, 128.6, 128.5, 128.4, 127.4, 126.5, 123.4, 122.9, 59.1, 58.3, 54.2, 43.2, 40.5, 36.22, 32.19, 30.3, 29.9, 27.9, 26.2, 25.8, 23.7, 10.1.

DI-66

Chemical Formula: C$_{39}$H$_{47}$FN$_6$O$_4$S
Exact Mass: 714.3364

Example 26

$^1$H NMR (300 MHz, CD3OD), δ 8.63 (d, J=7.3, 1H), 8.39-8.30 (m, 2H), 8.12 (d, J=7.0, 1H), 7.75 (d, J=8.0, 1H), 7.44-7.21 (m, 12H), 6.14 (d, J=8.1, 1H), 4.92-4.90 (m, 1H), 4.46-4.44 (m, 1H), 4.14-4.08 (m, 1H), 3.62-3.55 (m, 1H), 3.46-3.34 (m, 1H), 2.88 (t, J=7.5, 2H), 2.28-2.14 (m, 3H), 2.03-1.25 (m, 14H), 1.06 (t, J=7.6, 3H); $^{13}$C NMR (75 MHz, CD3OD).

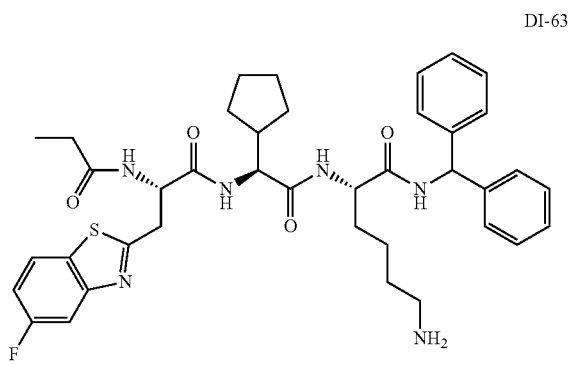

DI-63

Chemical Formula: $C_{39}H_{47}FN_6O_4S$
Exact Mass: 714.3364

Example 27

$^1$H NMR (300 MHz, CD3OD), δ 8.65 (d, J=8.2, 1H), 8.39-8.30 (m, 2H), 8.09 (d, J=7.3, 1H), 7.95-7.91 (m, 1H), 7.64 (dd, J=2.4, 11.9, 1H), 7.35-7.20 (m, 11H), 6.14 (d, J=8.1, 1H), 4.93-4.90 (m, 1H), 4.47-4.44 (m, 1H), 4.16-4.11 (m, 1H), 3.61-3.54 (m, 1H), 3.45-3.37 (m, 1H), 2.86 (t, J=7.4, 2H), 2.27-2.14 (m, 3H), 1.84-1.24 (m, 14H), 1.06 (t, J=7.6, 3H); $^{13}$C NMR (75 MHz, CD3OD).

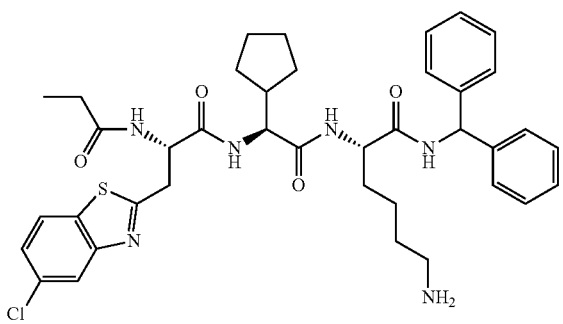

DI-65

Chemical Formula: $C_{39}H_{47}ClN_6O_4S$
Exact Mass: 730.3068

Example 29

$^1$H NMR (300 MHz, CD3OD), δ 8.65 (d, J=8.1, 1H), 8.30 (t, J=7.8, 1H), 8.09 (d, J=7.3, 1H), 7.92-7.89 (m, 2H), 7.40 (dd, J=1.7, 8.6, 1H), 7.34-7.20 (m, 10H), 6.13 (d, J=8.0, 1H), 4.92-4.91 (m, 1H), 4.45-4.41 (m, 1H), 4.14-4.10 (m, 1H), 3.60-3.37 (m, 2H), 2.84 (t, J=7.4, 2H), 2.26-2.13 (m, 3H), 1.83-1.23 (m, 14H), 1.05 (t, J=7.6, 3H); $^{13}$C NMR (75 MHz, CD3OD), δ177.2, 173.9, 172.8, 172.5, 171.5, 155.0, 142.8, 142.7, 135.1, 133.3, 129.6, 129.5, 128.8, 128.6, 128.5, 128.4, 126.7, 124.0, 123.1, 59.0, 58.3, 54.2, 54.1, 43.3, 40.5, 36.3, 32.2, 30.3, 29.9, 28.0, 26.2, 25.8, 23.7, 10.2.

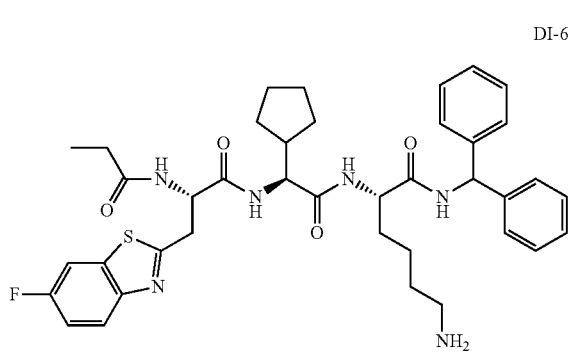

DI-67

Chemical Formula: $C_{39}H_{47}FN_6O_4S$
Exact Mass: 714.3364

Example 28

$^1$H NMR (300 MHz, CD3OD), δ 8.64 (d, J=7.9, 1H), 8.30 (d, J=8.0, 1H), 8.08 (d, J=7.5, 1H), 7.94-7.89 (m, 1H), 7.72 (dd, J=2.6, 8.4, 1H), 7.36-7.22 (m, 11H), 6.16-6.13 (m, 1H), 4.82-4.80 (m, 1H), 4.47-4.42 (m, 1H), 4.15-4.10 (m, 1H), 3.59-3.53 (m, 1H), 3.44-3.36 (m, 1H), 2.86 (t, J=7.4, 2H), 2.28-2.17 (m, 3H), 1.82-1.29 (m, 14H), 1.06 (t, J=7.6, 3H); $^{13}$C NMR (75 MHz, CD3OD).

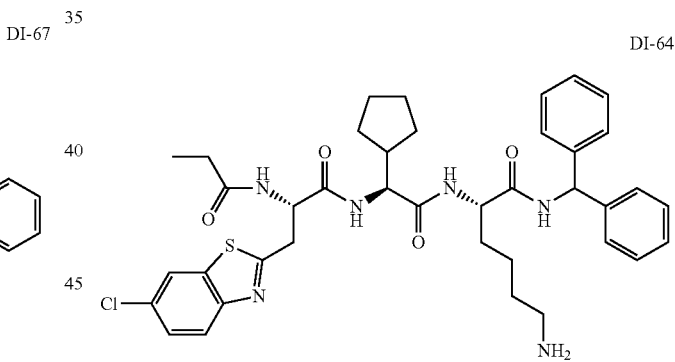

DI-64

Chemical Formula: $C_{39}H_{47}ClN_6O_4S$
Exact Mass: 730.3068

Example 30

$^1$H NMR (300 MHz, CD3OD:CCl$_3$D=1:1), δ 8.54 (d, J=8.1, 1H), 8.35 (t, J=7.5, 1H), 8.11-8.06 (m, 3H), 7.68 (dd, J=1.9, 8.7, 1H), 7.57-7.41 (m, 10H), 6.36 (d, J=8.1, 1H), 5.09-5.04 (m, 1H), 4.66-4.61 (m, 1H), 4.30-4.25 (m, 1H), 3.77-3.61 (m, 2H), 3.07 (t, J=7.1, 2H), 2.51-2.33 (m, 3H), 2.09-1.38 (m, 14H), 1.31 (t, J=7.6, 3H); $^{13}$C NMR (75 MHz, CD3OD:CCl$_3$D=1:1), δ 176.4, 173.1, 171.8, 171.7, 168.9, 151.7, 141.7, 141.6, 136.9, 131.9, 129.1, 129.0, 128.0, 127.97, 127.6, 123.7, 121.9, 58.5, 57.6, 53.34, 53.26, 42.3, 39.9, 35.4, 31.3, 29.7, 29.6, 29.5, 27.1, 25.6, 25.3, 22.8, 9.9.

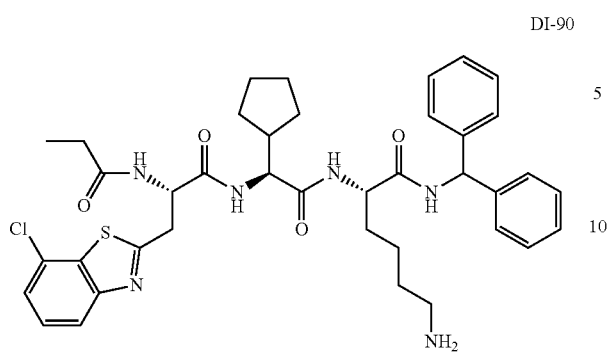

Chemical Formula: C₃₉H₄₇ClN₆O₄S
Exact Mass: 730.3068

Example 31

¹H NMR (300 MHz, CD3OD), δ 8.64 (d, J=8.2, 1H), 8.10 (t, J=7.2, 1H), 7.88 (d, J=7.7, 1H), 7.52-7.43 (m, 2H), 7.35-7.21 (m, 10H), 6.15-6.14 (m, 1H), 4.94-4.93 (m, 1H), 4.47-4.42 (m, 1H), 4.13-4.10 (m, 1H), 3.63-3.39 (m, 2H), 2.86 (t, J=7.3, 2H), 2.28-2.16 (m, 3H), 1.84-1.29 (m, 14H), 1.06 (t, J=7.6, 3H); ¹³C NMR (75 MHz, CD3OD), δ 177.2, 173.9, 172.8, 172.5, 169.9, 154.9, 142.8, 142.7, 136.5, 129.6, 129.5, 128.8, 128.6, 128.4, 127.7, 126.1, 122.2, 59.1, 58.3, 54.2, 54.1, 43.3, 40.5, 36.4, 32.2, 30.3, 29.9, 28.0, 26.2, 25.8, 23.7, 10.2.

4. Synthesis of Example 32.

Scheme 5. Synthesis of Example 32.

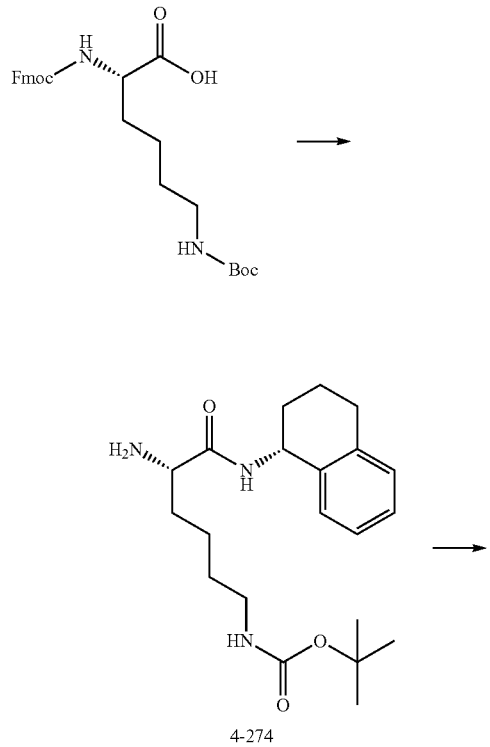

4-274

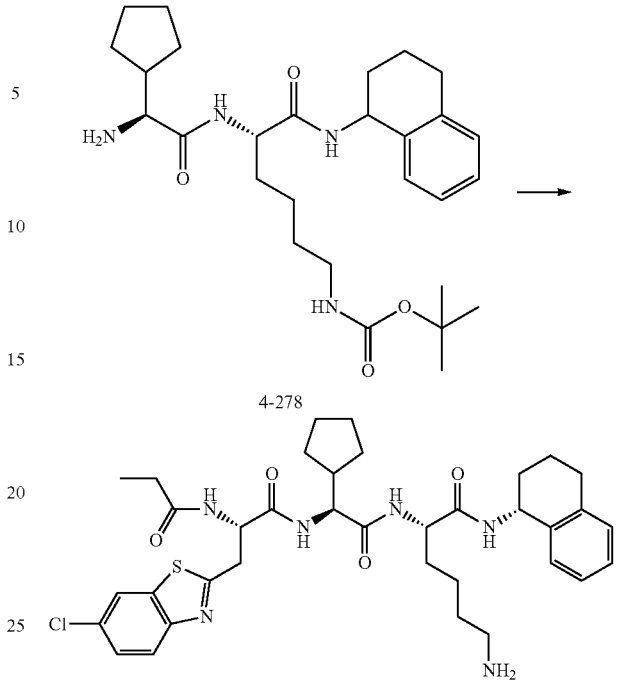

4-278

Example 32 was prepared from Fmoc-Lys(Boc)-OH using a similar procedure as that for Example 25.

4-274:

¹H NMR (300 MHz, CDCl₃), δ 7.63 (d, J=8.8, 1H), 7.32-7.05 (m, 4H), 5.15-5.10 (m, 1H), 4.96 (brd., 1H), 3.37-3.33 (m, 1H), 3.11-3.09 (m, 2H), 2.82-2.70 (m, 2H), 2.03-1.99 (m, 1H), 1.84-1.75 (m, 6H), 1.57-1.41 (m, 14H); ¹³C NMR (75 MHz, CDCl₃), δ 174.3, 156.1, 137.4, 136.9, 129.1, 128.4, 127.1, 126.1, 78.9, 55.0, 46.9, 40.1, 34.7, 30.2, 29.8, 29.2, 28.4, 22.9, 20.1.

4-278:

¹HNMR (300 MHz, CDCl₃), δ 7.77 (d, J=8.5, 1H), 7.58 (d, J=8.1, 1H), 7.18-7.04 (m, 4H), 5.14-5.09 (m, 1H), 4.92 (br, 1H), 4.62-4.54 (m, 1H), 3.08-3.06 (m, 2H), 2.76-2.72 (m, 3H), 2.03-2.01 (m, 2H), 1.82-1.77 (m, 4H), 1.66-1.20 (m, 24H); ¹³C NMR (75 MHz, CDCl₃), δ 175.1, 171.1, 156.1, 137.4, 136.5, 129.0, 128.5, 127.0, 126.1, 78.9, 58.3, 52.3, 47.4, 43.5, 40.3, 32.9, 30.2, 29.4, 29.3, 28.4, 27.5, 25.6, 25.4, 22.7, 20.2.

Example 32

¹H NMR (300 MHz, CD₃OD), δ 8.00 (d, J=2.0, 1H), 7.89 (d, J=8.7, 1H), 7.49 (dd, J=2.1, 8.7, 1H), 7.17-7.08 (m, 2H), 5.05-5.04 (m, 1H), 4.80-4.74 (m, 1H), 4.35-4.31 (m, 1H), 4.13 (d, J=8.8, 1H), 3.54-3.36 (m, 2H), 2.94-2.81 (m, 4H), 2.27-2.20 (m, 3H), 1.98-1.29 (m, 18H), 1.06 (t, J=7.6, 3H); 13C NMR (75 MHz, CD3OD), δ 177.2, 173.9, 172.9, 170.1, 152.7, 138.7, 138.0, 137.5, 132.2, 130.1, 129.5, 128.3, 128.0, 127.1, 124.4, 122.5, 59.2, 54.3, 43.2, 40.6, 36.1, 32.3, 31.2, 30.4, 30.3, 30.2, 29.9, 28.0, 26.2, 25.9, 23.8, 21.4, 10.2.

5. Synthesis of Examples 33 and 34.

Scheme 6. Synthesis of Example 33 and 34.

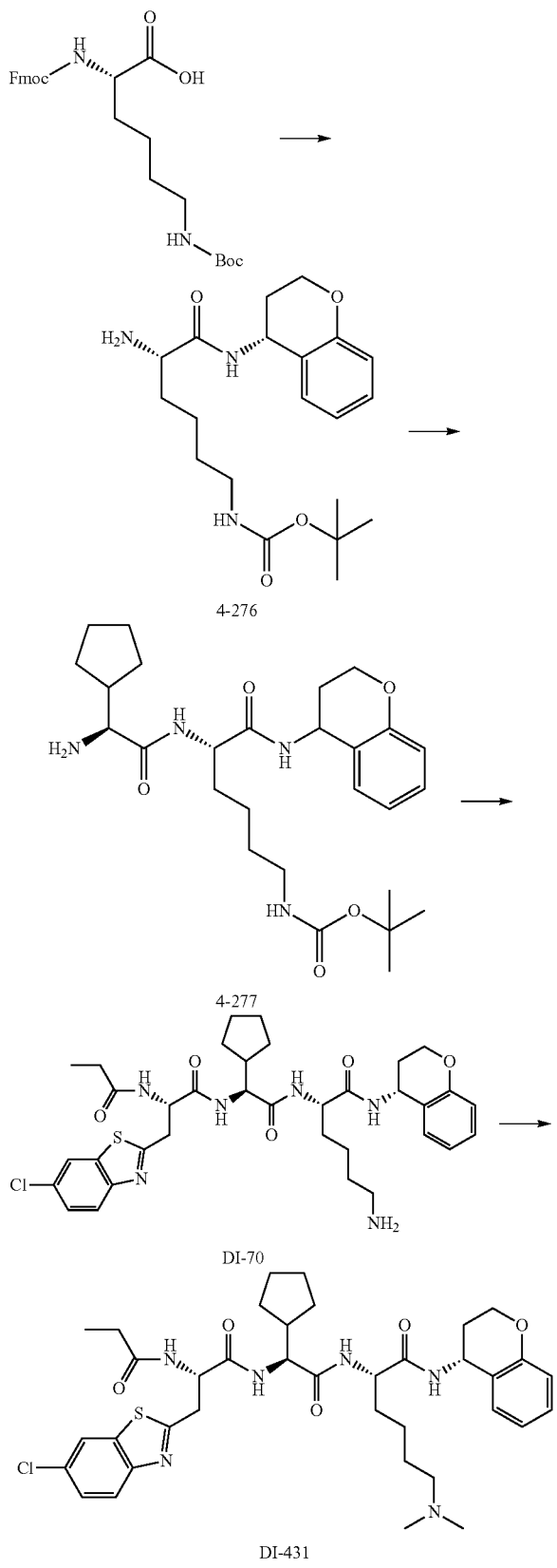

Example 33 was prepared from Fmoc-Lys(Boc)-OH using a similar procedure as that for compound Example 25.

4-276:

$^1$H NMR (300 MHz, CDCl$_3$), δ 7.74 (d, J=8.1, 1H), 7.16-7.12 (m, 2H), 6.89-6.78 (m, 2H), 5.08-5.06 (m, 1H), 4.25-4.12 (m, 1H), 3.35-3.31 (m, 1H), 3.11-3.09 (m, 2H), 2.19-2.17 (m, 1H), 2.00-1.84 (m, 2H), 1.62-1.41 (m, 16H); $^{13}$C NMR (75 MHz, CDCl$_3$), δ 174.7, 156.1, 154.9, 129.1, 128.9, 122.3, 120.6, 116.9, 78.8, 63.3, 54.9, 42.9, 40.1, 34.6, 29.8, 29.1, 28.4, 22.9.

4-277:

$^1$H NMR (300 MHz, CDCl$_3$), δ 7.95 (d, J=7.4, 1H), 7.80 (d, J=8.5, 1H), 7.14-7.10 (m, 2H), 6.87-6.77 (m, 2H), 5.11-5.05 (m, 1H), 4.94 (br, 1H), 4.67-4.57 (m, 1H), 4.26-4.15 (m, 2H), 3.07-3.05 (m, 2H), 2.71 (d, J=6.1, 1H), 2.19-2.13 (m, 1H), 2.03-1.99 (m, 2H), 1.81-1.77 (m, 1H), 1.67-1.17 (m, 24H); $^{13}$C NMR (75 MHz, CDCl$_3$), δ 175.2, 171.3, 156.1, 155.1, 129.4, 128.9, 121.9, 120.6, 116.9, 78.9, 77.5, 77.1, 76.7, 63.3, 58.1, 52.2, 43.5, 43.4, 40.3, 32.9, 29.4, 29.3, 29.1, 28.4, 27.5, 25.6, 25.4, 22.7.

Example 33

$^1$H NMR (300 MHz, CD$_3$OD), δ 8.35-8.22 (m, 2H), 8.06 (d, J=6.9, 1H), 8.00 (d, J=2.0, 1H), 7.88 (d, J=8.7, 1H), 7.48 (dd, J=2.1, 8.7, 1H), 7.14-7.08 (m, 2H), 6.85-6.75 (m, 2H), 5.07-5.00 (m, 1H), 4.80-4.74 (m, 1H), 4.34-4.31 (m, 1H), 4.23-4.20 (m, 2H), 4.13-4.08 (m, 1H), 3.54-3.36 (m, 2H), 2.91 (t, J=7.5, 2H), 2.27-1.28 (m, 19H), 1.06 (t, J=7.6, 3H); $^{13}$C NMR (75 MHz, DMSO-D6), δ 173.8, 171.3, 170.5, 169.6, 155.1, 151.7, 137.1, 129.9, 129.7, 129.1, 126.9, 123.8, 123.6, 122.2, 120.6, 116.9, 63.6, 56.3, 52.8, 52.4, 42.8, 36.1, 31.9, 29.1, 29.0, 28.8, 28.6, 27.2, 25.3, 25.0, 22.7, 10.2.

Example 34

Na(AcO)$_3$BH (4 equiv.) was added to as solution of Example 33 (1 equiv.) and formaldehyde (10 equiv.) in ClCH$_2$CH$_2$Cl and the resultant mixture was stirred at room temperature for 1 h. The reaction was quenched with 10% NaHCO$_3$ solution and evaporated. The residue was purified by HPLC to give Example 34.

Example 34

$^1$H NMR (400 MHz, DMSO-D6), δ 9.45 (br., 1H), 8.43 (d, J=8.3, 1H), 8.34 (d, J=8.4, 1H), 8.23 (d, J=2.2, 1H), 8.14 (d, J=8.1, 1H), 7.94-7.92 (m, 2H), 7.52 (dd, J=2.2, 8.7, 1H), 7.16-7.10 (m, 2H), 6.85-6.81 (m, 1H), 6.79-6.77 (m, 1H), 5.03-4.98 (m, 1H), 4.86-4.80 (m, 1H), 4.30-4.15 (m, 4H), 3.55-3.47 (m, 1H), 3.33-3.26 (m, 1H), 3.03-2.98 (m, 2H), 2.76 (d, J=3.6, 6H), 2.21-2.00 (m, 4H), 1.88-1.83 (m, 1H), 1.70-1.24 (m, 14H), 0.94 (t, J=7.6, 3H); $^{13}$C NMR (100 MHz, DMSO-D6), δ 173.8, 171.3, 171.2, 170.5, 169.6, 155.1, 151.7, 137.1, 129.9, 129.7, 129.1, 127.0, 123.8, 123.6, 122.2, 120.6, 116.9, 63.6, 56.9, 56.2, 52.7, 52.5, 42.8, 42.7, 42.6, 36.1, 31.9, 29.2, 29.0, 28.9, 28.6, 25.3, 25.0, 23.8, 22.8, 10.2.

6. Synthesis of Examples 35 & 36.

Scheme 7. Synthesis of Example 35.

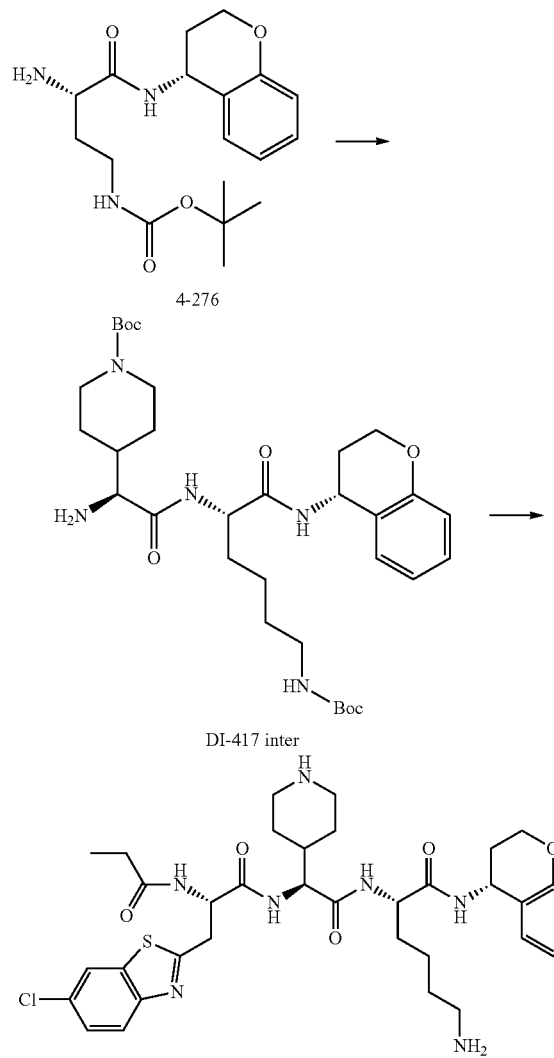

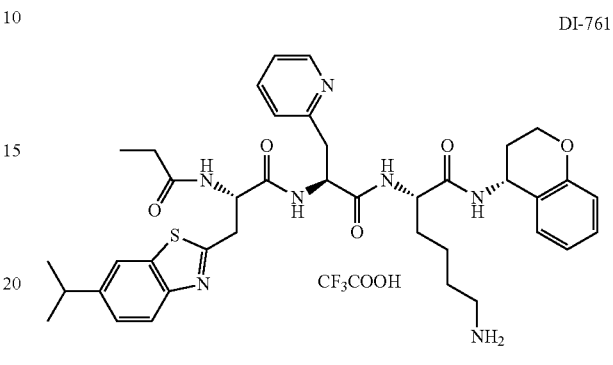

Example 35 was prepared using a similar procedure as that for Example 25.

Example 35 intermediate: H NMR (300 MHz, CDCl$_3$), δ 7.92-7.76 (m, 2H), 7.13-7.08 (m, 2H), 6.84-6.74 (m, 2H), 5.08-5.06 (m, 1H), 4.94 (br, 1H), 4.53-4.51 (m, 1H), 4.19-4.07 (m, 4H), 3.15-3.02 (m, 4H), 2.84-2.82 (m, 1H), 2.62-2.58 (m, 1H), 2.15-2.13 (m, 1H), 2.00-1.92 (m, 2H), 1.77-1.17 (m, 30H); $^{13}$C NMR (75 MHz, CDCl$_3$), δ 173.9, 171.2, 156.1, 155.0, 154.6, 129.3, 129.0, 121.8, 120.7, 117.0, 79.5, 79.0, 63.3, 58.9, 52.6, 43.5, 40.1, 39.3, 32.6, 29.5, 29.1, 28.8, 28.4, 26.1, 22.7.

Example 35

$^1$H NMR (300 MHz, CD$_3$OD), δ 8.49-8.40 (m, 2H), 8.25 (d, J=7.9, 1H), 7.99 (d, J=2.0, 1H), 7.90 (d, J=8.7, 1H), 7.48 (dd, J=2.0, 8.7, 1H), 7.18-7.10 (m, 2H), 6.85-6.82 (m, 1H), 6.76 (d, J=8.1, 1H), 5.08-5.00 (m, 1H), 4.80-4.73 (m, 1H), 4.37-4.32 (m, 1H), 4.23-4.14 (m, 3H), 3.62-3.34 (m, 4H), 3.06-2.88 (m, 4H), 2.29-2.21 (m, 2H), 2.09-1.23 (m, 15H), 1.07 (t, J=7.6, 3H); $^{13}$C NMR (75 MHz, CD3OD), δ 177.4, 173.4, 172.8, 171.9, 169.8, 156.5, 152.8, 138.0, 132.3, 130.4, 130.1, 128.1, 124.5, 123.3, 122.6, 121.6, 118.0, 64.5, 57.8, 54.8, 54.4, 44.9, 44.8, 40.5, 37.8, 36.2, 32.4, 30.2, 29.9, 28.2, 26.9, 26.0, 24.0, 10.2.

DI-761

Example 36 was prepared using a similar procedure as that for Example 25.

Example 36

$^1$H NMR (400 MHz, MeOD) δ 8.65 (d, J=4.9 Hz, 1H), 8.32 (td, J=7.9, 1.5 Hz, 1H), 7.97-7.68 (m, 4H), 7.41 (dd, J=8.5, 1.7 Hz, 1H), 7.25-7.05 (m, 2H), 6.85 (td, J=7.5, 1.1 Hz, 1H), 6.79 (d, J=8.2 Hz, 1H), 5.14 (t, J=5.8 Hz, 1H), 4.76 (dd, J=8.4, 5.2 Hz, 1H), 4.30 (dd, J=9.2, 5.2 Hz, 1H), 4.25-4.22 (m, 2H), 3.65 (dd, J=14.5, 5.5 Hz, 1H), 3.54 (dd, J=15.4, 5.2 Hz, 1H), 3.46-3.40 (m, 2H), 3.07 (dt, J=13.7, 6.9 Hz, 1H), 2.93 (t, J=7.7 Hz, 2H), 2.25 (q, J=7.6 Hz, 2H), 2.20-2.11 (m, 1H), 2.05-1.98 (m, 1H), 1.87-1.63 (m, 4H), 1.58-1.37 (m, 3H), 1.33 (d, J=6.9 Hz, 6H), 1.08 (t, J=7.6 Hz, 3H). $^{13}$C NMR (101 MHz, MeOD) δ 175.99, 172.13, 171.50, 170.21, 166.68, 155.15, 153.65, 150.89, 146.71, 144.47, 142.80, 135.24, 128.93, 128.66, 127.57, 125.20, 124.59, 121.92, 121.73, 120.19, 118.58, 116.56, 63.18, 53.71, 53.20, 52.71, 43.60, 39.08, 35.81, 34.50, 34.08, 30.92, 28.80, 28.44, 26.68, 23.16, 22.53, 8.67.

7. Synthesis of Examples 37 & 38

Scheme 8. Synthesis of Example 37 & 38

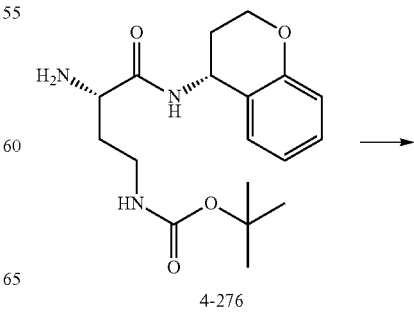

217
-continued

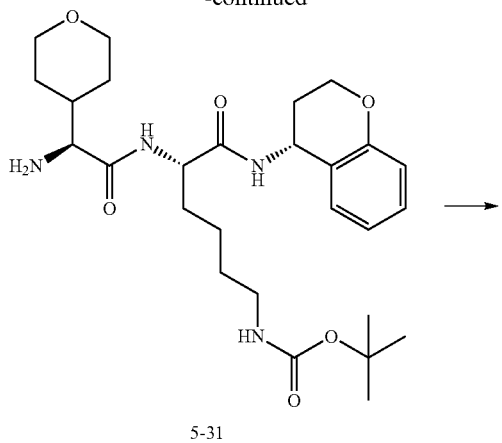

5-31

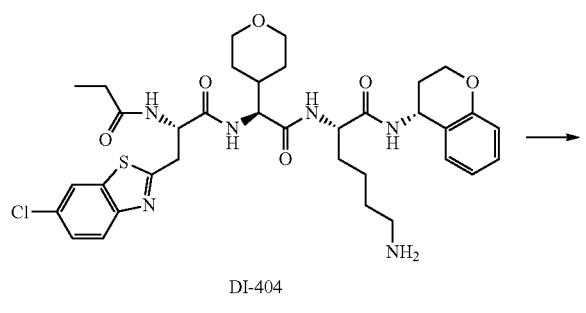

DI-404

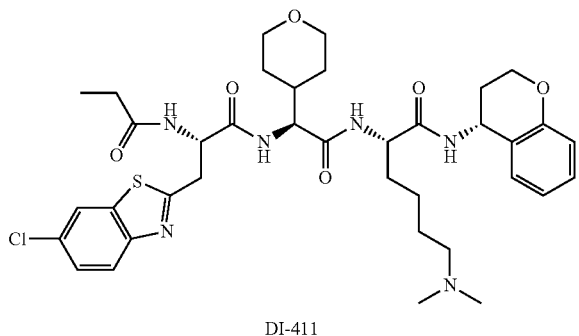

DI-411

218

Examples 37 & 38 were prepared using a similar procedure as that for compounds Examples 33 & 34.

5-31:

$^1$H NMR (300 MHz, CDCl$_3$), δ 7.91-7.81 (m, 2H), 7.13-7.08 (m, 2H), 6.85-6.75 (m, 2H), 5.09-5.07 (m, 1H), 4.90 (br, 1H), 4.58-4.51 (m, 1H), 4.24-4.14 (m, 2H), 3.96-3.92 (m, 2H), 3.36-3.26 (m, 2H), 3.04-3.02 (m, 1H), 2.70-2.69 (m, 1H), 2.17-2.14 (m, 1H), 2.01-1.97 (m, 1H), 1.82-1.75 (m, 2H), 1.66-1.29 (m, 20H); $^{13}$C NMR (75 MHz, CDCl$_3$), δ 174.0, 171.1, 156.1, 155.0, 129.3, 129.0, 121.9, 120.6, 117.0, 79.0, 67.7, 63.3, 58.9, 52.4, 43.4, 40.2, 38.3, 32.9, 29.5, 29.2, 28.4, 26.8, 22.8.

Example 37

$^1$H NMR (300 MHz, DMSO-D6), δ 8.45 (d, J=8.2, 1H), 8.36 (d, J=8.3, 1H), 8.24-8.21 (m, 2H), 7.95-7.92 (m, 2H), 7.71 (br., 3H), 7.53 (d, J=8.4, 1H), 7.17-7.08 (m, 2H), 6.86-6.76 (m, 2H), 5.01-4.99 (m, 1H), 4.85-4.84 (m, 1H), 4.31-4.20 (m, 4H), 3.86-3.83 (m, 2H), 3.35-3.18 (m, 3H), 2.78-2.73 (m, 2H), 2.15-1.89 (m, 5H), 1.65-1.14 (m, 11H), 0.94 (t, J=7.5, 3H); $^{13}$C NMR (75 MHz, DMSO-D6), δ 173.9, 171.3, 170.6, 170.4, 169.5, 155.1, 151.7, 137.1, 129.9, 129.6, 129.1, 126.9, 123.8, 123.7, 122.2, 120.6, 116.9, 67.4, 67.2, 63.6, 56.9, 53.0, 52.5, 42.8, 38.2, 36.1, 31.8, 29.5, 29.1, 28.9, 28.6, 27.1, 22.8, 10.2.

Example 38

$^1$H NMR (300 MHz, DMSO-D6), δ 9.42 (br., 1H), 8.49 (d, J=8.1, 1H), 8.36 (d, J=9.4, 1H), 8.27-8.24 (m, 2H), 7.94-7.90 (m, 2H), 7.54-7.51 (m, 1H), 7.17-7.08 (m, 2H), 6.86-6.76 (m, 2H), 6.57 (br., 1H), 5.01-4.99 (m, 1H), 4.86-4.83 (m, 1H), 4.32-4.02 (m, 4H), 3.84-3.82 (m, 2H), 3.52-3.48 (m, 1H), 3.27-3.22 (m, 2H), 3.02-2.95 (m, 2H), 2.76 (s, 6H), 2.15-1.88 (m, 6H), 1.61-1.15 (m, 10H), 0.94 (t, J=7.6, 3H); $^{13}$C NMR (75 MHz, DMSO-D6), δ 173.9, 171.2, 170.6, 170.4, 169.6, 155.1, 151.7, 137.1, 129.9, 129.6, 129.1, 127.0, 123.8, 123.7, 122.3, 120.6, 116.9, 67.2, 63.6, 56.9, 52.5, 51.8, 42.7, 42.6, 36.1, 31.8, 29.5, 29.2, 28.9, 28.6, 23.8, 22.8, 10.2.

9. Synthesis of Examples 39-42. If DI-75-2 is Described Somewhere, it Will have to be Numbered Near the End.

Scheme 8. Synthesis of Examples 39 & 40

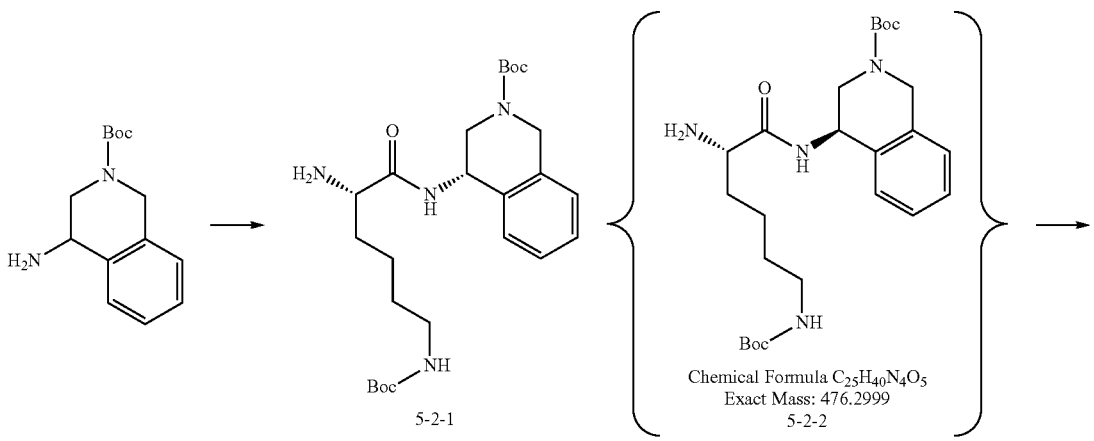

Chemical Formula C$_{25}$H$_{40}$N$_4$O$_5$
Exact Mass: 476.2999
5-2-2

-continued
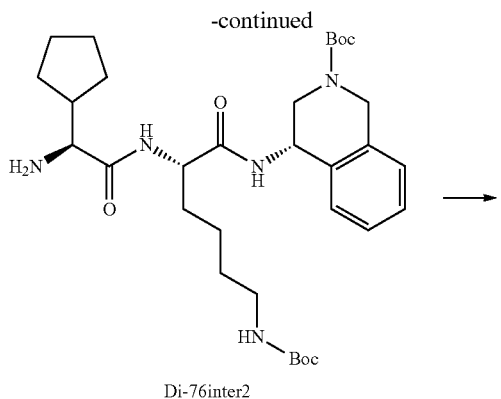
Di-76inter2
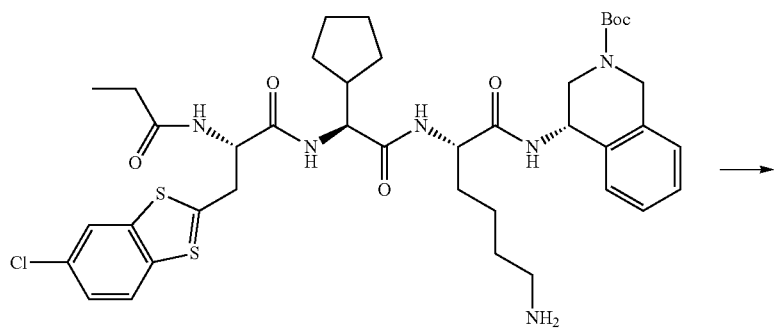
Chemical Formula: C_{35}H_{46}ClN_{7}O_{4}S
Exact Mass: 695.3021
DI-75-1
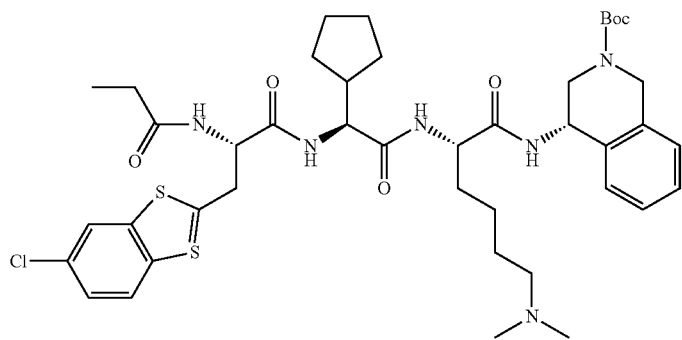
Chemical Formula: C_{38}H_{52}ClN_{7}O_{4}S
Exact Mass: 737.3490
DI-76
Compounds Examples 39 & 40 were prepared using a similar procedure as that for Examples 33 & 34.
5-2-1:
$^1$H NMR (300 MHz, CD3OD), δ 7.30-7.18 (m, 4H), 5.08-5.06 (m, 1H), 4.84-4.74 (m, 1H), 4.45-4.39 (m, 1H), 4.11-3.91 (m, 1H), 3.76 (t, J=6.7, 1H), 3.52-3.33 (m, 1H), 3.09-2.95 (m, 2H), 1.84-1.79 (m, 2H), 1.48-1.39 (m, 22H); $^{13}$C NMR (75 MHz, CD3OD), δ 169.6, 158.6, 156.9, 135.3, 134.3, 130.4, 129.4, 128.1, 127.5, 81.7, 80.0, 54.3, 48.3, 47.0, 46.2, 40.8, 32.4, 30.5, 28.8, 23.0.
5-2-2:
$^1$H NMR (300 MHz, CD3OD), δ 7.30-7.19 (m, 4H), 5.07-5.00 (m, 1H), 4.84-4.71 (m, 1H), 4.50-4.40 (m, 1H), 4.06-3.43 (m, 3H), 3.10 (t, J=6.7, 2H), 1.87-1.70 (m, 2H), 1.49-1.41 (m, 22H); $^{13}$C NMR (75 MHz, CD3OD), δ 168.3, 157.2, 155.6, 133.8, 132.9, 128.7, 127.9, 126.9, 126.1, 80.6, 78.6, 53.0, 46.9, 45.6, 44.9, 39.4, 30.9, 29.1, 27.4, 27.3, 21.8.

Example 39 Intermediate $^1$H NMR (300 MHz, CD3OD), δ 8.54-8.48 (m, 2H), 7.32-7.22 (m, 4H), 5.06-5.04 (m, 1H), 4.79-4.77 (m, 1H), 4.51-4.46 (m, 1H), 4.38-4.35 (m, 1H), 4.01-3.87 (m, 1H), 3.77-3.74 (m, 1H), 3.06-3.04 (m, 2H), 2.29-2.21 (m, 1H), 1.86-1.66 (m, 8H), 1.52-1.44 (m, 24H); 13C NMR (75 MHz, CD3OD), δ 171.6, 168.5, 157.2, 155.3, 133.7, 133.6, 128.5, 127.7, 126.6, 126.0, 80.3, 78.5, 56.7, 53.3, 46.7, 45.6, 44.8, 42.0, 39.7, 31.6, 29.2, 28.53, 28.49, 27.39, 27.38, 24.5, 24.4, 22.8.

Example 39

$^1$H NMR (300 MHz, CD$_3$OD), δ 8.40 (d, J=2.0, 1H), 8.23-8.20 (m, 2H), 8.00 (d, J=2.0, 1H), 7.89 (d, J=8.7, 1H), 7.48 (dd, J=2.1, 8.7, 1H), 7.33-7.23 (m, 4H), 5.23 (t, J=5.2, 1H), 4.66-4.62 (m, 1H), 4.49-4.33 (m, 2H), 4.31-4.26 (m, 1H), 4.06-4.01 (m, 1H), 3.65-3.59 (m, 1H), 3.50-3.34 (m, 3H), 2.90 (t, J=7.5, 2H), 2.26-2.18 (m, 3H), 1.87-1.26 (m, 14H), 1.04 (t, J=7.6, 3H); $^{13}$C NMR (75 MHz, CD3OD), δ 177.4, 174.4, 174.3, 173.2, 169.8, 152.8, 137.9, 132.9, 132.3, 129.89, 128.85, 129.7, 128.1, 127.8, 124.4, 122.6, 59.9, 54.9, 54.5, 46.9, 45.9, 45.4, 42.8, 40.5, 35.9, 31.7, 30.5, 30.3, 29.8, 28.0, 26.1, 25.8, 23.9, 101.

Example 40

$^1$H NMR (300 MHz, CD$_3$OD), δ 8.27-8.20 (m, 2H), 8.04 (d, J=1.8, 1H), 7.92 (d, J=8.8, 1H), 7.54-7.51 (m, 1H), 7.39-7.28 (m, 4H), 5.31-5.19 (m, 1H), 4.77-4.70 (m, 1H), 4.59-4.45 (m, 2H), 4.33-4.26 (m, 1H), 4.09-4.06 (m, 1H), 3.78-3.71 (m, 1H), 3.55-3.41 (m, 2H), 3.13-3.10 (m, 3H), 2.90 (s, 3H), 2.29-2.22 (m, 3H), 1.88-1.31 (m, 14H), 1.07 (t, J=7.5, 3H); $^{13}$C NMR (75 MHz, CD3OD), δ 177.4, 174.5, 174.4, 173.2, 169.9, 152.8, 138.0, 132.3, 130.1, 130.02, 129.96, 129.8, 128.1, 127.6, 124.4, 122.6, 58.7, 55.9, 54.7, 54.5, 46.0, 43.5, 42.9, 41.1, 38.9, 35.9, 31.7, 30.5, 30.3, 29.8, 26.2, 25.9, 25.0, 23.9, 10.1.

Scheme 8. Synthesis of Examples 41 & 42.

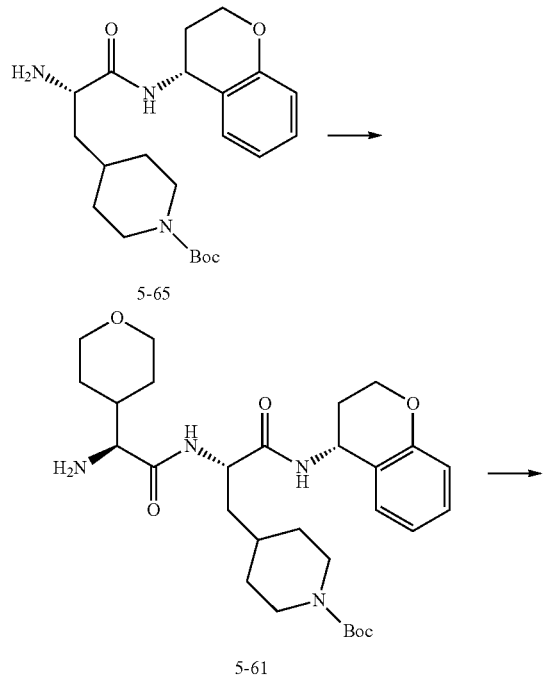

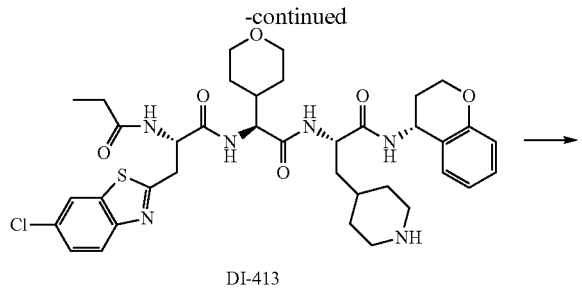

DI-413

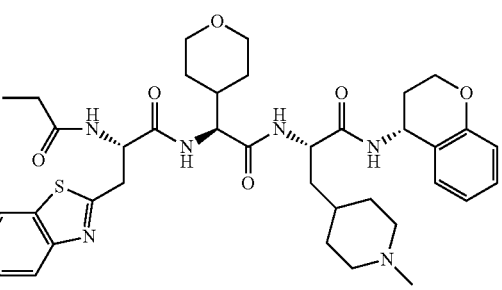

DI-415

Examples 41 & 42 were prepared using a similar procedure as that for compounds Examples 33 & 34.

5-65:

$^1$H NMR (300 MHz, CDCl$_3$), δ 7.68 (d, J=8.1, 1H), 7.15-7.10 (m, 2H), 6.87-6.82 (m, 1H), 6.78 (d, J=8.1, 1H), 5.09-5.03 (m, 1H), 4.25-4.02 (m, 4H), 3.46-3.42 (m, 1H), 2.66 (br, 2H), 2.18-1.94 (m, 4H), 1.78-1.62 (m, 4H), 1.47-1.30 (m, 10H), 1.21-1.06 (m, 2H); $^{13}$C NMR (75 MHz, CDCl$_3$), δ 174.8, 155.0, 154.8, 129.1, 122.2, 120.7, 117.1, 79.4, 63.3, 52.5, 43.8, 43.1, 41.8, 32.7, 31.2, 29.0, 28.4.

5-61:

$^1$H NMR (300 MHz, CD$_3$OD), δ 7.17-7.08 (m, 2H), 6.84-6.73 (m, 2H), 5.06-5.03 (m, 1H), 4.46 (t, J=7.4, 1H), 4.21-4.14 (m, 2H), 4.05-3.96 (m, 4H), 3.74 (d, J=6.5, 1H), 3.44-3.34 (m, 2H), 2.69 (br., 2H), 2.14-2.06 (m, 2H), 1.99-1.89 (m, 1H), 1.73-1.29 (m, 18H), 1.21-1.02 (m, 2H); $^{13}$C NMR (75 MHz, CD$_3$OD), δ 172.1, 172.0, 155.1, 155.0, 129.0, 128.6, 122.0, 120.1, 116.5, 79.6, 67.0, 66.9, 63.1, 56.9, 51.2, 43.5, 43.4, 38.2, 37.1, 32.4, 32.0, 31.1, 28.8, 28.4, 27.9, 27.3.

Example 41

$^1$H NMR (300 MHz, DMSO-D6), 8.58-8.51 (m, 2H), 8.37-8.23 (m, 4H), 7.95-7.92 (m, 2H), 7.54-7.51 (m, 1H), 7.17-7.08 (m, 2H), 6.86-6.77 (m, 2H), 5.00-4.98 (m, 1H), 4.84-4.83 (m, 1H), 4.36-4.20 (m, 6H), 3.87-3.83 (m, 2H), 3.53-3.26 (m, 3H), 2.80-2.77 (m, 2H), 2.15-1.76 (m, 8H), 1.56-1.24 (m, 9H), 0.94 (t, J=7.6, 3H); 1.21-1.0C NMR (75 MHz, DMSO-D6), δ 173.9, 171.3, 170.6, 170.4, 169.6, 155.1, 151.7, 137.1, 129.9, 129.7, 129.1, 126.9, 123.8, 123.6, 122.2, 120.6, 116.9, 67.4, 63.6, 57.0, 52.5, 50.6, 43.6, 42.8, 38.4, 38.1, 36.2, 30.4, 29.6, 29.1, 29.0, 28.9, 28.7, 28.2, 10.2.

Example 42 DI-415 needs to be inserted here.

8. Synthesis of Example 12X. DI-423 not in SAR Table. If being Added, Put at End.

Scheme 10. Synthesis of DI-423

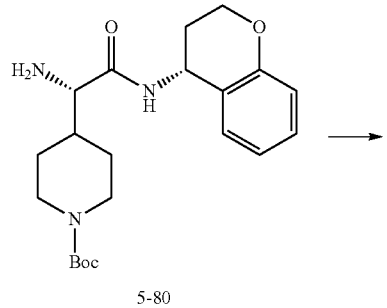

5-80

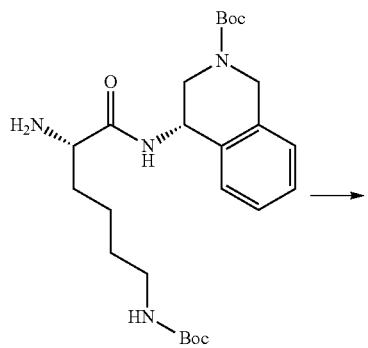

5-47

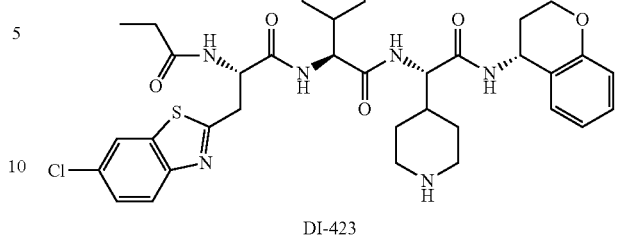

DI-423

Compounds DI-423 were prepared using a similar procedure as that for Example 33.

5-80:
$^1$H NMR (300 MHz, CDCl$_3$), δ 7.64 (d, J=7.8, 1H), 7.21-7.12 (m, 2H), 6.93-6.83 (m, 2H), 5.15-5.11 (m, 1H), 4.27-4.13 (m, 4H), 3.32 (d, J=3.8, 1H), 2.75-2.71 (m, 2H), 2.26-2.00 (m, 3H), 1.79-1.23 (m, 15H); $^{13}$C NMR (75 MHz, CDCl$_3$), δ 173.1, 155.1, 154.7, 129.2, 129.1, 122.1, 120.8, 117.2, 79.5, 63.3, 59.1, 43.7, 43.2, 39.3, 29.2, 28.5, 25.8.

5-47:
$^1$HNMR (300 MHz, CD$_3$OD), δ 8.76 (d, J=8.0, 1H), 7.18-7.13 (m, 2H), 6.88-6.78 (m, 2H), 5.14-5.08 (m, 1H), 4.47 (t, J=6.9, 1H), 4.27-4.19 (m, 3H), 4.15-4.01 (m, 4H), 3.81 (d, J=6.5, 1H), 3.48-3.39 (m, 2H), 2.77 (br., 2H), 2.20-2.07 (m, 2H), 2.03-1.82 (m, 3H), 1.70-1.20 (m, 17H); $^{13}$C NMR (75 MHz, CD$_3$OD), δ 170.4, 167.5, 155.1, 155.0, 128.9, 128.7, 121.9, 120.2, 116.6, 79.7, 67.0, 63.1, 57.8, 57.7, 56.9, 43.4, 38.0, 37.2, 28.9, 28.3, 28.1, 27.3.

Example 12XDI-423

$^1$HNMR (300 MHz, DMSO-D6), δ 8.76-8.64 (m, 2H), 8.38-8.33 (m, 3H), 8.23 (d, J=2.0, 1H), 7.99-7.91 (m, 2H), 7.52 (dd, J=2.1, 8.7, 1H), 7.18-7.13 (m, 1H), 7.06-6.99 (m, 1H), 6.85-6.77 (m, 2H), 5.03-5.01 (m, 1H), 4.88-4.81 (m, 1H), 4.33 (t, J=7.6, 1H), 4.25-4.20 (m, 2H), 4.07-4.00 (m, 1H), 3.86-3.84 (m, 2H), 3.53-3.48 (m, 1H), 3.34-3.22 (m, 2H), 2.85-2.73 (m, 2H), 2.14-1.67 (m, 9H), 1.46-1.15 (m, 8H), 0.94 (t, J=7.6, 3H); $^{13}$C NMR (75 MHz, DMSO-D6), δ 173.8, 170.7, 170.6, 169.60, 169.55, 155.1, 151.7, 137.1, 129.9, 129.5, 129.1, 126.9, 123.8, 123.5, 122.2, 120.6, 117.0, 67.4, 67.2, 63.5, 60.2, 56.6, 52.4, 43.0, 42.7, 38.3, 36.2, 29.5, 29.2, 28.9, 25.5, 21.2, 10.2.

9. Synthesis of Examples 43 & 44.

Scheme 11. Synthesis of Examples 43 & 44.

5-2-1

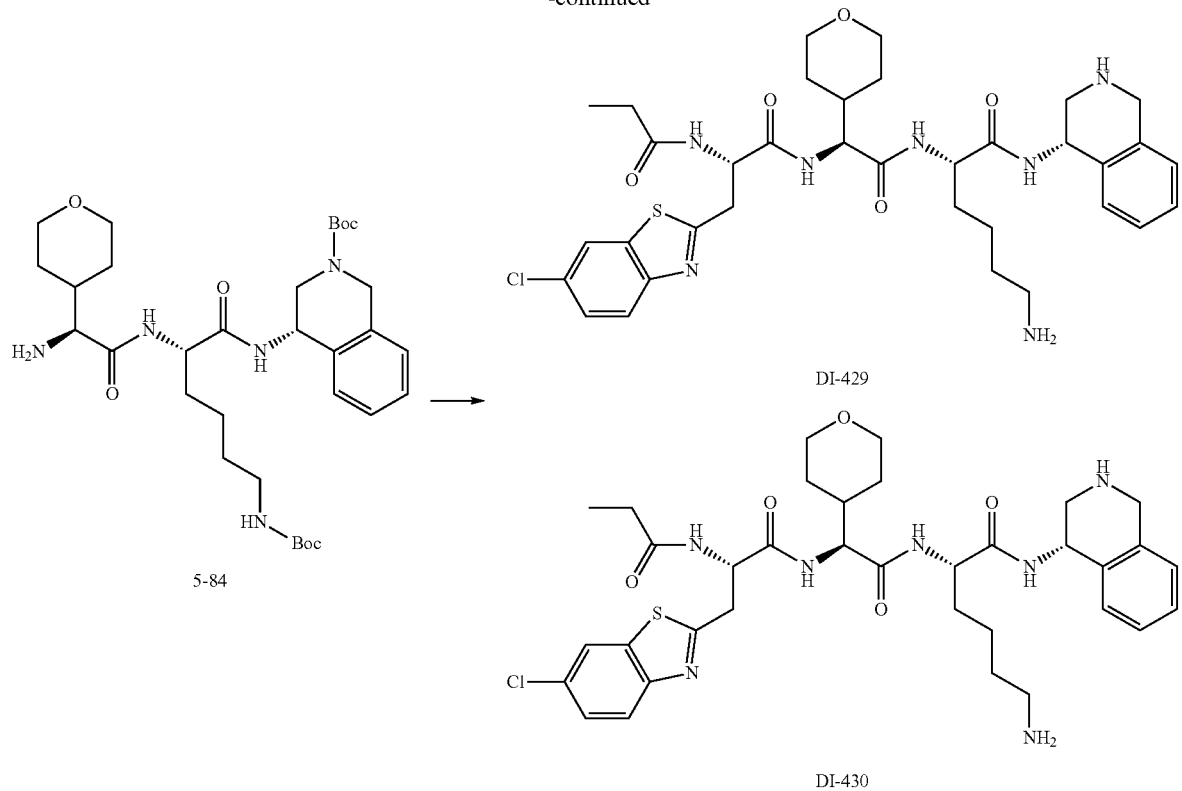
Compounds Examples 43 & 44 were prepared using a similar procedure as that for compounds Examples 33 & 34.
5-84:
¹HNMR (300 MHz, CD3OD), δ 8.61-8.53 (m, 2H), 7.33-7.19 (m, 4H), 5.05-4.97 (m, 1H), 4.91-4.79 (m, 1H), 4.52-4.46 (m, 1H), 4.37-4.32 (m, 1H), 4.03-4.00 (m, 3H), 3.77-3.74 (m, 1H), 3.48-3.37 (m, 3H), 3.06-3.04 (m, 2H), 2.16-2.14 (m, 1H), 1.83-1.65 (m, 4), 1.52-1.43 (m, 24H); ¹³C NMR (75 MHz, CD3OD), δ 171.8, 167.6, 157.2, 155.3, 133.7, 133.6, 128.5, 127.7, 126.6, 125.9, 80.2, 78.5, 67.0, 66.9, 57.0, 53.5, 46.7, 45.6, 44.8, 42.0, 39.7, 31.6, 29.2, 28.53, 28.49, 27.39, 27.38, 24.5, 24.4, 22.8.
Example 43
¹H NMR (300 MHz, CD₃OD), δ 8.33 (d, J=6.5, 1H), 8.22 (d, J=7.4, 1H), 8.01 (s, 1H), 7.91 (d, J=8.6, 1H), 7.50 (d, J=8.6, 1H), 7.36-7.27 (m, 4H), 5.24 (t, J=6.2, 1H), 4.74-4.69 (m, 1H), 4.49-4.27 (m, 3H), 4.14-4.13 (m, 1H), 3.90-3.88 (m, 2H), 3.67-3.37 (m, 6H), 2.90 (t, J=7.0, 2H), 2.24 (q, J=7.4, 2H), 1.99-1.30 (m, 11H), 1.06 (t, J=7.5, 3H); ¹³C NMR (75 MHz, CD3OD), δ 176.0, 172.9, 171.8, 171.7, 168.4, 151.4, 136.6, 131.6, 130.9, 128.5, 128.3, 128.2, 126.7, 126.4, 123.0, 121.2, 67.2, 67.1, 58.4, 53.5, 53.2, 45.4, 44.5, 44.0, 39.1, 36.9, 34.6, 30.4, 29.2, 28.9, 28.4, 26.6, 22.5, 8.7.
Example 44
¹H NMR (300 MHz, CD₃OD), δ 8.54 (d, J=6.7, 1H), 8.15-8.08 (m, 2H), 8.04 (s, 1H), 7.93 (d, J=8.7, 1H), 7.53 (d, J=8.7, 1H), 7.39-7.30 (m, 4H), 5.34-5.32 (m, 1H), 4.70 (t, J=7.3, 1H), 4.56-4.38 (m, 2H), 4.26-4.24 (m, 1H), 4.03-4.01 (m, 1H), 3.78-3.38 (m, 5H), 3.25-3.21 (m, 1H), 2.94-2.92 (m, 2H), 2.18-2.08 (m, 1H), 2.00-1.17 (m, 12H), 1.00 (t, J=7.5, 3H); ¹³C NMR (75 MHz, CD3OD), δ 175.7, 173.1, 172.8, 171.9, 167.9, 151.5, 136.6, 131.6, 131.0, 128.6, 128.5, 128.4, 126.8, 126.4, 123.1, 121.2, 67.1, 67.0, 58.9, 54.2, 53.7, 45.6, 44.5, 43.7, 39.0, 36.2, 34.4, 29.9, 29.0, 28.4, 28.0, 26.6, 22.7, 8.7.

Synthesis of Example 45.
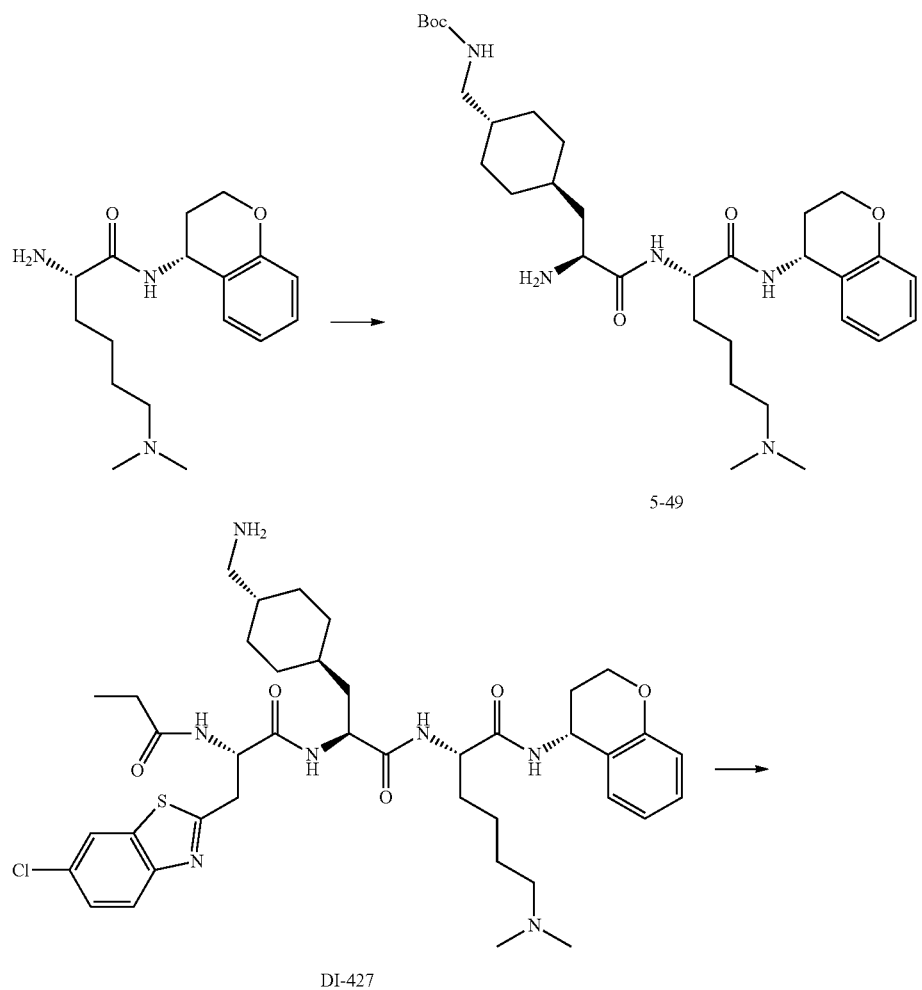
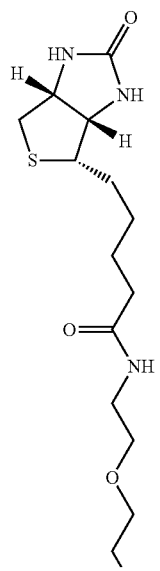

-continued
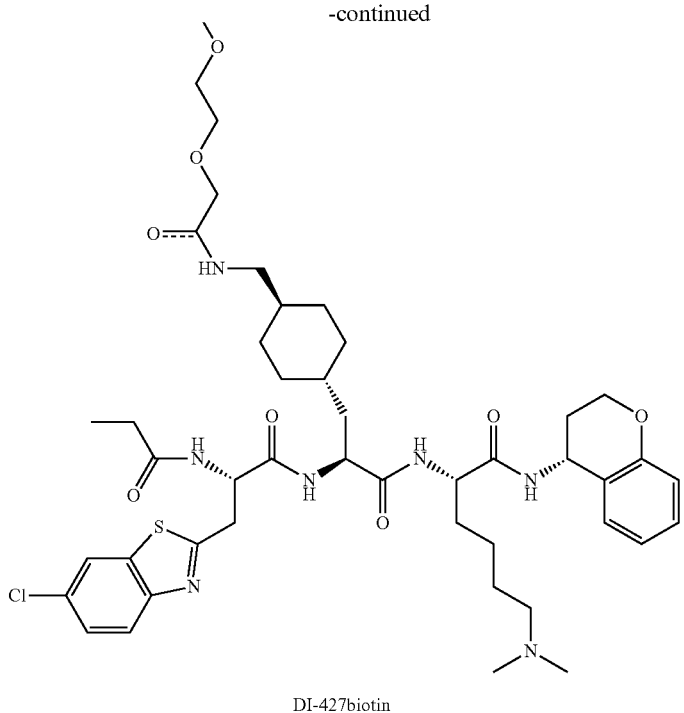
DI-427biotin
Example 45 was synthesized as shown in scheme 12. 5-49:
¹HNMR (300 MHz, CD3OD), δ 8.53 (d, J=7.9, 2H), 7.20-7.14 (m, 2H), 6.90-6.85 (m, 1H), 6.76 (d, J=8.02H), 5.13-5.09 ((m, 2H), 1H), 4.43-4.38 ((m, 1H), 4.28-4.18 (m, 7H); 2H), 4.05-4.00 (m, 1H), 3.78-3.69 (m, 1H), 3.27-3.20 (m, 1H), 3.15-3.10 (m, 2H), 2.91-2.89 (m, 8H), 2.16-2.13 (m, 1H), 2.03-1.66 (m, 11), 1.46-1.44 (m, 11H), 1.15-1.02 (m, 4H); ¹³C NMR (75 MHz, CD3OD), δ 171.5, 169.4, 157.3, 155.1, 128.9, 128.7, 122.0, 120.3, 116.6, 78.4, 63.1, 57.3, 54.4, 53.1, 50.9, 43.4, 42.0, 38.8, 38.1, 33.2, 32.6, 31.8, 31.3, 30.0, 29.9, 28.8, 27.4, 23.7, 22.3.
Example 45
¹H NMR (300 MHz, CD3OD), δ 8.02 (d, J=2.0, 1H), 7.93 (d, J=8.7, 1H), 7.51 (dd, J=2.1, 8.7, 1H), 7.16-7.11 (m, 2H), 6.88-6.77 (m, 2H), 5.07 (t, J=5.7, 1H), 4.82-4.78 (m, 1H), 4.41-4.31 (m, 2H), 4.24 (t, J=5.3, 2H), 3.58-3.38 (m, 2H), 3.11 (t, J=8.0, 2H), 2.89 (s, 6H), 2.76 (d, J=7.0, 2H), 2.30-2.22 (m, 2H), 2.16-1.24 (In, 16H), 1.11-0.85 (m, 7H); ¹³C NMR (75 MHz, CD3OD), δ 175.9, 173.3, 171.8, 171.5, 168.6, 155.2, 151.4, 136.6, 130.8, 129.0, 128.7, 126.7, 123.1, 121.9, 121.2, 120.2, 116.6, 63.0, 57.3, 52.9, 51.6, 44.9, 43.4, 42.0, 38.4, 35.9, 34.7, 33.4, 32.3, 30.84, 30.75, 29.6, 29.4, 28.8, 28.5, 23.6, 22.4, 8.8.
10. Synthesis of Examples 46-52.
Scheme 13. Synthesis of Examples 46-52. DI-831 is Ex 3.
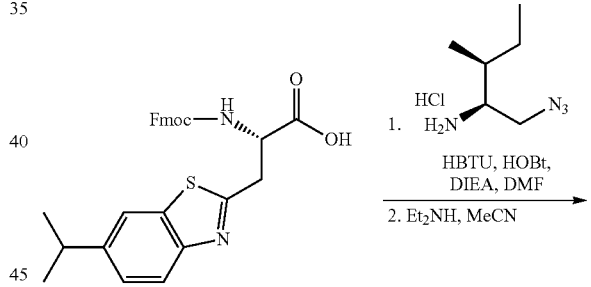
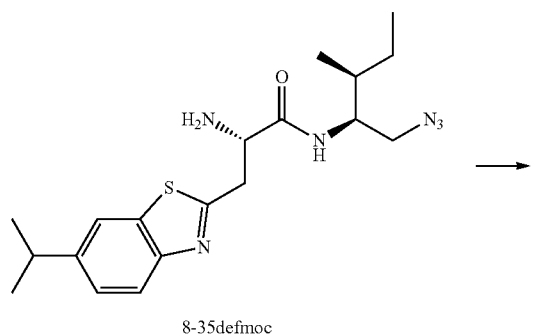
8-35defmoc -continued

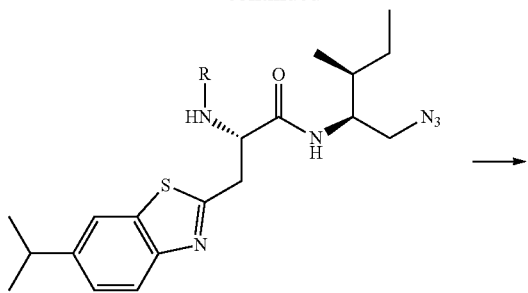

7-120-1, R = 

7-120-2, R = 

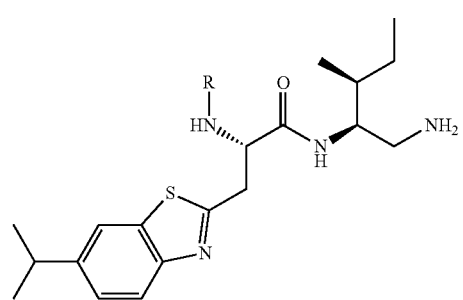

DI-829, R =

DI-833, R =

DI-834, R =

DI-830, R =

DI-835, R =

DI-836, R =

DI-837, R =

8-35defmoc (S)-2-amino-N-((2S,3S)-1-azido-3-methylpentan-2-yl)-3-(6-isopropylbenzo[d]thiazol-2-yl)propanamide, 8-35defmoc To a solution of the 6-85 (2.0 g, 4.1 mmol, 1 equiv.), HBTU (2.3 g, 6.2 mmol, 1.5 equiv.) and DIEA (2.1 mL, 12.3 mmol, 3 equiv.) in DMF (20 mL) was added (2S,3 S)-1-azido-3-methylpentan-2-amine hydrochloride (0.8 g, 4.5 mmol, 1.1 equiv.) and the resultant mixture was stirred at room temperature for 1 h. The solution was diluted with EtOAc and washed with $H_2O$, saturated sodium bicarbonate, 1.0 M HCl, brine and dried over sodium sulfate. After removal of the solvent under vacuum, the residue was treated with 3 mL diethylamine in Acetonitrile (27 mL) for 1 h. The reaction mixture was evaporated and the residue was purified by flash chromatography on silica gel to afford 8-35defmoc (1.2 g 77%). 8-35defmoc: $^1$H NMR (400 MHz, MeOD) δ 7.94 (d, J=8.5 Hz, 1H), 7.84 (d, J=1.7 Hz, 1H), 7.44 (dd, J=8.5, 1.7 Hz, 1H), 4.57 (dd, J=7.8, 5.2 Hz, 1H), 3.87 (td, J=7.3, 3.8 Hz, 1H), 3.77 (dd, J=16.6, 5.2 Hz, 1H), 3.68 (dd, J=16.6, 7.8 Hz, 1H), 3.47 (dd, J=12.8, 3.9 Hz, 1H), 3.41-3.35 (m, 1H), 3.06 (dq, J=13.6, 6.8 Hz, 1H), 1.70-1.60 (m, 1H), 1.58-1.50 (m, 1H), 1.32 (d, J=6.9 Hz, 6H), 1.24-1.12 (m, 1H), 0.96-0.91 (m, 6H). $^{13}$C NMR (101 MHz, MeOD) δ 167.35, 164.24, 151.02, 146.98, 135.29, 125.36, 122.10, 118.60, 53.74, 52.01, 36.06, 34.11, 34.05, 24.98, 23.15, 14.16, 10.11. UPLC-MS (ESI-MS) m/z: calculated for $C_{19}H_{29}N_6OS^+$ 389.21, found 389.36[M+H]$^+$.

7-120-1

(S)-2-acetamido-N-((2S,3S)-1-azido-3-methylpentan-2-yl)-3-(6-isopropylbenzo[d]thiazol-2-yl)propanamide, 7-120-1

Acetic anhydride (46 mg, 0.45 mmoL, 2 equiv.) was added to a solution of 8-35defmoc (87 mg, 0.22 mmoL, 1 equiv.) and DIEA (156 μL, 0.89 mmol, 4 equiv.) in DCM (10 mL). The resulting reaction mixture was stirred for half an hour and then was evaporated. The residue was purified by flash chromatography on silica gel to afford compounds 7-120-1 (89 mg, 92% yields). $^1$H NMR (400 MHz, CDCl$_3$) δ 7.91 (d, J=8.5 Hz, 1H), 7.72 (d, J=1.6 Hz, 1H), 7.59 (d, J=9.1 Hz, 1H), 7.47-7.36 (m, 2H), 5.06 (q, J=6.4 Hz, 1H), 4.02-3.82 (m, 1H), 3.64 (d, J=6.3 Hz, 2H), 3.37 (qd, J=12.6, 5.3 Hz, 2H), 3.08 (dt, J=13.8, 6.9 Hz, 1H), 2.08 (s, 3H), 1.65-1.58 (m, 1H), 1.51-1.39 (m, 1H), 1.33 (d, J=6.9 Hz, 6H), 1.21-1.03 (m, 1H), 0.92 (d, J=6.8 Hz, 3H), 0.88 (t, J=7.4 Hz, 3H). $^{13}$C NMR (101 MHz, CDCl$_3$) δ 171.12, 169.86, 168.43, 148.60, 147.43, 134.34, 126.28, 121.25, 118.98, 53.54, 52.41, 52.37, 36.15, 35.62, 34.29, 25.06, 24.10, 22.97, 15.39, 11.19. UPLC-MS (ESI-MS) m/z: calculated for $C_{21}H_{31}N_6O_2S^+$ 431.22, found 431.36[M+H]$^+$.

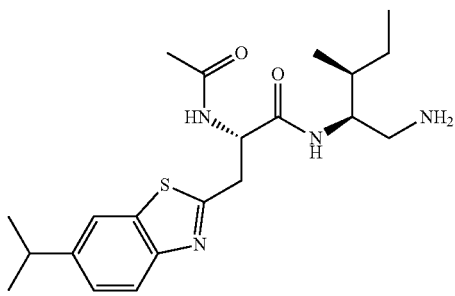

DI-829

Example 46. (S)-2-acetamido-N-((2S,3S)-1-amino-3-methylpentan-2-yl)-3-(6-isopropylbenzo[d]thiazol-2-yl)propanamide To a solution of compound 7-120-1 (45 mg, 0.11 mmol) in MeOH (10 mL) was added 10% Pd-C (20 mg). The solution was stirred under 1 atm of $H_2$ at room temperature for 3 hours before filtering through celite and being concentrated. The resulting amine was purified by HPLC to afford Example 46 (38 mg, 91%). $^1$H NMR (400 MHz, MeOD) δ 7.92-7.77 (m, 2H), 7.49-7.36 (m, 1H), 4.87-4.85 (m, 1H), 4.01-3.96 (m, 1H), 3.69 (dd, J=15.2, 5.9 Hz, 1H), 3.55 (dd, J=15.2, 6.9 Hz, 1H), 3.30-3.19 (m, 1H), 3.08 (dt, J=13.8, 6.9 Hz, 1H), 2.97 (dd, J=12.6, 11.3 Hz, 1H), 2.03 (s, 3H), 1.68-1.54 (m, 1H), 1.48-1.41 (m, 1H), 1.33 (d, J=6.9 Hz, 6H), 1.21-1.06 (m, 1H), 0.94 (d, J=6.8 Hz, 3H), 0.86 (t, J=7.4 Hz, 3H). 13C NMR (101 MHz, MeOD) δ 172.45, 171.81, 167.06, 150.90, 146.80, 135.18, 125.31, 121.29, 118.67, 53.09, 52.09, 41.76, 36.51, 34.60, 34.08, 24.77, 23.14, 21.18, 14.22, 9.75. UPLC-MS (ESI-MS) m/z: calculated for $C_{21}H_{33}N_4O_2S^+$ 405.23, found 405.25[M+H]$^+$.

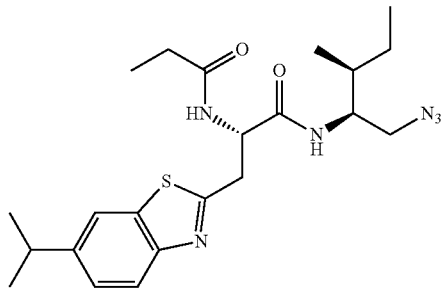

7-120-2

(S)—N-((2S,3S)-1-azido-3-methylpentan-2-yl)-3-(6-isopropylbenzo[d]thiazol-2-yl)-2-propionamidopropanamide, 7-120-2

Propionic anhydride (58 mg, 0.45 mmoL, 2 equiv.) was added to a solution of 8-35defmoc (87 mg, 0.22 mmoL, 1 equiv.) and DIEA (156 μL, 0.89 mmol, 4 equiv.) in DCM (10 mL). The resulting reaction mixture was stirred for half an hour and then was evaporated. The residue was purified by flash chromatography on silica gel to afford compounds 7-120-12 (86 mg, 89% yields). $^1$H NMR (400 MHz, CDCl$_3$) δ 7.94 (d, J=8.5 Hz, 1H), 7.73 (d, J=1.0 Hz, 1H), 7.54 (d, J=9.0 Hz, 1H), 7.50 (d, J=7.0 Hz, 1H), 7.45 (dd, J=8.4, 1.5 Hz, 1H), 5.08 (dd, J=12.7, 6.8 Hz, 1H), 4.00-3.88 (m, 1H), 3.75 (dd, J=15.3, 5.3 Hz, 1H), 3.63 (dd, J=15.3, 7.2 Hz, 1H), 3.39 (qd, J=12.6, 5.4 Hz, 2H), 3.08 (dt, J=13.8, 6.9 Hz, 1H), 2.31 (q, J=7.6 Hz, 2H), 1.68-1.56 (m, 1H), 1.48-1.42 (m, 1H), 1.33 (d, J=6.9 Hz, 6H), 1.20-1.05 (m, 4H), 0.92 (d, J=6.8 Hz, 3H), 0.88 (t, J=7.4 Hz, 3H). $^{13}$C NMR (101 MHz, CDCl$_3$) δ 175.27, 169.85, 169.08, 147.86, 147.47, 133.89, 126.67, 120.89, 119.04, 53.65, 52.49, 52.36, 36.20, 35.35, 34.30, 29.42, 25.07, 24.05, 24.04, 15.32, 11.17, 9.61. UPLC-MS (ESI-MS) m/z: calculated for $C_{22}H_{33}N_6O_2S^+$ 445.24, found 445.37[M+H]$^+$.

DI-830

Example 47. (S)—N-((2S,3S)-1-amino-3-methylpentan-2-yl)-3-(6-isopropylbenzo[d]thiazol-2-yl)-2-propionamidopropanamide To a solution of compound 7-120-2 (52 mg, 0.12 mmol) in MeOH (10 mL) was added 10% Pd-C (20 mg). The solution was stirred under 1 atm of $H_2$ at room temperature for 3 hours before filtering through celite and being concentrated. The resulting amine was purified by HPLC to afford Example 47 (36 mg, 86%). $^1$H NMR (400 MHz, MeOD) δ 7.90-7.80 (m, 2H), 7.43 (dd, J=8.5, 1.7 Hz, 1H), 4.91-4.89 (m, 1H), 4.09-3.92 (m, 1H), 3.69 (dd, J=15.2, 5.9 Hz, 1H), 3.55 (dd, J=15.2, 7.0 Hz, 1H), 3.29-3.20 (m, 1H), 3.08 (dt, J=13.8, 6.9 Hz, 1H), 3.02-2.93 (m, 1H), 2.30 (q, J=7.6 Hz, 2H), 1.67-1.56 (m, 1H), 1.48-1.42 (m, 1H), 1.33 (d, J=6.9 Hz, 6H), 1.20-1.07 (m, 4H), 0.95 (d, J=6.8 Hz, 3H), 0.86 (t, J=7.4 Hz, 3H). $^{13}$C NMR (101 MHz, MeOD) δ 176.05, 171.86, 167.09, 150.90, 146.78, 135.16, 125.30, 121.28, 118.66, 52.92, 52.07, 41.77, 36.54, 34.55, 34.07, 28.54, 24.74, 23.14, 14.24, 9.76, 8.71. UPLC-MS (ESI-MS) m/z: calculated for $C_{22}H_{35}N_4O_2S^+$ 419.25, found 419.29 [M+H]$^+$.

Example 48

DI-833

(S)—N-((2S,3S)-1-amino-3-methylpentan-2-yl)-2-formamido-3-(6-isopropylbenzo[d]thiazol-2-yl)propanamide 8-35 defmoc (100 mg, 0.26 mmol) was dissolved in a mixture of DIEA (1 mL) and Ethyl formate (5 mL) and the resulting reaction mixture was left stirring for 3 days. The solvents were removed in vacuo and the residue was dissolved in MeOH (10 ml). Then 10% Pd-C (20 mg) was added and the resulting reaction mixture was stirred under 1 atm of $H_2$ at room temperature for 3 hours before filtering through celite and being concentrated. The resulting amine was purified by HPLC to afford Example 48 (58 mg, 58%). $^1$H NMR (400 MHz, MeOD) δ 8.18 (d, J=0.7 Hz, 1H), 7.87-7.81 (m, 2H), 7.43 (dd, J=8.5, 1.7 Hz, 1H), 4.99 (t, J=5.6 Hz, 1H), 4.04-3.98 (m, 1H), 3.69 (dd, J=15.3, 5.8 Hz, 1H), 3.63 (dd, J=15.3, 6.1 Hz, 1H), 3.27 (dd, J=12.9, 2.4 Hz, 1H), 3.08 (dt, J=13.8, 6.9 Hz, 1H), 2.98 (dd, J=12.9, 11.1 Hz, 1H), 1.68-1.55 (m, 1H), 1.48-1.42 (m, 1H), 1.33 (d, J=6.9 Hz, 6H), 1.21-1.08 (m, 1H), 0.94 (d, J=6.8 Hz, 3H), 0.85 (t, J=7.4 Hz, 3H). $^{13}$C NMR (101 MHz, MeOD) δ 171.17, 166.62, 162.68, 150.95, 146.81, 135.20, 125.30, 121.29, 118.67, 52.15, 52.06, 51.53, 41.84, 36.56, 34.73, 34.07, 24.76, 23.13, 14.20, 9.73. UPLC-MS (ESI-MS) m/z: calculated for $C_{20}H_{31}N_4O_2S^+$ 391.22, found 391.22 [M+H]$^+$.

Example 49

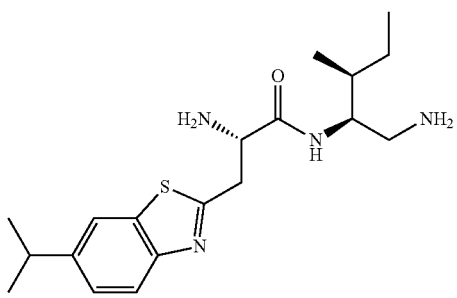

DI-834

(S)-2-amino-N-((2S,3S)-1-amino-3-methylpentan-2-yl)-3-(6-isopropylbenzo[d]thiazol-2-yl)propanamide To a solution of compound 8-35defmoc (36 mg, 0.09 mmol) in MeOH (10 mL) was added 10% Pd-C (20 mg). The solution was stirred under 1 atm of $H_2$ at room temperature for 3 hours before filtering through celite and being concentrated. The resulting amine was purified by HPLC to afford Example 49 (28 mg, 83%). $^1$H NMR (400 MHz, MeOD) δ 7.97-7.83 (m, 2H), 7.48 (dd, J=8.6, 1.6 Hz, 1H), 4.54 (t, J=5.8 Hz, 1H), 4.14-4.09 (m, 1H), 3.82-3.80 (m, 2H), 3.29-3.28 (m, 1H), 3.13-3.03 (m, 2H), 1.73-1.67 (m, 1H), 1.60-1.47 (m, 1H), 1.34 (d, J=6.9 Hz, 6H), 1.28-1.20 (m, 1H), 1.01 (d, J=6.8 Hz, 3H), 0.95 (t, J=7.4 Hz, 3H). $^{13}$C NMR (101 MHz, MeOD) δ 168.43, 164.33, 151.03, 147.22, 135.21, 125.60, 121.54, 118.81, 52.49, 52.02, 41.45, 36.70, 34.10, 33.67, 24.83, 23.10, 14.05, 10.01. UPLC-MS (ESI-MS) m/z: calculated for $C_{19}H_{32}N_4OS^{2+}$ 182.11, found 182.21 [M+2H]$^{2+}$.

Example 50

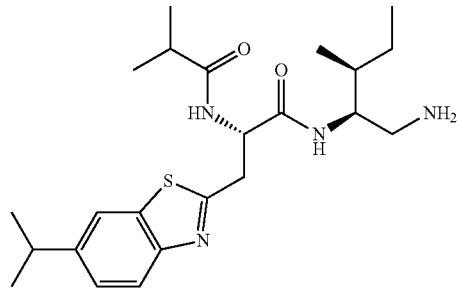

DI-835

(S)—N-((2S,3S)-1-amino-3-methylpentan-2-yl)-2-isobutyramido-3-(6-isopropylbenzo[d]thiazol-2-yl)propanamide: Example 50 was prepared from 8-35defmoc in 72% yield over two steps by a similar procedure as that for compound Example 46. $^1$H NMR (400 MHz, MeOD) δ 8.33 (d, J=7.3 Hz, 1H), 7.99 (d, J=8.9 Hz, 1H), 7.85-7.83 (m, 2H), 7.43 (dd, J=8.6, 1.6 Hz, 1H), 4.91-4.88 (m, 1H), 4.09-3.90 (m, 1H), 3.69 (dd, J=15.2, 5.9 Hz, 1H), 3.55 (dd, J=15.2, 7.1 Hz, 1H), 3.26 (dd, J=13.4, 3.1 Hz, 1H), 3.08 (dt, J=13.8, 6.9 Hz, 1H), 3.02-2.93 (m, 1H), 2.53 (dt, J=13.7, 6.9 Hz, 1H), 1.68-1.57 (m, 1H), 1.50-1.42 (m, 1H), 1.33 (d, J=6.9 Hz, 6H), 1.23-1.04 (m, 7H), 0.95 (d, J=6.8 Hz, 3H), 0.88 (t, J=7.4 Hz, 3H). $^{13}$C NMR (101 MHz, MeOD) δ 179.04, 171.85, 167.11, 150.91, 146.78, 135.14, 125.30, 121.24, 118.67, 52.71, 52.02, 41.85, 36.59, 34.59, 34.45, 34.07, 24.69, 23.13, 18.48, 18.17, 14.25, 9.78. UPLC-MS (ESI-MS) m/z: calculated for $C_{23}H_{37}N_4O_2S^+$ 433.26, found 433.29 [M+H]$^+$.

Example 51

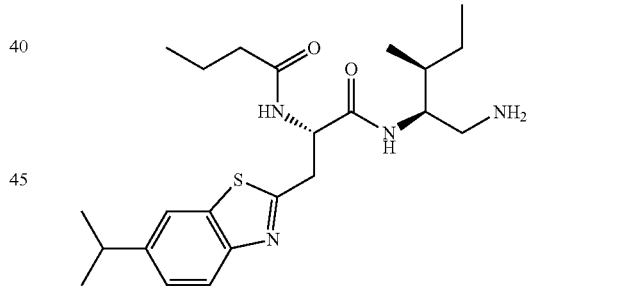

DI-836

N—((S)-1-(((2S,3 S)-1-amino-3-methylpentan-2-yl)amino)-3-(6-isopropylbenzo[d]thiazol-2-yl)-1-oxopropan-2-yl)butyramide: Example 51was prepared from 8-35defmoc in 70% yield over two steps by a similar procedure as that for compound Example 46. $^1$H NMR (400 MHz, MeOD) δ 7.91-7.75 (m, 2H), 7.43 (dd, J=8.6, 1.6 Hz, 1H), 4.91-4.88 (m, 1H), 4.02-3.96 (m, 1H), 3.69 (dd, J=15.2, 5.9 Hz, 1H), 3.54 (dd, J=15.2, 7.2 Hz, 1H), 3.25 (dd, J=13.1, 3.1 Hz, 1H), 3.08 (dt, J=13.8, 6.9 Hz, 1H), 2.98 (dd, J=12.8, 11.1 Hz, 1H), 2.35-2.18 (m, 2H), 1.71-1.55 (m, 3H), 1.49-1.41 (m, 1H), 1.33 (d, J=6.9 Hz, 6H), 1.19-1.12 (m, 1H), 0.96-0.85 (m, 9H). $^{13}$C NMR (101 MHz, MeOD) δ 175.14, 171.86, 167.08, 150.93, 146.77, 135.17, 125.29, 121.28, 118.66, 52.90, 52.06, 41.78, 37.32, 36.56, 34.61, 34.07, 24.74, 23.14, 18.76, 14.23, 12.56, 9.78. UPLC-MS (ESI-MS) m/z: calculated for $C_{23}H_{37}N_4O_2S^+$ 433.26, found 433.29 $[M+H]^+$.

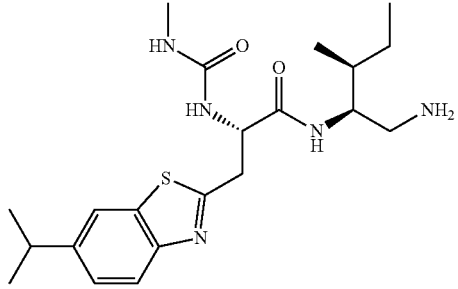

DI-837

Example 52. (S)—N-((2S,3S)-1-amino-3-methyl-pentan-2-yl)-3-(6-isopropylbenzo[d]thiazol-2-yl)-2-(3-methylureido)propanamide Methyl isocyanate (18 mg, 0.31 mmol, 2 equiv.) was added to a solution of 8-35defmoc (60 mg, 0.15 mmol, 1 equiv.) and DIEA (54 μL, 0.31 mmol, 2 equiv) in $CH_2Cl_2$ (5 mL) and the resulting solution was stirred at room temperature for overnight. The reaction mixture was concentrated and the residue was dissolved in MeOH (10 ml). Then 10% Pd-C (20 mg) was added and the resulting reaction mixture was stirred under 1 atm of $H_2$ at room temperature for 3 hours before filtering through celite and being concentrated. The resulting amine was purified by HPLC to afford Example 52 (58 mg, 74%). $^1$H NMR (400 MHz, MeOD) δ 7.85 (d, J=8.5 Hz, 1H), 7.83 (d, J=1.7 Hz, 1H), 7.42 (dd, J=8.5, 1.7 Hz, 1H), 4.74 (t, J=5.8 Hz, 1H), 3.99-3.94 (m, 1H), 3.61 (d, J=5.8 Hz, 2H), 3.24 (dd, J=12.9, 3.0 Hz, 1H), 3.07 (dt, J=13.8, 6.9 Hz, 1H), 2.98 (dd, J=12.8, 11.3 Hz, 1H), 2.74 (s, 3H), 1.58 (dtd, J=8.8, 7.3, 3.7 Hz, 1H), 1.44-1.35 (m, 1H), 1.32 (d, J=6.9 Hz, 6H), 1.12-1.04 (m, 1H), 0.91 (d, J=6.8 Hz, 3H), 0.79 (t, J=7.4 Hz, 3H). $^{13}$C NMR (101 MHz, MeOD) δ 172.94, 167.09, 159.77, 150.97, 146.68, 135.23, 125.18, 121.40, 118.59, 53.78, 52.00, 41.73, 36.52, 35.24, 34.07, 25.54, 24.79, 23.15, 14.24, 9.70. UPLC-MS (ESI-MS) m/z: calculated for $C_{21}H_{34}N_5O_2S^+$ 420.24, found 419.29 $[M+H]^+$.

11. Synthesis of Examples 53-55 and Analogs.

Scheme 14. Synthesis compounds Example 53-55 and analogs.

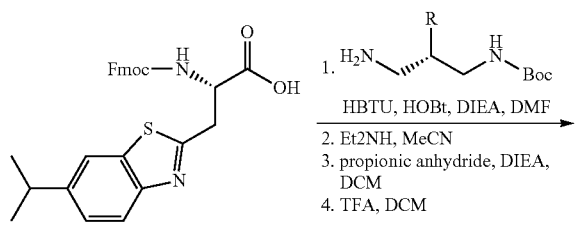

1. $H_2N$\\\~\~\~\~$N$-Boc, R
   HBTU, HOBt, DIEA, DMF
2. Et2NH, MeCN
3. propionic anhydride, DIEA, DCM
4. TFA, DCM -continued

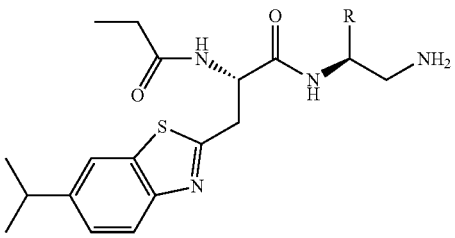

Example 53

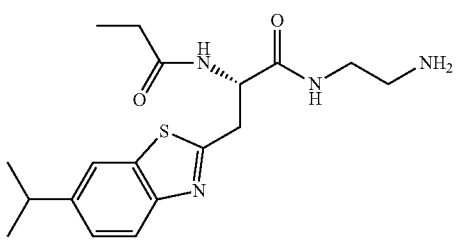

DI-739

Example 53. (S)—N-(2-aminoethyl)-3-(6-isopropyl-benzo[d]thiazol-2-yl)-2-propionamidopropanamide To a solution of the 6-85 (120 mg, 0.25 mmol, 1 equiv.), HBTU (140 mg, 0.37 mmol, 1.5 equiv.) and DIEA (129 μL, 0.74 mmol, 3 equiv.) in DMF (5 mL) was added tert-butyl (2-aminoethyl)carbamate (43 mg, 0.27 mmol, 1.1 equiv.) and the resultant mixture was stirred at room temperature for 1 h. The solution was diluted with EtOAc and washed with $H_2O$, saturated sodium bicarbonate, 1.0 M HCl, brine and dried over sodium sulfate. After removal of the solvent under vacuum, the residue was treated with 1 mL diethyl-amine in Acetonitrile (9 mL) for 1 h. The reaction mixture was evaporated and dissolved in DCM (5 mL). This solution was treated with propionic anhydride (64 mg, 0.49 mmoL, 2 equiv.) and DIEA (171 μL, 0.99 mmol, 4 equiv.). The resulting reaction mixture was stirred for half an hour and then was evaporated. The residue was treated with TFA (1 ml) in DCM (5 mL) and stirred for 5 h. This reaction mixture was concentrated and purified by HPLC to afford Example 53 (54 mg, 61%). H NMR (400 MHz, MeOD) δ 7.86 (d, J=8.5 Hz, 1H), 7.82 (d, J=1.7 Hz, 1H), 7.42 (dd, J=8.5, 1.7 Hz, 1H), 4.83 (dd, J=8.2, 5.5 Hz, 1H), 3.67 (dd, J=15.1, 5.5 Hz, 1H), 3.56-3.43 (m, 3H), 3.10-3.03 (m, 3H), 2.28 (q, J=7.6 Hz, 2H), 1.32 (d, J=6.9 Hz, 6H), 1.09 (t, J=7.6 Hz, 3H). $^{13}$C NMR (101 MHz, MeOD) δ 176.04, 172.38, 166.94, 150.80, 146.73, 135.22, 125.26, 121.46, 118.60, 53.15, 39.46, 36.83, 34.93, 34.07, 28.50, 23.14, 8.56. UPLC-MS (ESI-MS) m/z: calculated for $C_{18}H_{27}N_4O_2S^+$ 363.18, found 363.18 $[M+H]^+$.

Example 54

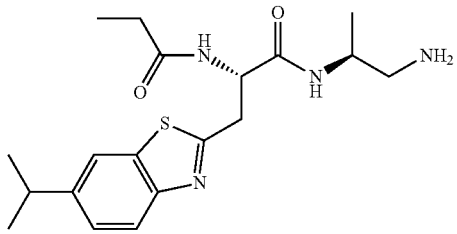

DI-832

(S)—N—((S)-1-aminopropan-2-yl)-3-(6-isopropyl-benzo[d]thiazol-2-yl)-2-propionamidopropanamide Example 54 was prepared from 6-85 in 57% yield over four steps by a similar procedure as that for compound Example 53. $^1$H NMR (400 MHz, MeOD) δ 7.86-7.83 (m, 2H), 7.42 (dd, J=8.5, 1.7 Hz, 1H), 4.84 (dd, J=7.1, 5.8 Hz, 1H), 4.31-4.15 (m, 1H), 3.69 (dd, J=15.0, 5.8 Hz, 1H), 3.51 (dd, J=15.0, 7.2 Hz, 1H), 3.17-2.91 (m, 3H), 2.28 (q, J=7.6 Hz, 2H), 1.32 (d, J=6.9 Hz, 6H), 1.25 (d, J=6.9 Hz, 3H), 1.10 (t, J=7.6 Hz, 3H). $^{13}$C NMR (101 MHz, MeOD) δ 175.90, 171.51, 166.97, 150.86, 146.75, 135.21, 125.29, 121.29, 118.65, 52.91, 44.65, 43.71, 35.02, 34.07, 28.52, 23.14, 16.39, 8.65. UPLC-MS (ESI-MS) m/z: calculated for $C_{19}H_{29}N_4O_2S^+$ 377.20, found 377.23 [M+H]$^+$.

Example 55

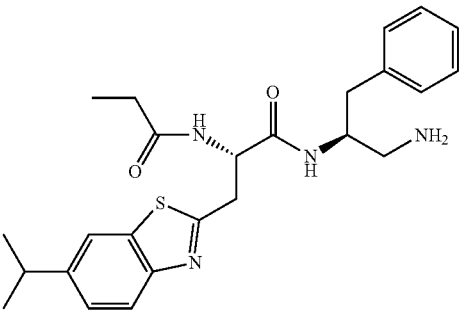

DI-517

(S)—N—((S)-1-amino-3-phenylpropan-2-yl)-3-(6-isopropylbenzo[d]thiazol-2-yl)-2-propionamidopropanamide Example 55 was prepared from 6-85 in 53% yield over four steps by a similar procedure as that for Example 53. $^1$H NMR (400 MHz, MeOD) δ 7.86-7.80 (m, 2H), 7.42 (dd, J=8.5, 1.6 Hz, 1H), 7.33-7.18 (m, 5H), 4.81 (dd, J=7.6, 5.5 Hz, 1H), 4.47-4.32 (m, 1H), 3.58 (dd, J=15.2, 5.5 Hz, 1H), 3.42 (dd, J=15.2, 7.6 Hz, 1H), 3.18 (dd, J=13.0, 3.6 Hz, 1H), 3.10-3.04 (m, 2H), 2.93-2.84 (m, 2H), 2.24 (q, J=7.6 Hz, 2H), 1.32 (d, J=6.9 Hz, 6H), 1.08 (t, J=7.6 Hz, 3H). $^{13}$C NMR (101 MHz, MeOD) δ 175.96, 171.68, 167.04, 150.86, 146.74, 136.78, 135.18, 128.77, 128.31, 126.58, 125.27, 121.31, 118.64, 52.86, 49.38, 43.08, 37.43, 34.73, 34.07, 28.49, 23.14, 8.60. UPLC-MS (ESI-MS) m/z: calculated for $C_{25}H_{33}N_4O_2S^+$ 453.23, found 453.24 [M+H]$^+$.

12. Synthesis of Example 56-79.

Scheme 15. Synthesis of Example 56-79.

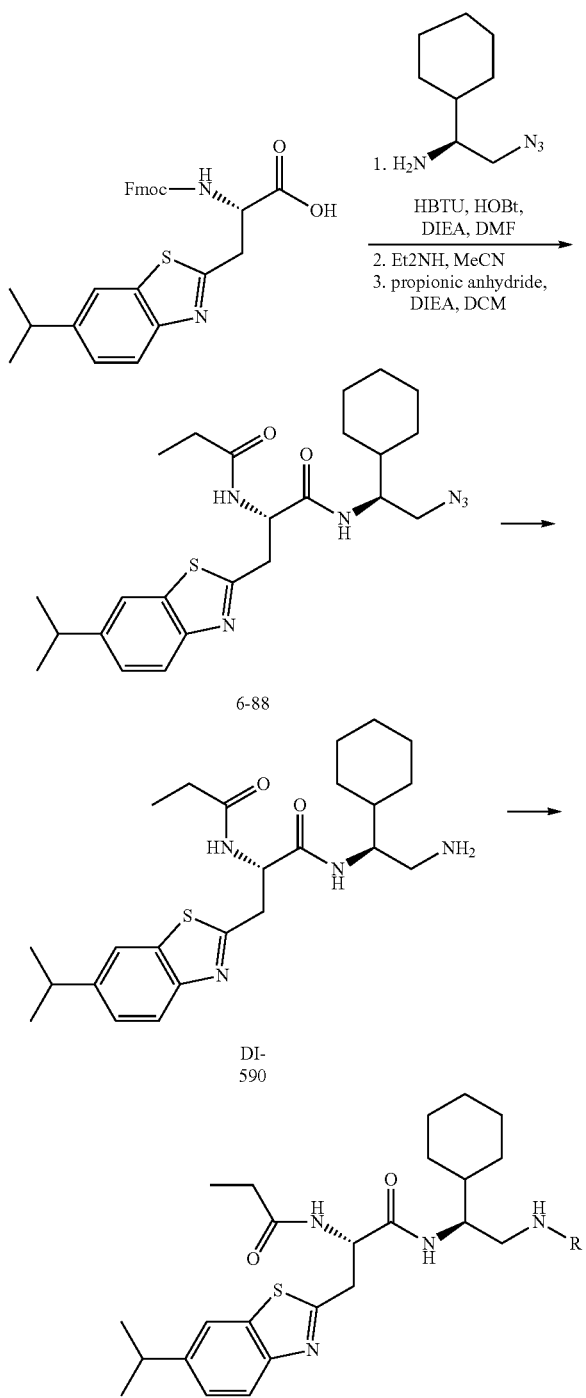

These compounds were synthesized using the synthetic route shown above.

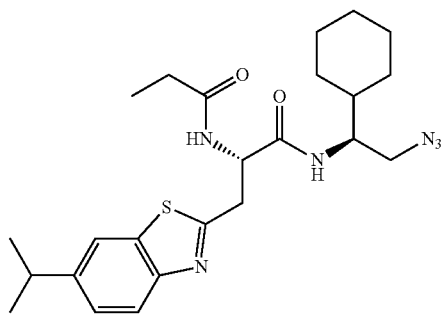

(S)—N—((S)-2-azido-1-cyclohexylethyl)-3-(6-isopropylbenzo[d]thiazol-2-yl)-2-propionamidopropanamide, 6-88

Compound 6-88 was prepared from 6-85 in 65% yield three steps by a similar procedure as that for compound 7-120-2. $^1$H NMR (400 MHz, CDCl$_3$) δ 7.84 (d, J=8.4 Hz, 1H), 7.69 (d, J=1.7 Hz, 1H), 7.50 (d, J=9.1 Hz, 1H), 7.39 (d, J=7.1 Hz, 1H), 7.34 (dd, J=8.5, 1.7 Hz, 1H), 5.04 (td, J=7.0, 4.8 Hz, 1H), 3.91-3.76 (m, 1H), 3.66 (dd, J=15.9, 4.7 Hz, 1H), 3.43 (dd, J=15.9, 7.0 Hz, 1H), 3.35 (dd, J=5.0, 1.1 Hz, 2H), 3.04 (dt, J=13.8, 6.9 Hz, 1H), 2.32 (q, J=7.6 Hz, 2H), 1.70-1.60 (dd, J=28.1, 15.3 Hz, 6H), 1.52-1.41 (m, 1H), 1.32-0.87 (m, 14H). $^{13}$C NMR (101 MHz, CDCl$_3$) δ 174.11, 170.30, 167.09, 150.97, 146.46, 135.25, 125.39, 121.98, 118.79, 53.54, 52.31, 51.92, 38.95, 35.50, 34.24, 29.69, 29.65, 28.51, 26.09, 25.91, 25.85, 24.18, 9.68. UPLC-MS (ESI-MS) m/z: calculated for C$_{24}$H$_{35}$N$_6$O$_2$S$^+$ 471.25, found 471.27 [M+H]$^+$.

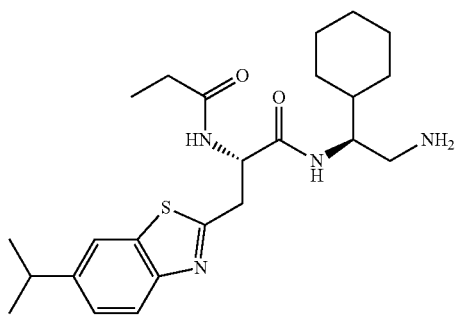

Example 56. (S)—N—((S)-2-amino-1-cyclohexylethyl)-3-(6-isopropylbenzo[d]thiazol-2-yl)-2-propionamidopropanamide Example 56 was prepared from 6-88 in 88% yield by a similar procedure as that for Example 47. $^1$H NMR (400 MHz, MeOD) δ 7.99 (d, J=8.9 Hz, 1H), 7.86-7.84 (m, 2H), 7.43 (d, J=8.5 Hz, 1H), 4.87-4.84 (m, 1H), 3.94-3.90 (m, 1H), 3.68 (dd, J=15.3, 5.8 Hz, 1H), 3.56 (dd, J=15.2, 6.9 Hz, 1H), 3.29-3.20 (m, 1H), 3.12-2.91 (m, 2H), 2.31 (q, J=7.6 Hz, 2H), 1.75-1.63 (m, 5H), 1.54-1.46 (m, 1H), 1.36-0.90 (m, 14H). $^{13}$C NMR (101 MHz, MeOD) δ 176.08, 171.86, 167.03, 150.94, 146.76, 135.15, 125.30, 121.33, 118.65, 52.99, 52.48, 41.73, 39.59, 34.51, 34.08, 29.39, 28.57, 28.25, 25.70, 25.50, 25.43, 23.14, 8.70. UPLC-MS (ESI-MS) m/z: calculated for C$_{24}$H$_{37}$N$_4$O$_2$S$^+$ 445.26, found 445.27 [M+H]$^+$.

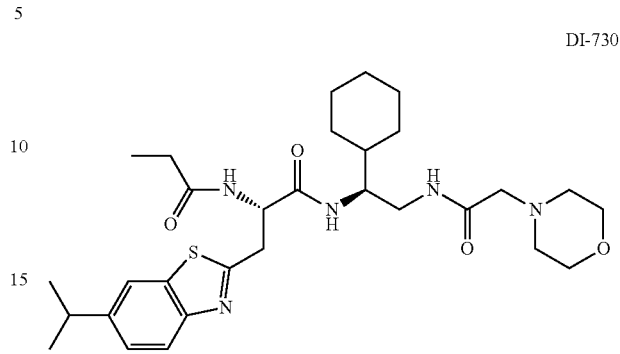

Example 57. (S)—N—((S)-1-cyclohexyl-2-(2-morpholinoacetamido)ethyl)-3-(6-isopropylbenzo[d]thiazol-2-yl)-2-propionamidopropanamide Example 56 (40 mg, 0.09 mmol, 1 equiv.) was added to a solution of the 2-morpholinoacetic acid (16 mg, 0.11 mmol, 1.2 equiv.), HBTU (51 mg, 0.13 mmol, 1.5 equiv.) and DIEA (47 µL, 0.27 mmol, 3 equiv.) in DCM (5 mL). The resultant mixture was stirred at room temperature for 1 h and concentrated. The residue was purified by HPLC to afford Example 57 (45 mg, 87%). $^1$H NMR (400 MHz, MeOD) δ 7.88 (d, J=8.4 Hz, 1H), 7.84 (s, 1H), 7.44 (d, J=8.5 Hz, 1H), 4.93-4.91 (s, 1H), 4.14-3.75 (m, 8H), 3.65 (dd, J=15.5, 5.4 Hz, 1H), 3.58-3.46 (m, 4H), 3.17-3.04 (m, 3H), 2.35 (q, J=7.5 Hz, 2H), 1.73-1.62 (m, 6H), 1.38-0.86 (m, 15H). $^{13}$C NMR (101 MHz, MeOD) δ 176.25, 171.48, 167.27, 164.01, 150.97, 146.76, 135.17, 125.30, 121.58, 118.68, 63.38, 56.94, 53.98, 53.03, 52.57, 40.82, 39.59, 34.73, 34.09, 29.59, 28.74, 28.41, 25.85, 25.62, 25.54, 23.16, 23.14, 8.75. UPLC-MS (ESI-MS) m/z: calculated for C$_{30}$H$_{46}$N$_5$O$_4$S$^+$ 572.33, found 572.21[M+H]$^+$.

Example 58

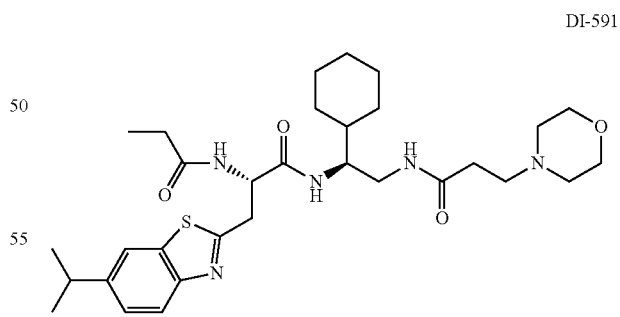

(S)—N—((S)-1-cyclohexyl-2-(3-morpholinopropanamido)ethyl)-3-(6-isopropylbenzo[d]thiazol-2-yl)-2-propionamidopropanamide: Example 58 was prepared from Example 56 in 81% yield by a similar procedure as that for Example 57. $^1$H NMR (400 MHz, MeOD) δ 7.87 (d, J=8.5 Hz, 1H), 7.83 (d, J=1.6 Hz, 1H), 7.43 (dd, J=8.5, 1.7 Hz, 1H), 4.86 (dd, J=7.8, 5.4 Hz, 1H), 4.07-4.04 (m, 2H), 3.88-3.76 (m, 3H), 3.64 (dd, J=15.4, 5.3 Hz, 1H), 3.57-3.37

(m, 6H), 3.17-3.06 (m, 4H), 2.69 (t, J=6.4 Hz, 2H), 2.34 (q, J=7.5 Hz, 2H), 1.72-1.60 (m, 5H), 1.39-0.86 (m, 15H). $^{13}$C NMR (101 MHz, MeOD) δ 176.00, 171.58, 170.51, 167.14, 150.98, 146.74, 135.17, 125.28, 121.57, 118.63, 63.61, 54.19, 53.25, 53.18, 51.89, 40.78, 39.66, 34.80, 34.09, 29.55, 28.72, 28.47, 28.43, 25.87, 25.66, 25.58, 23.16, 23.15, 8.73. UPLC-MS (ESI-MS) m/z: calculated for $C_{31}H_{48}N_5O_4S^+$ 586.34, found 586.29 $[M+H]^+$.

Example 59

DI-731

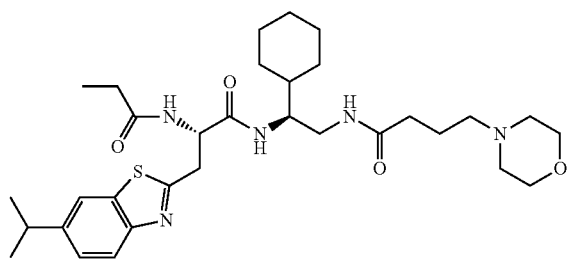

N—((S)-2-cyclohexyl-2-((S)-3-(6-isopropylbenzo[d]thi-azol-2-yl)-2-propionamidopropanamido)ethyl)-4-morpholinobutanamide: Example 59 was prepared from Example 56 in 79% yield by a similar procedure as that for compound Example 57. $^1$H NMR (400 MHz, MeOD) δ 7.87 (d, J=8.5 Hz, 1H), 7.84 (s, 1H), 7.65 (d, J=9.5 Hz, 1H), 7.43 (d, J=8.5 Hz, 1H), 4.91-4.89 (m, 1H), 4.15-4.00 (m, 2H), 3.89-3.72 (m, 3H), 3.65 (dd, J=15.3, 5.7 Hz, 1H), 3.60-3.50 (m, 3H), 3.47 (dd, J=15.3, 7.7 Hz, 1H), 3.18-2.93 (m, 6H), 2.46-2.25 (m, 4H), 1.99-1.89 (m, 2H), 1.74-1.64 (m, 5H), 1.39-0.89 (m, 15H). $^{13}$C NMR (101 MHz, MeOD) δ 175.91, 173.84, 171.45, 167.24, 150.96, 146.75, 135.20, 125.28, 121.56, 118.64, 63.91, 57.05, 53.74, 53.10, 51.88, 51.83, 40.98, 39.69, 34.90, 34.09, 32.56, 29.60, 28.65, 28.43, 25.91, 25.64, 25.58, 23.16, 18.89, 8.74. UPLC-MS (ESI-MS) m/z: calculated for $C_{32}H_{50}N_5O_4S^+$ 600.36, found 600.24 $[M+H]^+$.

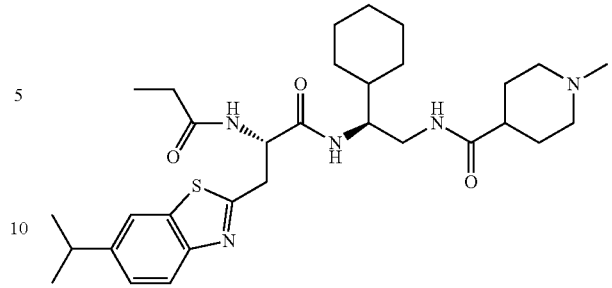

Example 60 was prepared from Example 56 in 86% yield by a similar procedure as that for compound Example 57. $^1$H NMR (400 MHz, MeOD) δ 7.94-7.93 (m, 1H), 7.87 (d, J=8.5 Hz, 1H), 7.84 (s, 1H), 7.66-7.62 (m, 1H), 7.43 (d, J=8.4 Hz, 1H), 4.92-4.90 (m, 1H), 3.84-3.77 (m, 1H), 3.62 (dd, J=15.4, 5.3 Hz, 1H), 3.57-3.43 (m, 4H), 3.13-3.04 (m, 2H), 3.01-2.76 (m, 5H), 2.46-2.36 (m, 1H), 2.32 (q, J=7.6 Hz, 2H), 2.05-185 (m, 4H), 1.72-1.62 (m, 5H), 1.39-0.87 (m, 15H). $^{13}$C NMR (101 MHz, MeOD) δ 175.91, 174.22, 171.37, 167.17, 151.01, 146.72, 135.23, 125.25, 121.60, 118.64, 54.34, 53.47, 53.03, 42.51, 40.67, 39.79, 39.28, 34.96, 34.08, 29.53, 28.66, 28.33, 26.21, 26.11, 25.89, 25.71, 25.65, 23.17, 23.15, 8.69.

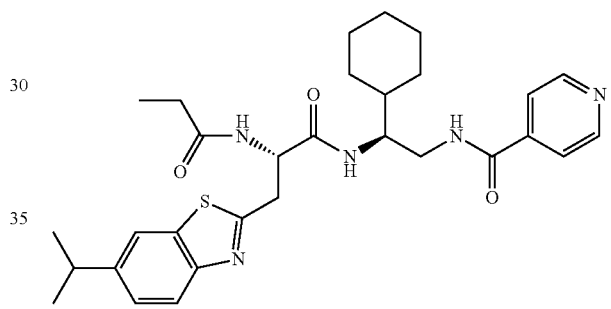

Example 61 was prepared from Example 56 by a similar procedure as that for Example 57. $^1$H NMR (400 MHz, MeOD) δ 8.80 (d, J=5.5 Hz, 2H), 8.07 (d, J=5.3 Hz, 2H), 7.78-7.76 (m, 2H), 7.37 (d, J=8.4 Hz, 1H), 4.91-4.89 (m, 1H), 4.04-3.88 (m, 1H), 3.69 (dd, J=13.6, 3.2 Hz, 1H), 3.61 (dd, J=15.4, 5.7 Hz, 1H), 3.46-3.38 (m, 2H), 3.05 (dt, J=13.8, 6.9 Hz, 1H), 2.30 (q, J=7.5 Hz, 2H), 1.81-1.63 (m, 5H), 1.56-1.45 (m, 1H), 1.35-0.95 (m, 14H). $^{13}$C NMR (101 MHz, MeOD) δ 175.69, 171.60, 167.02, 165.10, 150.85, 146.60, 146.04, 135.13, 125.15, 123.26, 121.51, 118.54, 54.44, 52.85, 41.86, 39.72, 34.92, 34.04, 29.60, 28.60, 28.46, 25.90, 25.72, 25.66, 23.14, 8.71.

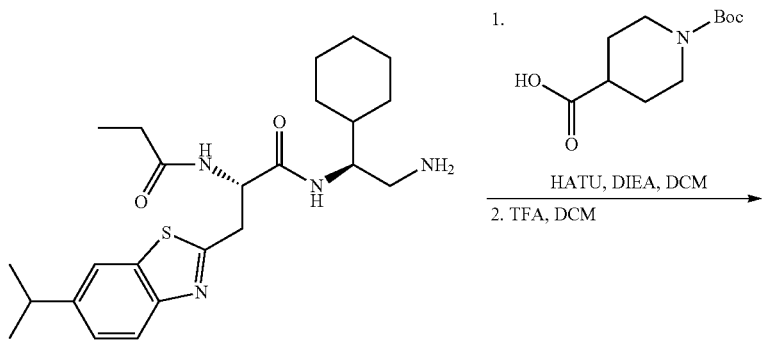

Exact Mass: 444.2559
Molecular Weight: 444.6380

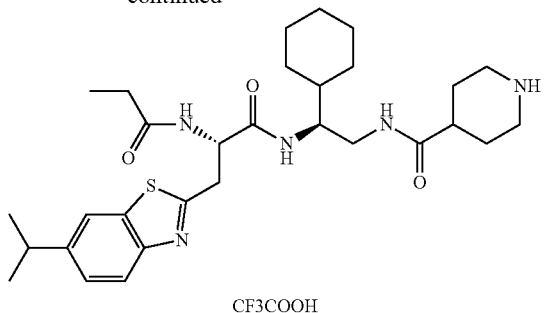

CF3COOH

Exact Mass: 669.3172
Molecular Weight: 669.8052

Example 62: N—((S)-2-cyclohexyl-2-((S)-3-(6-isopropylbenzo[d]thiazol-2-yl)-2-propionamidopropanamido)ethyl)piperidine-4-carboxamide Example 56 (150 mg, 0.34 mmol, 1 equiv.) was added to a solution of the 1-(tert-butoxycarbonyl)piperidine-4-carboxylic acid (93 mg, 0.40 mmol, 1.2 equiv.), HBTU (192 mg, 0.51 mmol, 1.5 equiv.) and DIEA (176 μL, 1.01 mmol, 3 equiv.) in DCM (10 mL). The resultant mixture was stirred at room temperature for 1 h and concentrated. The residue was dissolve in EtOAc and washed with H$_2$O, saturated sodium bicarbonate, 1.0 M HCl, brine and dried over sodium sulfate. After removal of the solvent under vacuum, the residue was treated with TFA (2 ml) in DCM (10 mL) and stirred for 5 h. This reaction mixture was concentrated and purified by HPLC to afford Example 62 (139 mg, 74%). $^1$H NMR (400 MHz, MeOD) δ 7.87 (d, J=8.5 Hz, 1H), 7.83 (s, 1H), 7.42 (dd, J=8.5, 1.5 Hz, 1H), 4.89 (dd, J=7.8, 5.4 Hz, 1H), 3.80 (ddd, J=10.2, 7.0, 3.5 Hz, 1H), 3.63 (dd, J=15.4, 5.5 Hz, 1H), 3.53-3.36 (m, 4H), 3.12-3.04 (m, 2H), 2.98-2.90 (m, 2H), 2.49-2.38 (m, 1H), 2.32 (q, J=7.6 Hz, 2H), 1.98-1.81 (m, 4H), 1.72-1.62 (m, 5H), 1.39-0.92 (m, 15H). $^{13}$C NMR (101 MHz, MeOD) δ 175.87, 174.55, 171.35, 167.22, 150.93, 146.73, 135.21, 125.25, 121.57, 118.63, 54.31, 53.02, 42.89, 40.66, 39.79, 39.39, 34.95, 34.08, 29.54, 28.66, 28.32, 25.89, 25.72, 25.66, 25.14, 25.08, 23.16, 8.70. UPLC-MS (ESI-MS) m/z: calculated for C$_{30}$H$_{46}$N$_5$O$_3$S$^+$ 556.33, found 556.22 [M+H]$^+$.

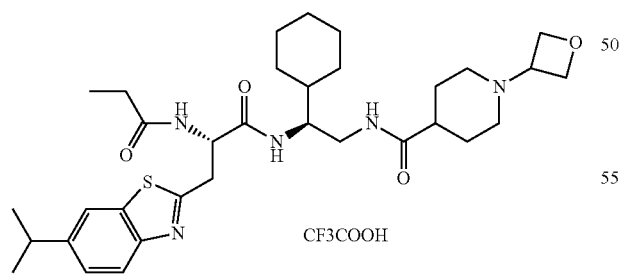

CF3COOH

Exact Mass: 725.3434
Molecular Weight: 725.8692

Example 63

$^1$H NMR (400 MHz, MeOD) δ 7.94-7.91 (m, 2H), 7.54 (d, J=7.9 Hz, 1H), 4.94-4.84 (m, 5H), 4.20-3.65 (m, 4H), 3.64-3.39 (m, 4H), 3.21-3.06 (m, 2H), 2.91-2.87 (m, 1H), 2.57-2.55 (m, 1H), 2.32 (dd, J=14.7, 7.3 Hz, 2H), 2.19-1.94 (m, 4H), 1.73-1.62 (m, 5H), 1.43-0.95 (m, 15H).

DI-763

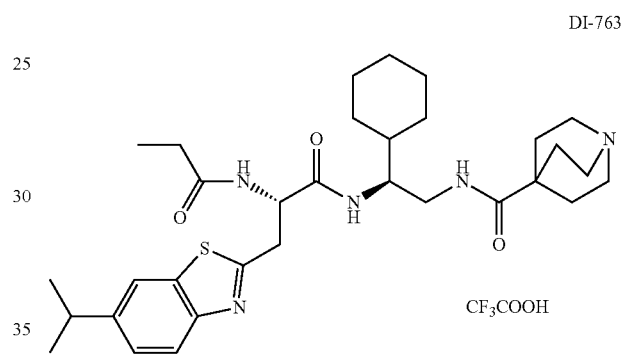

CF$_3$COOH

Molecular Weight: 695.8

Example 64

$^1$H NMR (400 MHz, MeOD) δ 7.87 (d, J=8.4 Hz, 1H), 7.84 (s, 1H), 7.58 (d, J=9.3 Hz, 1H), 7.43 (d, J=8.5 Hz, 1H), 4.91-4.88 (m, 1H), 3.82-3.78 (m, 1H), 3.63 (dd, J=15.0, 5.2 Hz, 1H), 3.50-3.35 (m, 9H), 3.16-3.03 (m, 2H), 2.33 (q, J=7.5 Hz, 2H), 2.13-1.98 (m, 6H), 1.72-1.61 (m, 5H), 1.39-0.91 (m, 15H).

DI-764

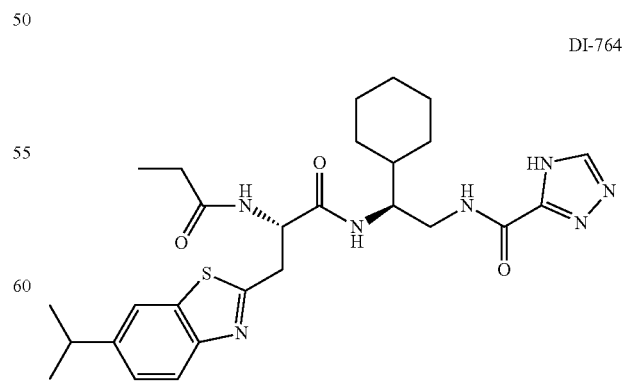

Molecular Weight: 539.7

Example 65

$^1$HNMR (400 MHz, MeOD) δ 8.39 (s, 1H), 7.81 (d, J=8.4 Hz, 1H), 7.76 (s, 1H), 7.37 (d, J=8.5 Hz, 1H), 4.92-4.88 (m, 1H), 3.94-3.92 (m, 1H), 3.65-3.55 (m, 2H), 3.48 (dd, J=13.6, 8.7 Hz, 1H), 3.39 (dd, J=15.2, 7.8 Hz, 1H), 3.05 (dt, J=13.9, 6.9 Hz, 1H), 2.26 (q, J=7.5 Hz, 2H), 1.84-1.63 (m, 5H), 1.56-1.48 (m, 1H), 1.36-0.99 (m, 15H).

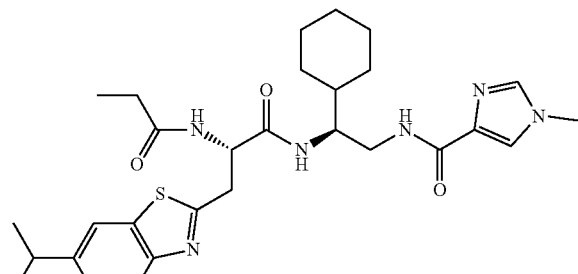

DI-766

Molecular Weight: 552.7

Example 66

$^1$H NMR (400 MHz, MeOD) δ 8.87 (s, 1H), 7.92 (s, 1H), 7.83-7.81 (m, 2H), 7.41 (d, J=8.6 Hz, 1H), 4.84-4.82 (m, 1H), 3.94 (s, 3H), 3.90-3.81 (m, 1H), 3.69-3.56 (m, 2H), 3.48-3.37 (m, 2H), 3.07 (dt, J=13.6, 6.8 Hz, 1H), 2.32 (q, J=7.5 Hz, 2H), 1.82-1.59 (m, 5H), 1.53-1.45 (m, 1H), 1.37-0.93 (m, 14H).

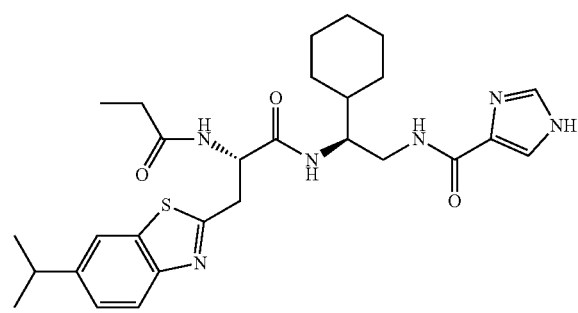

DI-767

Molecular Weight: 538.7

Example 67

$^1$H NMR (400 MHz, MeOD) δ 8.77 (s, 1H), 7.95 (s, 1H), 7.82-7.80 (m, 2H), 7.40 (d, J=8.4 Hz, 1H), 4.97-4.95 (m, 1H), 3.86-3.73 (m, 2H), 3.28-3.21 (m, 3H), 3.10-3.05 (m, 1H), 2.31 (dd, J=15.2, 7.5 Hz, 2H), 1.87-1.56 (m, 5H), 1.39-1.08 (m, 15H).

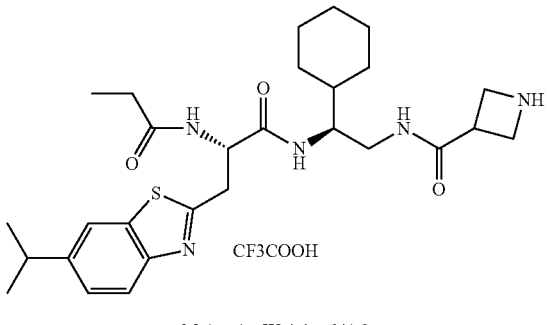

DI-769

CF3COOH

Molecular Weight: 641.8

Example 68

$^1$H NMR (400 MHz, MeOD) δ 7.86 (d, J=8.4 Hz, 1H), 7.82 (d, J=0.5 Hz, 1H), 7.42 (dd, J=8.4, 0.5 Hz, 1H), 4.85 (dd, J=7.7, 5.3 Hz, 1H), 4.31-4.11 (m, 4H), 3.87-3.76 (m, 1H), 3.67-3.55 (m, 2H), 3.53-3.46 (m, 2H), 3.15 (dd, J=13.7, 10.0 Hz, 1H), 3.06 (dt, J=13.8, 6.9 Hz, 1H), 2.34 (dt, J=15.0, 4.2 Hz, 2H), 1.71-1.60 (m, 5H), 1.38-0.88 (m, 15H).

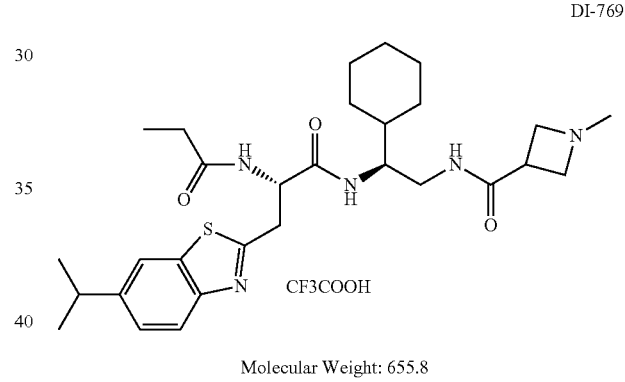

DI-769

CF3COOH

Molecular Weight: 655.8

Example 69

$^1$H NMR (400 MHz, MeOD) δ 7.87 (dd, J=8.5, 1.7 Hz, 1H), 7.83 (s, 1H), 7.43 (d, J=8.4 Hz, 1H), 4.86-4.82 (m, 1H), 4.49-4.36 (m, 2H), 4.16-4.04 (m, 2H), 3.88-3.78 (m, 1H), 3.65-3.45 (m, 4H), 3.19-2.89 (m, 5H), 2.40-2.28 (m, 2H), 1.72-1.60 (m, 6H), 1.37-0.92 (m, 15H).

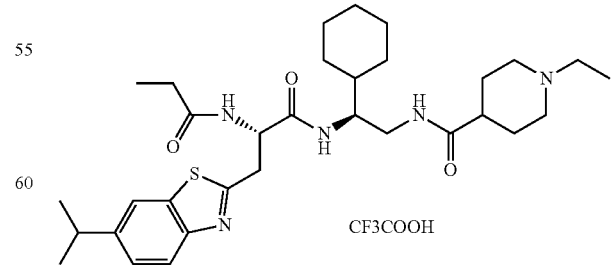

CF3COOH

Exact Mass: 697.3
Molecular Weight: 697.9

Example 70

$^1$H NMR (400 MHz, MeOD) δ 7.87 (dd, J=8.5, 2.5 Hz, 1H), 7.84 (d, J=1.5 Hz, 1H), 7.66 (d, J=9.3 Hz, 1H), 7.43 (dd, J=8.5, 1.6 Hz, 1H), 4.94-4.89 (m, 1H), 3.88-3.76 (m, 1H), 3.68-3.42 (m, 5H), 3.26-2.97 (m, 4H), 2.85 (td, J=13.2, 2.9 Hz, 2H), 2.47-2.40 (m, 1H), 2.32 (q, J=7.6 Hz, 2H), 2.12-1.82 (m, 4H), 1.72-1.62 (m, 6H), 1.40-0.92 (m, 18H).

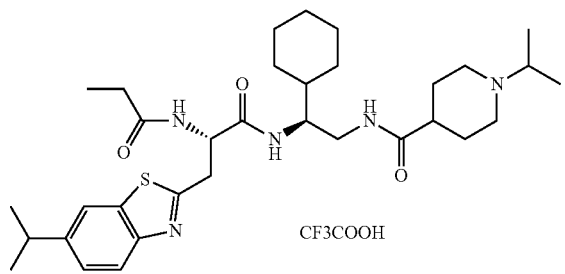

Exact Mass: 711.4
Molecular Weight: 711.9

Example 71

$^1$H NMR (400 MHz, MeOD) δ 7.87 (d, J=8.5 Hz, 1H), 7.84 (d, J=1.5 Hz, 1H), 7.66 (d, J=9.3 Hz, 1H), 7.43 (dd, J=8.5, 1.6 Hz, 1H), 4.90-4.88 (m, 1H), 3.84-3.78 (m, 1H), 3.63 (dd, J=15.4, 5.3 Hz, 1H), 3.55-3.42 (m, 5H), 3.13-3.04 (m, 2H), 2.99-2.92 (m, 2H), 2.44-2.40 (m, 1H), 2.35-2.30 (m, 2H), 2.15-1.85 (m, 4H), 1.72-1.62 (m, 5H), 1.38-0.99 (m, 21H).

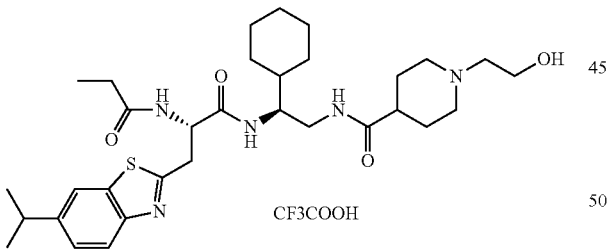

Exact Mass: 713.3
Molecular Weight: 713.9

Example 72

$^1$H NMR (400 MHz, MeOD) δ 7.87 (d, J=8.4 Hz, 1H), 7.84 (s, 1H), 7.43 (d, J=8.5 Hz, 1H), 4.92-4.89 (m, 1H), 3.91-3.76 (m, 3H), 3.72-3.55 (m, 3H), 3.53-3.38 (m, 3H), 3.24-3.19 (m, 1H), 3.14-2.89 (m, 4H), 2.49-2.38 (m, 1H), 2.32 (dd, J=15.2, 7.6 Hz, 2H), 2.11-1.85 (m, 4H), 1.72-1.62 (m, 5H), 1.38-0.93 (m, 15H).

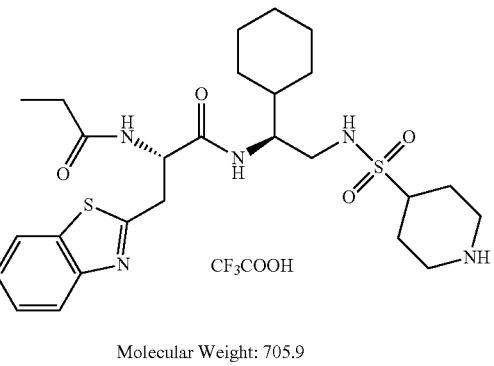

Molecular Weight: 705.9

Example 73

$^1$HNMR (400 MHz, MeOD) δ 7.89 (d, J=8.5 Hz, 1H), 7.82 (d, J=0.6 Hz, 1H), 7.79 (d, J=9.4 Hz, 1H), 7.41 (dd, J=8.4, 1.4 Hz, 1H), 4.94-4.90 (m, 1H), 3.78-3.65 (m, 2H), 3.54-3.46 (m, 3H), 3.39-3.35 (m, 2H), 3.29-3.22 (m, 1H), 3.16-3.02 (m, 4H), 2.37-2.23 (m, 4H), 1.99-1.91 (m, 2H), 1.69 (dd, J=25.9, 10.8 Hz, 6H), 1.35-0.94 (m, 15H). Not in DB but I added it at end.

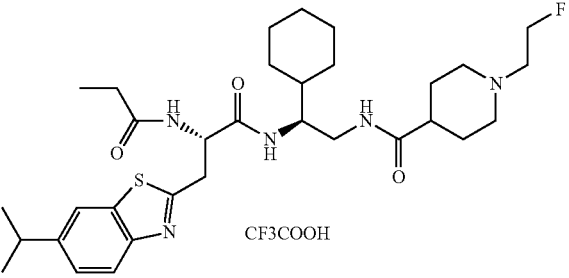

Molecular Weight: 715.8

Example 74

$^1$H NMR (400 MHz, MeOD) δ 7.87 (d, J=8.4 Hz, 1H), 7.84 (s, 1H), 7.65 (d, J=9.1 Hz, 1H), 7.43 (d, J=8.5 Hz, 1H), 4.99-4.94 (m, 1H), 4.81-4.74 (m, 1H), 3.82-3.79 (m, 1H), 3.72-3.59 (m, 3H), 3.57-3.41 (m, 5H), 3.13-3.00 (m, 4H), 2.46-2.43 (m, 1H), 2.33 (q, J=7.5 Hz, 2H), 2.11-1.90 (m, 4H), 1.66 (dd, J=33.3, 9.2 Hz, 6H), 1.40-0.91 (m, 15H).

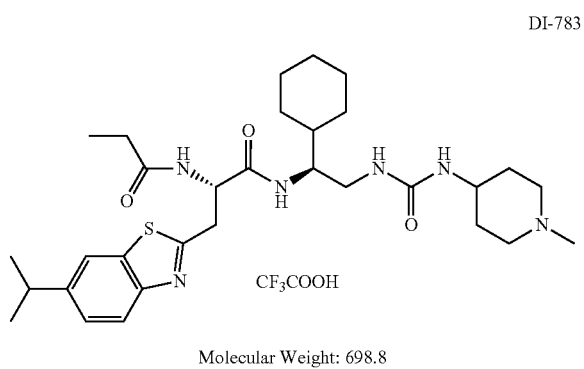 [SMILES: CCC(=O)N[C@@H](Cc1nc2ccc(C(C)C)cc2s1)C(=O)N[C@H](CNC(=O)NC1CCN(C)CC1)C1CCCCC1 ; "CF3COOH"]

DI-783

CF₃COOH

Molecular Weight: 698.8

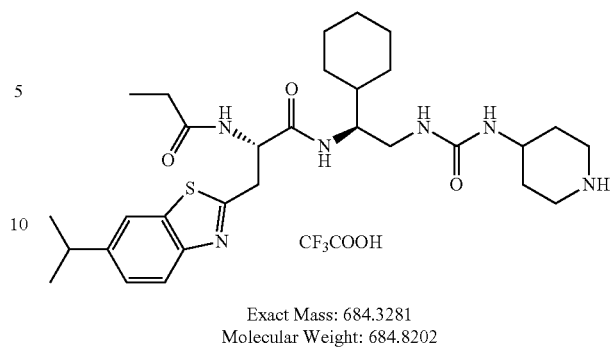

CF₃COOH

Exact Mass: 684.3281
Molecular Weight: 684.8202

Example 75

¹H NMR (400 MHz, MeOD) δ 7.86 (d, J=8.5 Hz, 1H), 7.82 (s, 1H), 7.42 (dd, J=8.5, 1.3 Hz, 1H), 4.93-4.90 (m, 1H), 3.79-3.66 (m, 2H), 3.61 (dd, J=15.3, 4.9 Hz, 1H), 3.56-3.43 (m, 3H), 3.38 (dd, J=13.9, 4.2 Hz, 1H), 3.15-3.04 (m, 4H), 2.86 (s, 3H), 2.38-2.24 (m, 2H), 2.17-1.98 (m, 3H), 1.72-1.60 (m, 7H), 1.42-0.97 (m, 15H).

¹³C NMR (101 MHz, MeOD) δ 175.77, 171.31, 167.15, 158.90, 150.97, 146.63, 135.27, 125.17, 121.60, 118.58, 54.95, 53.61, 53.58, 53.03, 44.53, 42.30, 40.87, 39.76, 35.22, 34.09, 30.01, 29.92, 29.55, 28.66, 28.35, 25.95, 25.81, 25.76, 23.16, 8.74.

Example 77

¹H NMR (400 MHz, MeOD) δ 7.86 (d, J=8.5 Hz, 1H), 7.82 (d, J=1.6 Hz, 1H), 7.41 (dd, J=8.5, 1.7 Hz, 1H), 4.94-4.90 (m, 1H), 3.80-3.69 (m, 2H), 3.61 (dd, J=15.3, 4.9 Hz, 1H), 3.48 (dd, J=15.3, 8.5 Hz, 1H), 3.42-3.34 (m, 3H), 3.18-2.99 (m, 4H), 2.30 (q, J=7.5 Hz, 2H), 2.14-2.08 (m, 2H), 1.78-1.54 (m, 7H), 1.41-0.93 (m, 15H).

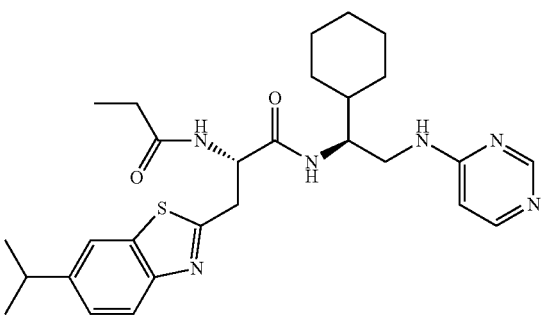 [SMILES: CCC(=O)N[C@@H](Cc1nc2ccc(C(C)C)cc2s1)C(=O)N[C@H](CNc1ccncn1)C1CCCCC1]

DI-784

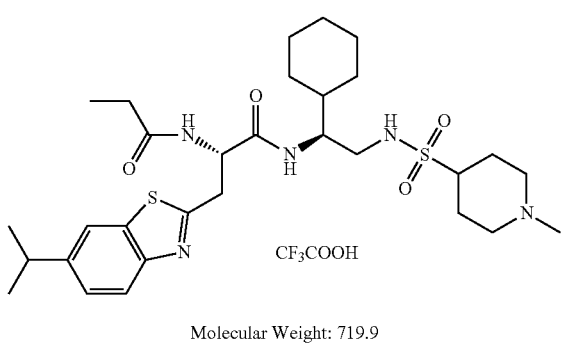

CF₃COOH

Molecular Weight: 719.9

Example 78

¹H NMR (400 MHz, MeOD) δ 8.66 (s, 1H), 7.95 (dd, J=7.3, 1.5 Hz, 1H), 7.85-7.81 (m, 2H), 7.42 (dd, J=8.5, 1.7 Hz, 1H), 6.68 (dd, J=7.3, 0.8 Hz, 1H), 4.82 (dd, J=5.1, 2.4 Hz, 1H), 4.05-3.86 (m, 2H), 3.59-3.49 (m, 2H), 3.42 (dd, J=15.2, 7.7 Hz, 1H), 3.08 (dt, J=13.8, 6.9 Hz, 1H), 2.29 (q, J=7.7 Hz, 2H), 1.80-1.64 (m, 5H), 1.52-1.48 (m, 1H), 1.34-1.04 (m, 14H).

Example 76

¹H NMR (400 MHz, MeOD) δ 7.89 (d, J=8.5 Hz, 1H), 7.82 (d, J=1.3 Hz, 1H), 7.42 (dd, J=8.5, 1.7 Hz, 1H), 4.93-4.91 (m, 1H), 3.79-3.58 (m, 4H), 3.49 (dd, J=15.4, 8.3 Hz, 1H), 3.4-3.36 (m, 2H), 3.30-3.22 (m, 1H), 3.15-3.02 (m, 4H), 2.90 (s, 3H), 2.39-2.35 (m, 2H), 2.29 (q, J=7.6 Hz, 2H), 2.03-1.89 (m, 2H), 1.73-1.64 (m, 5H), 1.42-0.95 (m, 15H).

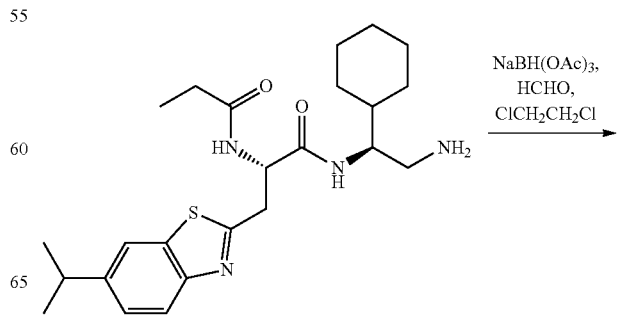

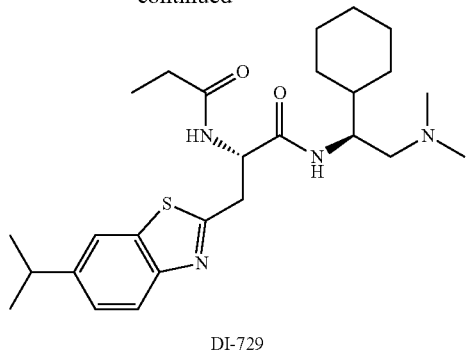

DI-729

Example 79. (S)—N—((S)-1-cyclohexyl-2-(dimethylamino)ethyl)-3-(6-isopropylbenzo[d]thiazol-2-yl)-2-propionamidopropanamide Example 56 (45 mg, 0.1 mmol) and formaldehyde solution 37 wt. % in H$_2$O (66 mg, 0.8 mmol) were mixed in 1,2-dichloroethane (5 mL) and then treated with sodium triacetoxyborohydride (86 mg, 0.4 mmol). The mixture was stirred at room temperature for 3 h until Example 56 was consumed. Then the reaction mixture was quenched by adding 1N NaOH, and concentrated. The residue was purified by HPLC to give 729 (40 mg, 83%). Example 79: $^1$H NMR (400 MHz, MeOD) δ 7.87 (d, J=8.4 Hz, 1H), 7.83 (d, J=0.5 Hz, 1H), 7.42 (d, J=8.4 Hz, 1H), 4.92-4.90 (m, 1H), 4.01-3.96 (m, 1H), 3.67 (dd, J=15.5, 6.1 Hz, 1H), 3.55 (dd, J=15.4, 7.6 Hz, 1H), 3.36-3.33 (m, 1H), 3.11-3.02 (m, 2H), 2.93 (s, 6H), 2.32 (q, J=7.6 Hz, 2H), 1.74-1.47 (m, 6H), 1.36-0.84 (m, 14H). $^{13}$C NMR (101 MHz, MeOD) δ 176.63, 172.01, 166.81, 151.01, 146.72, 135.19, 125.24, 121.61, 118.62, 59.32, 53.34, 50.15, 40.15, 34.09, 34.06, 29.23, 28.55, 28.02, 25.63, 25.49, 25.42, 23.15, 23.14, 8.62. UPLC-MS (ESI-MS) m/z: calculated for C$_{26}$H$_{41}$N$_4$O$_2$S$^+$ 473.29, found 473.32 [M+H]$^+$.

13. Synthesis of Examples 80-.

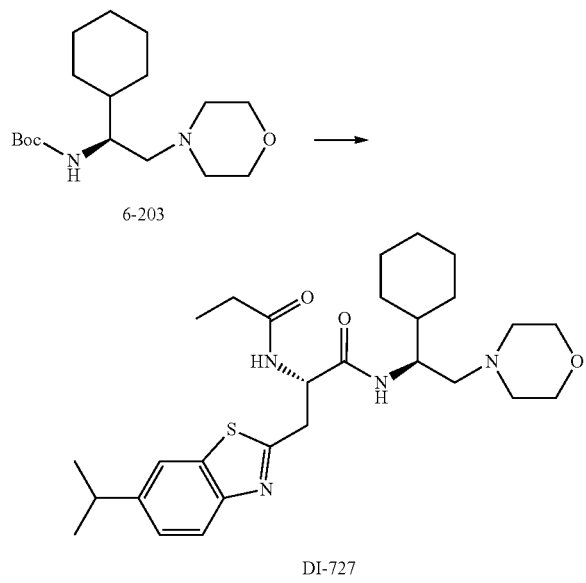

6-203

DI-727

Example 80. (S)—N—((S)-1-cyclohexyl-2-morpholinoethyl)-3-(6-isopropylbenzo[d]thiazol-2-yl)-2-propionamidopropanamide Hydrogen chloride solution (4.0 M in dioxane, 1 mL) was added to a solution of tert-butyl (S)-(1-cyclohexyl-2-morpholinoethyl)carbamate(Wang, S.; Seto, C. T. Enantioselective addition of vinylzinc reagents to 3,4-dihydroisoquinoline N-oxide. Org Lett 2006, 8, 3979-3982). $^2$ (30 mg, 0.1 mmol, 1 equiv.) in MeOH (5 mL). The solution was stirred for overnight and concentrated. The residue in DMF (2 mL) was added to a solution of the 6-85 (47 mg, 0.1 mmol, 1 equiv.), HBTU (55 mg, 0.14 mmol, 1.5 equiv.) and DIEA (50 µL, 0.29 mmol, 3 equiv.) in DMF (20 mL). The resultant mixture was stirred at room temperature for 1 h. The solution was diluted with EtOAc and washed with H$_2$O, saturated sodium bicarbonate, 1.0 M HCl, brine and dried over sodium sulfate. After removal of the solvent under vacuum, the residue was treated with 0.5 mL diethylamine in Acetonitrile (5 mL) for 1 h. The reaction mixture was evaporated and dissolved in DCM (5 mL). This solution was treated with propionic anhydride (25 mg, 0.2 mmoL, 2 equiv.) and DIEA (69 µL, 0.4 mmol, 4 equiv.). The resulting reaction mixture was stirred for half an hour and then was evaporated. The residue was purified by HPLC to afford Example 80 (31 mg, 63%). $^1$H NMR (400 MHz, MeOD) δ 7.87 (d, J=8.4 Hz, 1H), 7.82 (d, J=1.2 Hz, 1H), 7.41 (dd, J=8.4, 1.5 Hz, 1H), 4.78 (t, J=6.9 Hz, 1H), 4.18-3.71 (m, 6H), 3.68-3.63 (m, 2H), 3.56 (dd, J=15.4, 7.0 Hz, 1H), 3.41-3.33 (m, 2H), 3.25-3.01 (m, 3H), 2.35 (q, J=7.6 Hz, 2H), 1.70-1.45 (m, 6H), 1.35-0.87 (m, 14H). $^{13}$C NMR (101 MHz, MeOD) δ 176.80, 171.98, 166.40, 151.02, 146.77, 135.22, 125.26, 121.71, 118.63, 63.35, 59.00, 53.99, 49.33, 39.92, 34.10, 33.98, 29.21, 28.46, 28.12, 25.59, 25.46, 25.39, 23.16, 8.62. UPLC-MS (ESI-MS) m/z: calculated for C$_{28}$H$_{43}$N$_4$O$_3$S$^+$ 515.31, found 515.26 [M+H]$^+$.

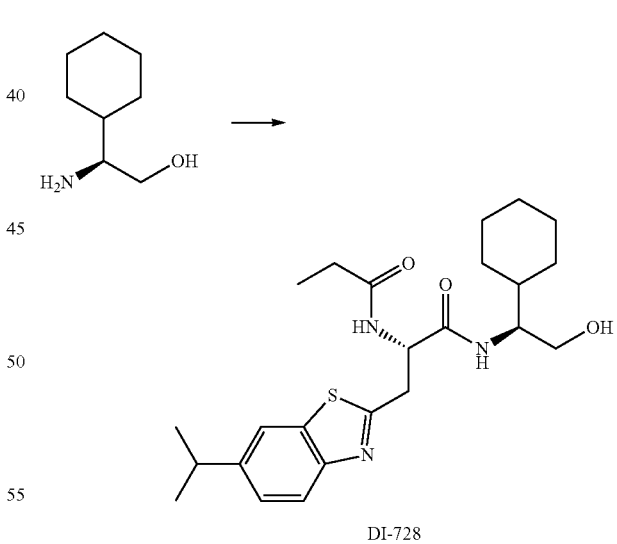

DI-728

Example 81 was synthesized using a similar method to that for Example 80.

(S)—N—((S)-1-cyclohexyl-2-hydroxyethyl)-3-(6-isopropylbenzo[d]thiazol-2-yl)-2-propionamidopropanamide $^1$H NMR (400 MHz, MeOD) δ 7.86 (d, J=8.5 Hz, 1H), 7.82 (d, J=1.7 Hz, 1H), 7.41 (dd, J=8.5, 1.7 Hz, 1H), 4.93

(dd, J=7.9, 5.5 Hz, 1H), 3.97-3.89 (m, 1H), 3.77-3.64 (m, 2H), 3.49 (dd, J=15.1, 7.9 Hz, 1H), 3.24-3.14 (m, 1H), 3.07 (dt, J=13.8, 6.9 Hz, 1H), 2.31-2.23 (m, 3H), 1.99-1.83 (m, 3H), 1.65-1.49 (m, 3H), 1.36-1.10 (m, 14H). $^{13}$C NMR (101 MHz, MeOD) δ 175.61, 170.95, 167.09, 150.92, 146.58, 135.24, 125.13, 121.56, 118.51, 61.34, 54.45, 52.81, 38.24, 35.24, 34.08, 29.67, 28.63, 28.47, 26.01, 25.84, 25.80, 23.15, 8.81. UPLC-MS (ESI-MS) m/z: calculated for $C_{24}H_{36}N_3O_3S^+$ 446.25, found 446.27 $[M+H]^+$.

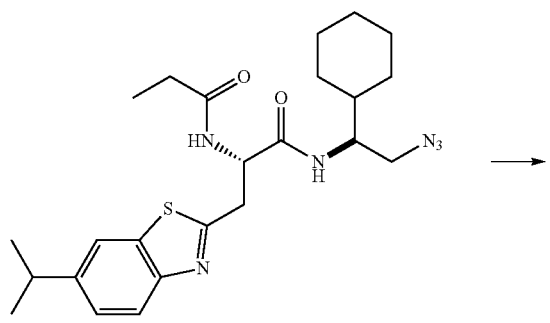

6-88

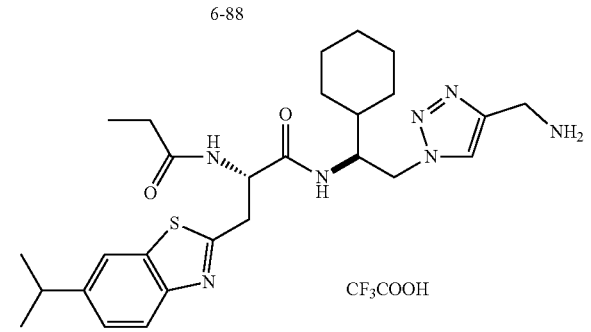

CF$_3$COOH

Exact Mass: 639.3
Molecular Weight: 639.7
DI-775

Example 82

$^1$H NMR (400 MHz, MeOD) δ 7.97 (s, 1H), 7.86 (d, J=8.5 Hz, 1H), 7.82 (d, J=1.5 Hz, 1H), 7.42 (dd, J=8.5, 1.6 Hz, 1H), 4.75 (dd, J=8.8, 4.6 Hz, 1H), 4.69 (dd, J=14.0, 3.9 Hz, 1H), 4.45 (dd, J=14.0, 10.1 Hz, 1H), 4.23 (s, 2H), 4.16-4.12 (m, 1H), 3.46 (dd, J=15.5, 4.6 Hz, 1H), 3.41-3.34 (m, 1H), 3.07 (dt, J=13.8, 6.9 Hz, 1H), 2.37-2.23 (m, 2H), 1.85-1.61 (m, 5H), 1.55-1.47 (m, 1H), 1.37-0.94 (m, 15H).

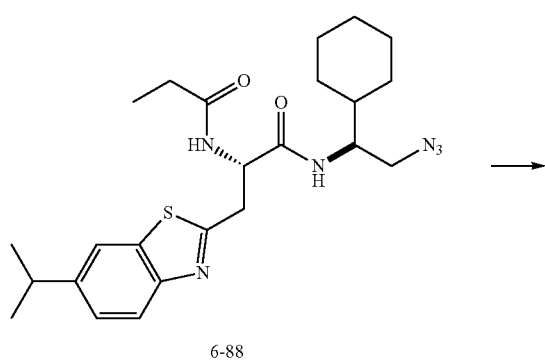

6-88

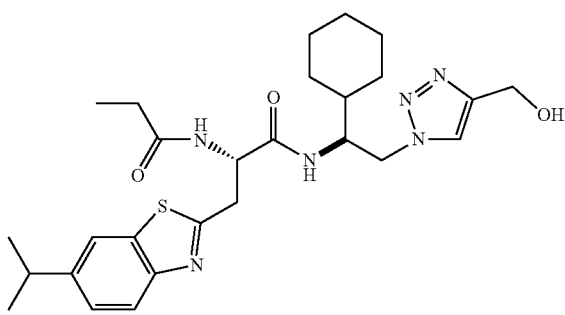

Exact Mass: 526.3
Molecular Weight: 526.7
DI-776

Example 83

$^1$H NMR (400 MHz, MeOD) δ 7.89 (s, 1H), 7.84 (d, J=8.5 Hz, 1H), 7.82 (d, J=1.3 Hz, 1H), 7.41 (dd, J=8.4, 1.5 Hz, 1H), 4.84-4.82 (m, 1H), 4.73-4.55 (m, 3H), 4.51-4.46 (m, 1H), 4.24-4.07 (m, 1H), 3.43 (dd, J=15.3, 5.0 Hz, 1H), 3.32-3.23 (m, 1H), 3.07 (dt, J=13.8, 6.9 Hz, 1H), 2.25 (q, J=7.6 Hz, 2H), 1.87-1.65 (m, 5H), 1.54-1.43 (m, 1H), 1.40-0.86 (m, 15H).

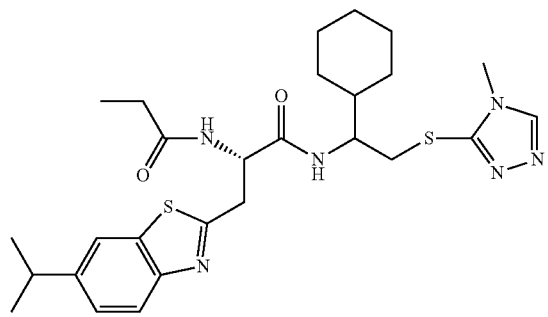

DI-762

Molecular Weight: 542.8

Example 84

$^1$HNMR (400 MHz, MeOD) δ 8.96 (s, 1H), 7.86 (d, J=8.4 Hz, 1H), 7.81 (d, J=1.6 Hz, 1H), 7.40 (dd, J=8.5, 1.6 Hz, 1H), 4.98 (dd, J=7.6, 6.3 Hz, 1H), 3.94-3.89 (m, 1H), 3.67-3.59 (m, 2H), 3.52 (s, 3H), 3.46 (dd, J=15.3, 7.7 Hz, 1H), 3.18 (dd, J=13.5, 10.2 Hz, 1H), 3.06 (dt, J=13.8, 6.9 Hz, 1H), 2.28 (q, J=7.6 Hz, 2H), 1.74-1.63 (m, 5H), 1.57-1.49 (m, 1H), 1.37-0.96 (m, 14H).

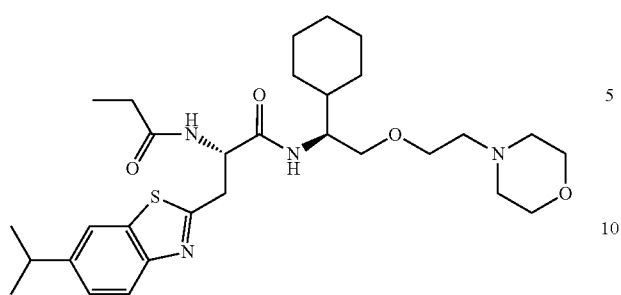

Example 85

¹H NMR (400 MHz, MeOD) δ 7.87 (d, J=8.6 Hz, 1H), 7.84 (s, 1H), 7.78-7.72 (m, 1H), 7.58 (dd, J=8.2, 7.1 Hz, 1H), 7.51 (dd, J=8.2, 7.1 Hz, 1H), 7.43 (d, J=8.5 Hz, 1H), 4.93-4.91 (m, 1H), 4.06-4.03 (m, 2H), 3.87-3.73 (m, 4H), 3.70-3.44 (m, 7H), 3.31-3.23 (m, 2H), 3.21-3.01 (m, 3H), 2.37-2.27 (m, 2H), 1.72-1.62 (m, 5H), 1.42-0.96 (m, 15H).

14. Synthesis of Examples 86-91

These compounds were synthesized using the similar methods as for Examples 56 & 58.

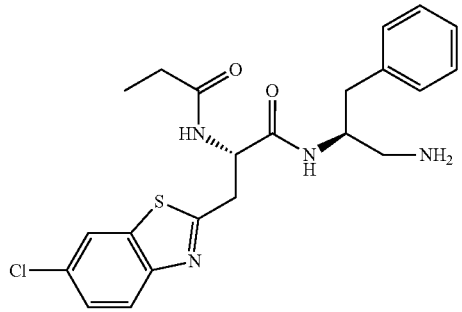 [SMILES: CCC(=O)N[C@@H](Cc1nc2ccc(Cl)cc2s1)C(=O)N[C@H](CN)Cc1ccccc1]

Example 86

¹H NMR (400 MHz, MeOD) δ 8.02 (d, J=2.0 Hz, 1H), 7.88 (d, J=8.7 Hz, 1H), 7.51 (dd, J=8.7, 2.1 Hz, 1H), 7.38-7.14 (m, 5H), 4.84-4.82 (m, 1H), 4.46-4.32 (m, 1H), 3.59 (dd, J=15.4, 5.3 Hz, 1H), 3.43 (dd, J=15.4, 8.1 Hz, 1H), 3.17 (dd, J=13.0, 3.8 Hz, 1H), 3.08 (dd, J=12.9, 10.2 Hz, 1H), 2.98-2.79 (m, 2H), 2.24 (q, J=7.6 Hz, 2H), 1.07 (t, J=7.6 Hz, 3H). ¹³C NMR (101 MHz, MeOD) δ 176.05 (s), 171.66 (s), 168.80 (s), 151.27 (s), 136.79 (s), 136.46 (s), 130.93 (s), 128.79 (s), 128.31 (s), 126.65 (d, J=13.1 Hz), 122.76 (s), 121.21 (s), 52.76 (s), 49.42 (s), 42.95 (s), 37.43 (s), 34.72 (s), 28.50 (s), 8.59 (s).

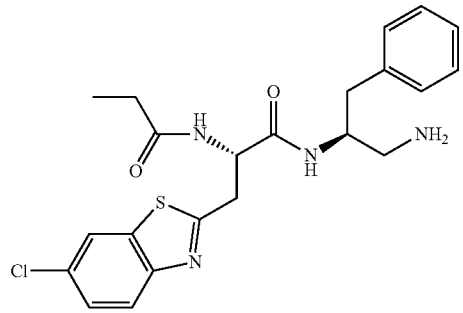 [SMILES: CCC(=O)N[C@@H](Cc1nc2ccc(Cl)cc2s1)C(=O)N[C@H](CN)Cc1ccccc1]

Example 87

¹H NMR (400 MHz, MeOD) δ 8.00 (d, J=1.9 Hz, 1H), 7.90 (d, J=8.7 Hz, 1H), 7.51 (dd, J=8.7, 2.1 Hz, 1H), 7.28-7.15 (m, 5H), 4.72-4.68 (m, 1H), 4.47-4.40 (m, 1H), 3.30-3.25 (m, 2H), 3.18 (dd, J=13.1, 3.5 Hz, 1H), 2.99 (dd, J=12.9, 10.6 Hz, 1H), 2.89 (dd, J=14.0, 6.0 Hz, 1H), 2.76 (dd, J=14.0, 9.0 Hz, 1H), 2.25 (q, J=7.6 Hz, 2H), 1.07 (t, J=7.6 Hz, 3H). ¹³C NMR (101 MHz, MeOD) δ 176.20, 171.97, 168.09, 151.34, 136.70, 136.54, 130.91, 128.73, 128.26, 126.68, 126.57, 123.00, 121.18, 53.29, 49.04, 43.17, 37.57, 34.92, 28.35, 8.56.

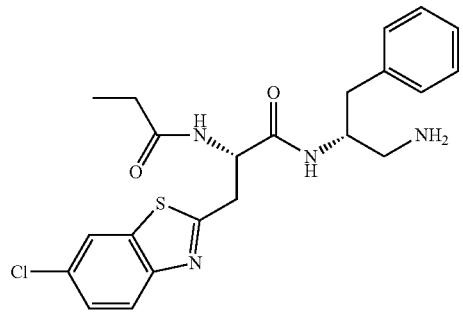 [SMILES: CCC(=O)N[C@@H](Cc1nc2ccc(Cl)cc2s1)C(=O)N[C@@H](CN)Cc1ccccc1]

Example 88

¹H NMR (400 MHz, MeOD) δ 8.01 (d, J=1.9 Hz, 1H), 7.88 (d, J=8.8 Hz, 1H), 7.50 (dd, J=8.7, 2.1 Hz, 1H), 7.34-7.18 (m, 5H), 4.83 (dd, J=8.0, 5.3 Hz, 1H), 4.44-4.32 (m, 1H), 3.58 (dd, J=15.4, 5.3 Hz, 1H), 3.42 (dd, J=15.4, 8.1 Hz, 1H), 3.17 (dd, J=13.0, 3.8 Hz, 1H), 3.08 (dd, J=12.9, 10.3 Hz, 1H), 2.95-2.84 (m, 2H), 2.24 (q, J=7.6 Hz, 2H), 1.07 (t, J=7.6 Hz, 3H).

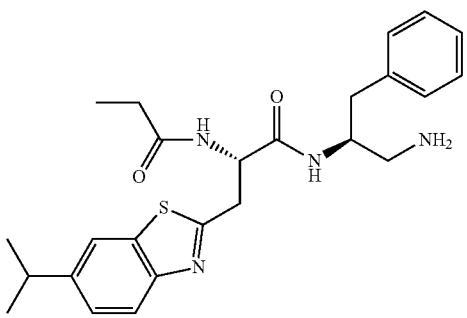 [SMILES: CCC(=O)N[C@@H](Cc1nc2ccc(C(C)C)cc2s1)C(=O)N[C@H](CN)Cc1ccccc1]

Example 89

¹H NMR (400 MHz, MeOD) δ 7.85 (d, J=8.5 Hz, 1H), 7.81 (d, J=1.5 Hz, 1H), 7.41 (dd, J=8.5, 1.6 Hz, 1H), 7.29-7.07 (m, 5H), 4.66 (t, J=7.1 Hz, 1H), 4.43-4.37 (m, 1H), 3.26 (d, J=7.1 Hz, 2H), 3.16 (dd, J=13.0, 3.3 Hz, 1H), 3.06 (dt, J-13.8, 6.9 Hz, 1H), 2.97 (dd, J=12.7, 10.7 Hz, 1H), 2.84 (dd, J=14.0, 6.1 Hz, 1H), 2.72 (dd, J=14.0, 8.8 Hz, 1H), 2.24 (q, J=7.6 Hz, 2H), 1.31 (d, J=6.9 Hz, 6H), 1.07 (t, J=7.6 Hz, 3H).

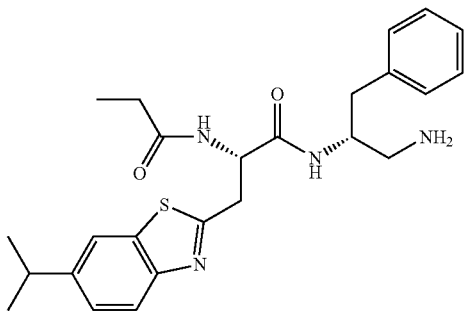 [SMILES: CCC(=O)N[C@@H](Cc1nc2ccc(C(C)C)cc2s1)C(=O)N[C@@H](CN)Cc1ccccc1]

Example 90

¹H NMR (400 MHz, MeOD) δ 7.85 (d, J=8.5 Hz, 1H), 7.81 (d, J=1.6 Hz, 1H), 7.41 (dd, J=8.5, 1.6 Hz, 1H), 7.28-7.09 (m, 5H), 4.68 (t, J=7.1 Hz, 1H), 4.44-4.38 (m, 1H), 3.30-3.24 (m, 2H), 3.17 (dd, J=13.0, 3.4 Hz, 1H), 3.06 (dt, J=13.8, 6.9 Hz, 1H), 2.99 (dd, J=12.8, 10.6 Hz, 1H), 2.85 (dd, J=14.0, 6.1 Hz, 1H), 2.73 (dd, J=14.0, 8.8 Hz, 1H), 2.25 (q, J=7.6 Hz, 2H), 1.32 (d, J=6.9 Hz, 6H), 1.07 (t, J=7.6 Hz, 3H).

Example 91

¹H NMR (400 MHz, MeOD) δ 7.83 (m, 2H), 7.42 (dd, J=8.6, 1.6 Hz, 1H), 7.33-7.17 (m, 5H), 4.81 (dd, J=7.6, 5.5 Hz, 1H), 4.49-4.32 (m, 1H), 3.58 (dd, J=15.2, 5.5 Hz, 1H), 3.42 (dd, J=15.2, 7.6 Hz, 1H), 3.18 (dd, J=13.0, 3.6 Hz, 1H), 3.12-3.01 (m, 2H), 2.94-2.81 (m, 2H), 2.24 (q, J=7.6 Hz, 2H), 1.32 (d, J=6.9 Hz, 6H), 1.08 (t, J=7.6 Hz, 3H).

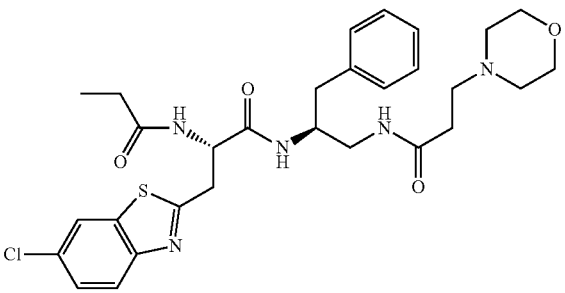 [SMILES: CCC(=O)N[C@@H](Cc1nc2ccc(Cl)cc2s1)C(=O)N[C@H](CNC(=O)CCN1CCOCC1)Cc1ccccc1]

Example 92

¹H NMR (400 MHz, MeOD) δ 8.02 (d, J=2.1 Hz, 1H), 7.90 (d, J=8.7 Hz, 1H), 7.51 (dd, J=8.7, 2.1 Hz, 1H), 7.32-7.15 (m, 5H), 4.83-4.78 (m, 1H), 4.42-4.22 (m, 1H), 4.04-3.84 (m, 4H), 3.55-3.40 (m, 8H), 3.18 (dd, J=13.7, 9.6 Hz, 2H), 2.81 (ddd, J=22.4, 14.0, 7.3 Hz, 2H), 2.69 (t, J=6.6 Hz, 2H), 2.27 (q, J=7.6 Hz, 2H), 1.08 (t, J=7.6 Hz, 3H).

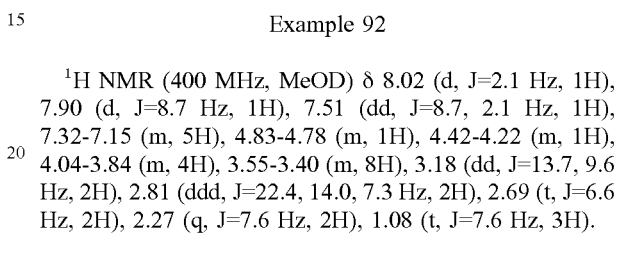

Example 93

¹H NMR (400 MHz, MeOD) δ 7.85 (d, J=8.5 Hz, 1H), 7.82 (d, J=1.6 Hz, 1H), 7.42 (dd, J=8.5, 1.7 Hz, 1H), 7.34-7.10 (m, 5H), 4.80 (dd, J=8.6, 5.3 Hz, 1H), 4.43-4.21 (m, 1H), 4.05 (d, J=12.3 Hz, 2H), 3.80 (t, J=12.4 Hz, 2H), 3.59-3.36 (m, 6H), 3.23-3.00 (m, 4H), 2.86-2.74 (m, 2H), 2.70 (t, J=6.5 Hz, 2H), 2.28 (q, J=7.6 Hz, 2H), 1.32 (d, J=6.9 Hz, 6H), 1.08 (t, J=7.6 Hz, 3H).

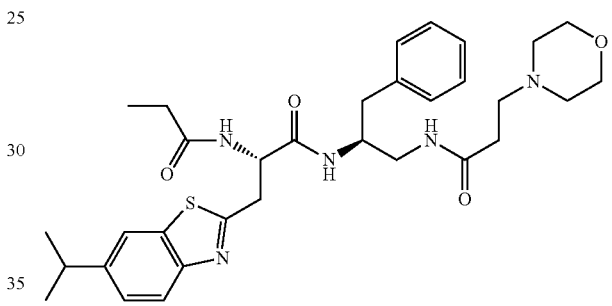

Example 94

¹H NMR (400 MHz, MeOD) δ 7.85 (d, J=8.5 Hz, 1H), 7.81 (d, J=0.5 Hz, 1H), 7.41 (dd, J=8.4, 0.5 Hz, 1H), 7.28-7.17 (m, 5H), 4.80 (dd, J=8.5, 5.3 Hz, 1H), 4.40-4.21

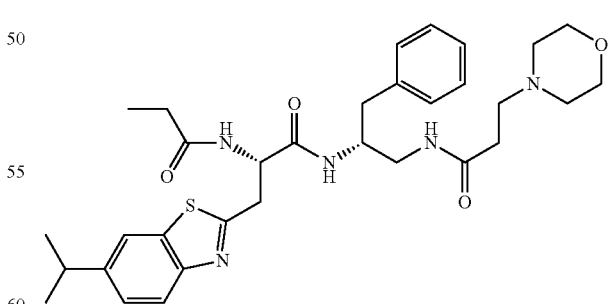

(m, 1H), 4.04 (d, J=12.4 Hz, 2H), 3.79 (t, J=11.9 Hz, 2H), 3.60-3.37 (m, 6H), 3.24-2.95 (m, 4H), 2.80 (ddd, J=22.2, 13.9, 7.2 Hz, 2H), 2.69 (t, J=6.6 Hz, 2H), 2.27 (q, J=7.6 Hz, 2H), 1.32 (d, J=6.9 Hz, 6H), 1.08 (t, J=7.6 Hz, 3H).

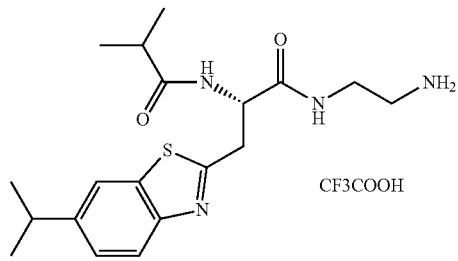

Molecular Weight: 490.5422

Example 95

¹HNMR (400 MHz, MeOD) δ 7.85 (d, J=8.5 Hz, 1H), 7.83 (s, 1H), 7.42 (d, J=8.5 Hz, 1H), 4.84-4.77 (m, 1H), 3.66 (dd, J=15.0, 5.3 Hz, 1H), 3.51 (dd, J=13.8, 8.0 Hz, 3H), 3.17-2.99 (m, 3H), 2.52 (dt, J=13.7, 6.8 Hz, 1H), 1.40-1.27 (m, 6H), 1.16-0.99 (m, 6H).

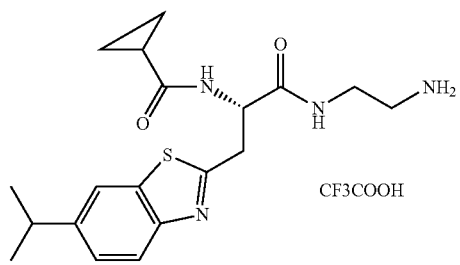

Molecular Weight: 488.5262

Example 96

¹H NMR (400 MHz, MeOD) δ 8.41 (t, J=5.5 Hz, 1H), 7.86 (d, J=8.5 Hz, 1H), 7.83 (s, 1H), 7.42 (d, J=8.5 Hz, 1H), 4.82 (dd, J=7.8, 5.8 Hz, 1H), 3.66 (dd, J=15.1, 5.8 Hz, 1H), 3.55-3.47 (m, 3H), 3.17-2.97 (m, 3H), 1.80-1.59 (m, 1H), 1.33 (d, J=6.9 Hz, 6H), 0.95-0.73 (m, 4H).

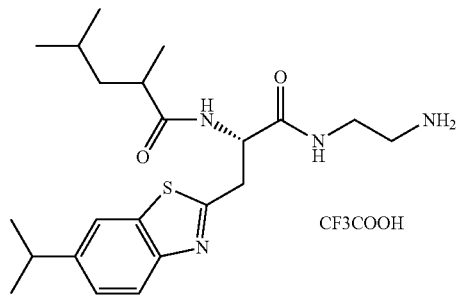

Molecular Weight: 532.6232

Example 97

¹H NMR (400 MHz, MeOD) δ 7.85 (d, J=8.5 Hz, 1H), 7.82 (s, 1H), 7.42 (d, J=8.5 Hz, 1H), 4.95-4.91 (m, 1H), 3.64 (dd, J=15.1, 5.3 Hz, 1H), 3.59-3.40 (m, 3H), 3.18-2.98 (m, 3H), 2.51-2.39 (m, 1H), 1.63-1.24 (m, 8H), 1.20-0.92 (m, 5H), 0.84 (dd, J=17.8, 5.9 Hz, 2H), 0.62 (d, J=6.4 Hz, 3H).

Example 98

¹H NMR (400 MHz, MeOD) δ 7.86 (d, J=8.5 Hz, 1H), 7.83 (s, 1H), 7.43 (d, J=8.5 Hz, 1H), 4.81 (dd, J=8.4, 5.4 Hz, 1H), 3.64 (dd, J=15.0, 5.6 Hz, 1H), 3.55-3.45 (m, 3H), 3.11-3.04 (m, 3H), 2.51-2.46 (m, 1H), 1.55-1.44 (m, 2H), 1.33 (d, J=6.9 Hz, 6H), 1.20-1.10 (m, 1H), 1.05 (d, J=6.8 Hz, 3H), 0.85 (dd, J=17.9, 6.1 Hz, 6H).

15. Synthesis of Examples 99-107.

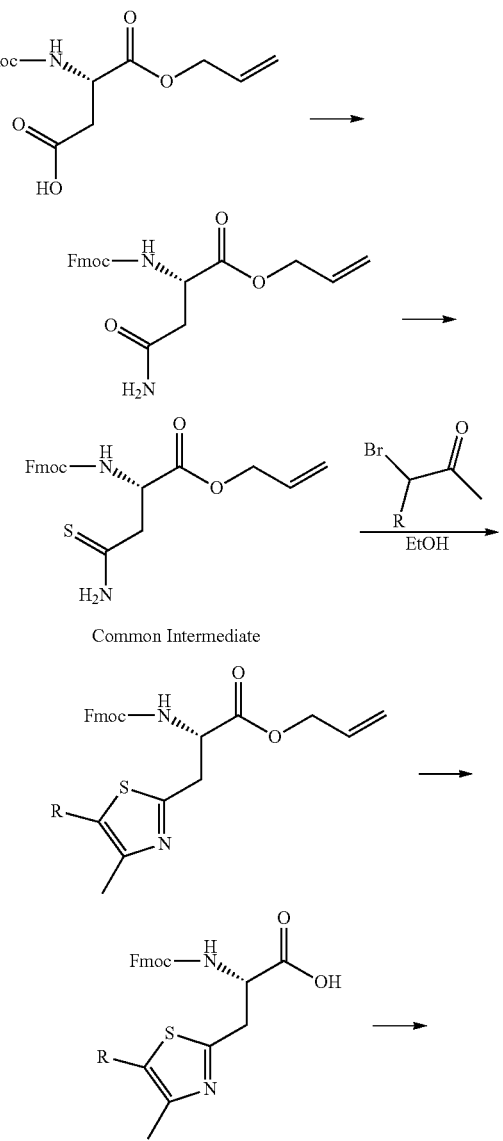

Scheme: Synthesis of Example 100 and analogs.

Common Intermediate

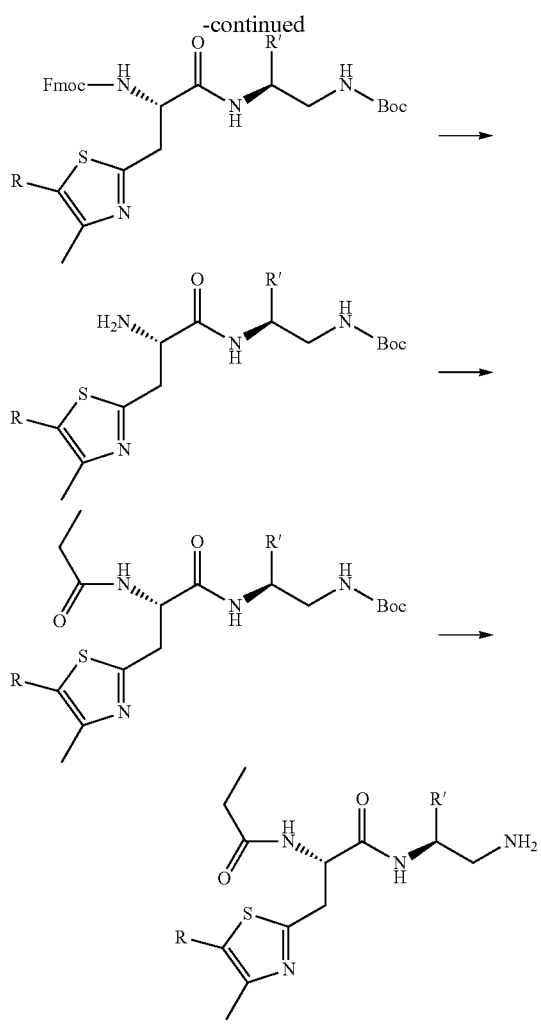

Example 100 and its analogs were made according to the above synthetic route.

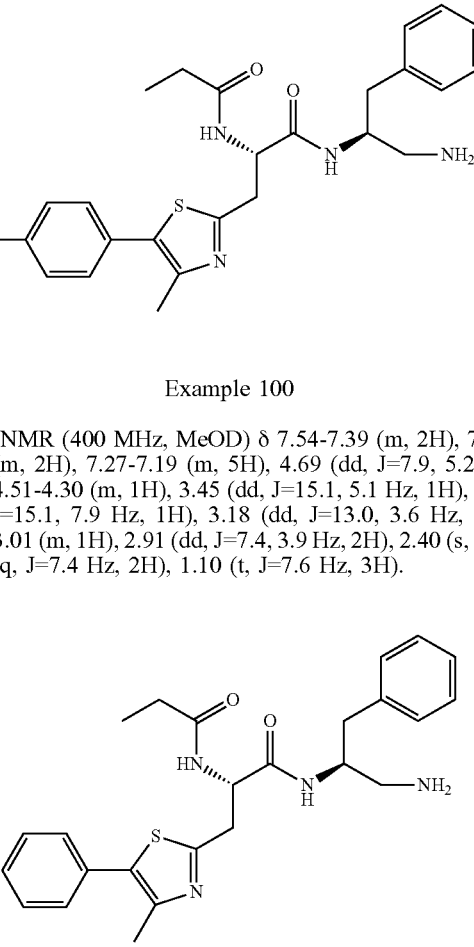

Example 100

¹H NMR (400 MHz, MeOD) δ 7.54-7.39 (m, 2H), 7.34-7.30 (m, 2H), 7.27-7.19 (m, 5H), 4.69 (dd, J=7.9, 5.2 Hz, 1H), 4.51-4.30 (m, 1H), 3.45 (dd, J=15.1, 5.1 Hz, 1H), 3.28 (dd, J=15.1, 7.9 Hz, 1H), 3.18 (dd, J=13.0, 3.6 Hz, 1H), 3.12-3.01 (m, 1H), 2.91 (dd, J=7.4, 3.9 Hz, 2H), 2.40 (s, 3H), 2.26 (q, J=7.4 Hz, 2H), 1.10 (t, J=7.6 Hz, 3H).

Example 101

¹H NMR (400 MHz, MeOD) δ 7.50-7.37 (m, 5H), 7.34-7.28 (m, 2H), 7.28-7.17 (m, 3H), 4.70 (dd, J=7.8, 5.2 Hz, 1H), 4.48-4.33 (m, 1H), 3.47 (dd, J=15.1, 5.2 Hz, 1H), 3.32-3.25 (m, 1H), 3.18 (dd, J=13.0, 3.6 Hz, 1H), 3.09 (dd, J=12.9, 10.4 Hz, 1H), 2.91 (dd, J=7.4, 3.3 Hz, 2H), 2.43 (s, 3H), 2.26 (dt, J=15.0, 7.4 Hz, 2H), 1.10 (t, J=7.6 Hz, 3H).

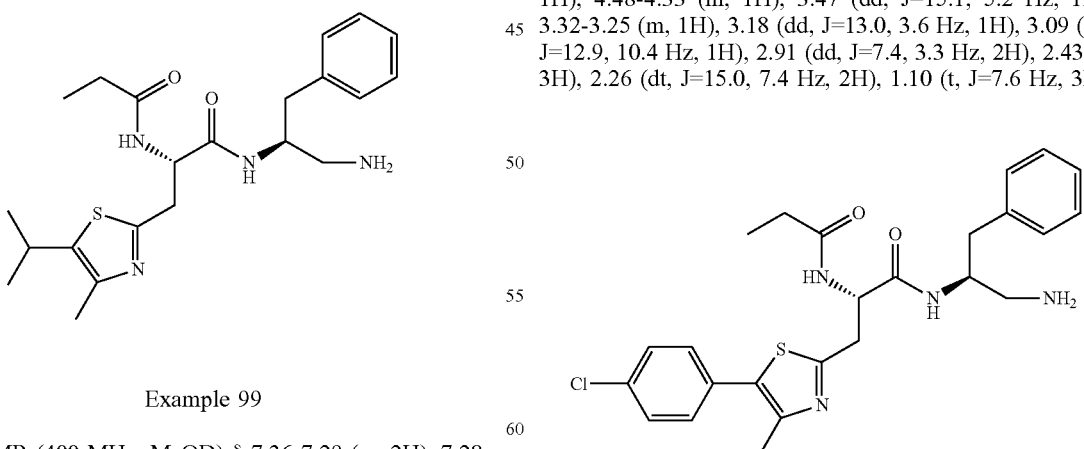

Example 99

¹H NMR (400 MHz, MeOD) δ 7.36-7.29 (m, 2H), 7.28-7.21 (m, 3H), 4.64 (dd, J=8.0, 5.1 Hz, 1H), 4.47-4.26 (m, 1H), 3.44 (dd, J=15.1, 5.1 Hz, 1H), 3.28-3.22 (m, 2H), 3.16 (dd, J=13.0, 3.6 Hz, 1H), 3.06 (dd, J=12.9, 10.4 Hz, 1H), 2.90 (dd, J=7.4, 3.4 Hz, 2H), 2.34 (d, J=6.4 Hz, 3H), 2.23 (q, J=7.6 Hz, 2H), 1.28 (dd, J=6.8, 2.0 Hz, 6H), 1.09 (t, J=7.6 Hz, 3H).

Example 102

¹H NMR (400 MHz, MeOD) δ 7.54-7.45 (m, 2H), 7.44-7.39 (m, 2H), 7.35-7.28 (m, 2H), 7.28-7.18 (m, 3H), 4.69

(dd, J=7.9, 5.2 Hz, 1H), 4.48-4.32 (m, 1H), 3.45 (dd, J=15.1, 5.1 Hz, 1H), 3.28 (dd, J=15.1, 7.9 Hz, 1H), 3.18 (dd, J=13.0, 3.6 Hz, 1H), 3.08 (dd, J=12.9, 10.4 Hz, 1H), 2.91 (dd, J=7.4, 3.7 Hz, 2H), 2.42 (s, 3H), 2.25 (q, J=7.5 Hz, 2H), 1.10 (t, J=7.6 Hz, 3H).

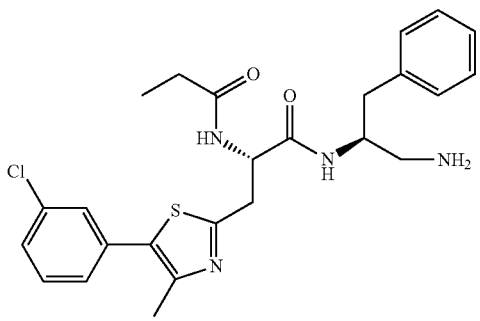 [SMILES: CCC(=O)N[C@@H](Cc1nc(C)c(-c2cccc(Cl)c2)s1)C(=O)N[C@H](CN)Cc1ccccc1]

Example 103

$^1$H NMR (400 MHz, MeOD) δ 7.54-7.40 (m, 3H), 7.39-7.29 (m, 3H), 7.28-7.15 (m, 3H), 4.70 (dd, J=7.8, 5.2 Hz, 1H), 4.42-4.39 (m, 1H), 3.45 (dd, J=15.1, 5.2 Hz, 1H), 3.31-3.23 (m, 1H), 3.18 (dd, J=13.0, 3.4 Hz, 1H), 3.07 (dd, J=15.8, 7.6 Hz, 1H), 2.98-2.84 (m, 2H), 2.43 (s, 3H), 2.26 (q, J=7.6 Hz, 2H), 1.10 (t, J=7.6 Hz, 3H).

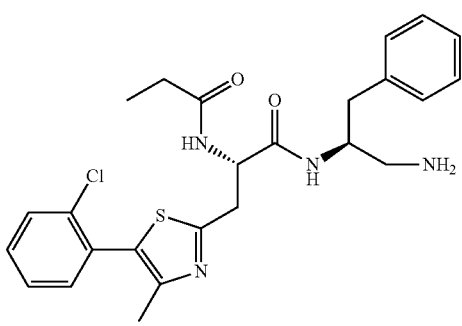 [SMILES: CCC(=O)N[C@@H](Cc1nc(C)c(-c2ccccc2Cl)s1)C(=O)N[C@H](CN)Cc1ccccc1]

Example 104

$^1$H NMR (400 MHz, MeOD) δ 7.59-7.53 (m, 1H), 7.48-7.37 (m, 3H), 7.35-7.19 (m, 5H), 4.59 (dd, J=8.5, 5.8 Hz, 1H), 4.49-4.32 (m, 1H), 3.22-3.09 (m, 3H), 3.00 (dd, J=12.9, 10.6 Hz, 1H), 2.92 (dd, J=13.9, 6.4 Hz, 1H), 2.82 (dd, J=13.9, 8.7 Hz, 1H), 2.34-2.16 (m, 5H), 1.10 (t, J=7.6 Hz, 3H).

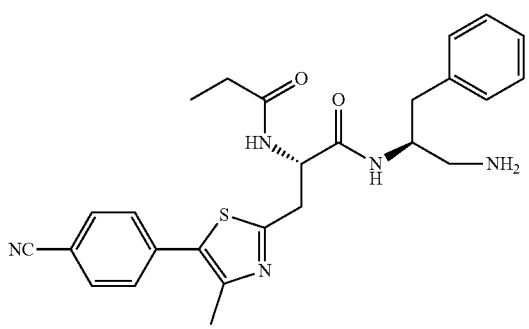 [SMILES: CCC(=O)N[C@@H](Cc1nc(C)c(-c2ccc(C#N)cc2)s1)C(=O)N[C@H](CN)Cc1ccccc1]

Example 105

$^1$H NMR (400 MHz, MeOD) δ 7.92-7.78 (m, 2H), 7.68-7.59 (m, 2H), 7.37-7.28 (m, 2H), 7.28-7.18 (m, 3H), 4.71 (dd, J=8.1, 5.1 Hz, 1H), 4.41-4.38 (m, 1H), 3.46 (dd, J=15.2, 5.1 Hz, 1H), 3.31-3.25 (m, 1H), 3.18 (dd, J=13.1, 3.7 Hz, 1H), 3.11-3.02 (m, 1H), 2.92-2.90 (m, 2H), 2.47 (s, 3H), 2.25 (q, J=7.5 Hz, 2H), 1.10 (t, J=7.6 Hz, 3H).

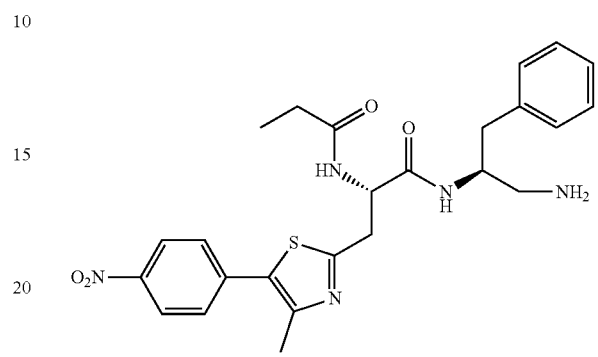

Example 106

$^1$H NMR (400 MHz, MeOD) δ 8.47-8.26 (m, 2H), 7.79-7.56 (m, 2H), 7.38-7.29 (m, 2H), 7.25 (dd, J=7.5, 4.2 Hz, 2H), 4.72 (dd, J=8.1, 5.1 Hz, 1H), 4.40 (d, J=6.9 Hz, 1H), 3.47 (dd, J=15.2, 5.1 Hz, 1H), 3.32-3.26 (m, 1H), 3.18 (dd, J=13.0, 3.6 Hz, 1H), 3.13-3.03 (m, 1H), 2.91 (dd, J=7.4, 3.8 Hz, 2H), 2.49 (s, 3H), 2.26 (q, J=7.6 Hz, 2H), 1.10 (t, J=7.6 Hz, 3H).

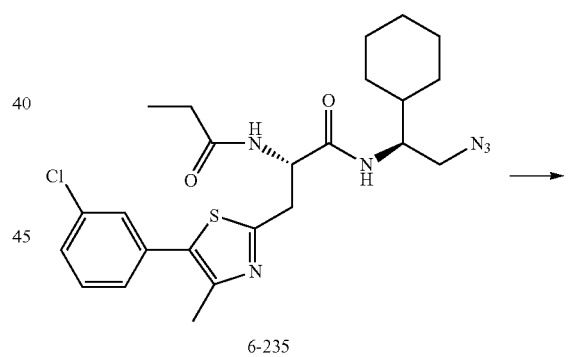

6-235

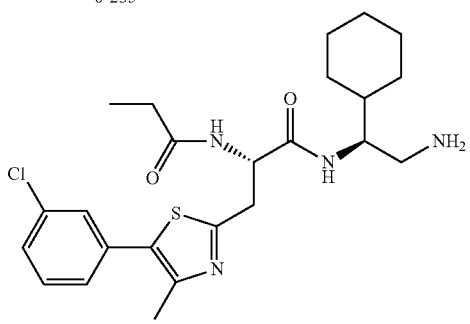

DI-738

6-235: $^1$H NMR (400 MHz, CDCl$_3$) δ 7.68 (d, J=9.0 Hz, 1H), 7.42-7.40 (m, 2H), 7.37-7.28 (m, 2H), 4.95 (dd, J=12.5, 6.6 Hz, 1H), 4.35 (br., 3H), 4.00-3.83 (m, 1H), 3.65 (dd,

J=15.3, 5.5 Hz, 1H), 3.57-3.26 (m, 3H), 2.54 (s, 3H), 2.33 (q, J=7.6 Hz, 2H), 1.78-1.67 (m, 5H), 1.59-1.44 (m, 1H), 1.42-0.78 (m, 8H).
Example 107
$^1$H NMR (400 MHz, MeOD) δ 7.52-7.33 (m, 4H), 4.82-4.81 (m, 1H), 3.75-3.68 (m, 1H), 3.61-3.58 (m, 2H), 3.51 (dd, J=15.0, 5.6 Hz, 1H), 3.38-3.36 (m, 1H), 2.45 (s, 3H), 2.29 (q, J=7.6 Hz, 2H), 1.81-1.55 (m, 6H), 1.31-0.98 (m, 8H).
$^{13}$C NMR (101 MHz, MeOD) δ 175.58, 170.92, 164.54, 147.55, 134.34, 133.56, 130.71, 130.08, 128.54, 127.77, 127.24, 61.30, 56.07, 53.03, 38.27, 34.52, 29.68, 28.64, 28.51, 26.04, 25.85, 14.43, 8.88.
16. Synthesis of Example 108.
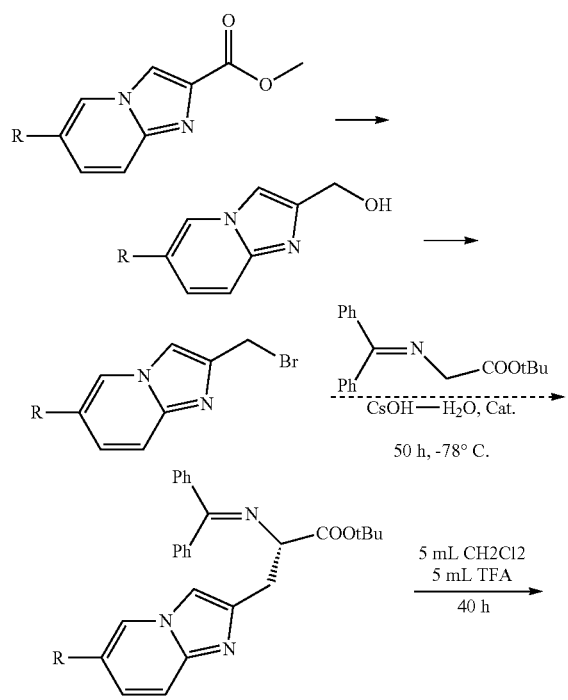
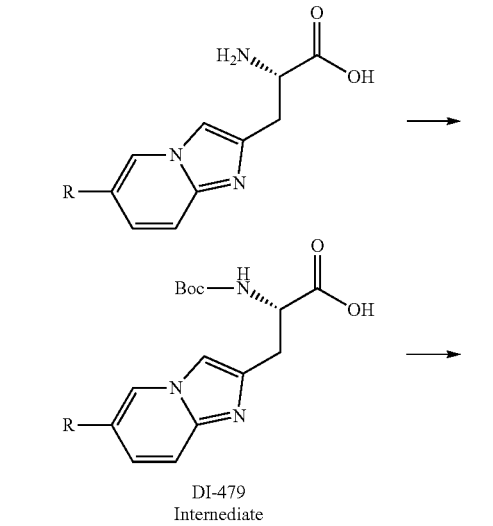
DI-479
Intermediate
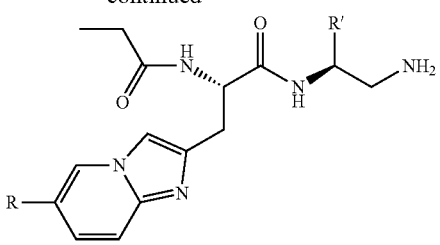
-continued
Example 108 and analogs were synthesized using the synthetic routes as shown above.
DI-589
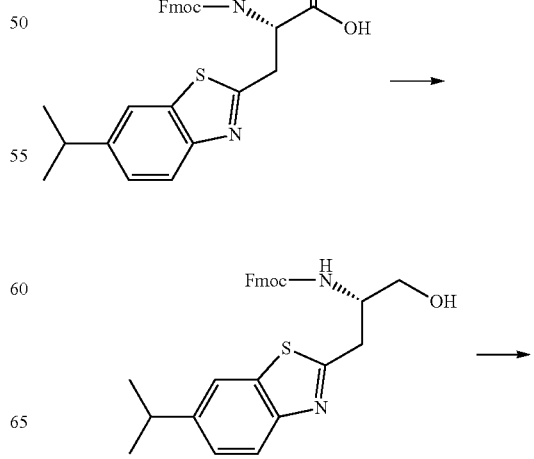
Example 108
$^1$H NMR (400 MHz, MeOD) δ 8.89 (d, J=0.8 Hz, 1H), 7.87-7.84 (m, 3H), 7.35-7.16 (m, 5H), 4.70 (dd, J=8.4, 5.4 Hz, 1H), 4.42-4.35 (m, 1H), 3.24-2.99 (m, 4H), 2.91 (d, J=7.5 Hz, 2H), 2.22 (q, J=7.6 Hz, 2H), 1.05 (td, J=7.5, 0.6 Hz, 3H). $^{13}$C NMR (101 MHz, MeOD) δ 176.06, 171.65, 139.36, 136.91, 136.30, 132.72, 128.84, 128.27, 126.54, 126.31, 124.21, 113.31, 112.91, 52.51, 49.47, 42.73, 37.41, 28.35, 27.52, 8.50.
17. Synthesis of Example 109-119.

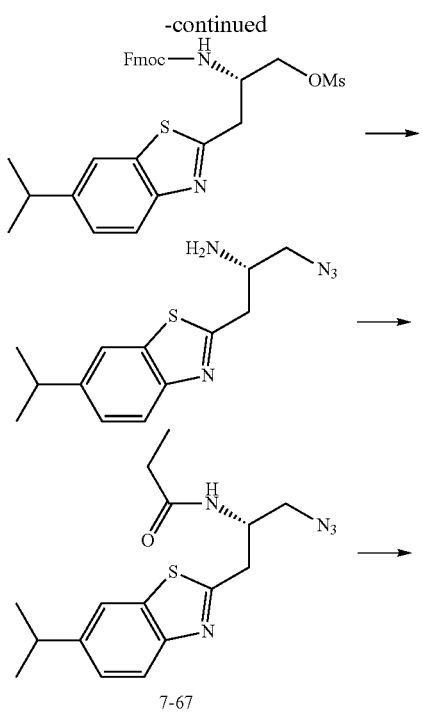

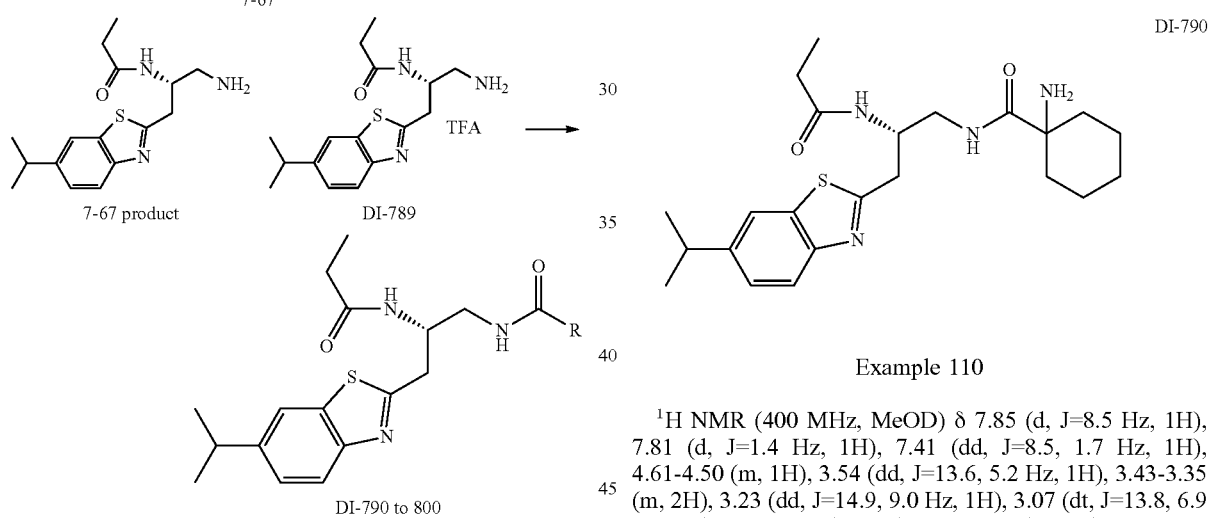

These compounds were synthesized shown in the above synthetic route.

7-67:

¹H NMR (400 MHz, CDCl₃) δ 7.86 (d, J=8.4 Hz, 1H), 7.67 (d, J=0.6 Hz, 1H), 7.39-7.21 (m, 1H), 6.93 (d, J=8.0 Hz, 1H), 4.56-4.48 (m, 1H), 3.54 (dd, J=12.3, 5.1 Hz, 1H), 3.44 (dd, J=12.3, 5.9 Hz, 1H), 3.33 (qd, J=15.2, 6.1 Hz, 2H), 3.01 (dt, J=13.8, 6.9 Hz, 1H), 2.22 (q, J=7.6 Hz, 2H), 1.28 (dd, J=6.9, 0.6 Hz, 6H), 1.12 (td, J=7.5, 0.5 Hz, 3H).

¹³C NMR (101 MHz, CDCl₃) δ 173.87, 165.96, 151.47, 146.41, 135.29, 125.37, 122.34, 118.72, 52.97, 48.64, 35.14, 34.20, 29.66, 24.18, 9.65.

7-67 Product:

¹H NMR (400 MHz, CDCl₃) δ 7.45 (d, J=8.3 Hz, 1H), 7.26 (s, 1H), 6.90 (d, J=8.1 Hz, 1H), 6.72 (d, J=7.8 Hz, 1H), 3.96-3.93 (m, 1H), 2.96-2.87 (m, 2H), 2.62-2.57 (m, 2H), 2.49-2.34 (m, 2H), 2.25-2.10 (m, 2H), 1.85-1.79 (m, 2H), 0.89 (d, J=6.7 Hz, 6H), 0.71 (t, J=7.4 Hz, 3H).

¹³C NMR (101 MHz, CDCl₃) δ 174.22, 166.99, 151.33, 146.16, 135.38, 125.20, 122.15, 118.66, 50.97, 44.26, 35.82, 34.14, 29.69, 24.16, 9.83.

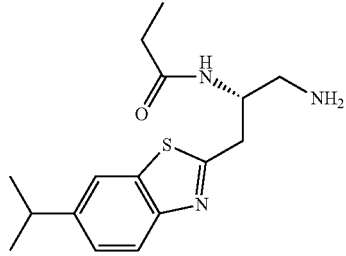

DI-789

Example 109

¹H NMR (400 MHz, MeOD) δ 7.87 (d, J=8.4 Hz, 1H), 7.82 (s, 1H), 7.42 (d, J=8.5 Hz, 1H), 7.42 (d, J=8.5 Hz, 1H), 4.70-4.54 (m, 1H), 3.47-3.36 (m, 2H), 3.14 (dd, J=12.9, 10.0 Hz, 1H), 3.07 (dt, J=13.8, 6.9 Hz, 1H), 2.25 (q, J=7.6 Hz, 2H), 1.32 (d, J=6.9 Hz, 6H), 1.06 (t, J=7.6 Hz, 3H).

DI-790

Example 110

¹H NMR (400 MHz, MeOD) δ 7.85 (d, J=8.5 Hz, 1H), 7.81 (d, J=1.4 Hz, 1H), 7.41 (dd, J=8.5, 1.7 Hz, 1H), 4.61-4.50 (m, 1H), 3.54 (dd, J=13.6, 5.2 Hz, 1H), 3.43-3.35 (m, 2H), 3.23 (dd, J=14.9, 9.0 Hz, 1H), 3.07 (dt, J=13.8, 6.9 Hz, 1H), 2.22-2.12 (m, 3H), 1.81-1.74 (m, 6H), 1.65-1.59 (m, 3H), 1.32 (d, J=6.9 Hz, 6H), 1.05 (t, J=7.6 Hz, 3H).

DI-792

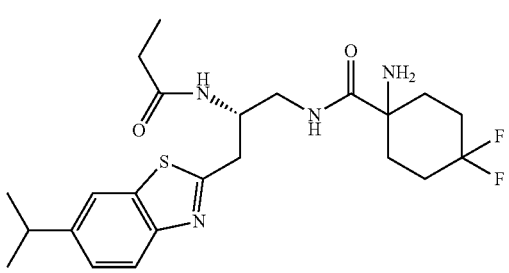

Example 111

¹H NMR (400 MHz, MeOD) δ 7.85 (d, J=8.5 Hz, 1H), 7.81 (d, J=1.7 Hz, 1H), 7.41 (dd, J=8.5, 1.7 Hz, 1H), 4.63-4.49 (m, 1H), 3.56 (dd, J=13.6, 4.9 Hz, 1H), 3.40-3.35 (m, 2H), 3.23 (dd, J=14.9, 9.1 Hz, 1H), 3.06 (dt, J=13.8, 6.9 Hz, 1H), 2.36-2.30 (m, 2H), 2.22-2.10 (m, 5H), 2.07-1.99 (m, 3H), 1.32 (d, J=6.9 Hz, 6H), 1.05 (t, J=7.6 Hz, 3H).

DI-793

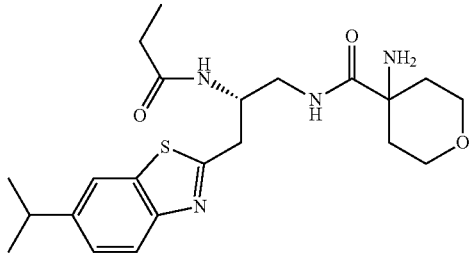

Example 112

$^1$H NMR (400 MHz, MeOD) δ 7.85 (d, J=8.5 Hz, 1H), 7.81 (d, J=1.6 Hz, 1H), 7.42 (dd, J=8.5, 1.7 Hz, 1H), 4.62-4.51 (m, 1H), 3.88-3.82 (m, 2H), 3.78-3.72 (m, 2H), 3.58 (dd, J=13.6, 5.0 Hz, 1H), 3.44-3.35 (m, 2H), 3.25 (dd, J=14.9, 9.1 Hz, 1H), 3.07 (dt, J=13.8, 6.9 Hz, 1H), 2.39-2.25 (m, 2H), 2.19 (q, J=7.6 Hz, 2H), 1.83-1.79 (m, 2H), 1.32 (d, J=6.9 Hz, 6H), 1.06 (t, J=7.6 Hz, 3H).

DI-794

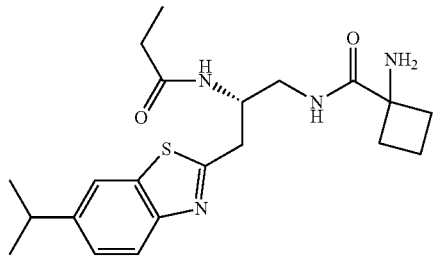

Example 113

$^1$H NMR (400 MHz, MeOD) δ 7.85 (d, J=8.5 Hz, 1H), 7.81 (d, J=1.5 Hz, 1H), 7.41 (dd, J=8.5, 1.7 Hz, 1H), 4.66-4.53 (m, 1H), 3.59 (dd, J=13.6, 5.0 Hz, 1H), 3.47-3.36 (m, 2H), 3.26 (dd, J=14.9, 9.1 Hz, 1H), 3.07 (dt, J=13.8, 6.9 Hz, 1H), 2.75-2.59 (m, 2H), 2.44-2.36 (m, 2H), 2.31-2.11 (m, 4H), 1.32 (d, J=6.9 Hz, 6H), 1.06 (t, J=7.6 Hz, 3H).

DI-795

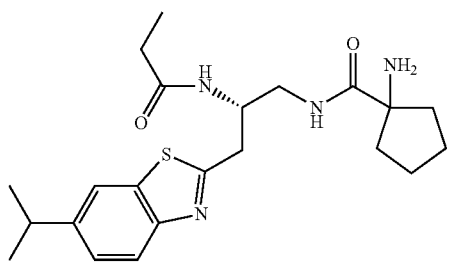

Example 114

$^1$H NMR (400 MHz, MeOD) δ 7.85 (d, J=8.5 Hz, 1H), 7.81 (d, J=1.2 Hz, 1H), 7.41 (dd, J=8.5, 1.7 Hz, 1H), 4.59-4.52 (m, 1H), 3.54 (dd, J=13.6, 5.0 Hz, 1H), 3.43-3.35 (m, 2H), 3.24 (dd, J=14.9, 9.1 Hz, 1H), 3.06 (dt, J=13.8, 6.9 Hz, 1H), 2.23-2.16 (m, 4H), 2.02-1.86 (m, 6H), 1.32 (d, J=6.9 Hz, 6H), 1.05 (t, J=7.6 Hz, 3H).

DI-796

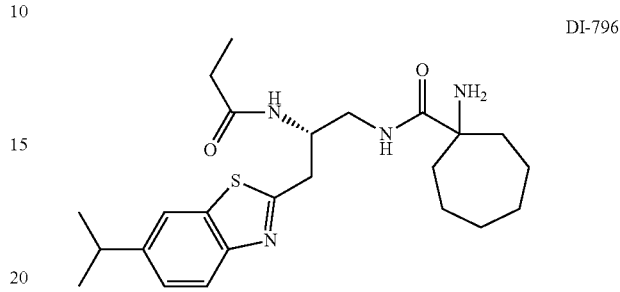

Example 115

$^1$H NMR (400 MHz, MeOD) δ 7.85 (d, J=8.5 Hz, 1H), 7.81 (d, J=0.7 Hz, 1H), 7.41 (dd, J=8.4, 1.5 Hz, 1H), 4.62-4.49 (m, 1H), 3.54 (dd, J=13.6, 5.0 Hz, 1H), 3.43-3.34 (m, 2H), 3.24 (dd, J=14.8, 9.0 Hz, 1H), 3.07 (dt, J=13.8, 6.9 Hz, 1H), 2.17 (ddd, J=20.6, 15.4, 7.9 Hz, 4H), 1.90-1.84 (m, 2H), 1.77-1.67 (m, 8H), 1.32 (d, J=6.9 Hz, 6H), 1.06 (t, J=7.6 Hz, 3H).

DI-797

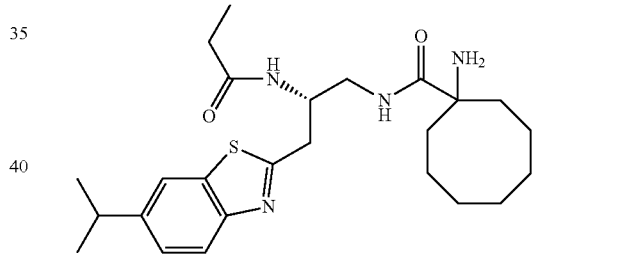

Example 116

$^1$H NMR (400 MHz, MeOD) δ 7.85 (d, J=8.5 Hz, 1H), 7.81 (d, J=1.6 Hz, 1H), 7.41 (dd, J=8.5, 1.7 Hz, 1H), 4.59-4.52 (m, 1H), 3.55 (dd, J=13.6, 5.1 Hz, 1H), 3.45-3.35 (m, 2H), 3.24 (dd, J=14.9, 8.9 Hz, 1H), 3.06 (dt, J=13.8, 6.9 Hz, 1H), 2.25-2.10 (m, 4H), 1.98-1.85 (m, 2H), 1.69-1.58 (m, 10H), 1.32 (d, J=6.9 Hz, 6H), 1.06 (t, J=7.6 Hz, 3H).

DI-798

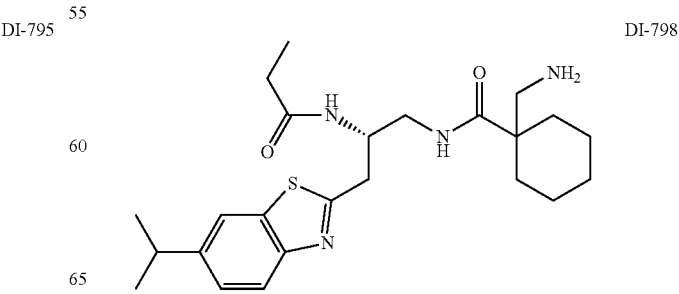

Example 117

¹H NMR (400 MHz, MeOD) δ 7.85 (d, J=8.5 Hz, 1H), 7.81 (s, 1H), 7.41 (d, J=8.5 Hz, 1H), 4.67-4.61 (m, 1H), 3.57 (dd, J=13.5, 4.3 Hz, 1H), 3.38 (dd, J=14.9, 5.0 Hz, 1H), 3.30-3.18 (m, 2H), 3.13-2.99 (m, 3H), 2.20 (q, J=7.6 Hz, 2H), 2.09-1.89 (m, 2H), 1.59-1.47 (m, 8H), 1.32 (d, J=6.9 Hz, 6H), 1.06 (t, J=7.6 Hz, 3H).

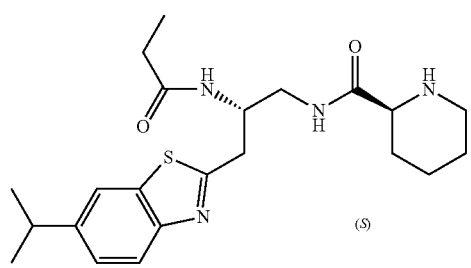

DI-799

Example 118

¹H NMR (400 MHz, MeOD) δ 7.85 (d, J=8.5 Hz, 1H), 7.81 (d, J=1.5 Hz, 1H), 7.41 (dd, J=8.5, 1.7 Hz, 1H), 4.54-4.47 (m, 1H), 3.80-3.72 (m, 1H), 3.56-3.48 (m, 1H), 3.46-3.35 (m, 3H), 3.23 (dd, J=14.9, 9.1 Hz, 1H), 3.10-2.99 (m, 2H), 2.22-2.16 (m, 3H), 1.98-1.84 (m, 2H), 1.77-1.58 (m, 3H), 1.32 (d, J=6.9 Hz, 6H), 1.05 (t, J=7.6 Hz, 3H).

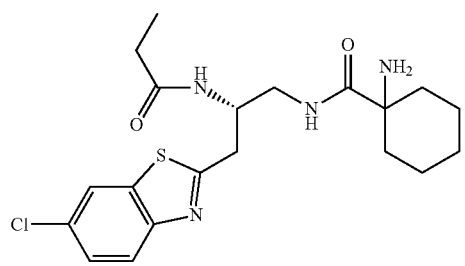 [SMILES: CCC(=O)N[C@H](CNC(=O)C1(N)CCCCC1)Cc1nc2ccc(Cl)cc2s1]

Example 119

¹H NMR (400 MHz, MeOD) δ 8.02 (d, J=1.7 Hz, 1H), 7.90 (d, J=8.7 Hz, 1H), 7.51 (dd, J=8.7, 2.0 Hz, 1H), 4.58-4.44 (m, 1H), 3.61 (d, J=8.4 Hz, 1H), 3.55 (dd, J=13.7, 5.0 Hz, 1H), 3.44-3.40 (m, 1H), 3.25 (dd, J=15.0, 9.0 Hz, 1H), 2.26-2.16 (m, 3H), 1.790-1.65 (m, 6H), 1.40-1.31 (m, 3H), 1.05 (t, J=7.6 Hz, 3H).

18. Synthesis of Examples 120 & 121.

Examples 120 & 121 were synthesized as shown in the following schemes.

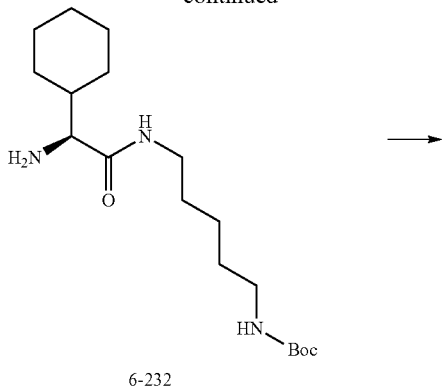

6-232

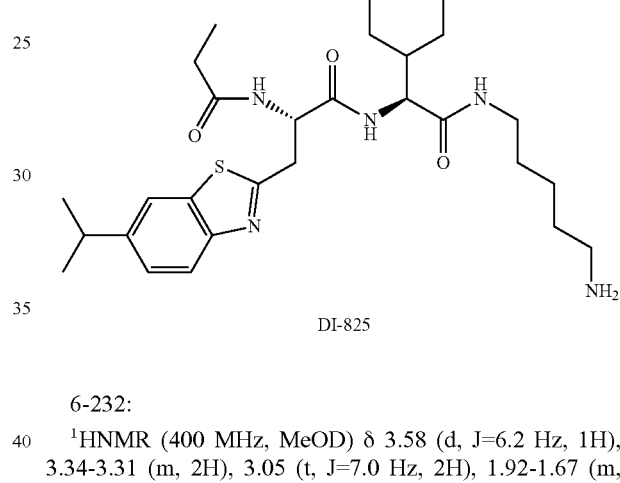

DI-825

6-232:

¹HNMR (400 MHz, MeOD) δ 3.58 (d, J=6.2 Hz, 1H), 3.34-3.31 (m, 2H), 3.05 (t, J=7.0 Hz, 2H), 1.92-1.67 (m, 6H), 1.65-0.99 (m, 20H).

Example 120

¹H NMR (400 MHz, MeOD) δ 7.86 (d, J=8.4 Hz, 1H), 7.82 (s, 1H), 7.42 (d, J=8.5 Hz, 1H), 4.97 (dd, J=7.6, 5.9 Hz, 1H), 4.11 (d, J=7.0 Hz, 1H), 3.62 (dd, J=15.1, 5.4 Hz, 1H), 3.47 (dd, J=15.7, 8.4 Hz, 1H), 3.18 (t, J=6.8 Hz, 2H), 3.07 (dt, J=13.8, 6.9 Hz, 1H), 2.91 (t, J=7.6 Hz, 2H), 2.37-2.21 (m, 2H), 1.79-1.47 (m, 10H), 1.40-0.96 (m, 15H).

¹³C NMR (101 MHz, MeOD) δ 175.80, 171.82, 171.11, 166.97, 146.65, 135.25, 125.15, 121.63, 118.56, 58.61, 52.78, 39.93, 39.21, 38.32, 34.76, 34.09, 29.40, 28.57, 28.28, 26.63, 25.68, 23.16, 23.11, 8.78.

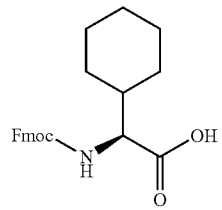

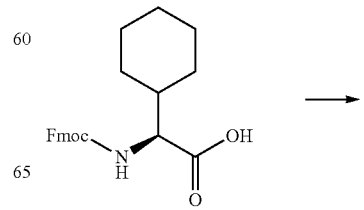

-continued

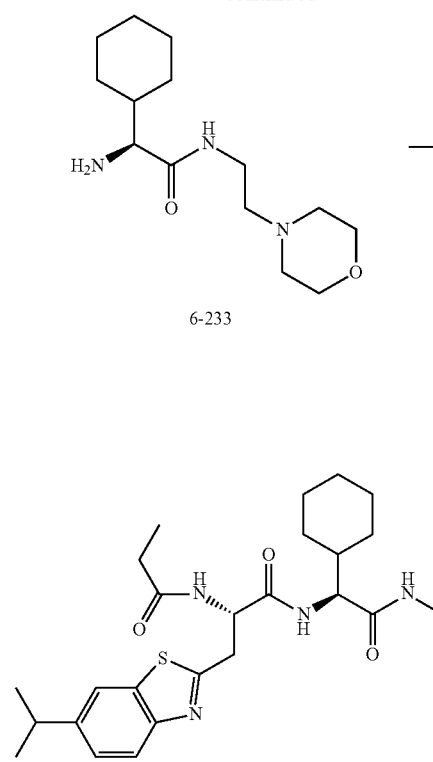

6-233

6-233:

¹H NMR (400 MHz, MeOD) δ 4.33-2.90 (m, 13H), 2.11-1.54 (m, 6H), 1.47-0.90 (m, 5H).

Example 121

¹H NMR (400 MHz, MeOD) δ 7.87 (d, J=8.5 Hz, 1H), 7.84 (d, J=1.0 Hz, 1H), 7.43 (dd, J=8.4, 1.6 Hz, 1H), 4.97-4.92 (m, 1H), 4.17-3.94 (m, 3H), 3.91-3.35 (m, 10H), 3.31-3.23 (m, 2H), 3.23-2.99 (m, 3H), 2.30 (q, J=7.6 Hz, 2H), 1.84-1.55 (m, 6H), 1.34-1.00 (m, 13H).

¹³C NMR (101 MHz, MeOD) δ 175.98, 173.34, 172.08, 166.94, 150.94, 146.76, 135.25, 125.26, 121.62, 118.64, 63.68, 59.51, 56.76, 52.92, 52.28, 39.30, 34.63, 34.09, 33.51, 29.23, 28.57, 28.52, 25.65, 25.61, 23.15, 8.76.

19. Synthesis of Examples 122-125.

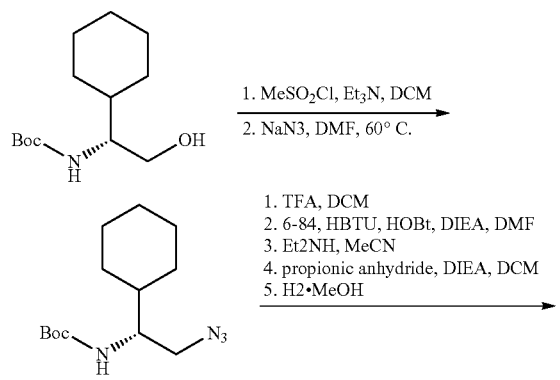

-continued

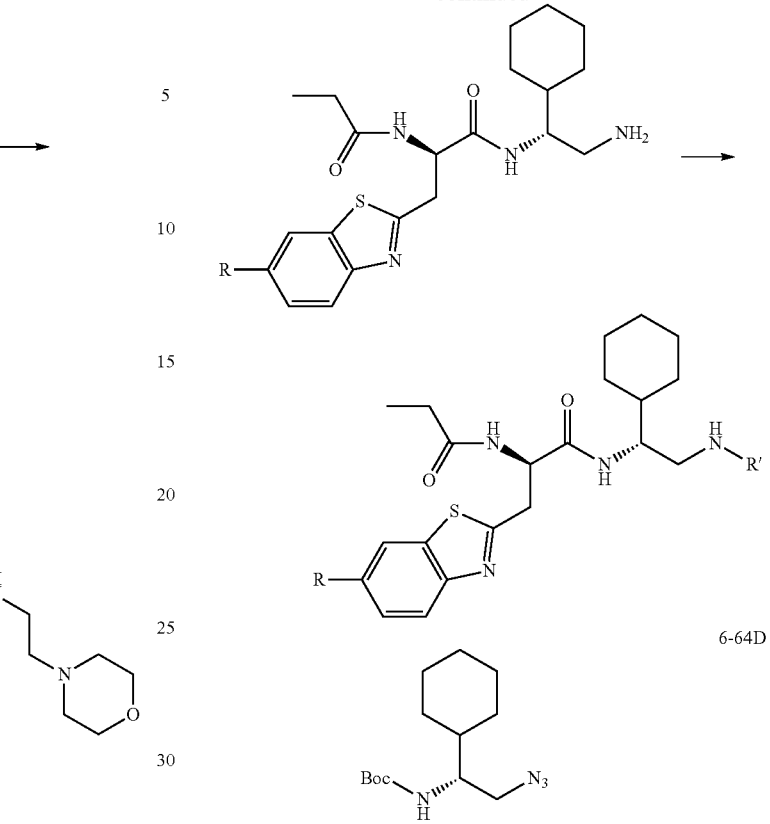

tert-butyl (R)-(2-azido-1-cyclohexylethyl)carbamate, 6-64D 6-64D was made by referring a reported method.³ MsCl (710 mg, 6.2 mmol, 1.5 equiv.) was added dropwise to a solution of N-Boc-D-cyclohexylglycinol (1.00 g, 4.1 mmol, 1 equiv.) and Et₃N (1.7 mL, 12.3 mmol, 3 equiv.) in CH₂Cl₂ (20 mL) at 0° C. The mixture was stirred 3 h at 0° C. and diluted with CH₂Cl₂. The mixture was washed with sat. aq NaHCO₃ (2×20 mL), 1M HCl, and brine. The organic layer was dried (Na₂SO4) and the solvent was removed in vacuo. The residue was dissolved in DMF and NaN₃ (802 mg, 12.3 mmol, 3 equiv.) was added. This reaction mixture was stirred at 60° C. for overnight and cooled to room temperature. EtOAc and H₂O were added to this mixture and the aqueous layer was extracted with EtOAc. The organic layer was washed with H₂O and brine. The organic layer was dried (Na₂SO₄) and the solvent was removed under vacuum. The crude product was purified by flash chromatography this gave 6-64D (617 mg, 56% over two steps). ¹H NMR (400 MHz, CDCl₃) δ 4.60 (d, J=8.6 Hz, 1H), 3.63-3.29 (m, 3H), 1.79-1.65 (m, 5H), 1.54-1.36 (m, 11H), 1.33-0.86 (m, 6H). 13C NMR (101 MHz, CDCl₃) δ 155.57, 79.48, 54.82, 52.72, 39.31, 29.77, 28.86, 28.36, 28.29, 26.16, 25.97, 25.96. UPLC-MS (ESI-MS) m/z: calculated for $C_{13}H_{25}N_4O_2^+$ 269.20, found [M+H]⁺.

DI-590DD

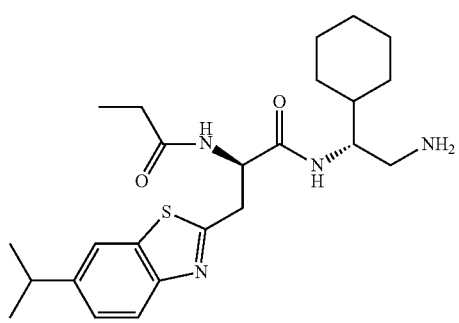

Example 122. (R)—N—((R)-2-amino-1-cyclohexylethyl)-3-(6-isopropylbenzo[d]thiazol-2-yl)-2-propionamidopropanamide Example 122 was prepared from 6-64D and 6-84 in 51% yield over 5 steps by a similar procedure as that for compound Example 56. $^1$H NMR (400 MHz, MeOD) δ 7.97 (d, J=9.0 Hz, 1H), 7.88-7.81 (m, 2H), 7.43 (dd, J=8.6, 1.5 Hz, 1H), 4.91 (m, 1H), 3.97-3.87 (m, 1H), 3.68 (dd, J=15.3, 5.9 Hz, 1H), 3.56 (dd, J=15.2, 6.9 Hz, 1H), 3.25 (dd, J=12.9, 3.0 Hz, 1H), 3.08 (dt, J=13.8, 6.9 Hz, 1H), 3.01-2.93 (m, 1H), 2.31 (q, J=7.6 Hz, 2H), 1.76-1.61 (m, 5H), 1.55-1.47 (m, 1H), 1.34-0.90 (m, 14H). $^{13}$C NMR (101 MHz, MeOD) δ 176.09, 171.87, 167.03, 150.95, 146.77, 135.15, 125.30, 121.31, 118.66, 52.97, 52.48, 41.77, 39.59, 34.49, 34.08, 29.40, 28.56, 28.24, 25.70, 25.49, 25.43, 23.14, 8.70. UPLC-MS (ESI-MS) m/z: calculated for $C_{24}H_{37}N_4O_2S^+$ 445.26, found 445.41 [M+H]$^+$.

Example 123

DI-591DD

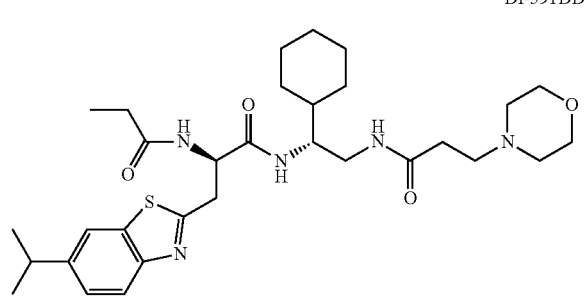

Example 123. (R)—N—((R)-1-cyclohexyl-2-(3-morpholinopropanamido)ethyl)-3-(6-isopropylbenzo[d]thiazol-2-yl)-2-propionamidopropanamide Example 123 was prepared from Example 122 in 83% yield by a similar procedure as that for compound Example 58. H NMR (400 MHz, MeOD) δ 7.87 (d, J=8.5 Hz, 1H), 7.84 (d, J=1.6 Hz, 1H), 7.43 (dd, J=8.5, 1.6 Hz, 1H), 4.87-4.82 (m, 1H), 4.08-4.05 (m, 2H), 3.87-3.76 (m, 3H), 3.64 (dd, J=15.4, 5.4 Hz, 1H), 3.56-3.37 (m, 6H), 3.20-3.03 (m, 4H), 2.69 (t, J=6.3 Hz, 2H), 2.34 (q, J=7.6 Hz, 2H), 1.72-1.60 (m, 5H), 1.38-0.87 (m, 16H). $^{13}$C NMR (101 MHz, MeOD) δ 176.01, 171.60, 170.52, 167.11, 151.01, 146.74, 135.17, 125.28, 121.57, 118.63, 63.61, 54.19, 53.25, 53.20, 51.89, 40.80, 39.67, 34.78, 34.09, 29.55, 28.72, 28.47, 28.38, 25.86, 25.65, 25.58, 23.15, 8.73. UPLC-MS (ESI-MS) m/z: calculated for $C_{31}H_{48}N_5O_4S^+$ 586.34, found 586.28 [M+H]$^+$.

DI-732DD

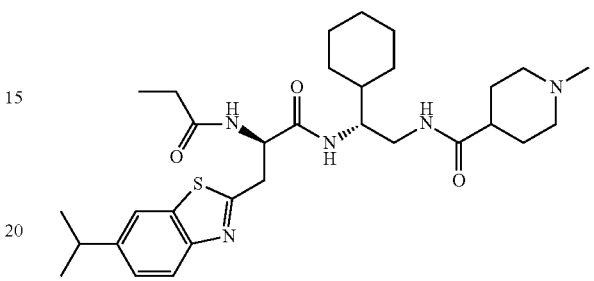

Example 124 was synthesized using a similar method as that for Example 123.

Example 124

$^1$H NMR (400 MHz, MeOD) δ 7.87 (d, J=8.5 Hz, 1H), 7.83 (d, J=1.5 Hz, 1H), 7.43 (dd, J=8.5, 1.7 Hz, 1H), 4.88 (dd, J=7.8, 5.4 Hz, 1H), 3.82-3.77 (m, 1H), 3.63 (dd, J=15.4, 5.4 Hz, 1H), 3.58-3.42 (m, 4H), 3.15-3.02 (m, 2H), 3.00-2.79 (m, 5H), 2.47-2.36 (m, 1H), 2.32 (q, J 7.6 Hz, 2H), 2.07-1.83 (m, 4H), 1.71-1.62 (m, 5H), 1.39-0.92 (m, 15H). $^{13}$C NMR (101 MHz, MeOD) δ 175.91, 174.22, 171.37, 167.17, 151.01, 146.72, 135.23, 125.25, 121.60, 118.64, 54.34, 53.47, 53.03, 42.51, 40.67, 39.79, 39.28, 34.96, 34.08, 29.53, 28.66, 28.33, 26.21, 26.11, 25.89, 25.71, 25.65, 23.17, 23.15, 8.69.

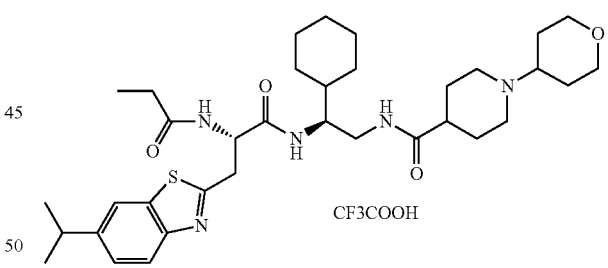

CF3COOH

Exact Mass: 753.3747
Molecular Weight: 753.9232

Example 125

$^1$H NMR (400 MHz, MeOD) δ 7.98 (s, 1H), 7.94 (d, J=8.1 Hz, 1H), 7.57 (d, J=8.7 Hz, 1H), 4.99-4.94 (s, 1H), 4.11-4.07 (m, 2H), 3.84-3.80 (m, 2H), 3.66-3.38 (m, 7H), 3.23-2.93 (m, 4H), 2.58-2.52 (m, 1H), 2.32 (q, J=7.5 Hz, 2H), 2.12-1.99 (m, 6H), 1.80-1.63 (m, 7H), 1.44-0.98 (m, 15H).

20. Synthesis of Fluorescein—Labeled or Biotin-Labeled DCN1 Inhibitors Examples 126 & 127.

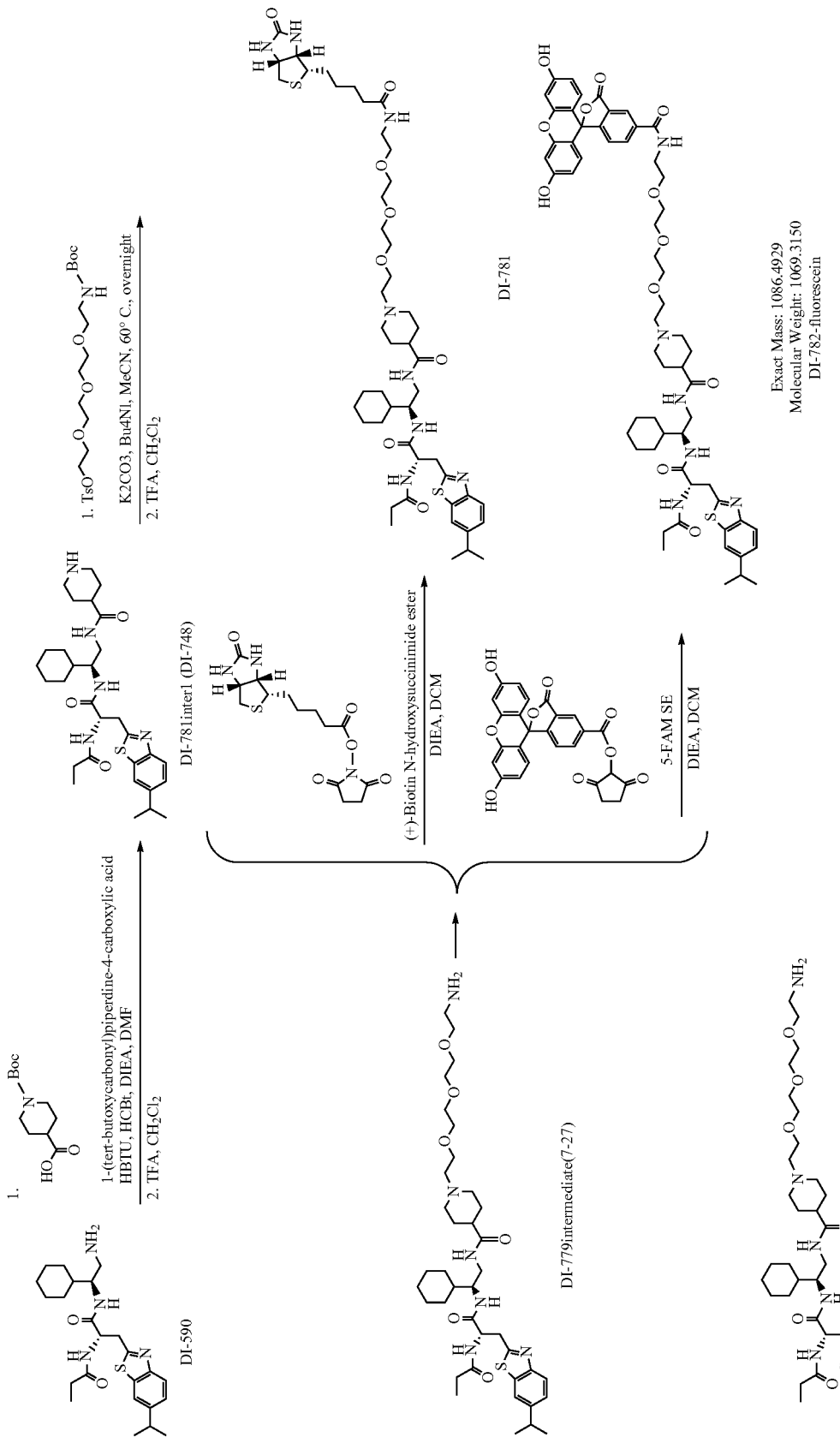

1-(2-(2-(2-(2-aminoethoxy)ethoxy)ethoxy)ethyl)-
N—((S)-2-cyclohexyl-2-((S)-3-(6-isopropylbenzo[d]
thiazol-2-yl)-2-propionamidopropanamido)ethyl)
piperidine-4-carboxamide, 7-27

A suspension of Example 62 (120 mg, 0.22 mmol, 1 equiv.), T-Boc-n-amido-peg4-tos (126 mg, 0.28 mmol, 1.3 equiv.), $K_2CO_3$ (89 mg, 0.65 mmol, 3 equiv.) and Tetrabutylammonium iodide (8.0 mg, 0.02 mmol, 0.1 equiv.) in DMF (10 mL) was stirred at 60° C. for overnight. The reaction was cooled and diluted with EtOAc and $H_2O$. The organic layer was washed with saturated sodium bicarbonate, 1.0 M HCl, brine and dried over sodium sulfate. After removal of the solvent under vacuum, the residue was treated with TFA (2 ml) in DCM (10 mL) and stirred for 5 h. This reaction mixture was concentrated and purified by HPLC to afford DI-78liner2 (7-27) (103 mg, 65%). DI-78liner 2 (7-27): $^1$H NMR (400 MHz, MeOD) δ 7.87 (d, J=8.4 Hz, 1H), 7.83 (s, 1H), 7.42 (dd, J=8.5, 1.4 Hz, 1H), 4.86 (dd, J=8.9, 3.5 Hz, 1H), 3.85-3.60 (m, 16H), 3.57-3.36 (m, 4H), 3.28-3.23 (m, 2H), 3.17-3.05 (m, 4H), 2.53-2.40 (m, 1H), 2.32 (q, J=7.6 Hz, 2H), 2.08-1.86 (m, 4H), 1.78-1.56 (m, 5H), 1.50-0.86 (m, 15H). UPLC-MS (ESI-MS) m/z: calculated for $C_{38}H_{63}N_6O_6S^+$ 366.23 found 366.36[M+H]$^{2+}$.

HRMS (ESI-MS) m/z: calculated for $C_{38}H_{63}N_6O_6S^+$ 731.4524, found 731.4515 [M+H]$^+$.

Example 126

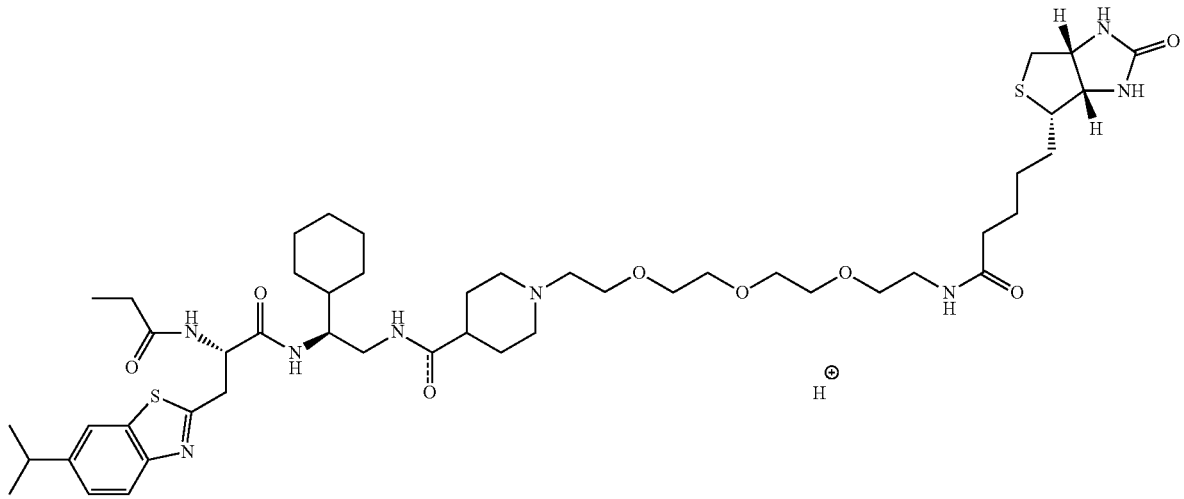

DI-781

N—((S)-2-cyclohexyl-2-((S)-3-(6-isopropylbenzo[d]
thiazol-2-yl)-2-propionamidopropanamido)ethyl)-1-
(13-oxo-17-((3aS,4S,6aR)-2-oxohexahydro-1H-
thieno [3,4-d] imidazol-4-yl)-3,6,9-trioxa-12-
azaheptadecyl)piperidine-4-carboxamide To a solution of 1-(2-(2-(2-(2-aminoethoxy)ethoxy)ethoxy)ethyl)-N—((S)-2-cyclohexyl-2-((S)-3-(6-isopropylbenzo[d]thiazol-2-yl)-2-propionamidopropanamido)ethyl)piperidine-4-carboxamide (30 mg, 0.04 mmol, 1 equiv.) and (+)-Biotin N-hydroxysuccinimide ester (21 mg, 0.06 mmol, 1.5 equiv.) in DCM (5 mL) was added DIEA (21 μL, 0.12 mmol, 3 equiv.). The reaction was stirred at room temperature overnight and concentrated. The residue was purified by HPLC to get Example 126 (25 mg, 64%). DI-781: $^1$H NMR (400 MHz, MeOD) δ 7.88 (d, J=8.4 Hz, 1H), 7.84 (s, 1H), 7.67 (d, J=9.5 Hz, 1H), 7.43 (d, J=8.4 Hz, 1H), 5.18-5.11 (m, 1H), 4.51 (dd, J=7.8, 5.0 Hz, 1H), 4.31 (dd, J=7.8, 4.5 Hz, 1H), 3.87-3.79 (m, 3H), 3.71-3.59 (m, 10H), 3.56-3.36 (m, 10H), 3.26-3.18 (m, 1H), 3.13-3.04 (m, 2H), 3.00-2.89 (m, 2H), 2.72 (d, J=12.8 Hz, 1H), 2.48-2.41 (m, 1H), 2.32 (q, J=7.6 Hz, 2H), 2.23 (t, J=7.3 Hz, 2H), 2.07-1.93 (m, 4H), 1.78-1.55 (m, 9H), 1.48-0.90 (m, 17H). HRMS (ESI-MS) m/z: calculated for $C_{48}H_{77}N_8O_8S_2^+$ 957.5300, found 957.5298 [M+H]$^+$.

Example 127

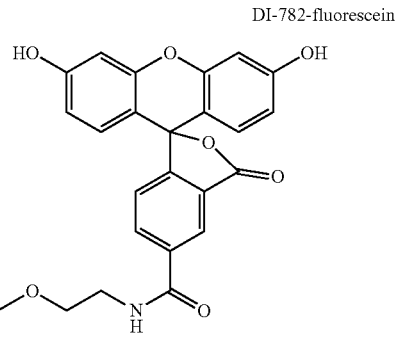
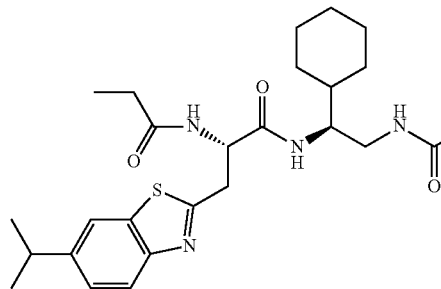

N—((S)-2-cyclohexyl-2-((S)-3-(6-isopropylbenzo[d] thiazol-2-yl)-2-propionamidopropanamido)ethyl)-1-(1-(3',6'-dihydroxy-3-oxo-3H-spiro [isobenzofuran-1,9'-xanthen]-5-yl)-1-oxo-5,8,11-trioxa-2-azatridecan-13-yl)piperidine-4-carboxamide, DI-782fluorescein To a solution of 1-(2-(2-(2-(2-aminoethoxy)ethoxy)ethoxy)ethyl)-N—((S)-2-cyclohexyl-2-((S)-3-(6-isopropyl-benzo[d]thiazol-2-yl)-2-propionamidopropanamido)ethyl) piperidine-4-carboxamide (30 mg, 0.04 mmol, 1 equiv.) and 5-Carboxyfluorescein N-hydroxysuccinimide ester (29 mg, 0.06 mmol, 1.5 equiv.) in DCM (5 mL) was added DIEA (21 µL, 0.12 mmol, 3 equiv.). The reaction was stirred at room temperature overnight and concentrated. The residue was purified by HPLC to get Example 127 (22 mg, 49%). $^1$H NMR (400 MHz, MeOD) δ 8.49 (s, 1H), 8.23 (dd, J=8.0, 1.4 Hz, 1H), 7.84 (d, J=8.4 Hz, 1H), 7.80 (s, 1H), 7.40 (dd, J=8.5, 1.4 Hz, 1H), 7.34 (d, J=8.0 Hz, 1H), 6.78 (d, J=2.2 Hz, 2H), 6.68 (d, J=8.7 Hz, 2H), 6.61 (dd, J=8.7, 2.1 Hz, 2H), 4.85-4.83 (m, 1H), 3.94-3.56 (m, 18H), 3.51-3.38 (m, 4H), 3.19-2.77 (m, 4H), 2.48-2.42 (m, 1H), 2.30 (q, J=7.6 Hz, 2H), 2.13-1.87 (m, 4H), 1.68-1.59 (m, 5H), 1.40-0.88 (m, 15H). HRMS (ESI-MS) m/z: calculated for $C_{59}H_{73}N_6O_{12}S^+$ 1089.5002, found 1089.4994 [M+H]$^+$.

To further demonstrate the activity of a DCN1 inhibitor of the present invention, compound Example 58 subjected to further tests and investigations.

A key function of cullin neddylation is to control E3 ubiquitin ligase activity of the cullin complex, which in turn regulates protein turnover in cells. DI-591 (Example 58) was evaluated for its effect on neddylation of 5 different cullins in the THLE2 liver cell line with the data shown in FIG. 1. Immortalized THLE2 liver cell line was treated by a dose-range of DCN1 inhibitor DI-591 or a dose-range of MLN4924 for 24 h. The protein levels of neddylated- and un-neddylated-cullin family proteins and several well-known substrates of cullins were examined by western blotting analysis. GAPDH was used as a loading control. Consistent with its pan-inhibitory activity on all cullins and data from a previous report (18), MLN4924 induces accumulation of cullin 3 substrate uclear factor erythroid 2-related factor 2 (NRF2) (32-34), as well as Cyclin E, BimEL, BIML, and BIMS, which are substrates of Cul-1, and CDT1 (35), which is a substrate of Cul-4A. In contrast, DI-591 (Example 58) selectively increased the abundance of NRF2 in a dose-dependent manner and has no or minimal effect on Cyclin E, BimEL, and CDT1 (FIG. 1). Significantly, negative control DI-591-DD (Example 123) had no effect on the substrates of cullins. Immunohistochemical data confirmed the increased NRF2 protein by Example 58 in liver cells.

Figure 2:
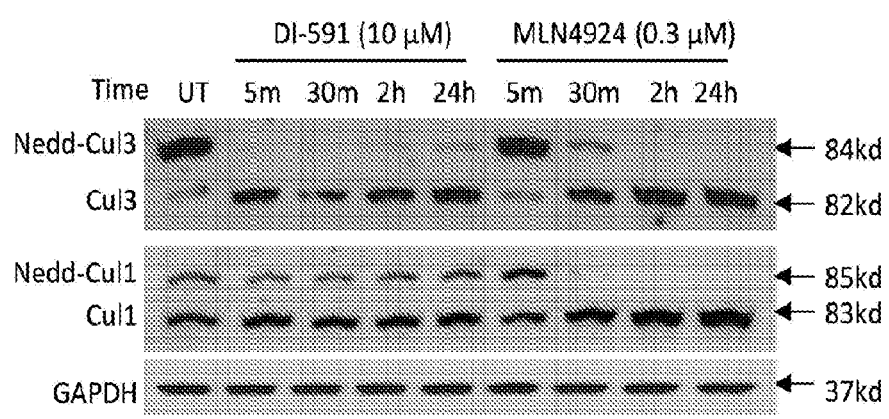
FIG. 2 shows that Example 58 (DI-591) rapidly inhibits the neddylation of cullin 3 and has little effect on the neddylation of cullin 1. THLE2 liver cell line was treated by Example 58 at 10 µM or MLN4924 at 0.3 µM for 5 minutes (5 m), 30 minutes (30 m), 2 hours (2 h) and 24 hours (24 h).

DI-591 (Example 58) was further compared to MLN4924 for their ability to inhibit neddylation of cullin 1 and cullin 3 in the THLE2 liver cell line with the data shown in FIG. 2. THLE2 liver cell line was treated by DI-591 at 10 µM or MLN4924 at 0.3 µM for 5 minutes (5m), 30 minutes (30 m), 2 hours (2h) and 24 hours (24h). The data showed that DI-591 rapidly inhibits the neddylation of cullin 3 and has little effect on the neddylation of cullin 1. In comparison, MLN4924 inhibits the neddylation of both cullin 1 and 3.

Figure 3:
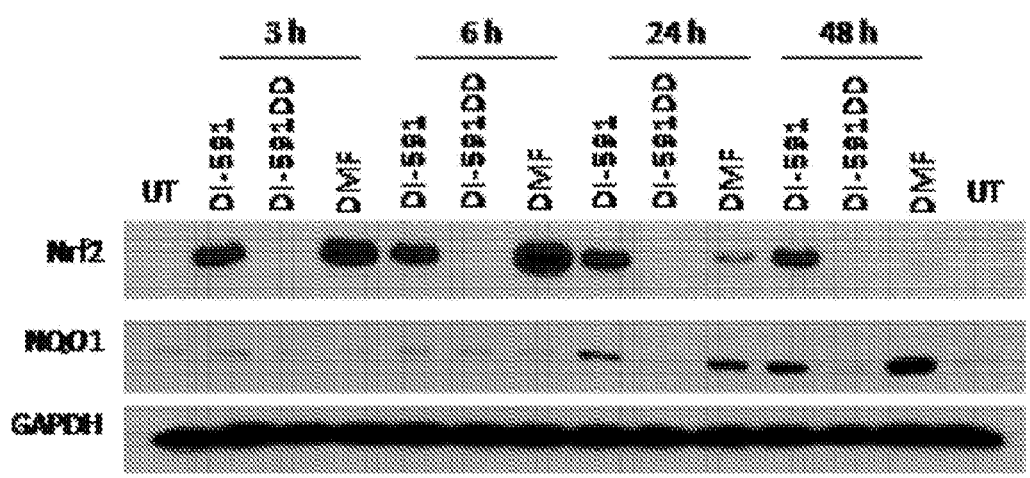
FIG. 3 provides western blot analyses, which showed the effect of Example 58 (DI-591) on NRF2 and NQ01 with dimethyl fumarate, a known NRF2 inhibitor, as a positive control and Example 123 as an inactive control. GAPDH was used as a loading control. DI-591 and Dimethyl fumarate (DMF), but not DI-591DD, stimulates the accumulation of NRF2 and NQ01 in liver cells. THLE2 liver cell line was treated by DI-591 at 10 µM, DI-591DD at 10 µM or DMF at 10 µM for different time points.
Figure 4:
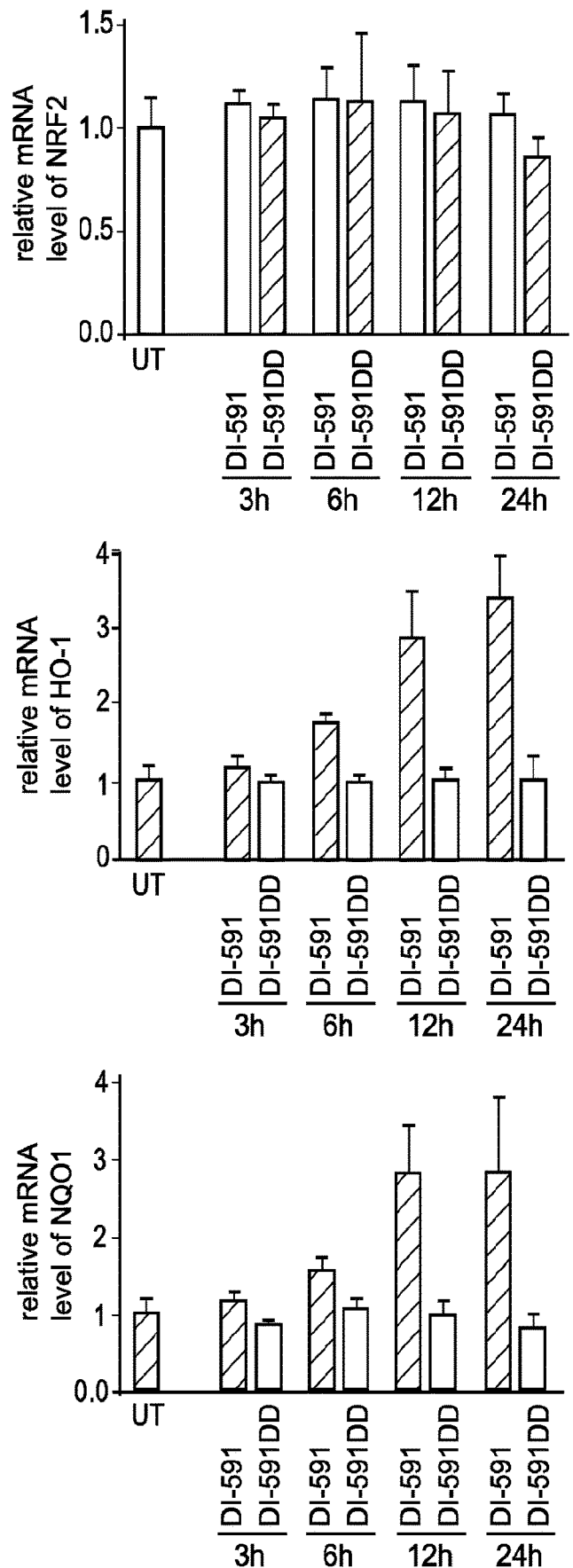
FIG. 4 provides qRT-PCR analysis of mRNA levels of NRF2 and NRF2-regulated genes in the THLE2 liver cell line. The data showed that Example 58 (DI-591) has no effect on mRNA level of NRF2 and upregulates of NRF2-regulated genes. THLE2 liver cell line was treated by DI-591 at 10 µM, DI-591DD at 10 µM or DMSO for different time points. The relative mRNA levels of NRF2, NQ01 and HO-1 were examined by quantitative real-time RT-PCR assay.

NRF2 is a transcriptional factor and a master regulator of antioxidant responses, regulating numerous detoxifying and antioxidant genes, such as the phase II detoxification enzymes heme oxygenase (HO1) and NAD(P)H:quinone oxidoreductase-1 (NQ01) (36). DI-591 (Example 58) was compared to dimethyl fumarate (DMF) for their effect on NRF2 and NQ01 protein levels in the THLE2 liver cell line with DI-591DD included as a control with the data shown in FIG. 3. THLE2 liver cell line was treated by DI-591 at 10 µM, DI-591DD at 10 µM or DMF at 10 µM for different time points. The data showed that DI-591 and dimethyl fumarate, but not DI-591DD, stimulate the accumulation of NRF2 and NQ01 in liver cells.

qRT-PCR analysis showed that DI-591 (Example 58) and Example 123 have no effect on the mRNA level of NRF2 (FIG. 4), suggesting that the increase of NRF2 protein by Example 58 (DI-591) is not due to the adaptive response of cells to oxidative stress (37). Example 58, but not Example 123, clearly increases the mRNA levels of NQ01 and HO1 (FIG. 4).

EXPERIMENTAL PROCEDURES

Competitive FP Binding Assay

The Fluorescence Polarization (FP) competitive binding assays were performed to accurately determine the binding affinities of our DCN1 inhibitors. A novel FAM labeled fluorescent probe compound (46) was designed and synthesized based on one of our potent small molecule DCN1 inhibitors. Equilibrium dissociation constants ($K_d$) values of 46 to both DCN1 and DCN2 proteins were determined from protein saturation experiments by monitoring the total FP values of mixtures composed with the fluorescent probe at a fixed concentration and proteins with increasing concentrations up to full saturation. Serial dilutions of proteins were mixed with 46 to a final volume of 200 µl in the assay buffer (100 mM phosphate buffer, pH=6.5, with 0.02% Tween-20 and 2% DMSO). Final probe concentration was 5 nM for both assays. Plates were incubated at room temperature for 30 minutes with gentle shaking to assure equilibrium. FP values in millipolarization units (mP) were measured using the Infinite M-1000 plate reader (Tecan U.S., Research Triangle Park, NC) in Microfluor 1 96-well, black, round-bottom plates (Thermo Scientific, Waltham, MA) at an excitation wavelength of 485 nm and an emission wavelength of 530 nm. $K_d$ values of 46 were calculated by fitting the sigmoidal dose-dependent FP increases as a function of protein concentrations using Graphpad Prism 6.0 software (Graphpad Software, San Diego, CA).

Cloning and Purification of DCN Proteins

Human DCN1 (residues 58-259) were cloned into a pDEST17 plasmid containing an N-terminal $His_6$ tag. DCN2 (residues 62-259), DCN3 (residues 86-304), DCN4 (residues 102-292) and DCN5 (residues 47-237) were cloned into an N-terminal $His_6$-TEV expression vector. Pure proteins were derived from the same expression and purification protocols. Plasmids were transformed into Rosetta2 cells, the cells were grown in Terrific Broth at 37° C. to an $O.D._{600}$>1.0 and induced with 0.4 mM Isopropyl (3-D-1-thiogalactopyranoside overnight at 20° C. The pelleted cells were resuspended in lysis buffer containing 25 mM Tris-HCl, pH 7.5, 200 mM NaCl and protease inhibitors, sonicated and centrifuged at 34,000×g for 45 minutes to remove debris. Cleared lysate was incubated with Ni-NTA resin (Qiagen) prewashed with lysis buffer, for 1 hr at 4° C. The matrix was loaded into a column then washed with 25 mM Tris-HCl, pH 7.5, 200 mM NaCl and 10 mM imidazole. Protein was eluted with 25 mM Tris-HCl, pH 7.5, 200 mM NaCl and 300 mM imidazole, concentrated and applied to a Superdex 75 (GE Healthcare) column pre-equilibrated with 25 mM Tris pH 7.5, 200 mM NaCl and 1 mM DTT. For DCN2-5, the N-terminal $His_6$ tag was removed prior to gel filtration. Tag removal was achieved through incubation with TEV protease during overnight dialysis against 25 mM Tris pH 7.5, 200 mM NaCl and 1 mM DTT and a second Ni-NTA column. DCN2-5 proteins were stored at −80° C. in 1 mg/mL fractions containing 5% glycerol. The uncleaved DCN1 protein was stored at −80° C. without glycerol.

Cell Lines and Culture Conditions.

Immortalized liver THLE2 (ATCC® CRL-2706™) cell lines was purchased from the ATCC (Rockville, MD). The cell line was maintained in BEGM Bronchial Epithelial Cell Growth Medium from Lonza/Clonetics Corporation (CC3170, Walkersville, MD) supplemented with 10% FBS and pen-strep at 37° C. in a humidified incubator with 5% $CO_2$. Esophageal cancer KYSE140 cell line (ACC 348) was purchased from DSMZ (Braunschweig, Germany). The cell line was maintained RPMI1640 supplemented with 10% FBS and pen-strep at 37° C. in a humidified incubator with 5% $CO_2$.

Western Blotting Analysis and Antibodies

Treated cells were lysed by RIPA buffer supplemented with protease inhibitor. The expression level of indicated proteins was examined by western blotting analysis. GAPDH was used as a loading control. Antibodies were purchased: Cullin 1 (sc-11384), Cullin2 (sc-10781), Cullin5 (sc-13014) and Cullin7 (sc-134565) from Santa Cruz Biotech. (Santa Cruz, CA); Cullin 4A (PA5-14542), Cullin 4B (PA5-35239), Cullin9 (PA5-20277), DCN2 (DCUN1D2, PA5-31607) and DCN3 (DCUN1D3, PA5-44000) from ThermoFisher Scientific (Wayne, MI); Cullin 3 (2759), NRF2 (12721), HO-1 (70081), NQO1 (3187), Cyclin E (4129), Bim (2819), Keap1 (8047) and UBC12 (4913) from Cell Signaling Technology (Boston, MA); DCN1 (GWB-E3D700) from GenWay Biotech (San Diego, CA). Results are representative of three independent experiments.

REFERENCES

1. Ciechanover, A. & Schwartz, A. L. The ubiquitin-proteasome pathway: the complexity and myriad functions of proteins death. *Proc Natl Acad Sci USA* 95, 2727-2730 (1998).
2. Hershko, A. The ubiquitin system for protein degradation and some of its roles in the control of the cell division cycle. *Cell Death and Differentiation* 12, 1191-1197, doi:10.1038/sj.cdd.4401702 (2005).
3. Bedford, L., Lowe, J., Dick, L. R., Mayer, R. J. & Brownell, J. E. Ubiquitin-like protein conjugation and the ubiquitin-proteasome system as drug targets. *Nat. Rev. Drug Discov.* 10, 29-46, doi:10.1038/nrd3321 (2011).
4. Nalepa, G., Rolfe, M. & Harper, J. W. Drug discovery in the ubiquitin-proteasome system. *Nat. Rev. Drug Discov.* 5, 596-613, doi:10.1038/nrd2056 (2006).
5. Kane, R. C., Bross, P. F., Farrell, A. T. & Pazdur, R. Velcade®: USFDA approval for the treatment of multiple myeloma progressing on prior therapy. *Oncologist* 8, 508-513, doi:DOI 10.1634/theoncologist.8-6-508 (2003).
6. Kane, R. C. et al. Bortezomib for the treatment of mantle cell lymphoma. *Clinical Cancer Research* 13, 5291-5294, doi:10.1158/1078-0432.CCR-07-0871 (2007).
7. McCormack, P. L. Carfilzomib: in relapsed, or relapsed and refractory, multiple myeloma. *Drugs* 72, 2023-2032, doi:10.2165/11209010-000000000-00000 (2012).
8. Petroski, M. D. & Deshaies, R. J. Function and regulation of cullin-RING ubiquitin ligases. *Nat Rev Mol Cell Biol* 6, 9-20, doi:10.1038/nrm 1547 (2005).
9. Gong, L. M. & Yeh, E. T. H. Identification of the activating and conjugating enzymes of the NEDD8 conjugation pathway. *J. Biol. Chem.* 274, 12036-12042, doi:DOI 10.1074/jbc.274.17.12036 (1999).
10. Deshaies, R. J., Emberley, E. D. & Saha, A. Control of Cullin-Ring Ubiquitin Ligase Activity by Nedd8. *Conjugation and Deconjugation of Ubiquitin Family Modifiers* 54, 41-56, doi:Book_Doi 10.1007/978-1-4419-6676-6 (2010).
11. Bulatov, E. & Ciulli, A. Targeting Cullin-RING E3 ubiquitin ligases for drug discovery: structure, assembly and small-molecule modulation. *Biochem J* 467, 365-386, doi:10.1042/BJ20141450 (2015).
12. Duda, D. M. et al. Structural insights into NEDD8 activation of Cullin-RING ligases: Conformational control of conjugation. *Cell* 134, 995-1006, doi:10.1016/j.cell.2008.07.022 (2008).

13 Scott, D. C. et al. A Dual E3 Mechanism for Rub 1 Ligation to Cdc53. *Molecular Cell* 39, 784-796, doi:10.1016/j.molcel.2010.08.030 (2010).

14 Soucy, T. A., Dick, L. R., Smith, P G., Milhollen, M. A. & Brownell, J. E. The NEDD8 Conjugation Pathway and Its Relevance in Cancer Biology and Therapy. *Genes Cancer* 1, 708-716, doi:10.1177/1947601910382898 (2010).

15 Watson, I. R., Irwin, M. S. & Ohh, M. NEDD8 Pathways in Cancer, Sine Quibus Non. *Cancer Cell* 19, 168-176, doi:10.1016/j.ccr.2011.01.002 (2011).

16 Zhao, Y C. & Sun, Y. Cullin-RING Ligases as Attractive Anti-cancer Targets. *Curr Pharm Design* 19, 3215-3225 (2013).

17 Zhao, Y C., Morgan, M. A. & Sun, Y Targeting Neddylation Pathways to Inactivate Cullin-RING Ligases for Anticancer Therapy. *Antioxid Redox Sign* 21, 2383-2400, doi:10.1089/ars.2013.5795 (2014).

18 Soucy, T. A. et al. An inhibitor of NEDD8-activating enzyme as a new approach to treat cancer. *Nature* 458, 732-U767, doi:10.1038/nature07884 (2009).

19 Brownell, J. E. et al. Substrate-Assisted Inhibition of Ubiquitin-like Protein-Activating Enzymes: The NEDD8 E1 Inhibitor MLN4924 Forms a NEDD8-AMP Mimetic In Situ. *Molecular Cell* 37, 102-111, doi:10. 1016/j.molcel.2009.12.024 (2010).

20 Soucy, T. A., Smith, P. G. & Rolfe, M. Targeting NEDD8-Activated Cullin-RING Ligases for the Treatment of Cancer. *Clinical Cancer Research* 15, 3912-3916, doi:10.1158/1078-0432.CCR-09-0343 (2009).

21 Huang, D. T. et al. A unique E1-E2 interaction required for optimal conjugation of the ubiquitin-like protein NEDD8. *Nature Structural & Molecular Biology* 11, 927-935, doi:10.1038/nsmb826 (2004).

22 Scott, D. C., Monda, J. K., Bennett, E. J., Harper, J. W. & Schulman, B. A. N-Terminal Acetylation Acts as an Avidity Enhancer Within an Interconnected Multiprotein Complex. *Science* 334, 674-678, doi:10.1126/science. 1209307 (2011).

23 Scott, D. C. et al. Structure of a RING E3 Trapped in Action Reveals Ligation Mechanism for the Ubiquitin-like Protein NEDD8. *Cell* 157, 1671-1684, doi:10.1016/j.cell.2014.04.037 (2014).

24 Yang, C. Y. & Wang, S. M. Computational Analysis of Protein Hotspots. *ACS Med. Chem. Lett.* 1, 125-129, doi:10.1021/ml100026a (2010).

25 Yang, C. Y. & Wang, S. M. Hydrophobic Binding Hot Spots of Bcl-xL Protein-Protein Interfaces by Cosolvent Molecular Dynamics Simulation. *ACS Med. Chem. Lett.* 2, 280-284, doi:10.1021/ml100276b (2011).

26 Yang, C. Y. & Wang, S. M. Analysis of Flexibility and Hotspots in Bcl-xL and Mcl-1 Proteins for the Design of Selective Small-Molecule Inhibitors. *ACS Med. Chem. Lett.* 3, 308-312, doi:10.1021/ml200301w (2012).

27 Monda, J. K. et al. Structural Conservation of Distinctive N-terminal Acetylation-Dependent Interactions across a Family of Mammalian NEDD8 Ligation Enzymes. *Structure* 21, 42-53, doi:10.1016/j.str.2012.10.013 (2013).

28 Keuss, M. J. et al. Characterization of the mammalian family of DCN-type NEDD8 E3 ligases. *J Cell Sci* 129, 1441-1454, doi:10.1242/jcs.181784 (2016).

29 Molina, D. M. et al. Monitoring Drug Target Engagement in Cells and Tissues Using the Cellular Thermal Shift Assay. *Science* 341, 84-87, doi:10.1126/science. 1233606 (2013).

30 Kim, A. Y et al. SCCRO (DCUN1D1) Is an Essential Component of the E3 Complex for Neddylation. *J. Biol. Chem.* 283, 33211-33220, doi:10.1074/jbc.M804440200 (2008).

31 Kurz, T. et al. Dcnl functions as a scaffold-type E3 ligase for cullin neddylation. *Molecular Cell* 29, 23-35, doi:10.1016/j.molcel.2007.12.012 (2008).

32 Kobayashi, A. et al. Oxidative stress sensor Keapl functions as an adaptor for Cul3-based E3 ligase to regulate for proteasomal degradation of Nrf2. *Molecular and Cellular Biology* 24, 7130-7139, doi:10.1128/Mcb.24.16.7130-7139.2004 (2004).

33 Cullinan, S. B., Gordan, J. D., Jin, J. O., Harper, J. W. & Diehl, J. A. The Keapl-BTB protein is an adaptor that bridges Nrf2 to a Cul3-based E3 ligase: Oxidative stress sensing by a Cul3-Keap1 ligase. *Molecular and Cellular Biology* 24, 8477-8486, doi:10.1128/Mcb.24.19.8477-8486.2004 (2004).

34 Venugopal, R. & Jaiswal, A. K. Nrf2 and Nrfl in association with Jun proteins regulate antioxidant response element-mediated expression and coordinated induction of genes encoding detoxifying enzymes. *Oncogene* 17, 3145-3156, doi:DOI 10.1038/sj.onc. 1202237 (1998).

35 Nishitani, H. et al. Two E3 ubiquitin ligases, SCF-Skp2 and DDB1-Cul4, target human Cdtl for proteolysis. *EMBO J* 25, 1126-1136, doi:10.1038/sj.emboj.7601002 (2006).

36 Gorrini, C., Harris, I. S. & Mak, T. W. Modulation of oxidative stress as an anticancer strategy. *Nat. Rev. Drug Discov.* 12, 931-947, doi:10.1038/nrd4002 (2013).

37 Ma, Q. Role of Nrf2 in Oxidative Stress and Toxicity. *Annu Rev Pharmacol* 53, 401-+, doi:10.1146/annurev-pharmtox-011112-140320 (2013).

38 Bomprezzi, R. Dimethyl fumarate in the treatment of relapsing-remitting multiple sclerosis: an overview. *Ther Adv Neurol Diso* 8, 20-30, doi:10.1177/1756285614564152 (2015).

39 Liby, K. T. & Sporn, M. B. Synthetic Oleanane Triterpenoids: Multifunctional Drugs with a Broad Range of Applications for Prevention and Treatment of Chronic Disease. *Pharmacol Rev* 64, 972-1003, doi:10.1124/pr.111.004846 (2012).

40 de Zeeuw, D. et al. Bardoxolone Methyl in Type 2 Diabetes and Stage 4 Chronic Kidney Disease. *New Engl J Med* 369, 2492-2503, doi:10.1056/Nejmoal306033 (2013).

41 Buendia, I. et al. Nrf2-ARE pathway: An emerging target against oxidative stress and neuroinflammation in neurodegenerative diseases. *Pharmacol Therapeut* 157, 84-104, doi:10.1016/j.pharmthera.2015.11.003 (2016).

42 Genschik, P., Sumara, I. & Lechner, E. The emerging family of CULLIN 3-RING ubiquitin ligases (CRL3s): cellular functions and disease implications. *EMBO J.* 32, 2307-2320, doi:10.1038/emboj.2013.173 (2013).

43 Anderica-Romero, A. C., Gonzalez-Herrera, I. G., Santamaria, A. & Pedraza-Chaverri, J. Cullin 3 as a novel target in diverse pathologies. *Redox Biology* 1, 366-372, doi:10.1016/j.redox.2013.07.003 (2013).

44 Canning, P. & Bullock, A. N. New strategies to inhibit KEAP1 and the Cul3-based E3 ubiquitin ligases. *Biochem Soc Trans* 42, 103-107, doi:10.1042/BST20130215 (2014).

45 Hayes, J. D. & Dinkova-Kostova, A. T. The Nrf2 regulatory network provides an interface between redox and intermediary metabolism. *Trends Biochem. Sci* 39, 199-218 (2014).

46 Suzuki, T., Motohashi, H. & Yamamoto, M. Toward clinical application of the Keap1-Nrf2 pathway. *Trends in Pharmacological Sciences* 34, 340-346, doi:10.1016/j.tips.2013.04.005 (2013).

47 Sporn, M. B. & Liby, K. T. NRF2 and cancer: the good, the bad and the importance of context. *Nat. Rev. Cancer* 12, 564-571, doi:10.1038/nrc3278 (2012).

48 Wang, J. M., Cieplak, P. & Kollman, P. A. How well does a restrained electrostatic potential (RESP) model perform in calculating conformational energies of organic and biological molecules? *J. Comput. Chem.* 21, 1049-1074, doi:Doi 10.1002/1096-987x(200009)21:12<1049::Aid-Jcc3>3.0.Co;2-F (2000).

49 Otwinowski, Z. & Minor, W. Processing of X-ray diffraction data collected in oscillation mode. *Method Enzymol* 276, 307-326, doi:Doi 10.1016/S0076-6879(97)76066-X (1997).

50 Vagin, A. & Teplyakov, A. Molecular replacement with MOLREP. *Acta Crystallogr D* 66, 22-25, doi:10.1107/S0907444909042589 (2010).

51 Emsley, P & Cowtan, K. Coot: model-building tools for molecular graphics. *Acta Crystallogr D* 60, 2126-2132, doi:10.1107/S0907444904019158 (2004).

52 Bricogne, G., Blanc, E., Brandl, M., Flensburg, C., Keller, P., Paciorek, W., Roversi, P., Sharff, A., Smart, O., Vonrhein, C. & Womack, T. (2011). BUSTER v.2.11.2. http://www.globalphasing.com.

53 Wu, K. et al. Suramin inhibits cullin-RING E3 ubiquitin ligases. *P Natl Acad Sci USA* 113, E2011-E2018, doi:10.1073/pnas.1601089113 (2016).

What is claimed:

1. A compound having a structural formula

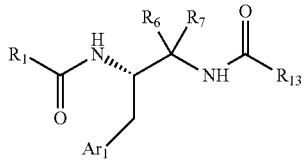

wherein;

$Ar_1$ is selected from the group consisting of

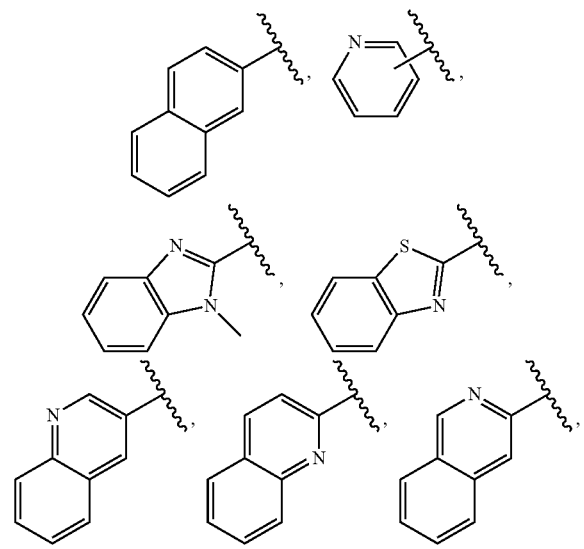

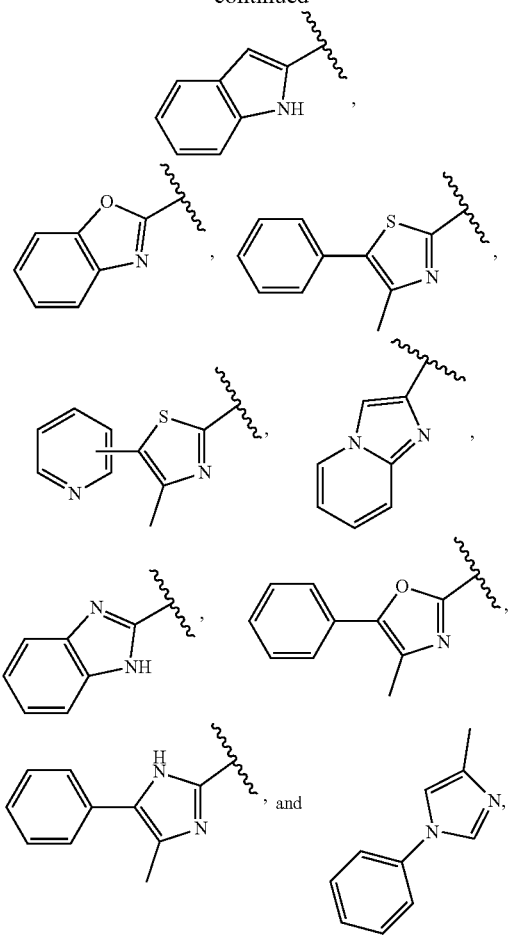

optionally substituted with up to four $R_2$ substituents;

$R_1$ is selected from the group consisting of $C_{1-6}$ alkyl, $C_{3-6}$ cycloalkyl, $C_{3-6}$ cycloalkylmethylene, NHMe, N(Me)$_2$, NHEt, NH-cyclopropyl, OMe, OEt, O-cyclopropyl;

$R_2$ are independently selected from the group consisting of halo, CN, $N_3$, $CF_3$, $NO_2$, H, $C_{1-6}$ alkyl, substituted $C_{1-6}$ alkyl, $C_{2-6}$ alkenyl, substituted $C_{2-6}$ alkenyl, $C_{2-6}$ alkynyl, substituted $C_{2-6}$ alkynyl, $C_{3-6}$ cycloalkyl, substituted $C_{3-6}$ cycloalkyl, $C_{4-6}$ cycloalkenyl substituted $C_{4-6}$ cycloalkenyl, phenyl, substituted phenyl, monocyclic heteroaryl, substituted monocyclic heteroaryl, $OR_5$, $NR_3R_4$, $COOR_5$, $CONR_3R_4$;

$R_3$ and $R_4$, independently, are selected from the group consisting of hydrogen, $C_{1-6}$ alkyl, allyl, $C_{3-6}$ cycloalkyl, $C_{4-6}$ heterocyclyl, aryl, heteroaryl, $C_{1-6}$ alkyl-$C_{3-6}$ cycloalkyl, $C_{1-6}$ alkyl-$C_{4-6}$ cycloalkenyl, $C_{1-6}$ alkyl-$C_{4-6}$ heterocyclyl, $C_{1-6}$ alkaryl, $C_{1-6}$ alkyl-heteroaryl, $C_{1-6}$ acyl, $C_{3-6}$ cycloalkylcarbonyl, $C_{4-6}$ heterocyclylcarbonyl, aroyl, heteroaroyl, or are taken together with the nitrogen atom to which they are attached to form a ring of four to seven members, optionally including any chemically stable combination of one to three O, C=O, $NR^5$ and S;

$R_5$ is selected from the group consisting of hydrogen, $C_{1-6}$ alkyl, allyl, propargyl, $C_{3-6}$ cycloalkyl, $C_{1-6}$ alkyl-$C_{4-6}$ cycloalkenyl, $C_{4-6}$ heterocyclyl, aryl, heteroaryl, $C_{1-6}$ alkyl-$C_{3-6}$ cycloalkyl, $C_{1-6}$ alkyl-$C_{4-6}$ heterocyclyl, $C_{1-6}$ alkaryl, $C_{1-6}$ alkyl-heteroaryl, $C_{1-6}$ acyl, $C_{3-6}$ cycloalkylcarbonyl, $C_{4-6}$ heterocyclylcarbonyl, aroyl, heteroaroyl, each optionally substituted with up to three substituents independently selected from halo, hydroxy, oxo, thio, thiono, amino, cyano, $C_{1-6}$ alkoxy, $C_{1-6}$ alkylthio, $C_{1-6}$ alkylamino, $C_{1-6}$ dialkylamino, $C_{4-6}$ heterocyclo, aryl, and heteroaryl;

$R_6$ and $R_7$, independently, are hydrogen or $C_{1-6}$ alkyl, or $R_6$ and $R_7$ are taken together to form =O, =S, or $R_6$ and $R_7$ are taken together with the carbon atom to which they are attached to form a three to six membered ring, optionally including any chemically stable combination of one to three of O, C=O, $S(O)_x$ or $NR_5$;

$R_{13}$ is $C_{1-6}$ alkyl, $C_{3-6}$ cycloalkyl, $C_{4-6}$ cycloalkenyl, $C_{4-6}$ heterocyclo, $C_{1-6}$ alkyl-$C_{3-6}$ cycloalkyl, $C_{1-6}$ alkyl-$C_{4-6}$ cycloalkenyl, $C_{4-6}$ heterocyclo, $C_{1-6}$ alkyl-$C_{4-6}$ heterocyclo, aryl, $C_{1-6}$ alkylaryl, heteroaryl, $C_{1-6}$ alkyl-heteroaryl, $C_{2-4}$ alkenylaryl, $C_{2-4}$ alkenylheteroaryl, with these groups optionally substituted with up to five substituents independently selected from the group consisting of $C_{1-6}$ alkyl, halo, hydroxy, oxo, thio, thiono, cyano, hydroxymethyl, aminomethyl, $C_{1-6}$ alkoxy, $C_{1-6}$ alkylamino, $C_{1-6}$ dialkylamino, $C_{1-6}$ alkylS$(O)_x$, $C_{1-6}$ aminoacyl, $C_{1-6}$ alkylaminosulfonyl, sulfonamido, $C_{4-6}$ heterocyclo(carbonyl), aryl, aroyl, heteroaryl, and heteroaroyl;

x is 0, 1, or 2;

or a pharmaceutically acceptable salt, hydrate, or solvate thereof.

2. The compound of claim 1 wherein $Ar_1$ is selected from the group consisting of 2-naphthyl, 2-benzoxazolyl, 2-imidazo[1,2-a]pyridinyl or 4-methyl-5-(3-halophenyl)thiazol-2-yl, wherein there are one or two $R_2$ substituents on the B-ring of the bicycle, selected from the group chloro, bromo, methyl, $CF_3$, methyl, ethyl, isopropyl, and cyclopropyl.

3. The compound of claim 1 wherein $R_1$ is selected from the group consisting of

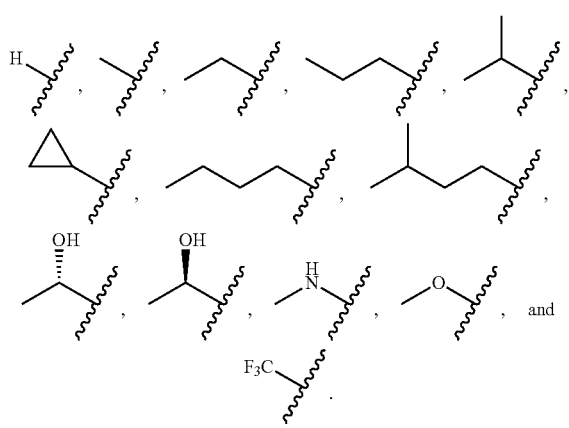

4. The compound of claim 3 wherein $R_1$ is selected from H, methyl, ethyl, propyl, isopropyl, cyclopropyl, methylamino and methoxy.

5. The compound of claim 1, wherein $R_{13}$ is selected from the group consisting of

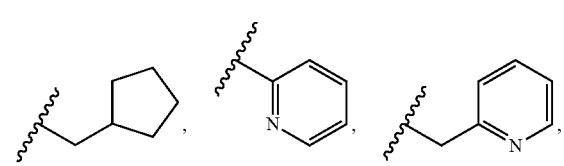

-continued

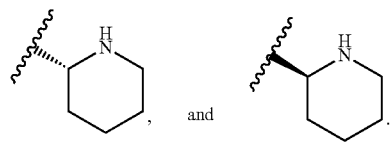

6. A compound selected from the group consisting of

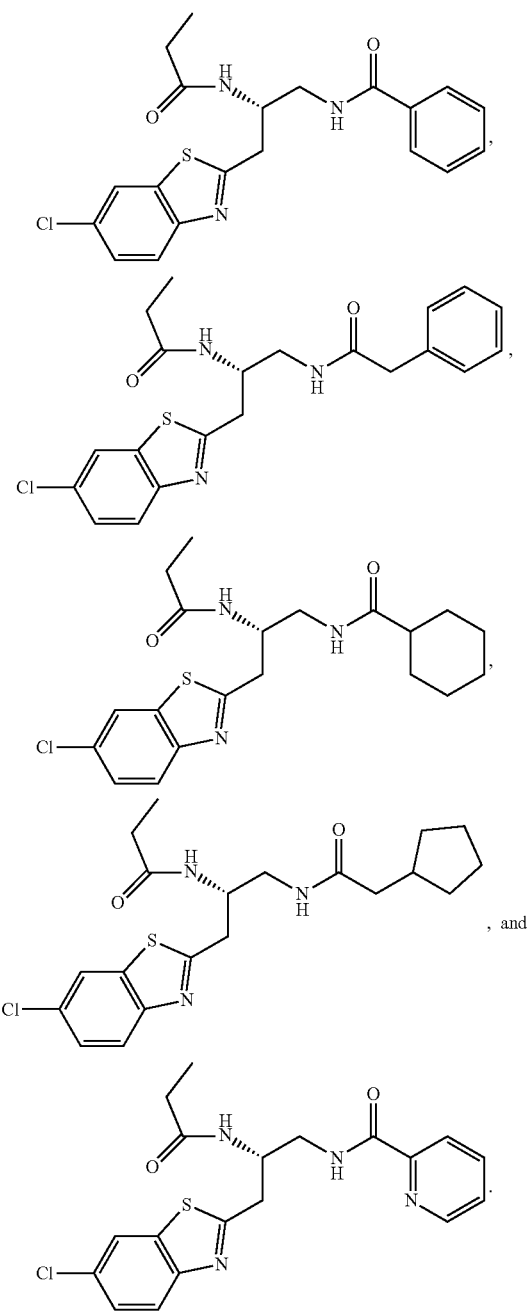

7. A pharmaceutical composition comprising a compound of claim 1 and a pharmaceutically acceptable carrier vehicle.

* * * * *